US007022481B2

(12) United States Patent
Phillips

(10) Patent No.: US 7,022,481 B2
(45) Date of Patent: Apr. 4, 2006

(54) METHODS OF USING GLUCAN SYNTHASE PATHWAY REPORTER GENES TO SCREEN FOR ANTIFUNGAL COMPOUNDS

(75) Inventor: John W. Phillips, New Providence, NJ (US)

(73) Assignee: Rosetta Inpharmatics LLC, Seattle, WA (US)

( * ) Notice: Subject to any disclaimer, the term of this patent is extended or adjusted under 35 U.S.C. 154(b) by 483 days.

(21) Appl. No.: 10/324,035

(22) Filed: Dec. 19, 2002

(65) Prior Publication Data
US 2005/0084848 A1  Apr. 21, 2005

(51) Int. Cl.
*C12Q 1/68* (2006.01)

(52) U.S. Cl. .................. 435/6; 435/32; 435/254.21; 536/24.1

(58) Field of Classification Search .............. 435/6, 435/32, 254.21; 536/24.1
See application file for complete search history.

(56) References Cited

U.S. PATENT DOCUMENTS

| | | | |
|---|---|---|---|
| 3,773,319 | A | 11/1973 | Hottendorf et al. |
| 4,485,045 | A | 11/1984 | Regen |
| 4,544,545 | A | 10/1985 | Ryan et al. |
| 5,569,588 | A | 10/1996 | Ashby et al. |
| 5,777,888 | A | 7/1998 | Rine et al. |
| 5,965,352 | A | 10/1999 | Stoughton et al. |
| 6,057,101 | A | 5/2000 | Nandabalan et al. |
| 6,064,754 | A | 5/2000 | Parekh et al. |
| 6,083,693 | A | 7/2000 | Nandabalan et al. |
| 6,165,709 | A | 12/2000 | Friend et al. |
| 6,187,535 | B1 | 2/2001 | LeGrain et al. |
| 6,271,002 | B1 | 8/2001 | Linsley et al. |
| 6,324,479 | B1 | 11/2001 | Friend et al. |

FOREIGN PATENT DOCUMENTS

| | | |
|---|---|---|
| DE | 32 18 121 A1 | 11/1983 |
| EP | 00 58 481 | 5/2003 |
| WO | WO 96/34099 | 10/1996 |
| WO | WO 98/38329 | 9/1998 |
| WO | WO 00/58521 | 10/2000 |

OTHER PUBLICATIONS

Arellano et al., 1996, "Rho1 GTPase activates the (1-3) β-D-glucan synthase and is involved in Schizosaacharomyces pombe morphogenesis", Embo. J. 15:5484-4594.
Alam et al., 1990, "Reporter Genes: Application to the Study of Mammalian Gene Transcription", Analytical Biochemistry 188:245-254.
Awald et al., 1994, "(1,3)β-Glucan synthase activity of Neurospora crasssa: identification of a substrate-binding protein", Biochim. Biophys. Acta 1201:312-320.
Bachmair et al., 2002, "Quantitation of Gene Expression by RT-PCR and HPLC Analysis of PCR Products", Methods Mol. Biol. 193:103-116.
Blanchard et al., 1996, "Sequence to array: Probing the genome's secrets", Nature Biotechnology. 14:1649.
Balkis et al., 2002, "Mechanisms of Fungal Resistance", Drugs 62:1025-1040.
Benton et al., 1977, "Screening λgt Recombinant Clones by Hybridization to Single Plaque in situ", Science 196:180-182.
Blondelle et al., 1996, "Novel antrimicrobial compounds identified using synthetic combinatorial library technology", Tib Tech 14:60.
Bojase et al., 2002, "Antimicrobial Flavonoids from *Bolusanthus speciosus*", Planta Med. 68:615-620.
Bussey et al., 1995, "The nucleotide sequence of chromosome I from *Saccharomyces cerevisiae*", Proc. Natl. Acad. Sci USA 92:3809-3813.
Castanotto et al., 1998, "Structural Similarities Between Hammerhead Ribozyme and the Spliceosomal RNAs Could Be Responsible for Lack of Ribozyme Clevage in Yeast", Antisense & Nucleic Acid Drug Development 8:1-13.
Cubitt et al., 1995, "Understanding, improving and using green fluorescent proteins", TIBS 20:448-455.
Dainese et al., 1997, "Probing protein function using a combination of gene knockout and proteome analysis by mass spectrometry", Electroporesis 18:432-442.
Dimster-Denk et al., 1999, "Comprehensive evaluation of isoprenoid biosyntheses regulation in *Saccharomyces cerevisiae* utilizing the Genome Reporter Matrix", J. Lipid Research 40:850-860.
Douglas et al., 1994, "A *Saccharomyces cerevisiae* Mutant with Echinocandin-Resistant 1,3-β-D-Glucan Synthase", J. Bacteriology 176:5686-5696.
Dujon et al., 1994, "Complete DNA sequence of yeast chromosome XI", Nature 369:371-378.

(Continued)

Primary Examiner—James Ketter
(74) Attorney, Agent, or Firm—Jones Day

(57) ABSTRACT

The present invention relates to methods of using nucleotide sequences from the promoter region of at least one of seven *S. cerevisiae* genes whose expression is an indicator of the inhibition or modulation of the glucan synthase pathway in *S. cerevisiae*. This invention envisions using at least one target polynucleotide sequence, each target polynucleotide sequence being operably linked to the promoter region of one of the seven glucan synthase pathway reporter genes, to screen chemical libraries and natural products for compounds which can be used as antifungal agents for use against a variety of fungal pathogens. This invention also envisions using the methods of the invention to assay the efficacy of and/or specificity of antifungal agents, and/or to monitor the activity of the glucan synthase pathway.

33 Claims, 38 Drawing Sheets

OTHER PUBLICATIONS

Figure 8:
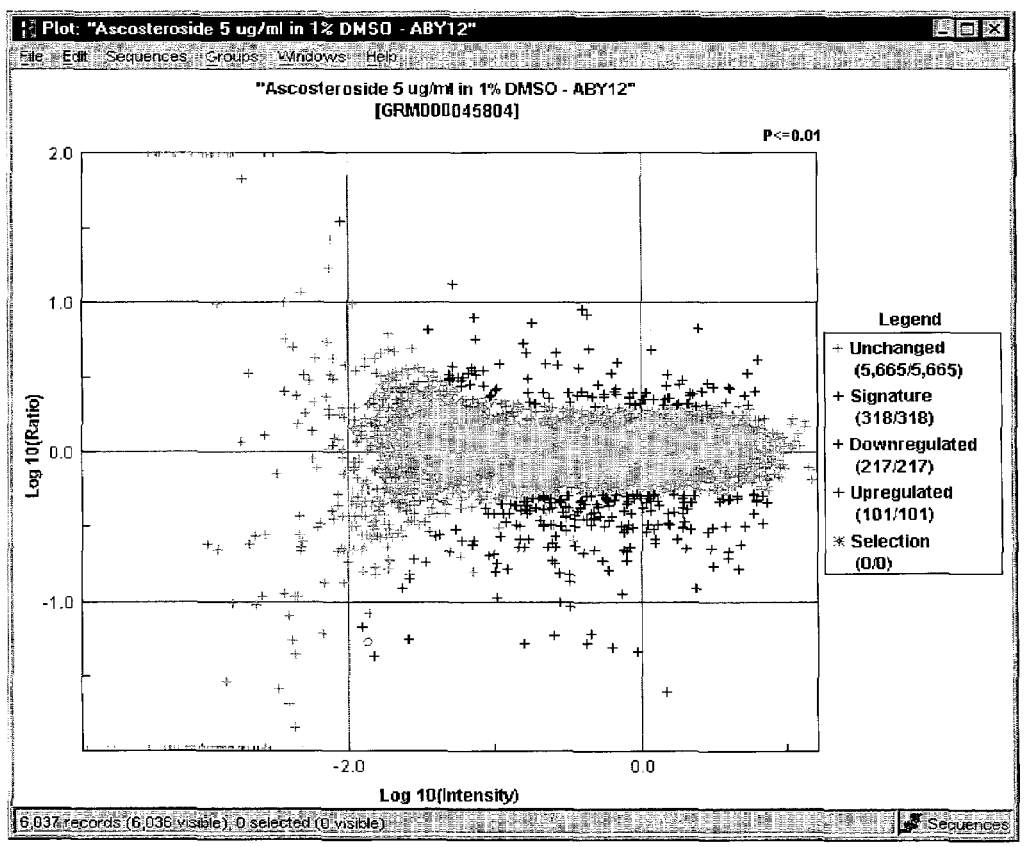

Feldmann et al., 1994, "Complete DNA sequence of yeast chromosome II", The EMBO Journal 13:5795-5809.

Froehler et al., 1986, "Synthesis of DNA via deoxynucleoside H-phosphonate intermediates", Nucleic Acids Research 14:5399-5407.

Galibert et al., 1996, "Complete nucleotide sequence of *Saccharomyces cerevisiae* chromosome X", The EMBO Journal 15:2031-2049.

Gorman et al., 1995, "Ascosteroside, a New Antifungal Agent from *Ascotricha amphitricha*", J. Antibotics 49:547-542.

Grunstein et al., 1975, "Colony hybridization: A method for the isolation of cloned DNAs that contain a specific gene", Proc. Natl. Acad. Sci. USA 72:3961-3965.

Heller et al., 1997, "Discovery and analysis of inflammatory disease-related genes using cDNA microarrays", Proc. Natl. Acad. Sci. USA 94:2150-2155.

Humphery-Smith et al., 1997, "Proteome research: Complementarity and limitations with respect to the RNA and DNA worlds", Electrophoresis 18:1217-1242.

Hussein et al., 2001, "Toxicity, metabolism, and impact of mycotoxins on humans and animals", Toxicology 167:101-134.

Hutchinson et al., 1978, "Mutagenesis at a Specific Position in a DNA Sequence", Journal of Biological Chemistry 253:6551-6560.

Hutchinson et al., 1986, "A complete library of point substitution mutations in the glucocorticoid response element of mouse mammary tumor virus", Proc. Natl. Acad. Sci. USA 83:710.

Inoue et al., 1995, "Characterization and gene cloning of 1,3-β-D-glucan synthase from *Saccharomyces cerevisiae*", Eur. J. Biochem. 231:845-854.

Johnston et al., 1994, "Complete Nucleotide Sequence of *Saccharomyces cerevisiae* Chromosome VIII", Science 265:2077-2082.

Kelly et al., 1996, "Isolation of a Gene Involved in 1,3-B-Glucan Synthesis in *Aspergillus nidulans* and Purification of the Corresponding Protein", Journal of Bacteriology 178:4381-4391.

Lashkari et al., 1997, "Yeast microarrays for enome wide parallel genetic and gene expression analysis", Proc. Natl. Acad. Sci. USA 94:13057-13062.

Liang et al., 1992, "Differential Display of Eukaryotic Messenger RNA by Means of the Polymerase Chain Reaction", Science 257:967-971.

Lockhart et al., 1996, "Expression monitoring by hybridization to high-density oligonucleotide arrays", Nature Biotechnolgy 14:1675-1680.

Martel et al., 2002, "Multiplexed chemiluminescent assays in arrayplates for high-throughput measurement of gene expression", Proc. SPIE 4626:35-43.

McBride et al., 1983, "An investigation of several deoxynucleoside phosphoramidites useful for synthesizing deoxyligonucleotides", Tetrahedron Letters 24:245-248.

McCormac et al., 1994, "Production of Antibacterial Compounds by Phylloplane-Inhabiting Yeasts and Yeastlike Fungi", Appl. Envir. Microbiology 60:927-931.

Mio et al., 1997, "Cloning of the Candida albicans Homolog of *Saccharomyces cervisiae* GSC1/FKS1 and Its Involvement in B-1, 3-Glucan Synthesis" Journal of Bacteriology 179:4096-4105.

Muller et al., 2002, "Processing of Gene Expression Data Generated by Quantitative eal-Time RT-PCR", Biotechniques 32:1372-1379.

O'Farrell, 1975, "High Resolution Two-Dimensional Electrophoresis of Proteins", The Journal of Biological Chemistry 250:4007-4021.

Oliphant et al., 1986, "Cloning of random-sequence oliogodeoxynucleotides", Gene 44:177-183.

Rahalison et al., 1991, "A bioautographic Agar Overlay Method for the Detection of Antifungal Compounds from Higher Plants", Phytochem. Anal. 2:199-203.

Rios et al., 1988, "Screening Methods for Natural Products with Antimicrobial activity: A review of the literature", Ethnopharmacol. 23:127-149.

Rose et al., 1983, "Construction and Use of Gene Fusions to lacZ (β-Galactosidase) That Are Expressed in Yeast", Meth. Enzymol. 167-180.

Rothstein, 1983, "One-Step Gene Disruption in Yeast", Meth. Enzymol. 101:202-211.

Schena et al., 1995, "Quantitative monitoring of gene expression patterns with a complementary DNA microarray", Science 270:467-470.

Sternberg, 1994, "The Emerging Fungal Threat", Science 266:1632-1634.

Terashima et al., 2000, "Up-regulation of genes encoding glycosylphosphatidylinositol (GPI)-attached proteins in response to cell wall damage caused by disruption of FKSI in *Saccharomyces cerevisiae*", Mol. Gen. Genet. 264:64-74.

Thompson et al., 1999, "A Glucan Synthase FKSI Homolog in Cryptococcus newformans Is Single Copy and Encodes an Essential Function", Journal of Bacteriology 181:444-453.

Velculescu et al., 1995, "Serial Analysis of Gene Expression", Science 270:484-487.

Wang et al., 1991, "A gene expression screen", Proc. Natl. Acad. Sci. USA 88:11505-11509.

Wills et al., 2000, "New potential targets for antifungal development", Emerging Therapeutic Targets 4:1-32.

Wodicka et al., 1997, "Genome-wide expression monitoring in *Saccharomyces cerevisiae*", Nature Biotechnology 15:1359-1367.

Zoller et al, 1984, "Oligonucleotide-Directed Mutagenesis: A Simple Method Using Two Oligonucleotide Primers and a Single-Stranded DNA Template", DNA 3:479-488.

Martel et al. 2002, "Multiplexed molecular profiling transcription assay in ArrayPlates for High-throughput measurement of gene expression". in *Gene Cloning and Expression Technologies*. Ch. 36, pp549-564, Weiner & Lu eds. Eaton Publishing, Westborough, MA.

```
tgatgattat gaaataacga acccaccctgc taagaaggct aaaatagaag aaaaacctga    60
aagtgaaccg gccaagagaa atagtggaga gacatatatc actgtctcta gcgaagatga   120
tgatgaagat ggatataatc cttatacccct ttaatatgtg cctttttgtt taaatgatgc   180
actgaactgt acatcactgt gtacctggat agaatgtgtg tttaaatatg cgtattatgt   240
attaataatt gaatttaatt ttacttctgt ttttctttttt atcgctgtga acttttttgt   300
caagaagtcg ctctttgttg gctttctctt ttatttatt ccatttcttt gaggtctcag    360
cagtggtatc attaggaaat tggcacgttt gccgaatttc ttgaaccaac ttctcgaagc   420
attttaattt gttggtttcc cttgacctag tttcatcaga ttgaattact atagaatcgc   480
tgcccttagc gtagtatcga aacctgccgc tacttaagat gtttctcact tcctgaggaa   540
tccaagcaca gtttgataaa ccagaaagtg tcaaagtaca tttactattt accttattaa   600
cgttttggcc tcctggcccg ctggctctat cgtaacgtaa aataaattga tttaagggca   660
agcccgttac gttaagtgct cctacccagt ttcttgcctg gacgaagtca gatttctttc   720
cgatcttttt attactaatc aatctgactg cctcttcaac gaactgttgt ttcttgcagt   780
gcaacattgg ttgaagtaca aacagagggg agcgccagt  aagtttaaac tttcccatca   840
atgttgtcat atgatatttc ttggcgtgtt tccttcaat  ttactgaaag gcaaacagta   900
atgttaagga ttctgttgtt ttttttttacc gtatacgctt gatttcgtca gcccccttga   960
agacacgaaa tgttgactat ccgcttccag atctggtaaa agattgattt gcgataattc  1020
ctgttgttgt catcacgggt gttatggttt gttgtaaact aaaaaaagaa tgaaggaaca  1080
ggacgcagat tcatctaatc aagttctgtg gggaggtccc cagtggtaag tgaataaata  1140
ttcgctttat gaagacctac acctggtttt ctcaatggat cagacgataa gtacaatttt  1200
tgtagagcta tactcgagga caatcagaca aaacgaaaga atatctttcg atg aag    1256
                                                          Met Lys
                                                            1
ggc gta aaa aag gaa gga tgg ata tct tat aaa gtt gat gga ttg ttt   1304
Gly Val Lys Lys Glu Gly Trp Ile Ser Tyr Lys Val Asp Gly Leu Phe
      5              10                  15
tcg ttc tta tgg caa aag aga tac ttg gta ctg aat gat tcg tat tta   1352
Ser Phe Leu Trp Gln Lys Arg Tyr Leu Val Leu Asn Asp Ser Tyr Leu
   20                  25                  30
gca ttt tac aaa agt gat aag tgc aat gag gaa cca gtc tta tct gtg   1400
Ala Phe Tyr Lys Ser Asp Lys Cys Asn Glu Glu Pro Val Leu Ser Val
35                  40                  45                  50
cct ttg act agt ata aca aat gtt agc aga ata caa ttg aaa caa aat   1448
Pro Leu Thr Ser Ile Thr Asn Val Ser Arg Ile Gln Leu Lys Gln Asn
                55                  60                  65
tgt ttt gag att ctt cgg gca aca gat caa aaa gag aac ata tcc ccc   1496
Cys Phe Glu Ile Leu Arg Ala Thr Asp Gln Lys Glu Asn Ile Ser Pro
           70                  75                  80
ata aac tcc tac ttt tat gaa tca aat tcc aaa aga tcg ata ttc att   1544
Ile Asn Ser Tyr Phe Tyr Glu Ser Asn Ser Lys Arg Ser Ile Phe Ile
       85                  90                  95
tcc aca aga acc gaa cgg gat ttg cat ggc tgg ctt gat gcc att ttt   1592
Ser Thr Arg Thr Glu Arg Asp Leu His Gly Trp Leu Asp Ala Ile Phe
   100                 105                 110
gcc aaa tgt cct ctc ctt agt ggt gtt tca tca cca aca aat ttt aca   1640
Ala Lys Cys Pro Leu Leu Ser Gly Val Ser Ser Pro Thr Asn Phe Thr
115                 120                 125                 130
cac aaa gta cac gtt ggg ttc gac cca aaa gtg gga aac ttt gtt gga   1688
His Lys Val His Val Gly Phe Asp Pro Lys Val Gly Asn Phe Val Gly
                135                 140                 145
gta cct gat agt tgg gct aaa cta cta caa acc tca gaa att acg tac   1736
Val Pro Asp Ser Trp Ala Lys Leu Leu Gln Thr Ser Glu Ile Thr Tyr
           150                 155                 160
gac gat tgg aac aga aac tca aaa gct gtt att aaa gca ctg caa ttt   1784
Asp Asp Trp Asn Arg Asn Ser Lys Ala Val Ile Lys Ala Leu Gln Phe
       165                 170                 175
```

FIG. 1

```
tat gaa gat tac aat gga ctg gac aca atg caa ttc aat gat cac ctc    1832
Tyr Glu Asp Tyr Asn Gly Leu Asp Thr Met Gln Phe Asn Asp His Leu
    180                 185                 190
aac aca agc tta gac ttg aaa cct tta aaa agt ccg aca agg tat att    1880
Asn Thr Ser Leu Asp Leu Lys Pro Leu Lys Ser Pro Thr Arg Tyr Ile
195                 200                 205                 210
ata aac aag agg act aat tcc atc aag aga tca gta agt agg acg ctc    1928
Ile Asn Lys Arg Thr Asn Ser Ile Lys Arg Ser Val Ser Arg Thr Leu
                215                 220                 225
cga aaa ggc aaa aca gat tcc att tta ccc gtc tat caa tca gaa ctt    1976
Arg Lys Gly Lys Thr Asp Ser Ile Leu Pro Val Tyr Gln Ser Glu Leu
            230                 235                 240
aaa cca ttc cca agg cct agt gat gat gat tat aag ttt acc aac ata    2024
Lys Pro Phe Pro Arg Pro Ser Asp Asp Asp Tyr Lys Phe Thr Asn Ile
        245                 250                 255
gag gac aat aaa gta cgc gaa gaa ggc agg gtg cat gtt agt aaa gaa    2072
Glu Asp Asn Lys Val Arg Glu Glu Gly Arg Val His Val Ser Lys Glu
    260                 265                 270
agc acg gca gat tcc cag aca aag cag tta gga aag aag gaa cag aaa    2120
Ser Thr Ala Asp Ser Gln Thr Lys Gln Leu Gly Lys Lys Glu Gln Lys
275                 280                 285                 290
gtc att caa agc cat ctg cga agg cat gat aat aat tca aca ttt aga    2168
Val Ile Gln Ser His Leu Arg Arg His Asp Asn Asn Ser Thr Phe Arg
                295                 300                 305
cct cat cga cta gca cca tct gca cct gct aca aaa aat cat gat agt    2216
Pro His Arg Leu Ala Pro Ser Ala Pro Ala Thr Lys Asn His Asp Ser
            310                 315                 320
aaa act aaa tgg cat aag gag gat ctc ctt gaa ctt aag aat aat gat    2264
Lys Thr Lys Trp His Lys Glu Asp Leu Leu Glu Leu Lys Asn Asn Asp
        325                 330                 335
gat tcg aat gaa ata ata atg aag atg aaa act gtt gca att gat gta    2312
Asp Ser Asn Glu Ile Ile Met Lys Met Lys Thr Val Ala Ile Asp Val
    340                 345                 350
aac cca aga ccg tat ttc caa ctg gta gaa aag gct ggt caa gga gca    2360
Asn Pro Arg Pro Tyr Phe Gln Leu Val Glu Lys Ala Gly Gln Gly Ala
355                 360                 365                 370
agt ggt gca gta tac ctg tca aag cga ata aaa tta cct caa gaa aat    2408
Ser Gly Ala Val Tyr Leu Ser Lys Arg Ile Lys Leu Pro Gln Glu Asn
                375                 380                 385
gac ccg aga ttc ttg aaa tca cat tgc cac cga gtc gta ggc gaa aga    2456
Asp Pro Arg Phe Leu Lys Ser His Cys His Arg Val Val Gly Glu Arg
            390                 395                 400
gtg gcc att aag cag ata cgt tta tct gaa caa cca aag aaa caa ttg    2504
Val Ala Ile Lys Gln Ile Arg Leu Ser Glu Gln Pro Lys Lys Gln Leu
        405                 410                 415
att atg aat gaa ctc cta gtg atg aat gat tcg cgc caa gaa aat atc    2552
Ile Met Asn Glu Leu Leu Val Met Asn Asp Ser Arg Gln Glu Asn Ile
    420                 425                 430
gtt aat ttc ctt gaa gcc tat att att gat gac gaa gag tta tgg gtg    2600
Val Asn Phe Leu Glu Ala Tyr Ile Ile Asp Asp Glu Glu Leu Trp Val
435                 440                 445                 450
ata atg gag tac atg gaa ggt ggc tgc tta aca gat ata ttg gat gct    2648
Ile Met Glu Tyr Met Glu Gly Gly Cys Leu Thr Asp Ile Leu Asp Ala
                455                 460                 465
gta gca agg agc aat acc ggt gag cac tca tcg ccg tta aac gaa aac    2696
Val Ala Arg Ser Asn Thr Gly Glu His Ser Ser Pro Leu Asn Glu Asn
            470                 475                 480
```

FIG. 1

| | |
|---|---|
| caa atg gca tat ata gta aaa gag acg tgc caa ggt ttg aag ttt ttg<br>Gln Met Ala Tyr Ile Val Lys Glu Thr Cys Gln Gly Leu Lys Phe Leu<br>485                         490                     495 | 2744 |
| cat aac aag aaa att atc cat cga gat atc aaa tct gat aat atc ctt<br>His Asn Lys Lys Ile Ile His Arg Asp Ile Lys Ser Asp Asn Ile Leu<br>500                         505                     510 | 2792 |
| ctg aat tcc caa ggg tta gtg aaa att aca gac ttc ggt ttt tgt gtg<br>Leu Asn Ser Gln Gly Leu Val Lys Ile Thr Asp Phe Gly Phe Cys Val<br>515                     520                     525                     530 | 2840 |
| gaa tta aca gaa aaa aga agc aag cgt gcc aca atg gta ggt act cca<br>Glu Leu Thr Glu Lys Arg Ser Lys Arg Ala Thr Met Val Gly Thr Pro<br>                     535                     540                     545 | 2888 |
| tat tgg atg gca cct gaa ata gtg aat caa aag gga tat gat gaa aaa<br>Tyr Trp Met Ala Pro Glu Ile Val Asn Gln Lys Gly Tyr Asp Glu Lys<br>               550                     555                     560 | 2936 |
| gtc gac gtt tgg tct cta ggg ata atg ctt att gag atg ata gaa ggt<br>Val Asp Val Trp Ser Leu Gly Ile Met Leu Ile Glu Met Ile Glu Gly<br>               565                     570                     575 | 2984 |
| gaa ccg cct tac cta aat gag gat cct ttg aag gcg ctg tat ctg ata<br>Glu Pro Pro Tyr Leu Asn Glu Asp Pro Leu Lys Ala Leu Tyr Leu Ile<br>580                         585                     590 | 3032 |
| gct aac aac ggt tca cca aaa ttg cgt cat cca gag tca gtg tcc aag<br>Ala Asn Asn Gly Ser Pro Lys Leu Arg His Pro Glu Ser Val Ser Lys<br>595                         600                     605                     610 | 3080 |
| caa acc aaa caa ttc tta gat gcc tgt ttg caa gtg aat gtc gaa tca<br>Gln Thr Lys Gln Phe Leu Asp Ala Cys Leu Gln Val Asn Val Glu Ser<br>                     615                     620                     625 | 3128 |
| aga gca tcc gtg aga aaa cta cta acg ttt gaa ttt ttg tca atg gca<br>Arg Ala Ser Val Arg Lys Leu Leu Thr Phe Glu Phe Leu Ser Met Ala<br>               630                     635                     640 | 3176 |
| tgc agc cct gag cag ctc aaa gta tcc tta aag tgg cat tga<br>Cys Ser Pro Glu Gln Leu Lys Val Ser Leu Lys Trp His<br>               645                     650                     655 | 3218 |

FIG. 1

```
aagaacgaag aaagtagtag tgaagattac aattttgcct atgctatgaa gttatggggg    60
gccactatcg gtgaccagtc aatggaattg aggggtgact tgatgattag tataatgaag   120
gatgcaatga acgactattt ctattatcaa aatgacaaca cagttgagcc tgaagaaatc   180
ataggaaata aagtgagtgg tattttattc gataatatta tcgattatac tacttatttt   240
ggaacaaaca cagaatatat ccacggtatt catatgctac ctatcacacc agtttcttct   300
aatattcgtt ctgagctttt cgtcgaagaa gaatggcaga ctaaaatcga gccaattatt   360
gaatcgatag aaagcggctg gacaggcata ttgaagctga atcaagcact cttcgaccca   420
gtagattcgt atgcattttt cagtgattca acttttgatt catccacata tttggataac   480
ggaatgagtc gcacatgggc attagcattt tcaggggggac tggccaactc aattgcttag   540
aaagagaact tggcaagcag gtctgtcgag tctttcccac tacatacata ttttatagaa   600
taaatcattt ttacttaact tgaaagttgt tgcgttcgaa aagaccacgg ctaacggaga   660
ccacttaggt aaatgcatgc cagtaagagg tatattagta ctttaatgaa tgaacttagc   720
aaggtaatgc ctgcactaaa ataaaattct aacgtcatcc taagaagcat caattggaca   780
tagtgaggaa aagttttcac catttaaaat ttgttttgca gaataccatt ctagactatg   840
atcccttaga gattctcatt cttaaatat cagcttcaac agcatatctt tatagtatta    900
tcgtactact ggcgacatta gcaaatcaaa gtattttgc tcagtttcta gttttatctg    960
tttgattccc cattagatgg taaacacgtt gtcttgatga ctgaaaagga agtgaacatg  1020
gtcaactcaa aataaccaga ctcaaaataa ttgcaattac ctaggctaga tatttttaga  1080
atattatgag aatatttta gaatatttgc aacccaaaat atatttaaat gccgccaatt   1140
tgcaaccaaa agattatccg ctaccttttt tttagtcatt gaatcgtagc ataaagttcc  1200
gagctttgaa aaaaagcttt gaactaagaa aaggtaagag atcctcaatt atg ata     1256
                                                           Met Ile
                                                            1
tta ctc caa gtc ata tgc acg att tgg aca tgt ctc ttt att ccg tta     1304
Leu Leu Gln Val Ile Cys Thr Ile Trp Thr Cys Leu Phe Ile Pro Leu
        5              10              15
ctc aat gca gag gaa ttc gtc ccc aaa gta acg gag act ctt tca gaa     1352
Leu Asn Ala Glu Glu Phe Val Pro Lys Val Thr Glu Thr Leu Ser Glu
 20              25              30
tat tca ttt agt cta gag agc ttt gac gat tcc aac agt tta atc aga    1400
Tyr Ser Phe Ser Leu Glu Ser Phe Asp Asp Ser Asn Ser Leu Ile Arg
35              40              45              50
tta gat aat caa gtc gtg tgg ata agt tcc gat tct gga gaa aat tgg    1448
Leu Asp Asn Gln Val Val Trp Ile Ser Ser Asp Ser Gly Glu Asn Trp
                55              60              65
gaa gcg gtc aaa gaa att gaa ggg cat att ctc gaa tta att gtt gat    1496
Glu Ala Val Lys Glu Ile Glu Gly His Ile Leu Glu Leu Ile Val Asp
         70              75              80
cct ttg cat gga cag gac agg gct ttt gtt tcg ata cat tta tca ccc    1544
Pro Leu His Gly Gln Asp Arg Ala Phe Val Ser Ile His Leu Ser Pro
        85              90              95
aaa ttt tac gtc acc gat gat cgt gga aaa tca tgg agg gct ctg act    1592
Lys Phe Tyr Val Thr Asp Asp Arg Gly Lys Ser Trp Arg Ala Leu Thr
100             105             110
ata ccc gtc tct gaa aac tgt cgt ttg ggt act tct tgc tct ata gct    1640
Ile Pro Val Ser Glu Asn Cys Arg Leu Gly Thr Ser Cys Ser Ile Ala
115             120             125             130
acc cat ccg aca gat aaa aag tac ctt att gca gat tgc cct tgc ttt    1688
Thr His Pro Thr Asp Lys Lys Tyr Leu Ile Ala Asp Cys Pro Cys Phe
                135             140             145
ata aac gac aat ggt tat atc caa ata caa aat gaa act tac ttt acc    1736
Ile Asn Asp Asn Gly Tyr Ile Gln Ile Gln Asn Glu Thr Tyr Phe Thr
             150             155             160
aac gat ggg gaa tcc ttt tac aat atc gaa cct tcc ttg aaa aag aaa    1784
Asn Asp Gly Glu Ser Phe Tyr Asn Ile Glu Pro Ser Leu Lys Lys Lys
        165             170             175
```

FIG. 2

```
gaa gat gac cat ata aca agt tca agc tgc aac ttt gtc aaa tct agc    1832
Glu Asp Asp His Ile Thr Ser Ser Ser Cys Asn Phe Val Lys Ser Ser
    180             185                 190
aag gat tct gat att gag ggt aac gac gct tcg ata cta tgt ttg ttc    1880
Lys Asp Ser Asp Ile Glu Gly Asn Asp Ala Ser Ile Leu Cys Leu Phe
195             200                 205                     210
tcg aac cat ggt tac gat agc gat cgt cac tta agt gcc gca tat aca    1928
Ser Asn His Gly Tyr Asp Ser Asp Arg His Leu Ser Ala Ala Tyr Thr
                215                 220                 225
caa tta gcc tta agt act gat gga ggt aaa act ttc aaa aaa ttt gat    1976
Gln Leu Ala Leu Ser Thr Asp Gly Gly Lys Thr Phe Lys Lys Phe Asp
            230                 235                 240
gag ttt aat gat aaa att att tat caa tac aag ata tta aaa tca cat    2024
Glu Phe Asn Asp Lys Ile Ile Tyr Gln Tyr Lys Ile Leu Lys Ser His
        245                 250                 255
ata atc gtt tcg aca caa gat gat aga tac aat gaa atg tca ccc atg    2072
Ile Ile Val Ser Thr Gln Asp Asp Arg Tyr Asn Glu Met Ser Pro Met
    260                 265                 270
gac atc tgg ata tcc aat gat gcg tct act ttt caa aag gca cgt cta    2120
Asp Ile Trp Ile Ser Asn Asp Ala Ser Thr Phe Gln Lys Ala Arg Leu
275             280                 285                     290
cct gct caa gta cgg cac gtc cat atg tat gga att tat gaa gat tct    2168
Pro Ala Gln Val Arg His Val His Met Tyr Gly Ile Tyr Glu Asp Ser
                295                 300                 305
att gga aga ata atc att cct ata tct acg ata ttc aca gat gaa aaa    2216
Ile Gly Arg Ile Ile Ile Pro Ile Ser Thr Ile Phe Thr Asp Glu Lys
            310                 315                 320
aac gac caa cca gct ccc tca gaa att tta ata tca gat tct caa ggg    2264
Asn Asp Gln Pro Ala Pro Ser Glu Ile Leu Ile Ser Asp Ser Gln Gly
        325                 330                 335
ttg aaa ttt tta cct gtt gaa tgg aca ata aat cct cac ttt ggt tat    2312
Leu Lys Phe Leu Pro Val Glu Trp Thr Ile Asn Pro His Phe Gly Tyr
    340                 345                 350
att gat att gct tct cct cat ttc tta gaa gga aca ata att ggc tcg    2360
Ile Asp Ile Ala Ser Pro His Phe Leu Glu Gly Thr Ile Ile Gly Ser
355             360                 365                     370
ttt cat cct tcc ttt gac tac tct cat aac aaa gga aaa tat aat aaa    2408
Phe His Pro Ser Phe Asp Tyr Ser His Asn Lys Gly Lys Tyr Asn Lys
                375                 380                 385
aag ata gcc aga tat gaa act aaa ata tct gtt gat aac ggc ctc aca    2456
Lys Ile Ala Arg Tyr Glu Thr Lys Ile Ser Val Asp Asn Gly Leu Thr
            390                 395                 400
tgg tca aat ttg aaa gtg gtt gac gag gaa aat gca gat tca ttc cct    2504
Trp Ser Asn Leu Lys Val Val Asp Glu Glu Asn Ala Asp Ser Phe Pro
        405                 410                 415
tgt gat atc act agg cct gaa aga tgt tcg ctc cag aac cct ttt tat    2552
Cys Asp Ile Thr Arg Pro Glu Arg Cys Ser Leu Gln Asn Pro Phe Tyr
    420                 425                 430
agt atc taa                                                        2561
Ser Ile
435
```

FIG. 2

```
tggactcagg atgatgagag gttcctttgt accactaaga tcgactcgtc ctaaccctat    60
atcccaatcc caagactagg cgaaccaaca ttaactgggc tcgtaatagg gcaatgataa   120
tgcaaaagcg gctcctaaac agaaattctt cagtagtcaa atctcgaaat tgccttgctc   180
gtcatcaaca tgaatcgtct atatcaaaac tgcatgtttc tctacgtcta cacagatgtt   240
tgcgtccgat tgtgcgcttc gattttttac ataatgctgg aagcaaagtt tgctctcaga   300
attcctgccc ttcgcccag ttacacgtgg ggacaatggc gctctttcat acagtcttca    360
ttctatggcc gcacttttgt ggcattctct ggaccgtcca tgaaaaatta taaactatt    420
tgctttctat tgaagtctat tgaagttagc gtggatagaa cggcgttaca tggcacatca   480
gctgaagcta gcgcaagtaa ttttcaacgc attcaaacga aaacttatc taaatacaat    540
tgtaacatac cggcttgctg tgtgtgaacc cctttcccca attgtatatc agaaacgtct   600
gagtggaggg tgaggaatca ctcactacct tttctccatt cgacgcctat aagcagcgta   660
ttttaaagga aaggggaatt agtgcggaga tgggccagaa atgtactctt ttttggcag    720
agttttttccg ggcgggacaa acaatggcg tggggtgatg aaataagcaa aattcaatat   780
cccttatgac ggaatggcag aattggccac catttgtct tggcattcaa tatacataca    840
aatcttcact accgcgatat tgttggtaat ggagattgct ttttggcctc ctggcttata   900
gggctctgag tctcgtggta gtggaatccg gcacagaaac gagaatcgga tatttggggc   960
cgggccatgt acaggcaaaa gaaatagcga aaatatctct tatttttttc gcgcttcctt  1020
tgtagtagaa attattggcg atcggattac tattcgcgga aaagaaatta aaaatagcga  1080
agaacttaga actataagcc tcaaaggaa acttgtgtgg tcgaaggctg gacgccataa   1140
taatatatat atgtacgtat atatattata tatgaatatc tgtagccgct aacttgtgtg  1200
tttgtgaatt tatataggat aaatagagca aaattactcg gcattgaaaa atg aaa     1256
                                                           Met Lys
                                                            1
ctt caa ttg gcg gca gtg gct aca tta gca gtc tta act agt ccg gca    1304
Leu Gln Leu Ala Ala Val Ala Thr Leu Ala Val Leu Thr Ser Pro Ala
      5                  10                  15
ttc ggt aga gta ctt ccc gat ggg aaa tac gtc aag att ccc ttc aca    1352
Phe Gly Arg Val Leu Pro Asp Gly Lys Tyr Val Lys Ile Pro Phe Thr
 20                  25                  30
aaa aaa aag aac ggc gac aat ggt gaa ctc agc aag aga tcg aac ggc    1400
Lys Lys Lys Asn Gly Asp Asn Gly Glu Leu Ser Lys Arg Ser Asn Gly
 35                  40                  45                  50
cat gaa aaa ttt gta cta gct aac gag caa agc ttt tat tct gtt gag    1448
His Glu Lys Phe Val Leu Ala Asn Glu Gln Ser Phe Tyr Ser Val Glu
                 55                  60                  65
cta gcc att ggt aca cct tca caa aac ctc act gtg ctg tta gac aca    1496
Leu Ala Ile Gly Thr Pro Ser Gln Asn Leu Thr Val Leu Leu Asp Thr
         70                  75                  80
ggc tca gct gac tta tgg gtt cct ggc aag gga aac ccc tac tgc ggt    1544
Gly Ser Ala Asp Leu Trp Val Pro Gly Lys Gly Asn Pro Tyr Cys Gly
     85                  90                  95
tct gtg atg gac tgt gac cag tat ggc gtg ttc gac aag acc aag tcg    1592
Ser Val Met Asp Cys Asp Gln Tyr Gly Val Phe Asp Lys Thr Lys Ser
100                 105                 110
tcc acg ttc aaa gcc aac aag tcc tcg cct ttt tat gcc gct tac ggt    1640
Ser Thr Phe Lys Ala Asn Lys Ser Ser Pro Phe Tyr Ala Ala Tyr Gly
115                 120                 125                 130
gac gga acc tat gca gaa ggt gca ttt ggt caa gat aaa tta aag tac    1688
Asp Gly Thr Tyr Ala Glu Gly Ala Phe Gly Gln Asp Lys Leu Lys Tyr
                135                 140                 145
aac gaa tta gac ctc agt ggt cta tcg ttt gcc gtg gcc aac gaa tct    1736
Asn Glu Leu Asp Leu Ser Gly Leu Ser Phe Ala Val Ala Asn Glu Ser
            150                 155                 160
aac tca acc ttt ggt gtg ctc ggg atc ggc ctt tcc acg ctt gaa gtc    1784
Asn Ser Thr Phe Gly Val Leu Gly Ile Gly Leu Ser Thr Leu Glu Val
       165                 170                 175
```

FIG. 3

```
acc tat tct gga aaa gtc gct att atg gac aag aga agc tac gag tat      1832
Thr Tyr Ser Gly Lys Val Ala Ile Met Asp Lys Arg Ser Tyr Glu Tyr
        180                 185                 190
gat aac ttt ccc ctg ttc cta aaa cat tct gga gcc atc gat gca acc      1880
Asp Asn Phe Pro Leu Phe Leu Lys His Ser Gly Ala Ile Asp Ala Thr
195                 200                 205                 210
gca tac tct ctt ttc cta aat gac gag tca cag tcc tcc ggc agc atc      1928
Ala Tyr Ser Leu Phe Leu Asn Asp Glu Ser Gln Ser Ser Gly Ser Ile
                215                 220                 225
ctc ttc ggc gct gta gat cac agc aag tac gag ggc caa ctg tac act      1976
Leu Phe Gly Ala Val Asp His Ser Lys Tyr Glu Gly Gln Leu Tyr Thr
            230                 235                 240
atc ccg ttg gtt aat ctt tat aag tcg cag ggt tat cag cac ccg gtg      2024
Ile Pro Leu Val Asn Leu Tyr Lys Ser Gln Gly Tyr Gln His Pro Val
        245                 250                 255
gcg ttc gat gtc act tta cag ggc tta gga ctg caa acc gac aag cgc      2072
Ala Phe Asp Val Thr Leu Gln Gly Leu Gly Leu Gln Thr Asp Lys Arg
    260                 265                 270
aac atc aca ttg acc acc acc aag ctc cca gcc cta ctc gat tca ggc      2120
Asn Ile Thr Leu Thr Thr Thr Lys Leu Pro Ala Leu Leu Asp Ser Gly
275                 280                 285                 290
aca acg cta aca tat ctg ccc tcc cag gca gtg gct ttg cta gca aag      2168
Thr Thr Leu Thr Tyr Leu Pro Ser Gln Ala Val Ala Leu Leu Ala Lys
                295                 300                 305
agc ttg aat gcc tcg tat tcc aag aca ttg ggt tat tat gag tac acg      2216
Ser Leu Asn Ala Ser Tyr Ser Lys Thr Leu Gly Tyr Tyr Glu Tyr Thr
            310                 315                 320
tgt ccc tcg agc gac aac aaa acc agc gtg gcc ttc gac ttc ggt ggc      2264
Cys Pro Ser Ser Asp Asn Lys Thr Ser Val Ala Phe Asp Phe Gly Gly
        325                 330                 335
ttc cgt atc aac gct cct cta tcc gac ttt act atg cag acc agt gtg      2312
Phe Arg Ile Asn Ala Pro Leu Ser Asp Phe Thr Met Gln Thr Ser Val
    340                 345                 350
ggg acc tgt gtc ttg gca ata att cca caa gcg ggc aac gcc acc gct      2360
Gly Thr Cys Val Leu Ala Ile Ile Pro Gln Ala Gly Asn Ala Thr Ala
355                 360                 365                 370
atc ctt ggt gat tcc ttc ttg aga aac gcc tac gtg gtc tac gat ttg      2408
Ile Leu Gly Asp Ser Phe Leu Arg Asn Ala Tyr Val Val Tyr Asp Leu
                375                 380                 385
gat aac tac gag att tcc cta gct caa gcc aag tat ggc acg ggg aaa      2456
Asp Asn Tyr Glu Ile Ser Leu Ala Gln Ala Lys Tyr Gly Thr Gly Lys
            390                 395                 400
gag aac gtc gaa gtc atc aaa tct acc gtt ccc agt gca ata agg gcc      2504
Glu Asn Val Glu Val Ile Lys Ser Thr Val Pro Ser Ala Ile Arg Ala
        405                 410                 415
ccc agt tac aac aac act tgg tct aac tac gcc tcc gcc acg tcc ggt      2552
Pro Ser Tyr Asn Asn Thr Trp Ser Asn Tyr Ala Ser Ala Thr Ser Gly
    420                 425                 430
ggt aat att ttt acc acc gtg cgc act ttc aat ggc acc agt act gcc      2600
Gly Asn Ile Phe Thr Thr Val Arg Thr Phe Asn Gly Thr Ser Thr Ala
435                 440                 445                 450
acc act acg agg tca acc acc acc aag aag aca aac tct acc act act      2648
Thr Thr Thr Arg Ser Thr Thr Thr Lys Lys Thr Asn Ser Thr Thr Thr
                455                 460                 465
```

FIG. 3

```
gca aag tcg act cat aaa agc aag agg gca ctc cag agg gct gct acc    2696
Ala Lys Ser Thr His Lys Ser Lys Arg Ala Leu Gln Arg Ala Ala Thr
            470             475             480
aac tcc gct tcc agt ata cgc tct acc ttg ggt tta ctg cta gtc ccc    2744
Asn Ser Ala Ser Ser Ile Arg Ser Thr Leu Gly Leu Leu Leu Val Pro
            485             490             495
tcc tta ctc atc ctt tcc gtt ttc ttt tcg taa                        2777
Ser Leu Leu Ile Leu Ser Val Phe Phe Ser
            500             505
```

FIG. 3

```
aattgggtgc taactatgcc ccatgcatct tacctcaact acaagctgcc aaaagagggt      60
accaacaaaa tctatggttg ttcggcccag aaaagaacat cactgaggtt ggtactatga     120
acgtgttctt cgttttcctc aacaaagtca ctggcaagaa ggaattggtt accgctccat     180
tagatggtac cattttagaa ggtgttacca gagactctgt tttaacattg gctcgtgaca     240
aactagatcc tcaagaatgg gacatcaacg agcgttatta cactattact gaagtcgcca     300
ctagagcaaa acaaggtgaa ctattagaag ccttcggttc tggtactgct gctgtcgttt     360
cacctatcaa ggaaattggc tggaacaacg aagatattca tgttccacta ttgcctggtg     420
aacaatgtgg tgcattgacc aagcaagttg ctcaatggat tgctgatatc caatacggta     480
gagtcaatta tggtaactgg tcaaaaactg ttgccgactt gaactaatga taatgaaggt     540
aaacatcccc tccccccca aaaaaaaaa acgagaattc ctctcagagg atctgttttt      600
ctctcacttt attcacatag atacatactt ttttacaatt cctgttgagt ttatttatta     660
taagaaatat tggattacta ttattattat agcttatgca agccattgtg cggcttctta     720
cgcttttttga aattgttgac ctaacaactt ggcacattat tgaatttcat agagactgct     780
tgtaatttag ttgccaaggt atctcgctgg actttacatg taaaatgaat gcggcaagat     840
acccaagaga gttgattatg ccaaaaaaaa aaatctata aggatatccc tggtattttc      900
tgaagaataa attctagcgt agttcagaag aggtgcaagt acagtatgaa taatggtatg     960
ccttccatca tcgtggcata caggttcagg catgaagaga tgattatgtt ccctcaccgg    1020
tccataatcc tgatttaaac agttcattag tatatgttca gccaacacaa caacgagaag    1080
ctttgtagtg aaagttttcc acgatctata tttagcattc taattagcgg ccccaaggga    1140
acgtatataa acataaacaa acggcacgaa ctaaaggggc aaattcaagt taaccctttt    1200
acactcagta catcttcaaa gccagtcttc tgtcaatgga agaatccaga atg cct       1256
                                                         Met Pro
                                                         1
aaa act agt tat tta aac aaa aat ttt gaa tct gct cac tat aat aac      1304
Lys Thr Ser Tyr Leu Asn Lys Asn Phe Glu Ser Ala His Tyr Asn Asn
        5               10                  15
gta cgt ccc tct tac cct tta tct tta gtc aat gag ata atg aaa ttt      1352
Val Arg Pro Ser Tyr Pro Leu Ser Leu Val Asn Glu Ile Met Lys Phe
 20              25                  30
cac aaa ggc aca cgc aaa agt ttg gtt gat att gga tgt ggc aca gga      1400
His Lys Gly Thr Arg Lys Ser Leu Val Asp Ile Gly Cys Gly Thr Gly
35              40                  45                  50
aaa gca act ttt gtc gtt gaa ccc tat ttt aag gaa gtg att ggg att      1448
Lys Ala Thr Phe Val Val Glu Pro Tyr Phe Lys Glu Val Ile Gly Ile
                55                  60                  65
gat cct tct tct gct atg ctt tcg att gct gag aaa gaa aca aat gaa      1496
Asp Pro Ser Ser Ala Met Leu Ser Ile Ala Glu Lys Glu Thr Asn Glu
                70                  75                  80
cgt aga tta gat aaa aag att aga ttt att aat gcg cct ggt gaa gat      1544
Arg Arg Leu Asp Lys Lys Ile Arg Phe Ile Asn Ala Pro Gly Glu Asp
            85                  90                  95
tta tcc agc att cga cca gaa agt gta gat atg gtt att tca gca gaa      1592
Leu Ser Ser Ile Arg Pro Glu Ser Val Asp Met Val Ile Ser Ala Glu
        100                 105                 110
gcc atc cat tgg tgc aat tta gaa agg ctg ttt cag cag gtt tcc tct      1640
Ala Ile His Trp Cys Asn Leu Glu Arg Leu Phe Gln Gln Val Ser Ser
115                 120                 125                 130
ata tta cga agt gat gga act ttt gca ttc tgg ttt tat att cag ccg      1688
Ile Leu Arg Ser Asp Gly Thr Phe Ala Phe Trp Phe Tyr Ile Gln Pro
                135                 140                 145
gaa ttt gtg gac ttt ccc gaa gcc ttg aat gta tac aaa tat gga          1736
Glu Phe Val Asp Phe Pro Glu Ala Leu Asn Val Tyr Tyr Lys Tyr Gly
                150                 155                 160
tgg agc aag gat tat atg ggt aaa tat ctg aac gac aac caa cgg gaa      1784
Trp Ser Lys Asp Tyr Met Gly Lys Tyr Leu Asn Asp Asn Gln Arg Glu
        165                 170                 175
```

FIG. 4

| | | | | | | | | | | | | | | | |
|---|---|---|---|---|---|---|---|---|---|---|---|---|---|---|---|
| att | ttg | ttg | aat | tac | ggt | ggt | gaa | aag | cta | cgt | tct | tta | ttg | tca | gat | 1832 |
| Ile | Leu | Leu | Asn | Tyr | Gly | Gly | Glu | Lys | Leu | Arg | Ser | Leu | Leu | Ser | Asp |
| | 180 | | | | | 185 | | | | | 190 | | | | |
| cga | ttt | gga | gat | att | gaa | gtc | aca | att | tac | agt | cct | tcg | gac | cca | aat | 1880 |
| Arg | Phe | Gly | Asp | Ile | Glu | Val | Thr | Ile | Tyr | Ser | Pro | Ser | Asp | Pro | Asn |
| 195 | | | | | 200 | | | | | 205 | | | | | 210 |
| gca | tca | aca | gta | acg | gct | gaa | aac | agt | cag | ttt | ctc | tgg | aga | gca | gct | 1928 |
| Ala | Ser | Thr | Val | Thr | Ala | Glu | Asn | Ser | Gln | Phe | Leu | Trp | Arg | Ala | Ala |
| | | | | 215 | | | | | 220 | | | | | 225 | |
| att | act | ctc | aat | caa | ttt | aaa | gag | ttt | gtg | aaa | agc | tgg | agc | ata | tac | 1976 |
| Ile | Thr | Leu | Asn | Gln | Phe | Lys | Glu | Phe | Val | Lys | Ser | Trp | Ser | Ile | Tyr |
| | | | 230 | | | | | 235 | | | | | 240 | | |
| act | tct | tgg | gct | aga | gat | aat | ccc | tcg | aaa | ccg | gat | att | gcc | gat | ata | 2024 |
| Thr | Ser | Trp | Ala | Arg | Asp | Asn | Pro | Ser | Lys | Pro | Asp | Ile | Ala | Asp | Ile |
| | | 245 | | | | | 250 | | | | | 255 | | | |
| ttc | att | aac | gag | ctc | aaa | gaa | atc | tgt | cat | tgt | gaa | gat | ttg | aat | gta | 2072 |
| Phe | Ile | Asn | Glu | Leu | Lys | Glu | Ile | Cys | His | Cys | Glu | Asp | Leu | Asn | Val |
| | 260 | | | | | 265 | | | | | 270 | | | | |
| cct | tta | aaa | ata | gag | tgg | tca | acg | ttt | tat | tac | tta | tgt | agg | aaa | aga | 2120 |
| Pro | Leu | Lys | Ile | Glu | Trp | Ser | Thr | Phe | Tyr | Tyr | Leu | Cys | Arg | Lys | Arg |
| 275 | | | | | 280 | | | | | 285 | | | | | 290 |
| gaa | tga | | | | | | | | | | | | | | | 2126 |
| Glu | | | | | | | | | | | | | | | |

FIG. 4

```
gaatcctatt ctgtttactt cactgttcac ttactttcgg tcccacatct acaaaacatc    60
tacaacaaga acgtgggcga tacagcaaaa aatcacttga aataacagaa tcaagtttct   120
tatccgattt cctactttg  agctccggct tatgttgaag atgttacttt tctttgtctc   180
taagtgatct ttattttct  ggctccagtg aaatttggta atagcatagt cacttcaact   240
aaagtctgat agtaatactt gcaaatattg caaaacttgg aagaatgtta atgaatcatt   300
tcttgcacca ttctttcaat catctcaatc tcctgctgtg atgtttaagt ataacattga   360
agactatgcc ctaatttcca atgttattta gttttaagca tatctttgtt tctaacagga   420
aactcaggcc cacatccgca aaaaaatatg tgccaaaaaa ctttcaacac ttcaaagata   480
cttaccactg caggaaaata atctacgtgt aacggtttga aaataaattt gacttcataa   540
ttggacataa gtactccatc gccatccctt tttaaagaag tttccacaag aatgaatggc   600
taatcgcaac taaatctttt ccttgcaaac gtaacacagt atcgacattt cttactcaa    660
tccaacgaag gaataaccta tctaaaaaat aaacgccgta gttttcagcc cacaagacgt   720
cattaaaaga tttgttaatt ataaaatag  aaatatttct accagcatga ttattcgtta   780
cttgaaagtc cccaataaat ttcactgttt ccgttaactg ttgtagttat taaacgcagc   840
aaacagatta ttttgaacaa caccggagaa acacgcgcag acccattcga gttaaaaata   900
gtaactcgcg atcaatcaat gcaggaagca ccgtaggaat tagtaagaac tcgtattttg   960
attgaaaatg ccatgaaagc aattgacttg ctgcagtaaa aagcgctgcc acaaactttg  1020
taattttcga caatgacgtt cttttcagat ggttactgtc ttttttttgga agaaacaaaa  1080
gaaggtactt ttatgatgtt atactaggca aaaagcctat ttaatgtaag tcctaattgt  1140
cgtttgagac tggatgaaaa gggacaaaat ggaaggataa ctaaggtga cttaccgcca   1200
gattaattcg gcctggaata gtttgatatc gaagaaagat tcacaattaa atg gcg    1256
                                                         Met Ala
                                                         1 act gac acc gag agg tgt att ttc cgt gca ttc ggc caa gat ttt atc     1304
Thr Asp Thr Glu Arg Cys Ile Phe Arg Ala Phe Gly Gln Asp Phe Ile
      5                  10                  15
cta aat aaa cat ttt cat ttg aca ggt aag att ggt cgg ggc tca cac     1352
Leu Asn Lys His Phe His Leu Thr Gly Lys Ile Gly Arg Gly Ser His
 20                  25                  30
agc ctt att tgt tct tca act tac aca gaa tcg aac gag gaa act cac     1400
Ser Leu Ile Cys Ser Ser Thr Tyr Thr Glu Ser Asn Glu Glu Thr His
35                  40                  45                  50
gtg gct atc aga aaa ata cca aac gcg ttt ggc aat aaa cta tct tgc     1448
Val Ala Ile Arg Lys Ile Pro Asn Ala Phe Gly Asn Lys Leu Ser Cys
                 55                  60                  65
aag aga act ctt cgt gaa ttg aaa cta cta aga cat tta aga ggg cac     1496
Lys Arg Thr Leu Arg Glu Leu Lys Leu Leu Arg His Leu Arg Gly His
             70                  75                  80
cca aat ata gtg tgg ctc ttc gat act gat ata gta ttt tac cca aat     1544
Pro Asn Ile Val Trp Leu Phe Asp Thr Asp Ile Val Phe Tyr Pro Asn
         85                  90                  95
ggg gca cta aat ggc gtt tat tta tat gaa gaa cta atg gaa tgt gac     1592
Gly Ala Leu Asn Gly Val Tyr Leu Tyr Glu Glu Leu Met Glu Cys Asp
     100                 105                 110
ctt tct caa att ata agg tcc gaa caa cgc ctg gaa gac gca cac ttt     1640
Leu Ser Gln Ile Ile Arg Ser Glu Gln Arg Leu Glu Asp Ala His Phe
115                 120                 125                 130
caa agc ttc ata tat cag ata ctg tgt gct ctg aaa tac ata cat tct     1688
Gln Ser Phe Ile Tyr Gln Ile Leu Cys Ala Leu Lys Tyr Ile His Ser
                 135                 140                 145
gct aat gtt tta cat tgt gac ctg aaa cca aaa aac tta ctt gtt aat     1736
Ala Asn Val Leu His Cys Asp Leu Lys Pro Lys Asn Leu Leu Val Asn
             150                 155                 160
agt gat tgc caa cta aaa att tgt aat ttt ggg cta tcg tgt agt tat     1784
Ser Asp Cys Gln Leu Lys Ile Cys Asn Phe Gly Leu Ser Cys Ser Tyr
         165                 170                 175
```

FIG. 5

```
tca gaa aac cac aag gtt aac gac ggc ttc att aag ggt tat ata acc   1832
Ser Glu Asn His Lys Val Asn Asp Gly Phe Ile Lys Gly Tyr Ile Thr
    180                 185                 190
tcg ata tgg tat aaa gca cca gaa att ttg ctg aat tat caa gaa tgc   1880
Ser Ile Trp Tyr Lys Ala Pro Glu Ile Leu Leu Asn Tyr Gln Glu Cys
195                 200                 205                 210
aca aaa gct gtc gat att tgg tca aca ggc tgt atc ttg gcc gaa cta   1928
Thr Lys Ala Val Asp Ile Trp Ser Thr Gly Cys Ile Leu Ala Glu Leu
                215                 220                 225
ctt ggt agg aaa cca atg ttt gaa ggg aag gat tat gta gat cat ttg   1976
Leu Gly Arg Lys Pro Met Phe Glu Gly Lys Asp Tyr Val Asp His Leu
            230                 235                 240
aat cat att cta caa ata ctt gga aca cca cct gag gaa aca ttg cag   2024
Asn His Ile Leu Gln Ile Leu Gly Thr Pro Pro Glu Glu Thr Leu Gln
        245                 250                 255
gaa att gcc tct caa aag gtg tat aat tat atc ttt cag ttc ggt aat   2072
Glu Ile Ala Ser Gln Lys Val Tyr Asn Tyr Ile Phe Gln Phe Gly Asn
    260                 265                 270
atc ccg gga aga tcg ttt gaa agc ata cta cct ggt gct aat cca gaa   2120
Ile Pro Gly Arg Ser Phe Glu Ser Ile Leu Pro Gly Ala Asn Pro Glu
275                 280                 285                 290
gcg ctt gaa ttg cta aag aaa atg cta gaa ttt gat cct aaa aaa agg   2168
Ala Leu Glu Leu Leu Lys Lys Met Leu Glu Phe Asp Pro Lys Lys Arg
                295                 300                 305
att act gta gag gat gca cta gag cat cca tat ttg tca atg tgg cat   2216
Ile Thr Val Glu Asp Ala Leu Glu His Pro Tyr Leu Ser Met Trp His
            310                 315                 320
gat ata gat gag gaa ttc tca tgt caa aag acc ttt aga ttc gaa ttc   2264
Asp Ile Asp Glu Glu Phe Ser Cys Gln Lys Thr Phe Arg Phe Glu Phe
        325                 330                 335
gag cat atc gaa agt atg gcg gaa tta gga aac gaa gtt ata aag gaa   2312
Glu His Ile Glu Ser Met Ala Glu Leu Gly Asn Glu Val Ile Lys Glu
    340                 345                 350
gta ttt gat ttc agg aaa gtt gtt aga aaa cat cct att agc ggt gat   2360
Val Phe Asp Phe Arg Lys Val Val Arg Lys His Pro Ile Ser Gly Asp
355                 360                 365                 370
tcc cca tca tca tca cta tct tta gag gat gcc att cct caa gaa gtt   2408
Ser Pro Ser Ser Ser Leu Ser Leu Glu Asp Ala Ile Pro Gln Glu Val
                375                 380                 385
gta cag gtc cat cct tct agg aaa gtt tta ccc agt tat agt cct gaa   2456
Val Gln Val His Pro Ser Arg Lys Val Leu Pro Ser Tyr Ser Pro Glu
            390                 395                 400
ttt tcc tat gta agc caa ctt cca tca cta act aca acc cag cca tat   2504
Phe Ser Tyr Val Ser Gln Leu Pro Ser Leu Thr Thr Thr Gln Pro Tyr
        405                 410                 415
caa aac ctt atg gga ata agc tct aat tca ttt cag ggt gtt aac taa   2552
Gln Asn Leu Met Gly Ile Ser Ser Asn Ser Phe Gln Gly Val Asn
    420                 425                 430
```

FIG. 5

```
attagcacgg atttccttaa gtaatttaaa ttaccaaaga agatccacat cagcagtcga      60
atgttcaaga tgccgtaagt ttaaaatctt tcgtatcttt ccccgatcct gtctttcatc     120
aatgaacttg aatatcaaga gtgaaaaaaa ctcatatggc ttctcttgaa gagttagaaa     180
gataggcaca tgccaattgt gtgcatagca cttactactc aacgatttca caacctagca     240
taatacgcga aaaaaaaagt gcatttattt aggtaagtct cattacctaa acgccagttt     300
gtttcacgta attggtaacg atgagggaac cgcagtagaa aaaactttca ttcacaaacg     360
attaaagtgt tatgctagcc agtttcaggc tttttgtttt atgcaagaga acattcgact     420
agatgtccag ttaagtgtgc gtcactttc ctacggtgcc tcgcacatga atgttatccg      480
gcgcacgata cttatcaccg aaaaacctta ttctacggaa aaccttattt acattaaagt     540
tggaaaaatt tcctctttt cctaataagg tggagctttt ggcttccagt atgctttcac      600
ggaattattt ctcatgtaca tttagctcca tttccagtgc ctccgatagg gaggcatcat     660
ggtactaccg tgacggagaa tacgtaggct gactttttcg tcagtttgtt gtccgtttac     720
aaaattggtg aatgaattct agccttcctc tgctcattaa ttgccctcac aagaatttgg     780
aagtgcgtag acaggtaaaa gattgtacta cagaggtatt gtggaacctt ctacagtact     840
tcggaataca cctaaaaggt tgttggatgc taaatttagc aaaagtcttt tttagctcac     900
tattaggctt gttaaagtct gaaattgttg aaaggcactc aaaaagataa atcaacaatc     960
agcattaacg gcacagttga aagagtcacc cacttgaaat tagctcggtt atcaaatata    1020
attatctctg gtaaagagct ctgcagcagg gttaatctat tcgcatactt acgctgtagg    1080
aacatttttat tattaggatc cgactactgc ctacatattt attcggaagg catgatgtcg    1140
aaaattttg agcttataaa aggaacatat ttcactcttg ctcgttgatg taagctctct    1200
tccgggttct tatttttaat tcttgtcacc agtaaacaga acatccaaaa atg aca        1256
                                                         Met Thr
                                                             1
atg cct cat cgc tat atg ttt ttg gca gtc ttt aca ctt ctg gca cta      1304
Met Pro His Arg Tyr Met Phe Leu Ala Val Phe Thr Leu Leu Ala Leu
     5              10                      15
act agt gtg gcc tca gga gcc aca gag gcg tgc tta cca gca ggc cag      1352
Thr Ser Val Ala Ser Gly Ala Thr Glu Ala Cys Leu Pro Ala Gly Gln
 20              25                      30
agg aaa agt ggg atg aat ata aat ttt tac cag tat tca ttg aaa gat      1400
Arg Lys Ser Gly Met Asn Ile Asn Phe Tyr Gln Tyr Ser Leu Lys Asp
 35              40                      45              50
tcc tcc aca tat tcg aat gca gca tat atg gct tat gga tat gcc tca      1448
Ser Ser Thr Tyr Ser Asn Ala Ala Tyr Met Ala Tyr Gly Tyr Ala Ser
                 55                      60                      65
aaa acc aaa cta ggt tct gtc gga gga caa act gat atc tcg att gat      1496
Lys Thr Lys Leu Gly Ser Val Gly Gly Gln Thr Asp Ile Ser Ile Asp
             70                      75                  80
tat aat att ccc tgt gtt agt tca tca ggc aca ttt cct tgt cct caa      1544
Tyr Asn Ile Pro Cys Val Ser Ser Ser Gly Thr Phe Pro Cys Pro Gln
         85                      90                  95
gaa gat tcc tat gga aac tgg gga tgc aaa gga atg ggt gct tgt tct      1592
Glu Asp Ser Tyr Gly Asn Trp Gly Cys Lys Gly Met Gly Ala Cys Ser
 100                     105                     110
aat agt caa gga att gca tac tgg agt act gat tta ttt ggt ttc tat      1640
Asn Ser Gln Gly Ile Ala Tyr Trp Ser Thr Asp Leu Phe Gly Phe Tyr
 115                     120                     125             130
act acc cca aca aac gta acc cta gaa atg aca ggt tat ttt tta cca      1688
Thr Thr Pro Thr Asn Val Thr Leu Glu Met Thr Gly Tyr Phe Leu Pro
                 135                     140                 145
cca cag acg ggt tct tac aca ttc aag ttt gct aca gtt gac gac tct      1736
Pro Gln Thr Gly Ser Tyr Thr Phe Lys Phe Ala Thr Val Asp Asp Ser
             150                     155                 160
gca att cta tca gta ggt ggt gca acc gcg ttc aac tgt tgt gct caa      1784
Ala Ile Leu Ser Val Gly Gly Ala Thr Ala Phe Asn Cys Cys Ala Gln
         165                     170                 175
```

FIG. 6

```
cag caa ccg ccg atc aca tca acg aac ttt acc att gac ggt atc aag    1832
Gln Gln Pro Pro Ile Thr Ser Thr Asn Phe Thr Ile Asp Gly Ile Lys
        180             185                 190
cca tgg ggt gga agt ttg cca cct aat atc gaa gga acc gtc tat atg    1880
Pro Trp Gly Gly Ser Leu Pro Pro Asn Ile Glu Gly Thr Val Tyr Met
195                 200                 205                 210
tac gct ggc tac tat tat cca atg aag gtt gtt tac tcg aac gct gtt    1928
Tyr Ala Gly Tyr Tyr Tyr Pro Met Lys Val Val Tyr Ser Asn Ala Val
                215                 220                 225
tct tgg ggt aca ctt cca att agt gtg aca ctt cca gat ggt acc act    1976
Ser Trp Gly Thr Leu Pro Ile Ser Val Thr Leu Pro Asp Gly Thr Thr
            230                 235                 240
gta agt gat gac ttc gaa ggg tac gtc tat tcc ttt gac gat gac cta    2024
Val Ser Asp Asp Phe Glu Gly Tyr Val Tyr Ser Phe Asp Asp Asp Leu
        245                 250                 255
agt caa tct aac tgt act gtc cct gac cct tca aat tat gct gtc agt    2072
Ser Gln Ser Asn Cys Thr Val Pro Asp Pro Ser Asn Tyr Ala Val Ser
    260                 265                 270
acc act aca act aca acg gaa cca tgg acc ggt act ttc act tct aca    2120
Thr Thr Thr Thr Thr Thr Glu Pro Trp Thr Gly Thr Phe Thr Ser Thr
275                 280                 285                 290
tct act gaa atg acc acc gtc acc ggt acc aac ggc gtt cca act gac    2168
Ser Thr Glu Met Thr Thr Val Thr Gly Thr Asn Gly Val Pro Thr Asp
                295                 300                 305
gaa acc gtc att gtc atc aga act cca aca act gct agc acc atc ata    2216
Glu Thr Val Ile Val Ile Arg Thr Pro Thr Thr Ala Ser Thr Ile Ile
            310                 315                 320
act aca act gag cca tgg aac agc act ttt acc tct act tct acc gaa    2264
Thr Thr Thr Glu Pro Trp Asn Ser Thr Phe Thr Ser Thr Ser Thr Glu
        325                 330                 335
ttg acc aca gtc act ggc acc aat ggt gta cga act gac gaa acc atc    2312
Leu Thr Thr Val Thr Gly Thr Asn Gly Val Arg Thr Asp Glu Thr Ile
    340                 345                 350
att gta atc aga aca cca aca aca gcc act act gcc ata act aca act    2360
Ile Val Ile Arg Thr Pro Thr Thr Ala Thr Thr Ala Ile Thr Thr Thr
355                 360                 365                 370
gag cca tgg aac agc act ttt acc tct act tct acc gaa ttg acc aca    2408
Glu Pro Trp Asn Ser Thr Phe Thr Ser Thr Ser Thr Glu Leu Thr Thr
                375                 380                 385
gtc acc ggt acc aat ggt ttg cca act gat gag acc atc att gtc atc    2456
Val Thr Gly Thr Asn Gly Leu Pro Thr Asp Glu Thr Ile Ile Val Ile
            390                 395                 400
aga aca cca aca aca gcc act act gcc atg act aca act cag cca tgg    2504
Arg Thr Pro Thr Thr Ala Thr Thr Ala Met Thr Thr Thr Gln Pro Trp
        405                 410                 415
aac gac act ttt acc tct act tct acc gaa ttg acc aca gtc acc ggt    2552
Asn Asp Thr Phe Thr Ser Thr Ser Thr Glu Leu Thr Thr Val Thr Gly
    420                 425                 430
acc aat ggt ttg cca act gat gag acc atc att gtc atc aga aca cca    2600
Thr Asn Gly Leu Pro Thr Asp Glu Thr Ile Ile Val Ile Arg Thr Pro
435                 440                 445                 450
aca aca gcc act act gcc atg act aca act cag cca tgg aac gac act    2648
Thr Thr Ala Thr Thr Ala Met Thr Thr Thr Gln Pro Trp Asn Asp Thr
                455                 460                 465
ttt acc tct act tct acc gaa ttg acc aca gtc acc ggt acc aat ggt    2696
Phe Thr Ser Thr Ser Thr Glu Leu Thr Thr Val Thr Gly Thr Asn Gly
            470                 475                 480
```

FIG. 6

| | | | | | | | | | | | | | | | |
|---|---|---|---|---|---|---|---|---|---|---|---|---|---|---|---|
| ttg | cca | act | gat | gag | acc | atc | att | gtc | atc | aga | aca | cca | aca | aca | gcc | 2744 |
| Leu | Pro | Thr | Asp | Glu | Thr | Ile | Ile | Val | Ile | Arg | Thr | Pro | Thr | Thr | Ala | |
| | | 485 | | | | | 490 | | | | | 495 | | | | |
| act | act | gcc | atg | act | aca | act | cag | cca | tgg | aac | gac | act | ttt | acc | tct | 2792 |
| Thr | Thr | Ala | Met | Thr | Thr | Thr | Gln | Pro | Trp | Asn | Asp | Thr | Phe | Thr | Ser | |
| | | 500 | | | | | 505 | | | | | 510 | | | | |
| aca | tcc | act | gaa | atc | acc | acc | gtc | acc | ggt | acc | aat | ggt | ttg | cca | act | 2840 |
| Thr | Ser | Thr | Glu | Ile | Thr | Thr | Val | Thr | Gly | Thr | Asn | Gly | Leu | Pro | Thr | |
| 515 | | | | | 520 | | | | | 525 | | | | | 530 | |
| gat | gag | acc | atc | att | gtc | atc | aga | aca | cca | aca | aca | gcc | act | act | gcc | 2888 |
| Asp | Glu | Thr | Ile | Ile | Val | Ile | Arg | Thr | Pro | Thr | Thr | Ala | Thr | Thr | Ala | |
| | | | | 535 | | | | | 540 | | | | | 545 | | |
| atg | act | aca | cct | cag | cca | tgg | aac | gac | act | ttt | acc | tct | aca | tcc | act | 2936 |
| Met | Thr | Thr | Pro | Gln | Pro | Trp | Asn | Asp | Thr | Phe | Thr | Ser | Thr | Ser | Thr | |
| | | | 550 | | | | | 555 | | | | | 560 | | | |
| gaa | atg | acc | acc | gtc | acc | ggt | acc | aac | ggt | ttg | cca | act | gat | gaa | acc | 2984 |
| Glu | Met | Thr | Thr | Val | Thr | Gly | Thr | Asn | Gly | Leu | Pro | Thr | Asp | Glu | Thr | |
| | | 565 | | | | | 570 | | | | | 575 | | | | |
| atc | att | gtc | atc | aga | aca | cca | aca | aca | gcc | act | act | gcc | ata | act | aca | 3032 |
| Ile | Ile | Val | Ile | Arg | Thr | Pro | Thr | Thr | Ala | Thr | Thr | Ala | Ile | Thr | Thr | |
| | | 580 | | | | | 585 | | | | | 590 | | | | |
| act | gag | cca | tgg | aac | agc | act | ttt | acc | tct | aca | tcc | act | gaa | atg | acc | 3080 |
| Thr | Glu | Pro | Trp | Asn | Ser | Thr | Phe | Thr | Ser | Thr | Ser | Thr | Glu | Met | Thr | |
| 595 | | | | | 600 | | | | | 605 | | | | | 610 | |
| acc | gtc | acc | ggt | acc | aac | ggt | ttg | cca | act | gat | gaa | acc | atc | att | gtc | 3128 |
| Thr | Val | Thr | Gly | Thr | Asn | Gly | Leu | Pro | Thr | Asp | Glu | Thr | Ile | Ile | Val | |
| | | | | 615 | | | | | 620 | | | | | 625 | | |
| atc | aga | aca | cca | aca | aca | gcc | act | act | gcc | ata | act | aca | act | cag | cca | 3176 |
| Ile | Arg | Thr | Pro | Thr | Thr | Ala | Thr | Thr | Ala | Ile | Thr | Thr | Thr | Gln | Pro | |
| | | | 630 | | | | | 635 | | | | | 640 | | | |
| tgg | aac | gac | act | ttt | acc | tct | aca | tcc | act | gaa | atg | acc | acc | gtc | acc | 3224 |
| Trp | Asn | Asp | Thr | Phe | Thr | Ser | Thr | Ser | Thr | Glu | Met | Thr | Thr | Val | Thr | |
| | | 645 | | | | | 650 | | | | | 655 | | | | |
| ggt | acc | aac | ggt | ttg | cca | act | gat | gaa | acc | atc | att | gtc | atc | aga | aca | 3272 |
| Gly | Thr | Asn | Gly | Leu | Pro | Thr | Asp | Glu | Thr | Ile | Ile | Val | Ile | Arg | Thr | |
| | 660 | | | | | 665 | | | | | 670 | | | | | |
| cca | aca | aca | gcc | act | act | gcc | atg | act | aca | act | cag | cca | tgg | aac | gac | 3320 |
| Pro | Thr | Thr | Ala | Thr | Thr | Ala | Met | Thr | Thr | Thr | Gln | Pro | Trp | Asn | Asp | |
| 675 | | | | | 680 | | | | | 685 | | | | | 690 | |
| act | ttt | acc | tct | aca | tcc | act | gaa | atc | acc | acc | gtc | acc | ggt | acc | acc | 3368 |
| Thr | Phe | Thr | Ser | Thr | Ser | Thr | Glu | Ile | Thr | Thr | Val | Thr | Gly | Thr | Thr | |
| | | | | 695 | | | | | 700 | | | | | 705 | | |
| ggt | ttg | cca | act | gat | gag | acc | atc | att | gtc | atc | aga | aca | cca | aca | aca | 3416 |
| Gly | Leu | Pro | Thr | Asp | Glu | Thr | Ile | Ile | Val | Ile | Arg | Thr | Pro | Thr | Thr | |
| | | | | 710 | | | | | 715 | | | | | 720 | | |
| gcc | act | act | gcc | atg | act | aca | act | cag | cca | tgg | aac | gac | act | ttt | acc | 3464 |
| Ala | Thr | Thr | Ala | Met | Thr | Thr | Thr | Gln | Pro | Trp | Asn | Asp | Thr | Phe | Thr | |
| | | 725 | | | | | 730 | | | | | 735 | | | | |
| tct | aca | tcc | act | gaa | atg | acc | acc | gtc | acc | ggt | acc | aac | ggc | gtt | cca | 3512 |
| Ser | Thr | Ser | Thr | Glu | Met | Thr | Thr | Val | Thr | Gly | Thr | Asn | Gly | Val | Pro | |
| | 740 | | | | | 745 | | | | | 750 | | | | | |
| act | gac | gaa | acc | gtc | att | gtc | atc | aga | act | cca | act | agt | gaa | ggt | cta | 3560 |
| Thr | Asp | Glu | Thr | Val | Ile | Val | Ile | Arg | Thr | Pro | Thr | Ser | Glu | Gly | Leu | |
| 755 | | | | | 760 | | | | | 765 | | | | | 770 | |
| atc | agc | acc | acc | act | gaa | cca | tgg | act | ggt | act | ttc | acc | tct | aca | tcc | 3608 |
| Ile | Ser | Thr | Thr | Thr | Glu | Pro | Trp | Thr | Gly | Thr | Phe | Thr | Ser | Thr | Ser | |
| | | | | 775 | | | | | 780 | | | | | 785 | | |

FIG. 6

```
act gag atg acc acc gtc acc ggt act aac ggt caa cca act gac gaa     3656
Thr Glu Met Thr Thr Val Thr Gly Thr Asn Gly Gln Pro Thr Asp Glu
            790                 795                 800
acc gtg att gtt atc aga act cca acc agt gaa ggt ttg gtt aca acc     3704
Thr Val Ile Val Ile Arg Thr Pro Thr Ser Glu Gly Leu Val Thr Thr
            805                 810                 815
acc act gaa cca tgg act ggt act ttt act tct aca tct act gaa atg     3752
Thr Thr Glu Pro Trp Thr Gly Thr Phe Thr Ser Thr Ser Thr Glu Met
            820                 825                 830
acc acc att act gga acc aac ggc gtt cca act gac gaa acc gtc att     3800
Thr Thr Ile Thr Gly Thr Asn Gly Val Pro Thr Asp Glu Thr Val Ile
835                 840                 845                 850
gtc atc aga act cca acc agt gaa ggt cta atc agc acc acc act gaa     3848
Val Ile Arg Thr Pro Thr Ser Glu Gly Leu Ile Ser Thr Thr Thr Glu
                855                 860                 865
cca tgg act ggt act ttt act tct aca tct act gaa atg acc acc att     3896
Pro Trp Thr Gly Thr Phe Thr Ser Thr Ser Thr Glu Met Thr Thr Ile
                870                 875                 880
act gga acc aat ggt caa cca act gac gaa acc gtt att gtt atc aga     3944
Thr Gly Thr Asn Gly Gln Pro Thr Asp Glu Thr Val Ile Val Ile Arg
                885                 890                 895
act cca act agt gaa ggt cta atc agc act aca acg gaa cca tgg acc     3992
Thr Pro Thr Ser Glu Gly Leu Ile Ser Thr Thr Thr Glu Pro Trp Thr
900                 905                 910
ggt act ttc act tct aca tct act gaa atg acg cac gtc acc ggt acc     4040
Gly Thr Phe Thr Ser Thr Ser Thr Glu Met Thr His Val Thr Gly Thr
915                 920                 925                 930
aac ggc gtt cca act gac gaa acc gtc att gtc atc aga act cca acc     4088
Asn Gly Val Pro Thr Asp Glu Thr Val Ile Val Ile Arg Thr Pro Thr
                935                 940                 945
agt gaa ggt cta atc agc acc act gaa cca tgg act ggc act ttc         4136
Ser Glu Gly Leu Ile Ser Thr Thr Thr Glu Pro Trp Thr Gly Thr Phe
                950                 955                 960
act tcg act tcc act gag gtt acc acc atc act gga acc aac ggt caa    4184
Thr Ser Thr Ser Thr Glu Val Thr Thr Ile Thr Gly Thr Asn Gly Gln
                965                 970                 975
cca act gac gaa act gtg att gtt atc aga act cca acc agt gaa ggt    4232
Pro Thr Asp Glu Thr Val Ile Val Ile Arg Thr Pro Thr Ser Glu Gly
980                 985                 990
cta atc agc acc acc act gaa cca tgg act ggt act ttc act tct         4277
Leu Ile Ser Thr Thr Thr Glu Pro Trp Thr Gly Thr Phe Thr Ser
995                 1000                1005
aca tct act gaa atg acc acc gtc acc ggt act aac ggt caa cca         4322
Thr Ser Thr Glu Met Thr Thr Val Thr Gly Thr Asn Gly Gln Pro
1010                1015                1020
act gac gaa acc gtg att gtt atc aga act cca acc agt gaa ggt         4367
Thr Asp Glu Thr Val Ile Val Ile Arg Thr Pro Thr Ser Glu Gly
1025                1030                1035
ttg gtt aca acc acc act gaa cca tgg act ggt act ttt act tcg         4412
Leu Val Thr Thr Thr Glu Pro Trp Thr Gly Thr Phe Thr Ser
1040                1045                1050
act tcc act gaa atg tct act gtc act gga acc aat ggc ttg cca         4457
Thr Ser Thr Glu Met Ser Thr Val Thr Gly Thr Asn Gly Leu Pro
1055                1060                1065
act gat gaa act gtc att gtt gtc aaa act cca act act gcc atc         4502
Thr Asp Glu Thr Val Ile Val Val Lys Thr Pro Thr Thr Ala Ile
1070                1075                1080
```

FIG. 6

```
tca tcc agt ttg tca tca   tca tct tca gga caa   atc acc agc tct          4547
Ser Ser Ser Leu Ser Ser   Ser Ser Ser Gly Gln   Ile Thr Ser Ser
1085             1090                 1095
atc acg tct tcg cgt cca   att att acc cca ttc   tat cct agc aat          4592
Ile Thr Ser Ser Arg Pro   Ile Ile Thr Pro Phe   Tyr Pro Ser Asn
1100             1105                 1110
gga act tct gtg att tct   tcc tca gta att tct   tcc tca gtc act          4637
Gly Thr Ser Val Ile Ser   Ser Ser Val Ile Ser   Ser Ser Val Thr
1115             1120                 1125
tct tct cta ttc act tct   tct cca gtc att tct   tcc tca gtc att          4682
Ser Ser Leu Phe Thr Ser   Ser Pro Val Ile Ser   Ser Ser Val Ile
1130             1135                 1140
tct tct tct aca aca acc   tcc act tct ata ttt   tct gaa tca tct          4727
Ser Ser Ser Thr Thr Thr   Ser Thr Ser Ile Phe   Ser Glu Ser Ser
1145             1150                 1155
aaa tca tcc gtc att cca   acc agt agt tcc acc   tct ggt tct tct          4772
Lys Ser Ser Val Ile Pro   Thr Ser Ser Ser Thr   Ser Gly Ser Ser
1160             1165                 1170
gag agc gaa acg agt tca   gct ggt tct gtc tct   tct tcc tct ttt          4817
Glu Ser Glu Thr Ser Ser   Ala Gly Ser Val Ser   Ser Ser Ser Phe
1175             1180                 1185
atc tct tct gaa tca tca   aaa tct cct aca tat   tct tct tca tca          4862
Ile Ser Ser Glu Ser Ser   Lys Ser Pro Thr Tyr   Ser Ser Ser Ser
1190             1195                 1200
tta cca ctt gtt acc agt   gcg aca aca agc cag   gaa act gct tct          4907
Leu Pro Leu Val Thr Ser   Ala Thr Thr Ser Gln   Glu Thr Ala Ser
1205             1210                 1215
tca tta cca cct gct acc   act aca aaa acg agc   gaa caa acc act          4952
Ser Leu Pro Pro Ala Thr   Thr Thr Lys Thr Ser   Glu Gln Thr Thr
1220             1225                 1230
ttg gtt acc gtg aca tcc   tgc gag tct cat gtg   tgc act gaa tcc          4997
Leu Val Thr Val Thr Ser   Cys Glu Ser His Val   Cys Thr Glu Ser
1235             1240                 1245
atc tcc cct gcg att gtt   tcc aca gct act gtt   act gtt agc ggc          5042
Ile Ser Pro Ala Ile Val   Ser Thr Ala Thr Val   Thr Val Ser Gly
1250             1255                 1260
gtc aca aca gag tat acc   aca tgg tgc cct att   tct act aca gag          5087
Val Thr Thr Glu Tyr Thr   Thr Trp Cys Pro Ile   Ser Thr Thr Glu
1265             1270                 1275
aca aca aag caa acc aaa   ggg aca aca gag caa   acc aca gaa aca          5132
Thr Thr Lys Gln Thr Lys   Gly Thr Thr Glu Gln   Thr Thr Glu Thr
1280             1285                 1290
aca aaa caa acc acg gta   gtt aca att tct tct   tgt gaa tct gac          5177
Thr Lys Gln Thr Thr Val   Val Thr Ile Ser Ser   Cys Glu Ser Asp
1295             1300                 1305
gta tgc tct aag act gct   tct cca gcc att gta   tct aca agc act          5222
Val Cys Ser Lys Thr Ala   Ser Pro Ala Ile Val   Ser Thr Ser Thr
1310             1315                 1320
gct act att aac ggc gtt   act aca gaa tac aca   aca tgg tgt cct          5267
Ala Thr Ile Asn Gly Val   Thr Thr Glu Tyr Thr   Thr Trp Cys Pro
1325             1330                 1335
att tcc acc aca gaa tcg   agg caa caa aca acg   cta gtt act gtt          5312
Ile Ser Thr Thr Glu Ser   Arg Gln Gln Thr Thr   Leu Val Thr Val
1340             1345                 1350
act tcc tgc gaa tct ggt   gtg tgt tcc gaa act   gct tca cct gcc          5357
Thr Ser Cys Glu Ser Gly   Val Cys Ser Glu Thr   Ala Ser Pro Ala
1355             1360                 1365
```

FIG. 6

```
att gtt tcg acg gcc acg  gct act gtg aat gat  gtt gtt acg gtc         5402
Ile Val Ser Thr Ala Thr  Ala Thr Val Asn Asp  Val Val Thr Val
1370            1375                1380
tat cct aca tgg agg cca  cag act gcg aat gaa  gag tct gtc agc         5447
Tyr Pro Thr Trp Arg Pro  Gln Thr Ala Asn Glu  Glu Ser Val Ser
1385            1390                1395
tct aaa atg aac agt gct  acc ggt gag aca aca  acc aat act tta         5492
Ser Lys Met Asn Ser Ala  Thr Gly Glu Thr Thr  Thr Asn Thr Leu
1400            1405                1410
gct gct gaa acg act acc  aat act gta gct gct  gag acg att acc         5537
Ala Ala Glu Thr Thr Thr  Asn Thr Val Ala Ala  Glu Thr Ile Thr
1415            1420                1425
aat act gga gct gct gag  acg aaa aca gta gtc  acc tct tcg ctt         5582
Asn Thr Gly Ala Ala Glu  Thr Lys Thr Val Val  Thr Ser Ser Leu
1430            1435                1440
tca aga tct aat cac gct  gaa aca cag acg gct  tcc gcg acc gat         5627
Ser Arg Ser Asn His Ala  Glu Thr Gln Thr Ala  Ser Ala Thr Asp
1445            1450                1455
gtg att ggt cac agc agt  agt gtt gtt tct gta  tcc gaa act ggc         5672
Val Ile Gly His Ser Ser  Ser Val Val Ser Val  Ser Glu Thr Gly
1460            1465                1470
aac acc aag agt cta aca  agt tcc ggg ttg agt  act atg tcg caa         5717
Asn Thr Lys Ser Leu Thr  Ser Ser Gly Leu Ser  Thr Met Ser Gln
1475            1480                1485
cag cct cgt agc aca cca  gca agc agc atg gta  gga tat agt aca         5762
Gln Pro Arg Ser Thr Pro  Ala Ser Ser Met Val  Gly Tyr Ser Thr
1490            1495                1500
gct tct tta gaa att tca  acg tat gct ggc agt  gcc aac agc tta         5807
Ala Ser Leu Glu Ile Ser  Thr Tyr Ala Gly Ser  Ala Asn Ser Leu
1505            1510                1515
ctg gcc ggt agt ggt tta  agt gtc ttc att gcg  tcc tta ttg ctg         5852
Leu Ala Gly Ser Gly Leu  Ser Val Phe Ile Ala  Ser Leu Leu Leu
1520            1525                1530
gca att att taa                                                       5864
Ala Ile Ile
1535
```

FIG. 6

```
aaactttcca atgatttctt gataatatcg ggttcgcaaa acattcttaa tgtacacgac    60
atacaccaaa acggcaaact catctatacc tacgtgtcga gattccccat ccgatgcata   120
gacatagatc caaggtcgca gataatagcc tacggaatca ccggaaagga tagacataca   180
ggcgcggaac aagcattagt cgtgatccaa caaattacca gaaataaagt gactttggag   240
cccgagttcc ccccaccaat caccataaca cttccataca gagatcccat caataccata   300
caactttcgc acgacgccaa gtatctgaca tgttcgaccg cgctagagtc gcggttcttg   360
atcatatctt tgcagaaaat aaacgaacca agactgataa tgaaaagtgt tcggtccata   420
gacacttcct tagaatctga aggtatcact gacacaaaac ttttcccagg aaatccaaat   480
ctgatgtgta tcacatcaac agcattcaat tcatctccac tggtcataaa caccaaaatc   540
acccaaatta acggtgtacg gaccgtggca caaccatcca tgcttataag ggtagatgag   600
attggatgca agattcacaa gtgcgaaata tcaccaagaa acgacgcaat tgccttcctc   660
gaccgcaacg gatcagttta catcatgtgt gcccccacca tgatggacaa caacgaaaaa   720
agaaggacaa tcctcgttga aaccgtggca aatgcctaca gggcttatga atcagctact   780
ttgcggttta acccagaggg caacaagctt tatattctcg acagaaaggg gactttcttt   840
gtggaagact ttgcatatgg cttgccccaa tctcgcgaaa tcaccaaatg taagcaaata   900
ttccacaaat aatgcatcta aatatatacg tatgtttaag gttctggtat acaggtatta   960
aagaaaaaca ctatcaacat tcccaataag atataccaca ccacgtgagc ttatagaagc  1020
acgtgaccac aattcacccc acaggtgtgg cttttttggt gccgtagaaa agactcattc  1080
atgaatcgtc ggaaacccat agtcatcttc gagcaaaagg tatatataag caacagaggg  1140
cagtagttct cgagaccacc atctttgat tggaaatagt ttcgtttaga tggggtgcac  1200
atagttttt tcaactgctt ttcctcgagg tcacccaaat atacaacgag atg cca     1256
                                                           Met Pro
                                                            1
```

| | | | | | | | | | | | | | | | | |
|---|---|---|---|---|---|---|---|---|---|---|---|---|---|---|---|---|
| gtt | gag | ttt | gct | acc | aat | cct | ttt | ggc | gag | gcc | aaa | aat | gca | act | tca | 1304 |
| Val | Glu | Phe | Ala | Thr | Asn | Pro | Phe | Gly | Glu | Ala | Lys | Asn | Ala | Thr | Ser | |
| | 5 | | | | | 10 | | | | | 15 | | | | | |
| ctg | cca | aaa | tat | ggt | aca | ccc | gta | act | gcc | att | tca | tct | gtg | ctg | ttc | 1352 |
| Leu | Pro | Lys | Tyr | Gly | Thr | Pro | Val | Thr | Ala | Ile | Ser | Ser | Val | Leu | Phe | |
| | 20 | | | | 25 | | | | | 30 | | | | | | |
| aat | aac | gtg | gac | tcc | att | ttt | gct | tac | aag | tcc | ttt | tct | caa | ccc | gat | 1400 |
| Asn | Asn | Val | Asp | Ser | Ile | Phe | Ala | Tyr | Lys | Ser | Phe | Ser | Gln | Pro | Asp | |
| 35 | | | | | 40 | | | | 45 | | | | | | 50 | |
| ttg | cta | cac | caa | gat | cta | aaa | aaa | tgg | tct | gaa | aag | cgt | ggt | aac | gaa | 1448 |
| Leu | Leu | His | Gln | Asp | Leu | Lys | Lys | Trp | Ser | Glu | Lys | Arg | Gly | Asn | Glu | |
| | | | | 55 | | | | 60 | | | | | 65 | | | |
| tca | cgt | ggg | aag | cca | ttt | ttc | caa | gag | ctg | gat | atc | aga | tct | ggc | gct | 1496 |
| Ser | Arg | Gly | Lys | Pro | Phe | Phe | Gln | Glu | Leu | Asp | Ile | Arg | Ser | Gly | Ala | |
| | | 70 | | | | | 75 | | | | | 80 | | | | |
| ggt | ttg | gct | cct | tta | ggg | ttt | tct | cat | gga | ttg | aag | aac | act | aca | gca | 1544 |
| Gly | Leu | Ala | Pro | Leu | Gly | Phe | Ser | His | Gly | Leu | Lys | Asn | Thr | Thr | Ala | |
| | 85 | | | | | 90 | | | | | 95 | | | | | |
| att | gtt | gct | cca | ggg | ttt | tcg | ctg | cca | tac | ttc | att | aac | tct | ttg | aaa | 1592 |
| Ile | Val | Ala | Pro | Gly | Phe | Ser | Leu | Pro | Tyr | Phe | Ile | Asn | Ser | Leu | Lys | |
| 100 | | | | | 105 | | | | | 110 | | | | | | |
| acc | gtc | tct | cat | gat | ggt | aag | ttt | ctt | ttg | aat | gtt | ggt | gct | tta | aac | 1640 |
| Thr | Val | Ser | His | Asp | Gly | Lys | Phe | Leu | Leu | Asn | Val | Gly | Ala | Leu | Asn | |
| 115 | | | | | 120 | | | | | 125 | | | | | 130 | |
| tac | gac | aat | gct | acc | ggc | tct | gtc | acc | aac | gat | tat | gta | acc | gca | ttg | 1688 |
| Tyr | Asp | Asn | Ala | Thr | Gly | Ser | Val | Thr | Asn | Asp | Tyr | Val | Thr | Ala | Leu | |
| | | | | 135 | | | | | 140 | | | | | 145 | | |
| gat | gct | gct | tcc | aag | ctg | aag | tat | ggt | gtc | gtg | act | ccg | att | tcc | gct | 1736 |
| Asp | Ala | Ala | Ser | Lys | Leu | Lys | Tyr | Gly | Val | Val | Thr | Pro | Ile | Ser | Ala | |
| | | | 150 | | | | | 155 | | | | | 160 | | | |
| aac | gag | gta | caa | agt | gtc | gcc | tta | ctg | gca | ttg | gcg | att | gcc | act | ttc | 1784 |
| Asn | Glu | Val | Gln | Ser | Val | Ala | Leu | Leu | Ala | Leu | Ala | Ile | Ala | Thr | Phe | |
| | 165 | | | | | 170 | | | | | 175 | | | | | |

FIG. 7

| | | | | | | | | | | | | | | | |
|---|---|---|---|---|---|---|---|---|---|---|---|---|---|---|---|
| agt | aat | aac | tcc | gga | gct | atc | aat | tta | ttt | gac | gga | tta | aac | tac | tcg | 1832 |
| Ser | Asn | Asn | Ser | Gly | Ala | Ile | Asn | Leu | Phe | Asp | Gly | Leu | Asn | Tyr | Ser | |
| | 180 | | | | 185 | | | | | 190 | | | | | | |
| aaa | acc | gtc | ttg | ccg | ttg | gtc | gaa | tct | gtt | cct | gag | gca | tct | att | ttg | 1880 |
| Lys | Thr | Val | Leu | Pro | Leu | Val | Glu | Ser | Val | Pro | Glu | Ala | Ser | Ile | Leu | |
| 195 | | | | | 200 | | | | | 205 | | | | | 210 | |
| gca | aaa | cta | tcc | aaa | gtt | att | gca | cca | gat | gct | gcc | ttt | gat | gat | gtc | 1928 |
| Ala | Lys | Leu | Ser | Lys | Val | Ile | Ala | Pro | Asp | Ala | Ala | Phe | Asp | Asp | Val | |
| | | | | 215 | | | | | 220 | | | | | 225 | | |
| ttg | gat | aag | ttt | aat | gaa | ttg | act | gga | ttg | aga | cta | cat | aat | ttc | caa | 1976 |
| Leu | Asp | Lys | Phe | Asn | Glu | Leu | Thr | Gly | Leu | Arg | Leu | His | Asn | Phe | Gln | |
| | | | 230 | | | | | 235 | | | | | 240 | | | |
| tac | ttt | ggt | gct | cag | gat | gct | gaa | act | gtg | ttt | atc | act | tat | ggg | tct | 2024 |
| Tyr | Phe | Gly | Ala | Gln | Asp | Ala | Glu | Thr | Val | Phe | Ile | Thr | Tyr | Gly | Ser | |
| | | 245 | | | | | 250 | | | | | 255 | | | | |
| tta | gaa | tcc | gaa | ttg | ttc | aac | tct | gcg | att | agt | ggt | aat | aat | tcc | aaa | 2072 |
| Leu | Glu | Ser | Glu | Leu | Phe | Asn | Ser | Ala | Ile | Ser | Gly | Asn | Asn | Ser | Lys | |
| | 260 | | | | | 265 | | | | | 270 | | | | | |
| atc | ggg | tta | atc | aac | gtc | aga | gtg | cca | tta | cct | ttt | aac | gtt | gct | aag | 2120 |
| Ile | Gly | Leu | Ile | Asn | Val | Arg | Val | Pro | Leu | Pro | Phe | Asn | Val | Ala | Lys | |
| 275 | | | | | 280 | | | | | 285 | | | | | 290 | |
| ttt | gtc | act | cac | gtt | cca | tcc | act | acc | aaa | caa | att | gtt | gtt | ata | ggc | 2168 |
| Phe | Val | Thr | His | Val | Pro | Ser | Thr | Thr | Lys | Gln | Ile | Val | Val | Ile | Gly | |
| | | | | 295 | | | | | 300 | | | | | 305 | | |
| caa | act | ttg | gat | ggt | tct | tcg | cct | tct | ttc | ttg | aga | tct | caa | gtt | tca | 2216 |
| Gln | Thr | Leu | Asp | Gly | Ser | Ser | Pro | Ser | Phe | Leu | Arg | Ser | Gln | Val | Ser | |
| | | | 310 | | | | | 315 | | | | | 320 | | | |
| gcc | gcc | tta | ttt | tac | cac | ggc | cgc | acc | tca | att | agc | gtt | tct | gag | tac | 2264 |
| Ala | Ala | Leu | Phe | Tyr | His | Gly | Arg | Thr | Ser | Ile | Ser | Val | Ser | Glu | Tyr | |
| | | 325 | | | | | 330 | | | | | 335 | | | | |
| atc | tat | caa | cca | gat | ttc | att | tgg | tcc | cca | aaa | gct | gtc | aaa | tca | att | 2312 |
| Ile | Tyr | Gln | Pro | Asp | Phe | Ile | Trp | Ser | Pro | Lys | Ala | Val | Lys | Ser | Ile | |
| | 340 | | | | | 345 | | | | | 350 | | | | | |
| gta | tcg | tca | ttc | atc | cct | gaa | ttc | act | tac | aat | gcc | gat | tca | tct | ttc | 2360 |
| Val | Ser | Ser | Phe | Ile | Pro | Glu | Phe | Thr | Tyr | Asn | Ala | Asp | Ser | Ser | Phe | |
| 355 | | | | | 360 | | | | | 365 | | | | | 370 | |
| ggc | gaa | gga | ttc | att | tat | tgg | gcc | tct | gat | aag | agt | atc | aat | att | gat | 2408 |
| Gly | Glu | Gly | Phe | Ile | Tyr | Trp | Ala | Ser | Asp | Lys | Ser | Ile | Asn | Ile | Asp | |
| | | | | 375 | | | | | 380 | | | | | 385 | | |
| gtt | gcc | tcc | aaa | ctt | gtg | aaa | gct | ctg | tct | ttg | gaa | gat | ggg | aaa | ttt | 2456 |
| Val | Ala | Ser | Lys | Leu | Val | Lys | Ala | Leu | Ser | Leu | Glu | Asp | Gly | Lys | Phe | |
| | | | 390 | | | | | 395 | | | | | 400 | | | |
| gtg | tct | ttg | aga | acg | aaa | ttt | gat | aac | ttg | gct | aat | gct | ggt | acc | ttc | 2504 |
| Val | Ser | Leu | Arg | Thr | Lys | Phe | Asp | Asn | Leu | Ala | Asn | Ala | Gly | Thr | Phe | |
| | | 405 | | | | | 410 | | | | | 415 | | | | |
| caa | gct | caa | ttt | gtg | acc | tcg | aaa | gaa | cag | ata | cct | gtt | tca | aac | atc | 2552 |
| Gln | Ala | Gln | Phe | Val | Thr | Ser | Lys | Glu | Gln | Ile | Pro | Val | Ser | Asn | Ile | |
| | 420 | | | | | 425 | | | | | 430 | | | | | |
| gat | tct | acg | aaa | tta | tca | gtc | gtt | gaa | gat | gtc | agt | tta | ttg | aag | cat | 2600 |
| Asp | Ser | Thr | Lys | Leu | Ser | Val | Val | Glu | Asp | Val | Ser | Leu | Leu | Lys | His | |
| 435 | | | | | 440 | | | | | 445 | | | | | 450 | |
| tta | gac | gta | gct | gct | acc | gtc | gca | gaa | caa | ggt | tca | att | gcg | ttg | gtt | 2648 |
| Leu | Asp | Val | Ala | Ala | Thr | Val | Ala | Glu | Gln | Gly | Ser | Ile | Ala | Leu | Val | |
| | | | | 455 | | | | | 460 | | | | | 465 | | |
| tcc | caa | aag | gca | gtt | aaa | gat | ttg | gat | tta | aat | tct | gta | gaa | agt | tac | 2696 |
| Ser | Gln | Lys | Ala | Val | Lys | Asp | Leu | Asp | Leu | Asn | Ser | Val | Glu | Ser | Tyr | |
| | | | 470 | | | | | 475 | | | | | 480 | | | |

FIG. 7

```
gtc aag aat ttg gga att cct gaa tca ttc cta ata tct att gcg aag    2744
Val Lys Asn Leu Gly Ile Pro Glu Ser Phe Leu Ile Ser Ile Ala Lys
        485                 490                 495
aaa aac atc aaa ttg ttt atc atc gat ggt gag acc act aac gac gag    2792
Lys Asn Ile Lys Leu Phe Ile Ile Asp Gly Glu Thr Thr Asn Asp Glu
500                 505                 510
tcc aaa ttg tcc ttg ttt atc caa gcc gtt ttc tgg aaa ttg gcc ttc    2840
Ser Lys Leu Ser Leu Phe Ile Gln Ala Val Phe Trp Lys Leu Ala Phe
515                 520                 525                 530
ggt cta gat gtc gca gaa tgt acc aac cgt atc tgg aaa agc att gat    2888
Gly Leu Asp Val Ala Glu Cys Thr Asn Arg Ile Trp Lys Ser Ile Asp
                535                 540                 545
tca ggt gca gac att tca gca gcc tcg att tct gaa ttt ctc act ggt    2936
Ser Gly Ala Asp Ile Ser Ala Ala Ser Ile Ser Glu Phe Leu Thr Gly
                550                 555                 560
gca ttc aaa aac ttc ctc agt gag gtt ccg cta gcg ctg tac act aaa    2984
Ala Phe Lys Asn Phe Leu Ser Glu Val Pro Leu Ala Leu Tyr Thr Lys
            565                 570                 575
ttt tct gaa ata aac att gaa aag aaa gag gat gag gaa gag cct gca    3032
Phe Ser Glu Ile Asn Ile Glu Lys Lys Glu Asp Glu Glu Glu Pro Ala
        580                 585                 590
gct tta cca att ttc gtt aat gaa aca tct ttc ctc cca aat aac agt    3080
Ala Leu Pro Ile Phe Val Asn Glu Thr Ser Phe Leu Pro Asn Asn Ser
595                 600                 605                 610
acc att gaa gaa ata cca tta cct gag acc tct gag atc tct gat att    3128
Thr Ile Glu Glu Ile Pro Leu Pro Glu Thr Ser Glu Ile Ser Asp Ile
                615                 620                 625
gcc aag aag ttg tcc ttc aaa gag gca tat gaa gtt gag aat aaa cta    3176
Ala Lys Lys Leu Ser Phe Lys Glu Ala Tyr Glu Val Glu Asn Lys Leu
                630                 635                 640
aga ccc gat tta ccc gtc aag aac ttc gtc gtg aaa gtt aaa gaa aat    3224
Arg Pro Asp Leu Pro Val Lys Asn Phe Val Val Lys Val Lys Glu Asn
            645                 650                 655
aga cgt gtt acg cct gct gat tat gat aga tat att ttc cat att gaa    3272
Arg Arg Val Thr Pro Ala Asp Tyr Asp Arg Tyr Ile Phe His Ile Glu
        660                 665                 670
ttc gat att tct ggt act gga atg act tat gac atc ggt gaa gcc ctc    3320
Phe Asp Ile Ser Gly Thr Gly Met Thr Tyr Asp Ile Gly Glu Ala Leu
675                 680                 685                 690
ggt att cat gcc aga aac aat gaa tct ttg gtc aaa gaa ttc tta acc    3368
Gly Ile His Ala Arg Asn Asn Glu Ser Leu Val Lys Glu Phe Leu Thr
                695                 700                 705
ttc tat ggt cta aat gaa tcc gat gtt gtc tta gtc ccc aac aag gac    3416
Phe Tyr Gly Leu Asn Glu Ser Asp Val Val Leu Val Pro Asn Lys Asp
            710                 715                 720
aac cac cat ttg tta gaa aca aga acc gtc tta caa gca ttt gtg gaa    3464
Asn His His Leu Leu Glu Thr Arg Thr Val Leu Gln Ala Phe Val Glu
        725                 730                 735
aat ttg gat att ttc ggt aaa cca cca aaa aga ttt tac gaa tca ttg    3512
Asn Leu Asp Ile Phe Gly Lys Pro Pro Lys Arg Phe Tyr Glu Ser Leu
    740                 745                 750
att cca tat gcc tct aac gaa gag gag aag aaa aaa tta gag gat ttg    3560
Ile Pro Tyr Ala Ser Asn Glu Glu Glu Lys Lys Lys Leu Glu Asp Leu
755                 760                 765                 770
gtt act cct gcc ggt gca gta gat ttg aag aga ttt caa gat gtg gag    3608
Val Thr Pro Ala Gly Ala Val Asp Leu Lys Arg Phe Gln Asp Val Glu
                775                 780                 785
```

FIG. 7

```
tat tat aca tat gct gac att ttt gaa ttg ttc cca tct gtt cgc cca      3656
Tyr Tyr Thr Tyr Ala Asp Ile Phe Glu Leu Phe Pro Ser Val Arg Pro
            790                     795                 800
tct ctt gag gaa ctt gtt act atc att gaa cca ttg aag aga aga gaa      3704
Ser Leu Glu Glu Leu Val Thr Ile Ile Glu Pro Leu Lys Arg Arg Glu
        805                     810                 815
tac tca att gcc tcc tct cag aaa gtt cat cca aat gaa gtt cat tta      3752
Tyr Ser Ile Ala Ser Ser Gln Lys Val His Pro Asn Glu Val His Leu
        820                     825                 830
ttg atc gtt gtt gtt gat tgg gtg gat aat aaa gga aga aaa agg tac      3800
Leu Ile Val Val Val Asp Trp Val Asp Asn Lys Gly Arg Lys Arg Tyr
835                     840                 845                 850
ggt caa gct tct aag tat atc tca gac ctt gct gtc ggt tca gaa ttg      3848
Gly Gln Ala Ser Lys Tyr Ile Ser Asp Leu Ala Val Gly Ser Glu Leu
                855                     860                 865
gtc gtt agc gtt aaa cca tct gtt atg aaa tta cca cca tct cca aag      3896
Val Val Ser Val Lys Pro Ser Val Met Lys Leu Pro Pro Ser Pro Lys
                870                     875                 880
caa cca gtt att atg agt ggt tta ggt act ggt ttg gca cca ttc aag      3944
Gln Pro Val Ile Met Ser Gly Leu Gly Thr Gly Leu Ala Pro Phe Lys
            885                     890                 895
gcc att gtt gaa gag aaa tta tgg caa aag cag caa ggt tat gag att      3992
Ala Ile Val Glu Glu Lys Leu Trp Gln Lys Gln Gln Gly Tyr Glu Ile
    900                     905                 910
ggt gaa gtc ttc cta tat cta ggt tca aga cac aaa aga gaa gaa tat      4040
Gly Glu Val Phe Leu Tyr Leu Gly Ser Arg His Lys Arg Glu Glu Tyr
915                     920                 925                 930
tta tat ggt gag tta tgg gag gct tac aaa gat gca ggt att atc aca      4088
Leu Tyr Gly Glu Leu Trp Glu Ala Tyr Lys Asp Ala Gly Ile Ile Thr
                935                     940                 945
cac atc ggc gct gct ttc tca aga gac caa cct caa aaa att tac att      4136
His Ile Gly Ala Ala Phe Ser Arg Asp Gln Pro Gln Lys Ile Tyr Ile
                950                     955                 960
caa gat cgt atc aaa gag aat ttg gat gaa tta aaa act gca atg att      4184
Gln Asp Arg Ile Lys Glu Asn Leu Asp Glu Leu Lys Thr Ala Met Ile
            965                     970                 975
gat aat aaa ggt tca ttt tac ttg tgt ggc cct act tgg cca gtt cca      4232
Asp Asn Lys Gly Ser Phe Tyr Leu Cys Gly Pro Thr Trp Pro Val Pro
        980                     985                 990
gat att act caa gct ttg  caa gac att ctg gct  aaa gac gcc gag       4277
Asp Ile Thr Gln Ala Leu  Gln Asp Ile Leu Ala  Lys Asp Ala Glu
995                 1000                1005
gaa  aga ggc atc aaa gtc  gac ttg gat gcc gca  att gaa gaa tta      4322
Glu  Arg Gly Ile Lys Val  Asp Leu Asp Ala Ala  Ile Glu Glu Leu
1010                1015                1020
aag  gaa gca tca aga tac  att tta gaa gtc tac  taa                  4358
Lys  Glu Ala Ser Arg Tyr  Ile Leu Glu Val Tyr
1025                1030                1035
```

FIG. 7

SEQUENCE LISTING

```
<160> NUMBER OF SEQ ID NOS: 23

<210> SEQ ID NO 1
<211> LENGTH: 3218
<212> TYPE: DNA
<213> ORGANISM: Saccharomyces cerevisiae
<220> FEATURE:
<221> NAME/KEY: CDS
<222> LOCATION: (1251)..(3218)

<400> SEQUENCE: 1
tgatgattat gaaataacga acccacctgc taagaaggct aaaatagaag aaaaacctga      60
aagtgaaccg gccaagagaa atagtggaga gacatatatc actgtctcta gcgaagatga     120
tgatgaagat ggatataatc cttataccct ttaatatgtg cctttttgtt taaatgatgc     180
actgaactgt acatcactgt gtacctggat agaatgtgtg tttaaatatg cgtattatgt     240
attaataatt gaatttaatt ttacttctgt ttttctttt atcgctgtga acttttttgt      300
caagaagtcg ctctttgttg gctttctctt ttattttatt ccatttcttt gaggtctcag     360
cagtggtatc attaggaaat tggcacgttt gccgaatttc ttgaaccaac ttctcgaagc     420
```

```
attttaattt gttggtttcc cttgacctag tttcatcaga ttgaattact atagaatcgc      480
tgcccttagc gtagtatcga aacctgccgc tacttaagat gtttctcact tcctgaggaa      540
tccaagcaca gtttgataaa ccagaaagtg tcaaagtaca tttactattt accttattaa      600
cgttttggcc tcctggcccg ctggctctat cgtaacgtaa aataaattga tttaagggca      660
agcccgttac gttaagtgct cctacccagt ttcttgcctg dacgaagtca gatttctttc      720 cgatctttt attactaatc aatctgactg cctcttcaac gaactgttgt ttcttgcagt       780
gcaacattgg ttgaagtaca aacagagggg agcgcccagt aagtttaaac tttcccatca      840
atgttgtcat atgatatttc ttggcgtgtt tcccttcaat ttactgaaag gcaaacagta     900
atgttaagga ttctgttgtt tttttttacc gtatacgctt gatttcgtca gccccttgga      960
agacacgaaa tgttgactat ccgcttccag atctggtaaa agattgattt gcgataattc     1020
ctgttgttgt catcacgggt gttatggttt gttgtaaact aaaaaaagaa tgaaggaaca     1080
ggacgcagat tcatctaatc aagttctgtg gggaggtccc cagtggtaag tgaataaata     1140
ttcgctttat gaagacctac acctggtttt ctcaatggat cagacgataa gtacaatttt     1200
tgtagagcta tactcgagga caatcagaca aaacgaaaga atatctttcg atg aag       1256
                                                            Met Lys
                                                            1
```

```
ggc gta aaa aag gaa gga tgg ata tct tat aaa gtt gat gga ttg ttt       1304
Gly Val Lys Lys Glu Gly Trp Ile Ser Tyr Lys Val Asp Gly Leu Phe
    5                   10                  15 tcg ttc tta tgg caa aag aga tac ttg gta ctg aat gat tcg tat tta       1352
Ser Phe Leu Trp Gln Lys Arg Tyr Leu Val Leu Asn Asp Ser Tyr Leu
 20                  25                  30 gca ttt tac aaa agt gat aag tgc aat gag gaa cca gtc tta tct gtg       1400
Ala Phe Tyr Lys Ser Asp Lys Cys Asn Glu Glu Pro Val Leu Ser Val
35                  40                  45                  50 cct ttg act agt ata aca aat gtt agc aga ata caa ttg aaa caa aat       1448
Pro Leu Thr Ser Ile Thr Asn Val Ser Arg Ile Gln Leu Lys Gln Asn
                55                  60                  65 tgt ttt gag att ctt cgg gca aca gat caa aaa gag aac ata tcc ccc       1496
Cys Phe Glu Ile Leu Arg Ala Thr Asp Gln Lys Glu Asn Ile Ser Pro
        70                  75                  80 ata aac tcc tac ttt tat gaa tca aat tcc aaa aga tcg ata ttc att       1544
Ile Asn Ser Tyr Phe Tyr Glu Ser Asn Ser Lys Arg Ser Ile Phe Ile
                85                  90                  95 tcc aca aga acc gaa cgg gat ttg cat ggc tgg ctt gat gcc att ttt       1592
Ser Thr Arg Thr Glu Arg Asp Leu His Gly Trp Leu Asp Ala Ile Phe
100                 105                 110 gcc aaa tgt cct ctc ctt agt ggt gtt tca tca cca aca aat ttt aca       1640
Ala Lys Cys Pro Leu Leu Ser Gly Val Ser Ser Pro Thr Asn Phe Thr
115                 120                 125                 130 cac aaa gta cac gtt ggg ttc gac cca aaa gtg gga aac ttt gtt gga       1688
His Lys Val His Val Gly Phe Asp Pro Lys Val Gly Asn Phe Val Gly
                135                 140                 145 gta cct gat agt tgg gct aaa cta cta caa acc tca gaa att acg tac       1736
Val Pro Asp Ser Trp Ala Lys Leu Leu Gln Thr Ser Glu Ile Thr Tyr
            150                 155                 160 gac gat tgg aac aga aac tca aaa gct gtt att aaa gca ctg caa ttt       1784
Asp Asp Trp Asn Arg Asn Ser Lys Ala Val Ile Lys Ala Leu Gln Phe
                165                 170                 175 tat gaa gat tac aat gga ctg gac aca atg caa ttc aat gat cac ctc       1832
Tyr Glu Asp Tyr Asn Gly Leu Asp Thr Met Gln Phe Asn Asp His Leu
                180                 185                 190
```

```
aac aca agc tta gac ttg aaa cct tta aaa agt ccg aca agg tat att    1880
Asn Thr Ser Leu Asp Leu Lys Pro Leu Lys Ser Pro Thr Arg Tyr Ile
195                 200                 205                 210 ata aac aag agg act aat tcc atc aag aga tca gta agt agg acg ctc    1928
Ile Asn Lys Arg Thr Asn Ser Ile Lys Arg Ser Val Ser Arg Thr Leu
            215                 220                 225 cga aaa ggc aaa aca gat tcc att tta ccc gtc tat caa tca gaa ctt    1976
Arg Lys Gly Lys Thr Asp Ser Ile Leu Pro Val Tyr Gln Ser Glu Leu
            230                 235                 240 aaa cca ttc cca agg cct agt gat gat gat tat aag ttt acc aac ata    2024
Lys Pro Phe Pro Arg Pro Ser Asp Asp Asp Tyr Lys Phe Thr Asn Ile
            245                 250                 255 gag gac aat aaa gta cgc gaa gaa ggc agg gtg cat gtt agt aaa gaa    2072
Glu Asp Asn Lys Val Arg Glu Glu Gly Arg Val His Val Ser Lys Glu
260                 265                 270 agc acg gca gat tcc cag aca aag cag tta gga aag aag gaa cag aaa    2120
Ser Thr Ala Asp Ser Gln Thr Lys Gln Leu Gly Lys Lys Glu Gln Lys
275                 280                 285                 290 gtc att caa agc cat ctg cga agg cat gat aat aat tca aca ttt aga    2168
Val Ile Gln Ser His Leu Arg Arg His Asp Asn Asn Ser Thr Phe Arg
                295                 300                 305 cct cat cga cta gca cca tct gca cct gct aca aaa aat cat gat agt    2216
Pro His Arg Leu Ala Pro Ser Ala Pro Ala Thr Lys Asn His Asp Ser
            310                 315                 320 aaa act aaa tgg cat aag gag gat ctc ctt gaa ctt aag aat aat gat    2264
Lys Thr Lys Trp His Lys Glu Asp Leu Leu Glu Leu Lys Asn Asn Asp
        325                 330                 335 gat tcg aat gaa ata ata atg aag atg aaa act gtt gca att gat gta    2312
Asp Ser Asn Glu Ile Ile Met Lys Met Lys Thr Val Ala Ile Asp Val
340                 345                 350 aac cca aga ccg tat ttc caa ctg gta gaa aag gct ggt caa gga gca    2360
Asn Pro Arg Pro Tyr Phe Gln Leu Val Glu Lys Ala Gly Gln Gly Ala
355                 360                 365                 370 agt ggt gca gta tac ctg tca aag cga ata aaa tta cct caa gaa aat    2408
Ser Gly Ala Val Tyr Leu Ser Lys Arg Ile Lys Leu Pro Gln Glu Asn
                375                 380                 385 gac ccg aga ttc ttg aaa tca cat tgc cac cga gtc gta ggc gaa aga    2456
Asp Pro Arg Phe Leu Lys Ser His Cys His Arg Val Val Gly Glu Arg
            390                 395                 400 gtg gcc att aag cag ata cgt tta tct gaa caa cca aag aaa caa ttg    2504
Val Ala Ile Lys Gln Ile Arg Leu Ser Glu Gln Pro Lys Lys Gln Leu
        405                 410                 415 att atg aat gaa ctc cta gtg atg aat gat tcg cgc caa gaa aat atc    2552
Ile Met Asn Glu Leu Leu Val Met Asn Asp Ser Arg Gln Glu Asn Ile
420                 425                 430 gtt aat ttc ctt gaa gcc tat att att gat gac gaa gag tta tgg gtg    2600
Val Asn Phe Leu Glu Ala Tyr Ile Ile Asp Asp Glu Glu Leu Trp Val
435                 440                 445                 450 ata atg gag tac atg gaa ggt ggc tgc tta aca gat ata ttg gat gct    2648
Ile Met Glu Tyr Met Glu Gly Gly Cys Leu Thr Asp Ile Leu Asp Ala
                455                 460                 465 gta gca agg agc aat acc ggt gag cac tca tcg ccg tta aac gaa aac    2696
Val Ala Arg Ser Asn Thr Gly Glu His Ser Ser Pro Leu Asn Glu Asn
            470                 475                 480 caa atg gca tat ata gta aaa gag acg tgc caa ggt ttg aag ttt ttg    2744
Gln Met Ala Tyr Ile Val Lys Glu Thr Cys Gln Gly Leu Lys Phe Leu
        485                 490                 495 cat aac aag aaa att atc cat cga gat atc aaa tct gat aat atc ctt    2792
His Asn Lys Lys Ile Ile His Arg Asp Ile Lys Ser Asp Asn Ile Leu
500                 505                 510
```

-continued

```
ctg aat tcc caa ggg tta gtg aaa att aca gac ttc ggt ttt tgt gtg   2840
Leu Asn Ser Gln Gly Leu Val Lys Ile Thr Asp Phe Gly Phe Cys Val
515                 520                 525                 530 gaa tta aca gaa aaa aga agc aag cgt gcc aca atg gta ggt act cca   2888
Glu Leu Thr Glu Lys Arg Ser Lys Arg Ala Thr Met Val Gly Thr Pro
            535                 540                 545 tat tgg atg gca cct gaa ata gtg aat caa aag gga tat gat gaa aaa   2936
Tyr Trp Met Ala Pro Glu Ile Val Asn Gln Lys Gly Tyr Asp Glu Lys
        550                 555                 560 gtc gac gtt tgg tct cta ggg ata atg ctt att gag atg ata gaa ggt   2984
Val Asp Val Trp Ser Leu Gly Ile Met Leu Ile Glu Met Ile Glu Gly
565                 570                 575 gaa ccg cct tac cta aat gag gat cct ttg aag gcg ctg tat ctg ata   3032
Glu Pro Pro Tyr Leu Asn Glu Asp Pro Leu Lys Ala Leu Tyr Leu Ile
            580                 585                 590 gct aac aac ggt tca cca aaa ttg cgt cat cca gag tca gtg tcc aag   3080
Ala Asn Asn Gly Ser Pro Lys Leu Arg His Pro Glu Ser Val Ser Lys
595                 600                 605                 610 caa acc aaa caa ttc tta gat gcc tgt ttg caa gtg aat gtc gaa tca   3128
Gln Thr Lys Gln Phe Leu Asp Ala Cys Leu Gln Val Asn Val Glu Ser
            615                 620                 625 aga gca tcc gtg aga aaa cta cta acg ttt gaa ttt ttg tca atg gca   3176
Arg Ala Ser Val Arg Lys Leu Leu Thr Phe Glu Phe Leu Ser Met Ala
        630                 635                 640 tgc agc cct gag cag ctc aaa gta tcc tta aag tgg cat tga            3218
Cys Ser Pro Glu Gln Leu Lys Val Ser Leu Lys Trp His
        645                 650                 655

<210> SEQ ID NO 2
<211> LENGTH: 655
<212> TYPE: PRT
<213> ORGANISM: Saccharomyces cerevisiae

<400> SEQUENCE: 2

Met Lys Gly Val Lys Lys Glu Gly Trp Ile Ser Tyr Lys Val Asp Gly
1               5                   10                  15

Leu Phe Ser Phe Leu Trp Gln Lys Arg Tyr Leu Val Leu Asn Asp Ser
            20                  25                  30

Tyr Leu Ala Phe Tyr Lys Ser Asp Lys Cys Asn Glu Glu Pro Val Leu
        35                  40                  45

Ser Val Pro Leu Thr Ser Ile Thr Asn Val Ser Arg Ile Gln Leu Lys
    50                  55                  60

Gln Asn Cys Phe Glu Ile Leu Arg Ala Thr Asp Gln Lys Glu Asn Ile
65                  70                  75                  80

Ser Pro Ile Asn Ser Tyr Phe Tyr Glu Ser Asn Ser Lys Arg Ser Ile
                85                  90                  95

Phe Ile Ser Thr Arg Thr Glu Arg Asp Leu His Gly Trp Leu Asp Ala
            100                 105                 110

Ile Phe Ala Lys Cys Pro Leu Leu Ser Gly Val Ser Pro Thr Asn
        115                 120                 125

Phe Thr His Lys Val His Val Gly Phe Asp Pro Lys Val Gly Asn Phe
    130                 135                 140

Val Gly Val Pro Asp Ser Trp Ala Lys Leu Leu Gln Thr Ser Glu Ile
145                 150                 155                 160

Thr Tyr Asp Asp Trp Asn Arg Asn Ser Lys Ala Val Ile Lys Ala Leu
                165                 170                 175

Gln Phe Tyr Glu Asp Tyr Asn Gly Leu Asp Thr Met Gln Phe Asn Asp
```

-continued

```
            180                 185                 190
His Leu Asn Thr Ser Leu Asp Leu Lys Pro Leu Lys Ser Pro Thr Arg
        195                 200                 205
Tyr Ile Ile Asn Lys Arg Thr Asn Ser Ile Lys Arg Ser Val Ser Arg
        210                 215                 220
Thr Leu Arg Lys Gly Lys Thr Asp Ser Ile Leu Pro Val Tyr Gln Ser
225                 230                 235                 240
Glu Leu Lys Pro Phe Pro Arg Pro Ser Asp Asp Tyr Lys Phe Thr
                245                 250                 255
Asn Ile Glu Asp Asn Lys Val Arg Glu Gly Arg Val His Val Ser
            260                 265                 270
Lys Glu Ser Thr Ala Asp Ser Gln Thr Lys Gln Leu Gly Lys Lys Glu
        275                 280                 285
Gln Lys Val Ile Gln Ser His Leu Arg Arg His Asp Asn Asn Ser Thr
        290                 295                 300
Phe Arg Pro His Arg Leu Ala Pro Ser Ala Pro Ala Thr Lys Asn His
305                 310                 315                 320
Asp Ser Lys Thr Lys Trp His Lys Glu Asp Leu Leu Glu Leu Lys Asn
                325                 330                 335
Asn Asp Asp Ser Asn Glu Ile Ile Met Lys Met Lys Thr Val Ala Ile
            340                 345                 350
Asp Val Asn Pro Arg Pro Tyr Phe Gln Leu Val Glu Lys Ala Gly Gln
        355                 360                 365
Gly Ala Ser Gly Ala Val Tyr Leu Ser Lys Arg Ile Lys Leu Pro Gln
        370                 375                 380
Glu Asn Asp Pro Arg Phe Leu Lys Ser His Cys His Arg Val Val Gly
385                 390                 395                 400
Glu Arg Val Ala Ile Lys Gln Ile Arg Leu Ser Glu Gln Pro Lys Lys
                405                 410                 415
Gln Leu Ile Met Asn Glu Leu Leu Val Met Asn Asp Ser Arg Gln Glu
            420                 425                 430
Asn Ile Val Asn Phe Leu Glu Ala Tyr Ile Ile Asp Asp Glu Glu Leu
        435                 440                 445
Trp Val Ile Met Glu Tyr Met Glu Gly Gly Cys Leu Thr Asp Ile Leu
        450                 455                 460
Asp Ala Val Ala Arg Ser Asn Thr Gly Glu His Ser Ser Pro Leu Asn
465                 470                 475                 480
Glu Asn Gln Met Ala Tyr Ile Val Lys Glu Thr Cys Gln Gly Leu Lys
                485                 490                 495
Phe Leu His Asn Lys Lys Ile Ile His Arg Asp Ile Lys Ser Asp Asn
            500                 505                 510
Ile Leu Leu Asn Ser Gln Gly Leu Val Lys Ile Thr Asp Phe Gly Phe
        515                 520                 525
Cys Val Glu Leu Thr Glu Lys Arg Ser Lys Arg Ala Thr Met Val Gly
        530                 535                 540
Thr Pro Tyr Trp Met Ala Pro Glu Ile Val Asn Gln Lys Gly Tyr Asp
545                 550                 555                 560
Glu Lys Val Asp Val Trp Ser Leu Gly Ile Met Leu Ile Glu Met Ile
                565                 570                 575
Glu Gly Glu Pro Pro Tyr Leu Asn Glu Asp Pro Leu Lys Ala Leu Tyr
            580                 585                 590
Leu Ile Ala Asn Asn Gly Ser Pro Lys Leu Arg His Pro Glu Ser Val
        595                 600                 605
```

Ser Lys Gln Thr Lys Gln Phe Leu Asp Ala Cys Leu Gln Val Asn Val
    610                 615                 620

Glu Ser Arg Ala Ser Val Arg Lys Leu Leu Thr Phe Glu Phe Leu Ser
625                 630                 635                 640

Met Ala Cys Ser Pro Glu Gln Leu Lys Val Ser Leu Lys Trp His
                645                 650                 655

<210> SEQ ID NO 3
<211> LENGTH: 1121
<212> TYPE: DNA
<213> ORGANISM: Saccharomyces cerevisiae

<400> SEQUENCE: 3
ttataccctt taatatgtgc cttttttgttt aaatgatgca ctgaactgta catcactgtg      60
tacctggata gaatgtgtgt ttaaatatgc gtattatgta ttaataattg aatttaatttt    120
tacttctgtt tttctttttta tcgctgtgaa cttttttgtc aagaagtcgc tctttgttgg    180
ctttctcttt tattttattc catttctttg aggtctcagc agtggtatca ttaggaaatt    240
ggcacgtttg ccgaatttct tgaaccaact tctcgaagca ttttaatttg ttggtttccc    300
ttgacctagt ttcatcagat tgaattacta tagaatcgct gcccttagcg tagtatcgaa    360
acctgccgct acttaagatg tttctcactt cctgaggaat ccaagcacag tttgataaac    420
cagaaagtgt caaagtacat ttactattta ccttattaac gttttggcct cctggcccgc    480
tggctctatc gtaacgtaaa ataaattgat ttaaggcaa gcccgttacg ttaagtgctc    540
ctacccagtt tcttgcctgg acgaagtcag atttctttcc gatctttttta ttactaatca    600
atctgactgc ctcttcaacg aactgttgtt tcttgcagtg caacattggt tgaagtacaa    660
acagagggga gcgcccagta agtttaaact ttcccatcaa tgttgtcata tgatatttct    720
tggcgtgttt cccttcaatt tactgaaagg caaacagtaa tgttaaggat tctgttgttt    780
ttttttaccg tatacgcttg atttcgtcag ccccttggaa gacacgaaat gttgactatc    840
cgcttccaga tctggtaaaa gattgatttg cgataattcc tgttgttgtc atcacgggtg    900
ttatggtttg ttgtaaacta aaaaaagaat gaaggaacag gacgcagatt catctaatca    960
agttctgtgg ggaggtcccc agtggtaagt gaataaatat tcgctttatg aagacctaca   1020
cctggttttc tcaatggatc agacgataag tacaattttt gtagagctat actcgaggac   1080
aatcagacaa acgaaagaa tatctttcga tgaagggcgt a                         1121

<210> SEQ ID NO 4
<211> LENGTH: 2561
<212> TYPE: DNA
<213> ORGANISM: Saccharomyces cerevisiae
<220> FEATURE:
<221> NAME/KEY: CDS
<222> LOCATION: (1251)..(2561)

<400> SEQUENCE: 4
aagaacgaag aaagtagtag tgaagattac aattttgcct atgctatgaa gttatggggg      60
gccactatcg gtgaccagtc aatggaattg aggggtgact tgatgattag tataatgaag    120
gatgcaatga acgactattt ctattatcaa aatgacaaca cagttgagcc tgaagaaatc    180
ataggaaata aagtgagtgg tatttttattc gataatatta tcgattatac tacttatttt    240
ggaacaaaca cagaatatat ccacggtatt catatgctac ctatcacacc agtttcttct    300
aatattcgtt ctgagacttt cgtcgaagaa gaatggcaga ctaaaatcga gccaattatt    360

```
gaatcgatag aaagcggctg gacaggcata ttgaagctga atcaagcact cttcgaccca    420
gtagattcgt atgcattttt cagtgattca acttttgatt catccacata tttggataac    480
ggaatgagtc gcacatgggc attagcattt tcaggggggac tggccaactc aattgcttag   540
aaagagaact tggcaagcag gtctgtcgag tctttcccac tacatacata ttttatagaa    600
taaatcattt ttacttaact tgaaagttgt tgcgttcgaa aagaccacgg ctaacggaga    660
ccacttaggt aaatgcatgc cagtaagagg tatattagta cttaatgaa tgaacttagc     720
aaggtaatgc ctgcactaaa ataaaattct aacgtcatcc taagaagcat caattggaca    780
tagtgaggaa aagttttcac catttaaaat ttgttttgca aataccatt ctagactatg     840
atcccttaga gattctcatt ctttaaatat cagcttcaac agcatatctt tatagtatta    900
tcgtactact ggcgacatta gcaaatcaaa gtattttttgc tcagtttcta gtttatctg    960
tttgattccc cattagatgg taaacacgtt gtcttgatga ctgaaaagga agtgaacatg   1020
gtcaactcaa ataaccaga ctcaaaataa ttgcaattac ctaggctaga tattttaga     1080
atattatgag aatattttta gaatatttgc aacccaaaat atatttaaat gccgccaatt   1140
tgcaaccaaa agattatccg ctacctttt tttagtcatt gaatcgtagc ataaagttcc    1200
gagctttgaa aaaagcttt gaactaagaa aaggtaagag atcctcaatt atg ata      1256
                                                        Met Ile
                                                          1 tta ctc caa gtc ata tgc acg att tgg aca tgt ctc ttt att ccg tta    1304
Leu Leu Gln Val Ile Cys Thr Ile Trp Thr Cys Leu Phe Ile Pro Leu
      5                  10                  15 ctc aat gca gag gaa ttc gtc ccc aaa gta acg gag act ctt tca gaa    1352
Leu Asn Ala Glu Glu Phe Val Pro Lys Val Thr Glu Thr Leu Ser Glu
 20                  25                  30 tat tca ttt agt cta gag agc ttt gac gat tcc aac agt tta atc aga    1400
Tyr Ser Phe Ser Leu Glu Ser Phe Asp Asp Ser Asn Ser Leu Ile Arg
 35                  40                  45                  50 tta gat aat caa gtc gtg tgg ata agt tcc gat tct gga gaa aat tgg    1448
Leu Asp Asn Gln Val Val Trp Ile Ser Ser Asp Ser Gly Glu Asn Trp
              55                  60                  65 gaa gcg gtc aaa gaa att gaa ggg cat att ctc gaa tta att gtt gat    1496
Glu Ala Val Lys Glu Ile Glu Gly His Ile Leu Glu Leu Ile Val Asp
          70                  75                  80 cct ttg cat gga cag gac agg gct ttt gtt tcg ata cat tta tca ccc    1544
Pro Leu His Gly Gln Asp Arg Ala Phe Val Ser Ile His Leu Ser Pro
      85                  90                  95 aaa ttt tac gtc acc gat gat cgt gga aaa tca tgg agg gct ctg act    1592
Lys Phe Tyr Val Thr Asp Asp Arg Gly Lys Ser Trp Arg Ala Leu Thr
100                 105                 110 ata ccc gtc tct gaa aac tgt cgt ttg ggt act tct tgc tct ata gct    1640
Ile Pro Val Ser Glu Asn Cys Arg Leu Gly Thr Ser Cys Ser Ile Ala
115                 120                 125                 130 acc cat ccg aca gat aaa aag tac ctt att gca gat tgc cct tgc ttt    1688
Thr His Pro Thr Asp Lys Lys Tyr Leu Ile Ala Asp Cys Pro Cys Phe
              135                 140                 145 ata aac gac aat ggt tat atc caa ata caa aat gaa act tac ttt acc    1736
Ile Asn Asp Asn Gly Tyr Ile Gln Ile Gln Asn Glu Thr Tyr Phe Thr
          150                 155                 160 aac gat ggg gaa tcc ttt tac aat atc gaa cct tcc ttg aaa aag aaa    1784
Asn Asp Gly Glu Ser Phe Tyr Asn Ile Glu Pro Ser Leu Lys Lys Lys
      165                 170                 175 gaa gat gac cat ata aca agt tca agc tgc aac ttt gtc aaa tct agc    1832
Glu Asp Asp His Ile Thr Ser Ser Ser Cys Asn Phe Val Lys Ser Ser
180                 185                 190
```

```
aag gat tct gat att gag ggt aac gac gct tcg ata cta tgt ttg ttc      1880
Lys Asp Ser Asp Ile Glu Gly Asn Asp Ala Ser Ile Leu Cys Leu Phe
195                 200                 205                 210 tcg aac cat ggt tac gat agc gat cgt cac tta agt gcc gca tat aca      1928
Ser Asn His Gly Tyr Asp Ser Asp Arg His Leu Ser Ala Ala Tyr Thr
                215                 220                 225 caa tta gcc tta agt act gat gga ggt aaa act ttc aaa aaa ttt gat      1976
Gln Leu Ala Leu Ser Thr Asp Gly Gly Lys Thr Phe Lys Lys Phe Asp
        230                 235                 240 gag ttt aat gat aaa att att tat caa tac aag ata tta aaa tca cat      2024
Glu Phe Asn Asp Lys Ile Ile Tyr Gln Tyr Lys Ile Leu Lys Ser His
    245                 250                 255 ata atc gtt tcg aca caa gat gat aga tac aat gaa atg tca ccc atg      2072
Ile Ile Val Ser Thr Gln Asp Asp Arg Tyr Asn Glu Met Ser Pro Met
260                 265                 270 gac atc tgg ata tcc aat gat gcg tct act ttt caa aag gca cgt cta      2120
Asp Ile Trp Ile Ser Asn Asp Ala Ser Thr Phe Gln Lys Ala Arg Leu
275                 280                 285                 290 cct gct caa gta cgg cac gtc cat atg tat gga att tat gaa gat tct      2168
Pro Ala Gln Val Arg His Val His Met Tyr Gly Ile Tyr Glu Asp Ser
                295                 300                 305 att gga aga ata atc att cct ata tct acg ata ttc aca gat gaa aaa      2216
Ile Gly Arg Ile Ile Ile Pro Ile Ser Thr Ile Phe Thr Asp Glu Lys
        310                 315                 320 aac gac caa cca gct ccc tca gaa att tta ata tca gat tct caa ggg      2264
Asn Asp Gln Pro Ala Pro Ser Glu Ile Leu Ile Ser Asp Ser Gln Gly
    325                 330                 335 ttg aaa ttt tta cct gtt gaa tgg aca ata aat cct cac ttt ggt tat      2312
Leu Lys Phe Leu Pro Val Glu Trp Thr Ile Asn Pro His Phe Gly Tyr
340                 345                 350 att gat att gct tct cct cat ttc tta gaa gga aca ata att ggc tcg      2360
Ile Asp Ile Ala Ser Pro His Phe Leu Glu Gly Thr Ile Ile Gly Ser
355                 360                 365                 370 ttt cat cct tcc ttt gac tac tct cat aac aaa gga aaa tat aat aaa      2408
Phe His Pro Ser Phe Asp Tyr Ser His Asn Lys Gly Lys Tyr Asn Lys
                375                 380                 385 aag ata gcc aga tat gaa act aaa ata tct gtt gat aac ggc ctc aca      2456
Lys Ile Ala Arg Tyr Glu Thr Lys Ile Ser Val Asp Asn Gly Leu Thr
        390                 395                 400 tgg tca aat ttg aaa gtg gtt gac gag gaa aat gca gat tca ttc cct      2504
Trp Ser Asn Leu Lys Val Val Asp Glu Glu Asn Ala Asp Ser Phe Pro
    405                 410                 415 tgt gat atc act agg cct gaa aga tgt tcg ctc cag aac cct ttt tat      2552
Cys Asp Ile Thr Arg Pro Glu Arg Cys Ser Leu Gln Asn Pro Phe Tyr
420                 425                 430 agt atc taa                                                           2561
Ser Ile
435

<210> SEQ ID NO 5
<211> LENGTH: 436
<212> TYPE: PRT
<213> ORGANISM: Saccharomyces cerevisiae

<400> SEQUENCE: 5

Met Ile Leu Leu Gln Val Ile Cys Thr Ile Trp Thr Cys Leu Phe Ile
1               5                   10                  15

Pro Leu Leu Asn Ala Glu Glu Phe Val Pro Lys Val Thr Glu Thr Leu
            20                  25                  30
```

```
Ser Glu Tyr Ser Phe Ser Leu Glu Ser Phe Asp Asp Ser Asn Ser Leu
         35                  40                  45

Ile Arg Leu Asp Asn Gln Val Val Trp Ile Ser Ser Asp Ser Gly Glu
 50                  55                  60

Asn Trp Glu Ala Val Lys Glu Ile Glu Gly His Ile Leu Glu Leu Ile
 65                  70                  75                  80

Val Asp Pro Leu His Gly Gln Asp Arg Ala Phe Val Ser Ile His Leu
                 85                  90                  95

Ser Pro Lys Phe Tyr Val Thr Asp Asp Arg Gly Lys Ser Trp Arg Ala
                100                 105                 110

Leu Thr Ile Pro Val Ser Glu Asn Cys Arg Leu Gly Thr Ser Cys Ser
             115                 120                 125

Ile Ala Thr His Pro Thr Asp Lys Lys Tyr Leu Ile Ala Asp Cys Pro
 130                 135                 140

Cys Phe Ile Asn Asp Asn Gly Tyr Ile Gln Ile Gln Asn Glu Thr Tyr
145                 150                 155                 160

Phe Thr Asn Asp Gly Glu Ser Phe Tyr Asn Ile Glu Pro Ser Leu Lys
                 165                 170                 175

Lys Lys Glu Asp Asp His Ile Thr Ser Ser Ser Cys Asn Phe Val Lys
             180                 185                 190

Ser Ser Lys Asp Ser Asp Ile Glu Gly Asn Asp Ala Ser Ile Leu Cys
         195                 200                 205

Leu Phe Ser Asn His Gly Tyr Asp Ser Asp Arg His Leu Ser Ala Ala
         210                 215                 220

Tyr Thr Gln Leu Ala Leu Ser Thr Asp Gly Gly Lys Thr Phe Lys Lys
225                 230                 235                 240

Phe Asp Glu Phe Asn Asp Lys Ile Ile Tyr Gln Tyr Lys Ile Leu Lys
                 245                 250                 255

Ser His Ile Ile Val Ser Thr Gln Asp Asp Arg Tyr Asn Glu Met Ser
             260                 265                 270

Pro Met Asp Ile Trp Ile Ser Asn Asp Ala Ser Thr Phe Gln Lys Ala
         275                 280                 285

Arg Leu Pro Ala Gln Val Arg His Val His Met Tyr Gly Ile Tyr Glu
         290                 295                 300

Asp Ser Ile Gly Arg Ile Ile Ile Pro Ile Ser Thr Ile Phe Thr Asp
305                 310                 315                 320

Glu Lys Asn Asp Gln Pro Ala Pro Ser Glu Ile Leu Ile Ser Asp Ser
                 325                 330                 335

Gln Gly Leu Lys Phe Leu Pro Val Glu Trp Thr Ile Asn Pro His Phe
             340                 345                 350

Gly Tyr Ile Asp Ile Ala Ser Pro His Phe Leu Glu Gly Thr Ile Ile
         355                 360                 365

Gly Ser Phe His Pro Ser Phe Asp Tyr Ser His Asn Lys Gly Lys Tyr
         370                 375                 380

Asn Lys Lys Ile Ala Arg Tyr Glu Thr Lys Ile Ser Val Asp Asn Gly
385                 390                 395                 400

Leu Thr Trp Ser Asn Leu Lys Val Val Asp Glu Glu Asn Ala Asp Ser
                 405                 410                 415

Phe Pro Cys Asp Ile Thr Arg Pro Glu Arg Cys Ser Leu Gln Asn Pro
             420                 425                 430

Phe Tyr Ser Ile
         435
```

-continued

<210> SEQ ID NO 6
<211> LENGTH: 1212
<212> TYPE: DNA
<213> ORGANISM: Saccharomyces cerevisiae

<400> SEQUENCE: 6

| | | | | | |
|---|---|---|---|---|---|
| gttatggggg | gccactatcg | gtgaccagtc | aatggaattg | agggtgact | tgatgattag | 60 |
| tataatgaag | gatgcaatga | acgactattt | ctattatcaa | aatgacaaca | cagttgagcc | 120 |
| tgaagaaatc | ataggaaata | aagtgagtgg | tattttattc | gataatatta | tcgattatac | 180 |
| tacttatttt | ggaacaaaca | cagaatatat | ccacggtatt | catatgctac | ctatcacacc | 240 |
| agtttcttct | aatattcgtt | ctgagacttt | cgtcgaagaa | gaatggcaga | ctaaaatcga | 300 |
| gccaattatt | gaatcgatag | aaagcggctg | gacaggcata | ttgaagctga | atcaagcact | 360 |
| cttcgaccca | gtagattcgt | atgcattttt | cagtgattca | acttttgatt | catccacata | 420 |
| tttggataac | ggaatgagtc | gcacatgggc | attagcattt | tcaggggac | tggccaactc | 480 |
| aattgcttag | aaagagaact | tggcaagcag | gtctgtcgag | tctttcccac | tacatacata | 540 |
| ttttatagaa | taaatcattt | ttacttaact | tgaaagttgt | tgcgttcgaa | aagaccacgg | 600 |
| ctaacggaga | ccacttaggt | aaatgcatgc | cagtaagagg | tatattagta | ctttaatgaa | 660 |
| tgaacttagc | aaggtaatgc | ctgcactaaa | ataaaattct | aacgtcatcc | taagaagcat | 720 |
| caattggaca | tagtgaggaa | aagttttcac | catttaaaat | ttgttttgca | gaataccatt | 780 |
| ctagactatg | atcccttaga | gattctcatt | ctttaaatat | cagcttcaac | agcatatctt | 840 |
| tatagtatta | tcgtactact | ggcgacatta | gcaaatcaaa | gtattttgc | tcagtttcta | 900 |
| gttttatctg | tttgattccc | cattagatgg | taaacacgtt | gtcttgatga | ctgaaaagga | 960 |
| agtgaacatg | gtcaactcaa | aataaccaga | ctcaaaataa | ttgcaattac | ctaggctaga | 1020 |
| tatttttaga | atattatgag | aatattttta | gaatatttgc | aacccaaaat | atatttaaat | 1080 |
| gccgccaatt | tgcaaccaaa | agattatccg | ctacctttt | tttagtcatt | gaatcgtagc | 1140 |
| ataaagttcc | gagctttgaa | aaaaagcttt | gaactaagaa | aaggtaagag | atcctcaatt | 1200 |
| atgatattac | tc | | | | | 1212 |

<210> SEQ ID NO 7
<211> LENGTH: 2777
<212> TYPE: DNA
<213> ORGANISM: Saccharomyces cerevisiae
<220> FEATURE:
<221> NAME/KEY: CDS
<222> LOCATION: (1251)..(2777)

<400> SEQUENCE: 7

| | | | | | |
|---|---|---|---|---|---|
| tggactcagg | atgatgagag | gttcctttgt | accactaaga | tcgactcgtc | ctaaccctat | 60 |
| atcccaatcc | caagactagg | cgaaccaaca | ttaactgggc | tcgtaatagg | gcaatgataa | 120 |
| tgcaaaagcg | gctcctaaac | agaaattctt | cagtagtcaa | atctcgaaat | tgccttgctc | 180 |
| gtcatcaaca | tgaatcgtct | atatcaaaac | tgcatgtttc | tctacgtcta | cacagatgtt | 240 |
| tgcgtccgat | tgtgcgcttc | gatttttac | ataatgctgg | aagcaaagtt | tgctctcaga | 300 |
| attcctgccc | ttcgccccag | ttacacgtgg | ggacaatggc | gctctttcat | acagtcttca | 360 |
| ttctatggcc | gcacttttgt | ggcattctct | ggaccgtcca | tgaaaaatta | tataactatt | 420 |
| tgctttctat | tgaagtctat | tgaagttagc | gtggatagaa | cggcgttaca | tggcacatca | 480 |
| gctgaagcta | gcgcaagtaa | ttttcaacgc | attcaaacga | aaaacttatc | taaatacaat | 540 |
| tgtaacatac | cggcttgctg | tgtgtgaacc | ccttttcccca | attgtatatc | agaaacgtct | 600 |

-continued

```
gagtggaggg tgaggaatca ctcactacct tttctccatt cgacgcctat aagcagcgta    660
ttttaaagga aagggaatt agtgcggaga tgggccagaa atgtactctt ttttggcag     720 agttttccg gcgggacaa acaatggcg tgggtgatg aaataagcaa aattcaatat       780
cccttatgac ggaatggcag aattggccac cattttgtct tggcattcaa tatacataca   840
aatcttcact accgcgatat tgttggtaat ggagattgct ttttggcctc ctggcttata   900 ggctctgag tctcgtggta gtggaatccg gcacagaaac gagaatcgga tatttggggc    960
cgggccatgt acaggcaaaa gaaatagcga aaatatctct tattttttc gcgcttcctt    1020 tgtagtagaa attattggcg atcggattac tattcgcgga aaagaaatta aaaatagcga   1080 agaactaga actataagcc tcaaaaggaa acttgtgtgg tcgaaggctg gacgccataa    1140
taatatatat atgtacgtat atatattata tatgaatatc tgtagccgct aacttgtgtg   1200
tttgtgaatt tatataggat aaatagagca aaattactcg gcattgaaaa atg aaa     1256
                                                        Met Lys
                                                        1
```

| | | | | | | | | | | | | | | | | |
|---|---|---|---|---|---|---|---|---|---|---|---|---|---|---|---|---|
| ctt | caa | ttg | gcg | gca | gtg | gct | aca | tta | gca | gtc | tta | act | agt | ccg | gca | 1304 |
| Leu | Gln | Leu | Ala | Ala | Val | Ala | Thr | Leu | Ala | Val | Leu | Thr | Ser | Pro | Ala | |
| | 5 | | | | 10 | | | | | 15 | | | | | | |
| ttc | ggt | aga | gta | ctt | ccc | gat | ggg | aaa | tac | gtc | aag | att | ccc | ttc | aca | 1352 |
| Phe | Gly | Arg | Val | Leu | Pro | Asp | Gly | Lys | Tyr | Val | Lys | Ile | Pro | Phe | Thr | |
| | 20 | | | | | 25 | | | | | 30 | | | | | |
| aaa | aaa | aag | aac | ggc | gac | aat | ggt | gaa | ctc | agc | aag | aga | tcg | aac | ggc | 1400 |
| Lys | Lys | Lys | Asn | Gly | Asp | Asn | Gly | Glu | Leu | Ser | Lys | Arg | Ser | Asn | Gly | |
| 35 | | | | 40 | | | | | 45 | | | | | 50 | | |
| cat | gaa | aaa | ttt | gta | cta | gct | aac | gag | caa | agc | ttt | tat | tct | gtt | gag | 1448 |
| His | Glu | Lys | Phe | Val | Leu | Ala | Asn | Glu | Gln | Ser | Phe | Tyr | Ser | Val | Glu | |
| | | | | 55 | | | | | 60 | | | | | 65 | | |
| cta | gcc | att | ggt | aca | cct | tca | caa | aac | ctc | act | gtg | ctg | tta | gac | aca | 1496 |
| Leu | Ala | Ile | Gly | Thr | Pro | Ser | Gln | Asn | Leu | Thr | Val | Leu | Leu | Asp | Thr | |
| | | | 70 | | | | | 75 | | | | | 80 | | | |
| ggc | tca | gct | gac | tta | tgg | gtt | cct | ggc | aag | gga | aac | ccc | tac | tgc | ggt | 1544 |
| Gly | Ser | Ala | Asp | Leu | Trp | Val | Pro | Gly | Lys | Gly | Asn | Pro | Tyr | Cys | Gly | |
| | | 85 | | | | | 90 | | | | | 95 | | | | |
| tct | gtg | atg | gac | tgt | gac | cag | tat | ggc | gtg | ttc | gac | aag | acc | aag | tcg | 1592 |
| Ser | Val | Met | Asp | Cys | Asp | Gln | Tyr | Gly | Val | Phe | Asp | Lys | Thr | Lys | Ser | |
| | 100 | | | | | 105 | | | | | 110 | | | | | |
| tcc | acg | ttc | aaa | gcc | aac | aag | tcc | tcg | cct | ttt | tat | gcc | gct | tac | ggt | 1640 |
| Ser | Thr | Phe | Lys | Ala | Asn | Lys | Ser | Ser | Pro | Phe | Tyr | Ala | Ala | Tyr | Gly | |
| 115 | | | | 120 | | | | | 125 | | | | | 130 | | |
| gac | gga | acc | tat | gca | gaa | ggt | gca | ttt | ggt | caa | gat | aaa | tta | aag | tac | 1688 |
| Asp | Gly | Thr | Tyr | Ala | Glu | Gly | Ala | Phe | Gly | Gln | Asp | Lys | Leu | Lys | Tyr | |
| | | | | 135 | | | | | 140 | | | | | 145 | | |
| aac | gaa | tta | gac | ctc | agt | ggt | cta | tcg | ttt | gcc | gtg | gcc | aac | gaa | tct | 1736 |
| Asn | Glu | Leu | Asp | Leu | Ser | Gly | Leu | Ser | Phe | Ala | Val | Ala | Asn | Glu | Ser | |
| | | | 150 | | | | | 155 | | | | | 160 | | | |
| aac | tca | acc | ttt | ggt | gtg | ctc | ggg | atc | ggc | ctt | tcc | acg | ctt | gaa | gtc | 1784 |
| Asn | Ser | Thr | Phe | Gly | Val | Leu | Gly | Ile | Gly | Leu | Ser | Thr | Leu | Glu | Val | |
| | | 165 | | | | | 170 | | | | | 175 | | | | |
| acc | tat | tct | gga | aaa | gtc | gct | att | atg | gac | aag | aga | agc | tac | gag | tat | 1832 |
| Thr | Tyr | Ser | Gly | Lys | Val | Ala | Ile | Met | Asp | Lys | Arg | Ser | Tyr | Glu | Tyr | |
| | 180 | | | | | 185 | | | | | 190 | | | | | |
| gat | aac | ttt | ccc | ctg | ttc | cta | aaa | cat | tct | gga | gcc | atc | gat | gca | acc | 1880 |
| Asp | Asn | Phe | Pro | Leu | Phe | Leu | Lys | His | Ser | Gly | Ala | Ile | Asp | Ala | Thr | |
| 195 | | | | 200 | | | | | 205 | | | | | 210 | | |
| gca | tac | tct | ctt | ttc | cta | aat | gac | gag | tca | cag | tcc | tcc | ggc | agc | atc | 1928 |
| Ala | Tyr | Ser | Leu | Phe | Leu | Asn | Asp | Glu | Ser | Gln | Ser | Ser | Gly | Ser | Ile | |

```
                      215                 220                 225
ctc ttc ggc gct gta gat cac agc aag tac gag ggc caa ctg tac act    1976
Leu Phe Gly Ala Val Asp His Ser Lys Tyr Glu Gly Gln Leu Tyr Thr
            230                 235                 240 atc ccg ttg gtt aat ctt tat aag tcg cag ggt tat cag cac ccg gtg    2024
Ile Pro Leu Val Asn Leu Tyr Lys Ser Gln Gly Tyr Gln His Pro Val
        245                 250                 255 gcg ttc gat gtc act tta cag ggc tta gga ctg caa acc gac aag cgc    2072
Ala Phe Asp Val Thr Leu Gln Gly Leu Gly Leu Gln Thr Asp Lys Arg
    260                 265                 270 aac atc aca ttg acc acc acc aag ctc cca gcc cta ctc gat tca ggc    2120
Asn Ile Thr Leu Thr Thr Thr Lys Leu Pro Ala Leu Leu Asp Ser Gly
275                 280                 285                 290 aca acg cta aca tat ctg ccc tcc cag gca gtg gct ttg cta gca aag    2168
Thr Thr Leu Thr Tyr Leu Pro Ser Gln Ala Val Ala Leu Leu Ala Lys
                295                 300                 305 agc ttg aat gcc tcg tat tcc aag aca ttg ggt tat tat gag tac acg    2216
Ser Leu Asn Ala Ser Tyr Ser Lys Thr Leu Gly Tyr Tyr Glu Tyr Thr
            310                 315                 320 tgt ccc tcg agc gac aac aaa acc agc gtg gcc ttc gac ttc ggt ggc    2264
Cys Pro Ser Ser Asp Asn Lys Thr Ser Val Ala Phe Asp Phe Gly Gly
        325                 330                 335 ttc cgt atc aac gct cct cta tcc gac ttt act atg cag acc agt gtg    2312
Phe Arg Ile Asn Ala Pro Leu Ser Asp Phe Thr Met Gln Thr Ser Val
    340                 345                 350 ggg acc tgt gtc ttg gca ata att cca caa gcg ggc aac gcc acc gct    2360
Gly Thr Cys Val Leu Ala Ile Ile Pro Gln Ala Gly Asn Ala Thr Ala
355                 360                 365                 370 atc ctt ggt gat tcc ttc ttg aga aac gcc tac gtg gtc tac gat ttg    2408
Ile Leu Gly Asp Ser Phe Leu Arg Asn Ala Tyr Val Val Tyr Asp Leu
                375                 380                 385 gat aac tac gag att tcc cta gct caa gcc aag tat ggc acg ggg aaa    2456
Asp Asn Tyr Glu Ile Ser Leu Ala Gln Ala Lys Tyr Gly Thr Gly Lys
            390                 395                 400 gag aac gtc gaa gtc atc aaa tct acc gtt ccc agt gca ata agg gcc    2504
Glu Asn Val Glu Val Ile Lys Ser Thr Val Pro Ser Ala Ile Arg Ala
        405                 410                 415 ccc agt tac aac aac act tgg tct aac tac gcc tcc gcc acg tcc ggt    2552
Pro Ser Tyr Asn Asn Thr Trp Ser Asn Tyr Ala Ser Ala Thr Ser Gly
    420                 425                 430 ggt aat att ttt acc acc gtg cgc act ttc aat ggc acc agt act gcc    2600
Gly Asn Ile Phe Thr Thr Val Arg Thr Phe Asn Gly Thr Ser Thr Ala
435                 440                 445                 450 acc act acg agg tca acc acc acc aag aag aca aac tct acc act act    2648
Thr Thr Thr Arg Ser Thr Thr Thr Lys Lys Thr Asn Ser Thr Thr Thr
                455                 460                 465 gca aag tcg act cat aaa agc aag agg gca ctc cag agg gct gct acc    2696
Ala Lys Ser Thr His Lys Ser Lys Arg Ala Leu Gln Arg Ala Ala Thr
            470                 475                 480 aac tcc gct tcc agt ata cgc tct acc ttg ggt tta ctg cta gtc ccc    2744
Asn Ser Ala Ser Ser Ile Arg Ser Thr Leu Gly Leu Leu Leu Val Pro
        485                 490                 495 tcc tta ctc atc ctt tcc gtt ttc ttt tcg taa                        2777
Ser Leu Leu Ile Leu Ser Val Phe Phe Ser
    500                 505

<210> SEQ ID NO 8
<211> LENGTH: 508
<212> TYPE: PRT
<213> ORGANISM: Saccharomyces cerevisiae
```

<400> SEQUENCE: 8

```
Met Lys Leu Gln Leu Ala Ala Val Ala Thr Leu Ala Val Leu Thr Ser
1               5                   10                  15
Pro Ala Phe Gly Arg Val Leu Pro Asp Gly Lys Tyr Val Lys Ile Pro
            20                  25                  30
Phe Thr Lys Lys Asn Gly Asp Asn Gly Glu Leu Ser Lys Arg Ser
        35                  40                  45
Asn Gly His Glu Lys Phe Val Leu Ala Asn Glu Gln Ser Phe Tyr Ser
    50                  55                  60
Val Glu Leu Ala Ile Gly Thr Pro Ser Gln Asn Leu Thr Val Leu Leu
65                  70                  75                  80
Asp Thr Gly Ser Ala Asp Leu Trp Val Pro Gly Lys Gly Asn Pro Tyr
                85                  90                  95
Cys Gly Ser Val Met Asp Cys Asp Gln Tyr Gly Val Phe Asp Lys Thr
            100                 105                 110
Lys Ser Ser Thr Phe Lys Ala Asn Lys Ser Ser Pro Phe Tyr Ala Ala
        115                 120                 125
Tyr Gly Asp Gly Thr Tyr Ala Glu Gly Ala Phe Gly Gln Asp Lys Leu
    130                 135                 140
Lys Tyr Asn Glu Leu Asp Leu Ser Gly Leu Ser Phe Ala Val Ala Asn
145                 150                 155                 160
Glu Ser Asn Ser Thr Phe Gly Val Leu Gly Ile Gly Leu Ser Thr Leu
                165                 170                 175
Glu Val Thr Tyr Ser Gly Lys Val Ala Ile Met Asp Lys Arg Ser Tyr
            180                 185                 190
Glu Tyr Asp Asn Phe Pro Leu Phe Leu Lys His Ser Gly Ala Ile Asp
        195                 200                 205
Ala Thr Ala Tyr Ser Leu Phe Leu Asn Asp Glu Ser Gln Ser Ser Gly
    210                 215                 220
Ser Ile Leu Phe Gly Ala Val Asp His Ser Lys Tyr Glu Gly Gln Leu
225                 230                 235                 240
Tyr Thr Ile Pro Leu Val Asn Leu Tyr Lys Ser Gln Gly Tyr Gln His
                245                 250                 255
Pro Val Ala Phe Asp Val Thr Leu Gln Gly Leu Gly Leu Gln Thr Asp
            260                 265                 270
Lys Arg Asn Ile Thr Leu Thr Thr Lys Leu Pro Ala Leu Leu Asp
        275                 280                 285
Ser Gly Thr Thr Leu Thr Tyr Leu Pro Ser Gln Ala Val Ala Leu Leu
    290                 295                 300
Ala Lys Ser Leu Asn Ala Ser Tyr Ser Lys Thr Leu Gly Tyr Tyr Glu
305                 310                 315                 320
Tyr Thr Cys Pro Ser Ser Asp Asn Lys Thr Ser Val Ala Phe Asp Phe
                325                 330                 335
Gly Gly Phe Arg Ile Asn Ala Pro Leu Ser Asp Phe Thr Met Gln Thr
            340                 345                 350
Ser Val Gly Thr Cys Val Leu Ala Ile Ile Pro Gln Ala Gly Asn Ala
        355                 360                 365
Thr Ala Ile Leu Gly Asp Ser Phe Leu Arg Asn Ala Tyr Val Val Tyr
    370                 375                 380
Asp Leu Asp Asn Tyr Glu Ile Ser Leu Ala Gln Ala Lys Tyr Gly Thr
385                 390                 395                 400
Gly Lys Glu Asn Val Glu Val Ile Lys Ser Thr Val Pro Ser Ala Ile
```

-continued

```
              405                 410                 415
Arg Ala Pro Ser Tyr Asn Asn Thr Trp Ser Asn Tyr Ala Ser Ala Thr
            420                 425                 430
Ser Gly Gly Asn Ile Phe Thr Thr Val Arg Thr Phe Asn Gly Thr Ser
            435                 440                 445
Thr Ala Thr Thr Thr Arg Ser Thr Thr Thr Lys Lys Thr Asn Ser Thr
        450                 455                 460
Thr Thr Ala Lys Ser Thr His Lys Ser Lys Arg Ala Leu Gln Arg Ala
465                 470                 475                 480
Ala Thr Asn Ser Ala Ser Ser Ile Arg Ser Thr Leu Gly Leu Leu Leu
                485                 490                 495
Val Pro Ser Leu Leu Ile Leu Ser Val Phe Phe Ser
            500                 505
```

<210> SEQ ID NO 9
<211> LENGTH: 1063
<212> TYPE: DNA
<213> ORGANISM: Saccharomyces cerevisiae

<400> SEQUENCE: 9

```
tatatcaaaa ctgcatgttt ctctacgtct acacagatgt ttgcgtccga ttgtgcgctt      60
cgatttttta cataatgctg gaagcaaagt ttgctctcag aattcctgcc cttcgcccca    120
gttacacgtg gggacaatgg cgctctttca tacagtcttc attctatggc cgcacttttg    180
tggcattctc tggaccgtcc atgaaaaatt atataactat ttgctttcta ttgaagtcta    240
ttgaagttag cgtggataga acggcgttac atggcacatc agctgaagct agcgcaagta    300
attttcaacg cattcaaacg aaaaactat ctaaatacaa ttgtaacata ccggcttgct    360
gtgtgtgaac ccctttcccc aattgtatat cagaaacgtc tgagtggagg gtgaggaatc    420
actcactacc ttttctccat cgacgccta taagcagcgt atttaaagg aaagggaat     480
tagtgcggag atgggccaga atgtactct ttttttggca gagtttttcc gggcgggaca    540
aaacaatggc gtggggtgat gaaataagca aaattcaata tcccttatga cggaatggca    600
gaattggcca ccattttgtc ttggcattca atatacatac aaatcttcac taccgcgata    660
ttgttggtaa tggagattgc ttttttggcct cctggcttat agggctctga gtctcgtggt    720
agtggaatcc ggcacagaaa cgagaatcgg atatttgggg ccgggccatg tacaggcaaa    780
agaaatagcg aaaatatctc ttattttttt cgcgcttcct ttgtagtaga aattattggc    840
gatcggatta ctattcgcgg aaaagaaatt aaaaatagcg aagaacttag aactataagc    900
ctcaaaagga aacttgtgtg gtcgaaggct ggacgccata ataatatata tatgtacgta    960
tatatattat atatgaatat ctgtagccgc taacttgtgt gtttgtgaat ttatatagga   1020
taaatagagc aaaattactc ggcattgaaa atgaaacttt caa                    1063
```

<210> SEQ ID NO 10
<211> LENGTH: 2126
<212> TYPE: DNA
<213> ORGANISM: Saccharomyces cerevisiae
<220> FEATURE:
<221> NAME/KEY: CDS
<222> LOCATION: (1251)..(2126)

<400> SEQUENCE: 10

```
aattgggtgc taactatgcc ccatgcatct tacctcaact acaagctgcc aaaagagggt      60
accaacaaaa tctatggttg ttcggcccag aaaagaacat cactgaggtt ggtactatga    120
```

-continued

```
acgtgttctt cgttttcctc aacaaagtca ctggcaagaa ggaattggtt accgctccat    180
tagatggtac cattttagaa ggtgttacca gagactctgt tttaacattg gctcgtgaca    240
aactagatcc tcaagaatgg gacatcaacg agcgttatta cactattact gaagtcgcca    300
ctagagcaaa acaaggtgaa ctattagaag ccttcggttc tggtactgct gctgtcgttt    360
cacctatcaa ggaaattggc tggaacaacg aagatattca tgttccacta ttgcctggtg    420
aacaatgtgg tgcattgacc aagcaagttg ctcaatggat tgctgatatc caatacggta    480
gagtcaatta tggtaactgg tcaaaaactg ttgccgactt gaactaatga taatgaaggt    540
aaacatcccc tccccccca aaaaaaaaaa acgagaattc ctctcagagg atctgttttt    600
ctctcacttt attcacatag atacatactt ttttacaatt cctgttgagt ttatttatta    660
taagaaatat tggattacta ttattattat agcttatgca agccattgtg cggcttctta    720 cgcttttga aattgttgac ctaacaactt ggcacattat tgaatttcat agagactgct    780
tgtaatttag ttgccaaggt atctcgctgg actttacatg taaatgaat gcggcaagat    840 acccaagaga gttgattatg ccaaaaaaaa aaatctata aggatatccc tggtattttc    900
tgaagaataa attctagcgt agttcagaag aggtgcaagt acagtatgaa taatggtatg    960
ccttccatca tcgtggcata caggttcagg catgaagaga tgattatgtt ccctcaccgg   1020
tccataatcc tgatttaaac agttcattag tatatgttca gccaacacaa caacgagaag   1080
ctttgtagtg aaagttttcc acgatctata tttagcattc taattagcgg ccccaaggga   1140
acgtatataa acataaacaa acggcacgaa ctaaaggggc aaattcaagt taaccctttt   1200
acactcagta catcttcaaa gccagtcttc tgtcaatgga agaatccaga atg cct       1256
                                                       Met Pro
                                                         1 aaa act agt tat tta aac aaa aat ttt gaa tct gct cac tat aat aac      1304
Lys Thr Ser Tyr Leu Asn Lys Asn Phe Glu Ser Ala His Tyr Asn Asn
      5              10                 15 gta cgt ccc tct tac cct tta tct tta gtc aat gag ata atg aaa ttt      1352
Val Arg Pro Ser Tyr Pro Leu Ser Leu Val Asn Glu Ile Met Lys Phe
 20             25                 30 cac aaa ggc aca cgc aaa agt ttg gtt gat att gga tgt ggc aca gga      1400
His Lys Gly Thr Arg Lys Ser Leu Val Asp Ile Gly Cys Gly Thr Gly
35          40                 45                 50 aaa gca act ttt gtc gtt gaa ccc tat ttt aag gaa gtg att ggg att      1448
Lys Ala Thr Phe Val Val Glu Pro Tyr Phe Lys Glu Val Ile Gly Ile
                55                 60                 65 gat cct tct tct gct atg ctt tcg att gct gag aaa gaa aca aat gaa      1496
Asp Pro Ser Ser Ala Met Leu Ser Ile Ala Glu Lys Glu Thr Asn Glu
         70                 75                 80 cgt aga tta gat aaa aag att aga ttt att aat gcg cct ggt gaa gat      1544
Arg Arg Leu Asp Lys Lys Ile Arg Phe Ile Asn Ala Pro Gly Glu Asp
     85                 90                 95 tta tcc agc att cga cca gaa agt gta gat atg gtt att tca gca gaa      1592
Leu Ser Ser Ile Arg Pro Glu Ser Val Asp Met Val Ile Ser Ala Glu
 100                105                110 gcc atc cat tgg tgc aat tta gaa agg ctg ttt cag cag gtt tcc tct      1640
Ala Ile His Trp Cys Asn Leu Glu Arg Leu Phe Gln Gln Val Ser Ser
115            120                125                130 ata tta cga agt gat gga act ttt gca ttc tgg ttt tat att cag ccg      1688
Ile Leu Arg Ser Asp Gly Thr Phe Ala Phe Trp Phe Tyr Ile Gln Pro
                135                140                145 gaa ttt gtg gac ttt ccc gaa gcc ttg aat gta tat tac aaa tat gga      1736
Glu Phe Val Asp Phe Pro Glu Ala Leu Asn Val Tyr Tyr Lys Tyr Gly
            150                155                160
```

```
tgg agc aag gat tat atg ggt aaa tat ctg aac gac aac caa cgg gaa      1784
Trp Ser Lys Asp Tyr Met Gly Lys Tyr Leu Asn Asp Asn Gln Arg Glu
        165                 170                 175 att ttg ttg aat tac ggt ggt gaa aag cta cgt tct tta ttg tca gat      1832
Ile Leu Leu Asn Tyr Gly Gly Glu Lys Leu Arg Ser Leu Leu Ser Asp
    180                 185                 190 cga ttt gga gat att gaa gtc aca att tac agt cct tcg gac cca aat      1880
Arg Phe Gly Asp Ile Glu Val Thr Ile Tyr Ser Pro Ser Asp Pro Asn
195                 200                 205                 210 gca tca aca gta acg gct gaa aac agt cag ttt ctc tgg aga gca gct      1928
Ala Ser Thr Val Thr Ala Glu Asn Ser Gln Phe Leu Trp Arg Ala Ala
                215                 220                 225 att act ctc aat caa ttt aaa gag ttt gtg aaa agc tgg agc ata tac      1976
Ile Thr Leu Asn Gln Phe Lys Glu Phe Val Lys Ser Trp Ser Ile Tyr
        230                 235                 240 act tct tgg gct aga gat aat ccc tcg aaa ccg gat att gcc gat ata      2024
Thr Ser Trp Ala Arg Asp Asn Pro Ser Lys Pro Asp Ile Ala Asp Ile
    245                 250                 255 ttc att aac gag ctc aaa gaa atc tgt cat tgt gaa gat ttg aat gta      2072
Phe Ile Asn Glu Leu Lys Glu Ile Cys His Cys Glu Asp Leu Asn Val
260                 265                 270 cct tta aaa ata gag tgg tca acg ttt tat tac tta tgt agg aaa aga      2120
Pro Leu Lys Ile Glu Trp Ser Thr Phe Tyr Tyr Leu Cys Arg Lys Arg
275                 280                 285                 290 gaa tga                                                              2126
Glu

<210> SEQ ID NO 11
<211> LENGTH: 291
<212> TYPE: PRT
<213> ORGANISM: Saccharomyces cerevisiae

<400> SEQUENCE: 11

Met Pro Lys Thr Ser Tyr Leu Asn Lys Asn Phe Glu Ser Ala His Tyr
1               5                   10                  15

Asn Asn Val Arg Pro Ser Tyr Pro Leu Ser Leu Val Asn Glu Ile Met
            20                  25                  30

Lys Phe His Lys Gly Thr Arg Lys Ser Leu Val Asp Ile Gly Cys Gly
        35                  40                  45

Thr Gly Lys Ala Thr Phe Val Val Glu Pro Tyr Phe Lys Glu Val Ile
    50                  55                  60

Gly Ile Asp Pro Ser Ser Ala Met Leu Ser Ile Ala Glu Lys Glu Thr
65                  70                  75                  80

Asn Glu Arg Arg Leu Asp Lys Lys Ile Arg Phe Ile Asn Ala Pro Gly
                85                  90                  95

Glu Asp Leu Ser Ser Ile Arg Pro Glu Ser Val Asp Met Val Ile Ser
            100                 105                 110

Ala Glu Ala Ile His Trp Cys Asn Leu Glu Arg Leu Phe Gln Gln Val
        115                 120                 125

Ser Ser Ile Leu Arg Ser Asp Gly Thr Phe Ala Phe Trp Phe Tyr Ile
    130                 135                 140

Gln Pro Glu Phe Val Asp Phe Pro Glu Ala Leu Asn Val Tyr Tyr Lys
145                 150                 155                 160

Tyr Gly Trp Ser Lys Asp Tyr Met Gly Lys Tyr Leu Asn Asp Asn Gln
                165                 170                 175

Arg Glu Ile Leu Leu Asn Tyr Gly Gly Glu Lys Leu Arg Ser Leu Leu
            180                 185                 190
```

Ser Asp Arg Phe Gly Asp Ile Glu Val Thr Ile Tyr Ser Pro Ser Asp
        195                 200                 205

Pro Asn Ala Ser Thr Val Thr Ala Glu Asn Ser Gln Phe Leu Trp Arg
    210                 215                 220

Ala Ala Ile Thr Leu Asn Gln Phe Lys Glu Phe Val Lys Ser Trp Ser
225                 230                 235                 240

Ile Tyr Thr Ser Trp Ala Arg Asp Asn Pro Ser Lys Pro Asp Ile Ala
                245                 250                 255

Asp Ile Phe Ile Asn Glu Leu Lys Glu Ile Cys His Cys Glu Asp Leu
                260                 265                 270

Asn Val Pro Leu Lys Ile Glu Trp Ser Thr Phe Tyr Leu Cys Arg
            275                 280                 285

Lys Arg Glu
    290

<210> SEQ ID NO 12
<211> LENGTH: 1212
<212> TYPE: DNA
<213> ORGANISM: Saccharomyces cerevisiae

<400> SEQUENCE: 12

| | | | | | |
|---|---|---|---|---|---|
| aaaagagggt | accaacaaaa | tctatggttg | ttcggcccag | aaaagaacat | cactgaggtt | 60 |
| ggtactatga | acgtgttctt | cgttttcctc | aacaaagtca | ctggcaagaa | ggaattggtt | 120 |
| accgctccat | tagatggtac | cattttagaa | ggtgttacca | gagactctgt | tttaacattg | 180 |
| gctcgtgaca | aactagatcc | tcaagaatgg | gacatcaacg | agcgttatta | cactattact | 240 |
| gaagtcgcca | ctagagcaaa | acaaggtgaa | ctattagaag | ccttcggttc | tggtactgct | 300 |
| gctgtcgttt | cacctatcaa | ggaaattggc | tggaacaacg | aagatattca | tgttccacta | 360 |
| ttgcctggtg | aacaatgtgg | tgcattgacc | aagcaagttg | ctcaatggat | tgctgatatc | 420 |
| caatacggta | gagtcaatta | tggtaactgg | tcaaaaactg | ttgccgactt | gaactaatga | 480 |
| taatgaaggt | aaacatcccc | tcccccccca | aaaaaaaaa | acgagaattc | ctctcagagg | 540 |
| atctgttttt | ctctcacttt | attcacatag | atacatactt | ttttacaatt | cctgttgagt | 600 |
| ttatttatta | taagaaatat | tggattacta | ttattattat | agcttatgca | agccattgtg | 660 |
| cggcttctta | cgcttttttga | aattgttgac | ctaacaactt | ggcacattat | tgaatttcat | 720 |
| agagactgct | tgtaatttag | ttgccaaggt | atctcgctgg | actttacatg | taaaatgaat | 780 |
| gcggcaagat | acccaagaga | gttgattatg | ccaaaaaaaa | aaaatctata | aggatatccc | 840 |
| tggtattttc | tgaagaataa | attctagcgt | agttcagaag | aggtgcaagt | acagtatgaa | 900 |
| taatggtatg | ccttccatca | tcgtggcata | caggttcagg | catgaagaga | tgattatgtt | 960 |
| ccctcaccgg | tccataatcc | tgatttaaac | agttcattag | tatatgttca | gccaacacaa | 1020 |
| caacgagaag | ctttgtagtg | aaagttttcc | acgatctata | tttagcattc | taattagcgg | 1080 |
| ccccaaggga | acgtatataa | acataaacaa | acggcacgaa | ctaaagggc | aaattcaagt | 1140 |
| taaccctttt | acactcagta | catcttcaaa | gccagtcttc | tgtcaatgga | agaatccaga | 1200 |
| atgcctaaaa | ct | | | | | 1212 |

<210> SEQ ID NO 13
<211> LENGTH: 2552
<212> TYPE: DNA
<213> ORGANISM: Saccharomyces cerevisiae
<220> FEATURE:
<221> NAME/KEY: CDS

<222> LOCATION: (1251)..(2552)

<400> SEQUENCE: 13

| | |
|---|---:|
| gaatcctatt ctgtttactt cactgttcac ttactttcgg tcccacatct acaaaacatc | 60 |
| tacaacaaga acgtgggcga tacagcaaaa aatcacttga aataacagaa tcaagtttct | 120 |
| tatccgattt cctactttg agctccggct tatgttgaag atgttacttt tctttgtctc | 180 |
| taagtgatct ttatttttct ggctccagtg aaatttggta atagcatagt cacttcaact | 240 |
| aaagtctgat agtaatactt gcaaatattg caaaacttgg aagaatgtta atgaatcatt | 300 |
| tcttgcacca ttctttcaat catctcaatc tcctgctgtg atgtttaagt ataacattga | 360 |
| agactatgcc ctaatttcca atgttatta gttttaagca tatctttgtt ctaacagga | 420 |
| aactcaggcc cacatccgca aaaaatatg tgccaaaaaa ctttcaacac ttcaaagata | 480 |
| cttaccactg caggaaaata atctacgtgt aacggtttga aaataaattt gacttcataa | 540 |
| ttggacataa gtactccatc gccatcccctt tttaaagaag tttccacaag aatgaatggc | 600 |
| taatcgcaac taaatctttt ccttgcaaac gtaacacagt atcgacattt tcttactcaa | 660 |
| tccaacgaag aataaccta tctaaaaaat aaacgccgta gttttcagcc acaagacgt | 720 |
| cattaaaaga tttgttaatt ataaaaatag aaatatttct accagcatga ttattcgtta | 780 |
| cttgaaagtc cccaataaat ttcactgttt ccgttaactg ttgtagttat taaacgcagc | 840 |
| aaacagatta ttttgaacaa caccggagaa acacgcgcag acccattcga gttaaaaata | 900 |
| gtaactcgcg atcaatcaat gcaggaagca ccgtaggaat tagtaagaac tcgtattttg | 960 |
| attgaaaatg ccatgaaagc aattgacttg ctgcagtaaa aagcgctgcc acaaactttg | 1020 |
| taattttcga caatgacgtt cttttcagat ggttactgtc ttttttttgga agaaacaaaa | 1080 |
| gaaggtactt ttatgatgtt atactaggca aaaagcctat ttaatgtaag tcctaattgt | 1140 |
| cgtttgagac tggatgaaaa gggacaaaat ggaaggataa ctaaaggtga cttaccgcca | 1200 |
| gattaattcg gcctggaata gtttgatatc gaagaaagat tcacaattaa atg gcg | 1256 |

```
                                                              Met Ala
                                                                1
act gac acc gag agg tgt att ttc cgt gca ttc ggc caa gat ttt atc   1304
Thr Asp Thr Glu Arg Cys Ile Phe Arg Ala Phe Gly Gln Asp Phe Ile
        5                  10                  15 cta aat aaa cat ttt cat ttg aca ggt aag att ggt cgg ggc tca cac   1352
Leu Asn Lys His Phe His Leu Thr Gly Lys Ile Gly Arg Gly Ser His
 20                  25                  30 agc ctt att tgt tct tca act tac aca gaa tcg aac gag gaa act cac   1400
Ser Leu Ile Cys Ser Ser Thr Tyr Thr Glu Ser Asn Glu Glu Thr His
 35                  40                  45                  50 gtg gct atc aga aaa ata cca aac gcg ttt ggc aat aaa cta tct tgc   1448
Val Ala Ile Arg Lys Ile Pro Asn Ala Phe Gly Asn Lys Leu Ser Cys
                 55                  60                  65 aag aga act ctt cgt gaa ttg aaa cta cta aga cat tta aga ggg cac   1496
Lys Arg Thr Leu Arg Glu Leu Lys Leu Leu Arg His Leu Arg Gly His
             70                  75                  80 cca aat ata gtg tgg ctc ttc gat act gat ata gta ttt tac cca aat   1544
Pro Asn Ile Val Trp Leu Phe Asp Thr Asp Ile Val Phe Tyr Pro Asn
         85                  90                  95 ggg gca cta aat ggc gtt tat tta tat gaa gaa cta atg gaa tgt gac   1592
Gly Ala Leu Asn Gly Val Tyr Leu Tyr Glu Glu Leu Met Glu Cys Asp
    100                 105                 110 ctt tct caa att ata agg tcc gaa caa cgc ctg gaa gac gca cac ttt   1640
Leu Ser Gln Ile Ile Arg Ser Glu Gln Arg Leu Glu Asp Ala His Phe
115                 120                 125                 130
```

```
caa agc ttc ata tat cag ata ctg tgt gct ctg aaa tac ata cat tct      1688
Gln Ser Phe Ile Tyr Gln Ile Leu Cys Ala Leu Lys Tyr Ile His Ser
                135                 140                 145 gct aat gtt tta cat tgt gac ctg aaa cca aaa aac tta ctt gtt aat      1736
Ala Asn Val Leu His Cys Asp Leu Lys Pro Lys Asn Leu Leu Val Asn
        150                 155                 160 agt gat tgc caa cta aaa att tgt aat ttt ggg cta tcg tgt agt tat      1784
Ser Asp Cys Gln Leu Lys Ile Cys Asn Phe Gly Leu Ser Cys Ser Tyr
    165                 170                 175 tca gaa aac cac aag gtt aac gac ggc ttc att aag ggt tat ata acc      1832
Ser Glu Asn His Lys Val Asn Asp Gly Phe Ile Lys Gly Tyr Ile Thr
180                 185                 190 tcg ata tgg tat aaa gca cca gaa att ttg ctg aat tat caa gaa tgc      1880
Ser Ile Trp Tyr Lys Ala Pro Glu Ile Leu Leu Asn Tyr Gln Glu Cys
195                 200                 205                 210 aca aaa gct gtc gat att tgg tca aca ggc tgt atc ttg gcc gaa cta      1928
Thr Lys Ala Val Asp Ile Trp Ser Thr Gly Cys Ile Leu Ala Glu Leu
                215                 220                 225 ctt ggt agg aaa cca atg ttt gaa ggg aag gat tat gta gat cat ttg      1976
Leu Gly Arg Lys Pro Met Phe Glu Gly Lys Asp Tyr Val Asp His Leu
            230                 235                 240 aat cat att cta caa ata ctt gga aca cca cct gag gaa aca ttg cag      2024
Asn His Ile Leu Gln Ile Leu Gly Thr Pro Pro Glu Glu Thr Leu Gln
        245                 250                 255 gaa att gcc tct caa aag gtg tat aat tat atc ttt cag ttc ggt aat      2072
Glu Ile Ala Ser Gln Lys Val Tyr Asn Tyr Ile Phe Gln Phe Gly Asn
    260                 265                 270 atc ccg gga aga tcg ttt gaa agc ata cta cct ggt gct aat cca gaa      2120
Ile Pro Gly Arg Ser Phe Glu Ser Ile Leu Pro Gly Ala Asn Pro Glu
275                 280                 285                 290 gcg ctt gaa ttg cta aag aaa atg cta gaa ttt gat cct aaa aaa agg      2168
Ala Leu Glu Leu Leu Lys Lys Met Leu Glu Phe Asp Pro Lys Lys Arg
                295                 300                 305 att act gta gag gat gca cta gag cat cca tat ttg tca atg tgg cat      2216
Ile Thr Val Glu Asp Ala Leu Glu His Pro Tyr Leu Ser Met Trp His
            310                 315                 320 gat ata gat gag gaa ttc tca tgt caa aag acc ttt aga ttc gaa ttc      2264
Asp Ile Asp Glu Glu Phe Ser Cys Gln Lys Thr Phe Arg Phe Glu Phe
        325                 330                 335 gag cat atc gaa agt atg gcg gaa tta gga aac gaa gtt ata aag gaa      2312
Glu His Ile Glu Ser Met Ala Glu Leu Gly Asn Glu Val Ile Lys Glu
    340                 345                 350 gta ttt gat ttc agg aaa gtt gtt aga aaa cat cct att agc ggt gat      2360
Val Phe Asp Phe Arg Lys Val Val Arg Lys His Pro Ile Ser Gly Asp
355                 360                 365                 370 tcc cca tca tca tca cta tct tta gag gat gcc att cct caa gaa gtt      2408
Ser Pro Ser Ser Ser Leu Ser Leu Glu Asp Ala Ile Pro Gln Glu Val
                375                 380                 385 gta cag gtc cat cct tct agg aaa gtt tta ccc agt tat agt cct gaa      2456
Val Gln Val His Pro Ser Arg Lys Val Leu Pro Ser Tyr Ser Pro Glu
            390                 395                 400 ttt tcc tat gta agc caa ctt cca tca cta act aca acc cag cca tat      2504
Phe Ser Tyr Val Ser Gln Leu Pro Ser Leu Thr Thr Thr Gln Pro Tyr
        405                 410                 415 caa aac ctt atg gga ata agc tct aat tca ttt cag ggt gtt aac taa      2552
Gln Asn Leu Met Gly Ile Ser Ser Asn Ser Phe Gln Gly Val Asn
    420                 425                 430
```

<210> SEQ ID NO 14

<211> LENGTH: 433
<212> TYPE: PRT
<213> ORGANISM: Saccharomyces cerevisiae

<400> SEQUENCE: 14

```
Met Ala Thr Asp Thr Glu Arg Cys Ile Phe Arg Ala Phe Gly Gln Asp
 1               5                  10                  15

Phe Ile Leu Asn Lys His Phe His Leu Thr Gly Lys Ile Gly Arg Gly
                20                  25                  30

Ser His Ser Leu Ile Cys Ser Ser Thr Tyr Thr Glu Ser Asn Glu Glu
            35                  40                  45

Thr His Val Ala Ile Arg Lys Ile Pro Asn Ala Phe Gly Asn Lys Leu
    50                  55                  60

Ser Cys Lys Arg Thr Leu Arg Glu Leu Lys Leu Leu Arg His Leu Arg
65                  70                  75                  80

Gly His Pro Asn Ile Val Trp Leu Phe Asp Thr Asp Ile Val Phe Tyr
                85                  90                  95

Pro Asn Gly Ala Leu Asn Gly Val Tyr Leu Tyr Glu Glu Leu Met Glu
            100                 105                 110

Cys Asp Leu Ser Gln Ile Ile Arg Ser Glu Gln Arg Leu Glu Asp Ala
        115                 120                 125

His Phe Gln Ser Phe Ile Tyr Gln Ile Leu Cys Ala Leu Lys Tyr Ile
    130                 135                 140

His Ser Ala Asn Val Leu His Cys Asp Leu Lys Pro Lys Asn Leu Leu
145                 150                 155                 160

Val Asn Ser Asp Cys Gln Leu Lys Ile Cys Asn Phe Gly Leu Ser Cys
                165                 170                 175

Ser Tyr Ser Glu Asn His Lys Val Asn Asp Gly Phe Ile Lys Gly Tyr
            180                 185                 190

Ile Thr Ser Ile Trp Tyr Lys Ala Pro Glu Ile Leu Leu Asn Tyr Gln
        195                 200                 205

Glu Cys Thr Lys Ala Val Asp Ile Trp Ser Thr Gly Cys Ile Leu Ala
    210                 215                 220

Glu Leu Leu Gly Arg Lys Pro Met Phe Glu Gly Lys Asp Tyr Val Asp
225                 230                 235                 240

His Leu Asn His Ile Leu Gln Ile Leu Gly Thr Pro Pro Glu Glu Thr
                245                 250                 255

Leu Gln Glu Ile Ala Ser Gln Lys Val Tyr Asn Tyr Ile Phe Gln Phe
            260                 265                 270

Gly Asn Ile Pro Gly Arg Ser Phe Glu Ser Ile Leu Pro Gly Ala Asn
        275                 280                 285

Pro Glu Ala Leu Glu Leu Leu Lys Lys Met Leu Glu Phe Asp Pro Lys
    290                 295                 300

Lys Arg Ile Thr Val Glu Asp Ala Leu Glu His Pro Tyr Leu Ser Met
305                 310                 315                 320

Trp His Asp Ile Asp Glu Glu Phe Ser Cys Gln Lys Thr Phe Arg Phe
                325                 330                 335

Glu Phe Glu His Ile Glu Ser Met Ala Glu Leu Gly Asn Glu Val Ile
            340                 345                 350

Lys Glu Val Phe Asp Phe Arg Lys Val Arg Lys His Pro Ile Ser
        355                 360                 365

Gly Asp Ser Pro Ser Ser Ser Leu Ser Leu Glu Asp Ala Ile Pro Gln
    370                 375                 380

Glu Val Val Gln Val His Pro Ser Arg Lys Val Leu Pro Ser Tyr Ser
```

-continued

```
        385                 390                 395                 400
Pro Glu Phe Ser Tyr Val Ser Gln Leu Pro Ser Leu Thr Thr Thr Gln
                    405                 410                 415
Pro Tyr Gln Asn Leu Met Gly Ile Ser Ser Asn Ser Phe Gln Gly Val
                420                 425                 430
Asn
```

<210> SEQ ID NO 15
<211> LENGTH: 1212
<212> TYPE: DNA
<213> ORGANISM: Saccharomyces cerevisiae

<400> SEQUENCE: 15

```
acaaaacatc tacaacaaga acgtgggcga tacagcaaaa aatcacttga ataacagaa      60
tcaagtttct tatccgattt cctacttttg agctccggct tatgttgaag atgttacttt    120
tctttgtctc taagtgatct ttattttcct ggctccagtg aaatttggta atagcatagt    180
cacttcaact aaagtctgat agtaatactt gcaaatattg caaaacttgg aagaatgtta    240
atgaatcatt tcttgcacca ttctttcaat catctcaatc tcctgctgtg atgtttaagt    300
ataacattga agactatgcc ctaatttcca atgttattta gttttaagca tatctttgtt    360
tctaacagga aactcaggcc cacatccgca aaaaatatg tgccaaaaaa ctttcaacac     420
ttcaaagata cttaccactg caggaaaata atctacgtgt aacggtttga aaataaattt    480
gacttcataa ttggacataa gtactccatc gccatccctt tttaaagaag tttccacaag    540
aatgaatggc taatcgcaac taaatctttt ccttgcaaac gtaacacagt atcgacattt    600
tcttactcaa tccaacgaag gaataaccta tctaaaaaat aaacgccgta gttttcagcc    660
cacaagacgt cattaaaaga tttgttaatt ataaaaatag aaatatttct accagcatga    720
ttattcgtta cttgaaagtc cccaataaat ttcactgttt ccgttaactg ttgtagttat    780
taaacgcagc aaacagatta ttttgaacaa caccggagaa acacgcgcag acccattcga    840
gttaaaaata gtaactcgcg atcaatcaat gcaggaagca ccgtaggaat tagtaagaac    900
tcgtattttg attgaaaatg ccatgaaagc aattgacttg ctgcagtaaa aagcgctgcc    960
acaaactttg taattttcga caatgacgtt cttttcagat ggttactgtc ttttttttgga  1020
agaaacaaaa gaaggtactt ttatgatgtt atactaggca aaaagcctat ttaatgtaag   1080
tcctaattgt cgtttgagac tggatgaaaa gggacaaaat ggaaggataa ctaaaggtga   1140
cttaccgcca gattaattcg gcctggaata gtttgatatc aagaaagat tcacaattaa    1200
atggcgactg ac                                                       1212
```

<210> SEQ ID NO 16
<211> LENGTH: 5864
<212> TYPE: DNA
<213> ORGANISM: Saccharomyces cerevisiae
<220> FEATURE:
<221> NAME/KEY: CDS
<222> LOCATION: (1251)..(5864)

<400> SEQUENCE: 16

```
attagcacgg atttccttaa gtaatttaaa ttaccaaaga agatccacat cagcagtcga     60
atgttcaaga tgccgtaagt ttaaaatctt tcgtatcttt ccccgatcct gtctttcatc   120
aatgaacttg aatatcaaga gtgaaaaaaa ctcatatggc ttctcttgaa gagttagaaa   180
gataggcaca tgccaattgt gtgcatagca cttactactc aacgatttca caacctagca   240
```

-continued

```
taatacgcga aaaaaaagt gcatttattt aggtaagtct cattacctaa acgccagttt     300
gtttcacgta attggtaacg atgagggaac cgcagtagaa aaactttca ttcacaaacg     360 attaaagtgt tatgctagcc agtttcaggc tttttgtttt atgcaagaga acattcgact     420
agatgtccag ttaagtgtgc gtcactttc ctacggtgcc tcgcacatga atgttatccg     480
gcgcacgata cttatcaccg aaaaaccta ttctacggaa aaccttattt acattaaagt     540
tggaaaaatt tcctctttt cctaataagg tggagctttt ggcttccagt atgctttcac     600
ggaattattt ctcatgtaca tttagctcca tttccagtgc ctccgatagg gaggcatcat     660
ggtactaccg tgacggagaa tacgtaggct gactttttcg tcagtttgtt gtccgtttac     720
aaaattggtg aatgaattct agccttcctc tgctcattaa ttgccctcac aagaatttgg     780
aagtgcgtag acaggtaaaa gattgtacta cagaggtatt gtggaacctt ctacagtact     840
tcggaataca cctaaaaggt tgttggatgc taaatttagc aaaagtctttt tttagctcac     900 tattaggctt gttaaagtct gaaattgttg aaaggcactc aaaaagataa atcaacaatc     960
agcattaacg gcacagttga aagagtcacc cacttgaaat tagctcggtt atcaaatata    1020
attatctctg gtaaagagct ctgcagcagg gttaatctat tcgcatactt acgctgtagg    1080 aacatttat tattaggatc cgactactgc ctacatattt attcggaagg catgatgtcg    1140 aaaattttg agcttataaa aggaacatat ttcactcttg ctcgttgatg taagctctct    1200
tccgggttct tattttaat tcttgtcacc agtaaacaga acatccaaaa atg aca       1256
                                                         Met Thr
                                                           1 atg cct cat cgc tat atg ttt ttg gca gtc ttt aca ctt ctg gca cta    1304
Met Pro His Arg Tyr Met Phe Leu Ala Val Phe Thr Leu Leu Ala Leu
       5               10              15 act agt gtg gcc tca gga gcc aca gag gcg tgc tta cca gca ggc cag    1352
Thr Ser Val Ala Ser Gly Ala Thr Glu Ala Cys Leu Pro Ala Gly Gln
  20              25              30 agg aaa agt ggg atg aat ata aat ttt tac cag tat tca ttg aaa gat    1400
Arg Lys Ser Gly Met Asn Ile Asn Phe Tyr Gln Tyr Ser Leu Lys Asp
35              40              45              50 tcc tcc aca tat tcg aat gca gca tat atg gct tat gga tat gcc tca    1448
Ser Ser Thr Tyr Ser Asn Ala Ala Tyr Met Ala Tyr Gly Tyr Ala Ser
              55              60              65 aaa acc aaa cta ggt tct gtc gga gga caa act gat atc tcg att gat    1496
Lys Thr Lys Leu Gly Ser Val Gly Gly Gln Thr Asp Ile Ser Ile Asp
      70              75              80 tat aat att ccc tgt gtt agt tca tca ggc aca ttt cct tgt cct caa    1544
Tyr Asn Ile Pro Cys Val Ser Ser Ser Gly Thr Phe Pro Cys Pro Gln
          85              90              95 gaa gat tcc tat gga aac tgg gga tgc aaa gga atg ggt gct tgt tct    1592
Glu Asp Ser Tyr Gly Asn Trp Gly Cys Lys Gly Met Gly Ala Cys Ser
100             105             110 aat agt caa gga att gca tac tgg agt act gat tta ttt ggt ttc tat    1640
Asn Ser Gln Gly Ile Ala Tyr Trp Ser Thr Asp Leu Phe Gly Phe Tyr
115             120             125             130 act acc cca aca aac gta acc cta gaa atg aca ggt tat ttt tta cca    1688
Thr Thr Pro Thr Asn Val Thr Leu Glu Met Thr Gly Tyr Phe Leu Pro
              135             140             145 cca cag acg ggt tct tac aca ttc aag ttt gct aca gtt gac gac tct    1736
Pro Gln Thr Gly Ser Tyr Thr Phe Lys Phe Ala Thr Val Asp Asp Ser
      150             155             160 gca att cta tca gta ggt ggt gca acc gcg ttc aac tgt tgt gct caa    1784
Ala Ile Leu Ser Val Gly Gly Ala Thr Ala Phe Asn Cys Cys Ala Gln
165             170             175
```

-continued

| | | |
|---|---|---|
| cag caa ccg ccg atc aca tca acg aac ttt acc att gac ggt atc aag<br>Gln Gln Pro Pro Ile Thr Ser Thr Asn Phe Thr Ile Asp Gly Ile Lys<br>180                          185                     190 | 1832 |
| cca tgg ggt gga agt ttg cca cct aat atc gaa gga acc gtc tat atg<br>Pro Trp Gly Gly Ser Leu Pro Pro Asn Ile Glu Gly Thr Val Tyr Met<br>195                    200                   205                     210 | 1880 |
| tac gct ggc tac tat tat cca atg aag gtt gtt tac tcg aac gct gtt<br>Tyr Ala Gly Tyr Tyr Tyr Pro Met Lys Val Val Tyr Ser Asn Ala Val<br>                 215                     220                     225 | 1928 |
| tct tgg ggt aca ctt cca att agt gtg aca ctt cca gat ggt acc act<br>Ser Trp Gly Thr Leu Pro Ile Ser Val Thr Leu Pro Asp Gly Thr Thr<br>             230                     235                    240 | 1976 |
| gta agt gat gac ttc gaa ggg tac gtc tat tcc ttt gac gat gac cta<br>Val Ser Asp Asp Phe Glu Gly Tyr Val Tyr Ser Phe Asp Asp Asp Leu<br>245                          250                     255 | 2024 |
| agt caa tct aac tgt act gtc cct gac cct tca aat tat gct gtc agt<br>Ser Gln Ser Asn Cys Thr Val Pro Asp Pro Ser Asn Tyr Ala Val Ser<br>260                          265                     270 | 2072 |
| acc act aca act aca acg gaa cca tgg acc ggt act ttc act tct aca<br>Thr Thr Thr Thr Thr Thr Glu Pro Trp Thr Gly Thr Phe Thr Ser Thr<br>275                          280                     285                     290 | 2120 |
| tct act gaa atg acc acc gtc acc ggt acc aac ggc gtt cca act gac<br>Ser Thr Glu Met Thr Thr Val Thr Gly Thr Asn Gly Val Pro Thr Asp<br>                         295                     300                     305 | 2168 |
| gaa acc gtc att gtc atc aga act cca aca act gct agc acc atc ata<br>Glu Thr Val Ile Val Ile Arg Thr Pro Thr Thr Ala Ser Thr Ile Ile<br>                 310                     315                     320 | 2216 |
| act aca act gag cca tgg aac agc act ttt acc tct act tct acc gaa<br>Thr Thr Thr Glu Pro Trp Asn Ser Thr Phe Thr Ser Thr Ser Thr Glu<br>325                          330                     335 | 2264 |
| ttg acc aca gtc act ggc acc aat ggt gta cga act gac gaa acc atc<br>Leu Thr Thr Val Thr Gly Thr Asn Gly Val Arg Thr Asp Glu Thr Ile<br>       340                     345                     350 | 2312 |
| att gta atc aga aca cca aca aca gcc act act gcc ata act aca act<br>Ile Val Ile Arg Thr Pro Thr Thr Ala Thr Thr Ala Ile Thr Thr Thr<br>355                          360                     365                     370 | 2360 |
| gag cca tgg aac agc act ttt acc tct act tct acc gaa ttg acc aca<br>Glu Pro Trp Asn Ser Thr Phe Thr Ser Thr Ser Thr Glu Leu Thr Thr<br>                       375                     380                     385 | 2408 |
| gtc acc ggt acc aat ggt ttg cca act gat gag acc atc att gtc atc<br>Val Thr Gly Thr Asn Gly Leu Pro Thr Asp Glu Thr Ile Ile Val Ile<br>                 390                     395                     400 | 2456 |
| aga aca cca aca aca gcc act act gcc atg act aca act cag cca tgg<br>Arg Thr Pro Thr Thr Ala Thr Thr Ala Met Thr Thr Thr Gln Pro Trp<br>                 405                     410                     415 | 2504 |
| aac gac act ttt acc tct act tct acc gaa ttg acc aca gtc acc ggt<br>Asn Asp Thr Phe Thr Ser Thr Ser Thr Glu Leu Thr Thr Val Thr Gly<br>       420                     425                     430 | 2552 |
| acc aat ggt ttg cca act gat gag acc atc att gtc atc aga aca cca<br>Thr Asn Gly Leu Pro Thr Asp Glu Thr Ile Ile Val Ile Arg Thr Pro<br>435                          440                     445                     450 | 2600 |
| aca aca gcc act act gcc atg act aca act cag cca tgg aac gac act<br>Thr Thr Ala Thr Thr Ala Met Thr Thr Thr Gln Pro Trp Asn Asp Thr<br>                       455                     460                     465 | 2648 |
| ttt acc tct act tct acc gaa ttg acc aca gtc acc ggt acc aat ggt<br>Phe Thr Ser Thr Ser Thr Glu Leu Thr Thr Val Thr Gly Thr Asn Gly<br>                 470                     475                     480 | 2696 |
| ttg cca act gat gag acc atc att gtc atc aga aca cca aca aca gcc<br>Leu Pro Thr Asp Glu Thr Ile Ile Val Ile Arg Thr Pro Thr Thr Ala | 2744 |

```
                485                490                495
act act gcc atg act aca act cag cca tgg aac gac act ttt acc tct    2792
Thr Thr Ala Met Thr Thr Thr Gln Pro Trp Asn Asp Thr Phe Thr Ser
    500                 505                 510 aca tcc act gaa atc acc acc gtc acc ggt acc aat ggt ttg cca act    2840
Thr Ser Thr Glu Ile Thr Thr Val Thr Gly Thr Asn Gly Leu Pro Thr
515                 520                 525                 530 gat gag acc atc att gtc atc aga aca cca aca aca gcc act act gcc    2888
Asp Glu Thr Ile Ile Val Ile Arg Thr Pro Thr Thr Ala Thr Thr Ala
                535                 540                 545 atg act aca cct cag cca tgg aac gac act ttt acc tct aca tcc act    2936
Met Thr Thr Pro Gln Pro Trp Asn Asp Thr Phe Thr Ser Thr Ser Thr
            550                 555                 560 gaa atg acc acc gtc acc ggt acc aac ggt ttg cca act gat gaa acc    2984
Glu Met Thr Thr Val Thr Gly Thr Asn Gly Leu Pro Thr Asp Glu Thr
        565                 570                 575 atc att gtc atc aga aca cca aca aca gcc act act gcc ata act aca    3032
Ile Ile Val Ile Arg Thr Pro Thr Thr Ala Thr Thr Ala Ile Thr Thr
    580                 585                 590 act gag cca tgg aac agc act ttt acc tct aca tcc act gaa atg acc    3080
Thr Glu Pro Trp Asn Ser Thr Phe Thr Ser Thr Ser Thr Glu Met Thr
595                 600                 605                 610 acc gtc acc ggt acc aac ggt ttg cca act gat gaa acc atc att gtc    3128
Thr Val Thr Gly Thr Asn Gly Leu Pro Thr Asp Glu Thr Ile Ile Val
                615                 620                 625 atc aga aca cca aca aca gcc act act gcc ata act aca act cag cca    3176
Ile Arg Thr Pro Thr Thr Ala Thr Thr Ala Ile Thr Thr Thr Gln Pro
            630                 635                 640 tgg aac gac act ttt acc tct aca tcc act gaa atg acc acc gtc acc    3224
Trp Asn Asp Thr Phe Thr Ser Thr Ser Thr Glu Met Thr Thr Val Thr
        645                 650                 655 ggt acc aac ggt ttg cca act gat gaa acc atc att gtc atc aga aca    3272
Gly Thr Asn Gly Leu Pro Thr Asp Glu Thr Ile Ile Val Ile Arg Thr
    660                 665                 670 cca aca aca gcc act act gcc atg act aca act cag cca tgg aac gac    3320
Pro Thr Thr Ala Thr Thr Ala Met Thr Thr Thr Gln Pro Trp Asn Asp
675                 680                 685                 690 act ttt acc tct aca tcc act gaa atc acc acc gtc acc ggt acc acc    3368
Thr Phe Thr Ser Thr Ser Thr Glu Ile Thr Thr Val Thr Gly Thr Thr
                695                 700                 705 ggt ttg cca act gat gag acc atc att gtc atc aga aca cca aca aca    3416
Gly Leu Pro Thr Asp Glu Thr Ile Ile Val Ile Arg Thr Pro Thr Thr
            710                 715                 720 gcc act act gcc atg act aca act cag cca tgg aac gac act ttt acc    3464
Ala Thr Thr Ala Met Thr Thr Thr Gln Pro Trp Asn Asp Thr Phe Thr
        725                 730                 735 tct aca tcc act gaa atg acc acc gtc acc ggt acc aac ggc gtt cca    3512
Ser Thr Ser Thr Glu Met Thr Thr Val Thr Gly Thr Asn Gly Val Pro
    740                 745                 750 act gac gaa acc gtc att gtc atc aga act cca act agt gaa ggt cta    3560
Thr Asp Glu Thr Val Ile Val Ile Arg Thr Pro Thr Ser Glu Gly Leu
755                 760                 765                 770 atc agc acc acc act gaa cca tgg act ggt act ttc acc tct aca tcc    3608
Ile Ser Thr Thr Thr Glu Pro Trp Thr Gly Thr Phe Thr Ser Thr Ser
                775                 780                 785 act gag atg acc acc gtc acc ggt act aac ggt caa cca act gac gaa    3656
Thr Glu Met Thr Thr Val Thr Gly Thr Asn Gly Gln Pro Thr Asp Glu
            790                 795                 800 acc gtg att gtt atc aga act cca acc agt gaa ggt ttg gtt aca acc    3704
```

```
                                   -continued

Thr Val Ile Val Ile Arg Thr Pro Thr Ser Glu Gly Leu Val Thr Thr
            805                 810                 815 acc act gaa cca tgg act ggt act ttt act tct aca tct act gaa atg      3752
Thr Thr Glu Pro Trp Thr Gly Thr Phe Thr Ser Thr Ser Thr Glu Met
820                 825                 830 acc acc att act gga acc aac ggc gtt cca act gac gaa acc gtc att      3800
Thr Thr Ile Thr Gly Thr Asn Gly Val Pro Thr Asp Glu Thr Val Ile
835                 840                 845                 850 gtc atc aga act cca acc agt gaa ggt cta atc agc acc acc act gaa      3848
Val Ile Arg Thr Pro Thr Ser Glu Gly Leu Ile Ser Thr Thr Thr Glu
                855                 860                 865 cca tgg act ggt act ttt act tct aca tct act gaa atg acc acc att      3896
Pro Trp Thr Gly Thr Phe Thr Ser Thr Ser Thr Glu Met Thr Thr Ile
                870                 875                 880 act gga acc aat ggt caa cca act gac gaa acc gtt att gtt atc aga      3944
Thr Gly Thr Asn Gly Gln Pro Thr Asp Glu Thr Val Ile Val Ile Arg
                885                 890                 895 act cca act agt gaa ggt cta atc agc act aca acg gaa cca tgg acc      3992
Thr Pro Thr Ser Glu Gly Leu Ile Ser Thr Thr Thr Glu Pro Trp Thr
            900                 905                 910 ggt act ttc act tct aca tct act gaa atg acg cac gtc acc ggt acc      4040
Gly Thr Phe Thr Ser Thr Ser Thr Glu Met Thr His Val Thr Gly Thr
915                 920                 925                 930 aac ggc gtt cca act gac gaa acc gtc att gtc atc aga act cca acc      4088
Asn Gly Val Pro Thr Asp Glu Thr Val Ile Val Ile Arg Thr Pro Thr
                935                 940                 945 agt gaa ggt cta atc agc acc acc act gaa cca tgg act ggc act ttc      4136
Ser Glu Gly Leu Ile Ser Thr Thr Thr Glu Pro Trp Thr Gly Thr Phe
            950                 955                 960 act tcg act tcc act gag gtt acc acc atc act gga acc aac ggt caa      4184
Thr Ser Thr Ser Thr Glu Val Thr Thr Ile Thr Gly Thr Asn Gly Gln
            965                 970                 975 cca act gac gaa act gtg att gtt atc aga act cca acc agt gaa ggt      4232
Pro Thr Asp Glu Thr Val Ile Val Ile Arg Thr Pro Thr Ser Glu Gly
980                 985                 990 cta atc agc acc acc act  gaa cca tgg act ggt  act ttc act tct        4277
Leu Ile Ser Thr Thr Thr  Glu Pro Trp Thr Gly  Thr Phe Thr Ser
995                 1000                1005 aca tct act gaa atg acc  acc gtc acc ggt act  aac ggt caa cca        4322
Thr Ser Thr Glu Met Thr  Thr Val Thr Gly Thr  Asn Gly Gln Pro
1010                1015                1020 act gac gaa acc gtg att  gtt atc aga act cca  acc agt gaa ggt        4367
Thr Asp Glu Thr Val Ile  Val Ile Arg Thr Pro  Thr Ser Glu Gly
1025                1030                1035 ttg gtt aca acc acc act  gaa cca tgg act ggt  act ttt act tcg        4412
Leu Val Thr Thr Thr Thr  Glu Pro Trp Thr Gly  Thr Phe Thr Ser
1040                1045                1050 act tcc act gaa atg tct  act gtc act gga acc  aat ggc ttg cca        4457
Thr Ser Thr Glu Met Ser  Thr Val Thr Gly Thr  Asn Gly Leu Pro
1055                1060                1065 act gat gaa act gtc att  gtt gtc aaa act cca  act act gcc atc        4502
Thr Asp Glu Thr Val Ile  Val Val Lys Thr Pro  Thr Thr Ala Ile
1070                1075                1080 tca tcc agt ttg tca tca  tca tct tca gga caa  atc acc agc tct        4547
Ser Ser Ser Leu Ser Ser  Ser Ser Ser Gly Gln  Ile Thr Ser Ser
1085                1090                1095 atc acg tct tcg cgt cca  att att acc cca ttc  tat cct agc aat        4592
Ile Thr Ser Ser Arg Pro  Ile Ile Thr Pro Phe  Tyr Pro Ser Asn
1100                1105                1110
```

```
gga act tct gtg att tct tcc tca gta att tct tcc tca gtc act    4637
Gly Thr Ser Val Ile Ser Ser Ser Val Ile Ser Ser Ser Val Thr
1115                1120                1125 tct tct cta ttc act tct tct cca gtc att tct tcc tca gtc att    4682
Ser Ser Leu Phe Thr Ser Ser Pro Val Ile Ser Ser Ser Val Ile
1130                1135                1140 tct tct tct aca aca acc tcc act tct ata ttt tct gaa tca tct    4727
Ser Ser Ser Thr Thr Thr Ser Thr Ser Ile Phe Ser Glu Ser Ser
1145                1150                1155 aaa tca tcc gtc att cca acc agt agt tcc acc tct ggt tct tct    4772
Lys Ser Ser Val Ile Pro Thr Ser Ser Ser Thr Ser Gly Ser Ser
1160                1165                1170 gag agc gaa acg agt tca gct ggt tct gtc tct tcc tct ttt        4817
Glu Ser Glu Thr Ser Ser Ala Gly Ser Val Ser Ser Ser Ser Phe
1175                1180                1185 atc tct tct gaa tca tca aaa tct cct aca tat tct tct tca tca    4862
Ile Ser Ser Glu Ser Ser Lys Ser Pro Thr Tyr Ser Ser Ser Ser
1190                1195                1200 tta cca ctt gtt acc agt gcg aca aca agc cag gaa act gct tct    4907
Leu Pro Leu Val Thr Ser Ala Thr Thr Ser Gln Glu Thr Ala Ser
1205                1210                1215 tca tta cca cct gct acc act aca aaa acg agc gaa caa acc act    4952
Ser Leu Pro Pro Ala Thr Thr Thr Lys Thr Ser Glu Gln Thr Thr
1220                1225                1230 ttg gtt acc gtg aca tcc tgc gag tct cat gtg tgc act gaa tcc    4997
Leu Val Thr Val Thr Ser Cys Glu Ser His Val Cys Thr Glu Ser
1235                1240                1245 atc tcc cct gcg att gtt tcc aca gct act gtt act gtt agc ggc    5042
Ile Ser Pro Ala Ile Val Ser Thr Ala Thr Val Thr Val Ser Gly
1250                1255                1260 gtc aca aca gag tat acc aca tgg tgc cct att tct act aca gag    5087
Val Thr Thr Glu Tyr Thr Thr Trp Cys Pro Ile Ser Thr Thr Glu
1265                1270                1275 aca aca aag caa acc aaa ggg aca aca gag caa acc aca gaa aca    5132
Thr Thr Lys Gln Thr Lys Gly Thr Thr Glu Gln Thr Thr Glu Thr
1280                1285                1290 aca aaa caa acc acg gta gtt aca att tct tct tgt gaa tct gac    5177
Thr Lys Gln Thr Thr Val Val Thr Ile Ser Ser Cys Glu Ser Asp
1295                1300                1305 gta tgc tct aag act gct tct cca gcc att gta tct aca agc act    5222
Val Cys Ser Lys Thr Ala Ser Pro Ala Ile Val Ser Thr Ser Thr
1310                1315                1320 gct act att aac ggc gtt act aca gaa tac aca aca tgg tgt cct    5267
Ala Thr Ile Asn Gly Val Thr Thr Glu Tyr Thr Thr Trp Cys Pro
1325                1330                1335 att tcc acc aca gaa tcg agg caa caa aca acg cta gtt act gtt    5312
Ile Ser Thr Thr Glu Ser Arg Gln Gln Thr Thr Leu Val Thr Val
1340                1345                1350 act tcc tgc gaa tct ggt gtg tgt tcc gaa act gct tca cct gcc    5357
Thr Ser Cys Glu Ser Gly Val Cys Ser Glu Thr Ala Ser Pro Ala
1355                1360                1365 att gtt tcg acg gcc acg gct act gtg aat gat gtt gtt acg gtc    5402
Ile Val Ser Thr Ala Thr Ala Thr Val Asn Asp Val Val Thr Val
1370                1375                1380 tat cct aca tgg agg cca cag act gcg aat gaa gag tct gtc agc    5447
Tyr Pro Thr Trp Arg Pro Gln Thr Ala Asn Glu Glu Ser Val Ser
1385                1390                1395 tct aaa atg aac agt gct acc ggt gag aca aca acc aat act tta    5492
Ser Lys Met Asn Ser Ala Thr Gly Glu Thr Thr Thr Asn Thr Leu
1400                1405                1410
```

-continued

```
gct gct gaa acg act acc aat act gta gct gct gag acg att acc        5537
Ala Ala Glu Thr Thr Thr Asn Thr Val Ala Ala Glu Thr Ile Thr
1415                1420                1425 aat act gga gct gct gag acg aaa aca gta gtc acc tct tcg ctt        5582
Asn Thr Gly Ala Ala Glu Thr Lys Thr Val Val Thr Ser Ser Leu
1430                1435                1440 tca aga tct aat cac gct gaa aca cag acg gct tcc gcg acc gat        5627
Ser Arg Ser Asn His Ala Glu Thr Gln Thr Ala Ser Ala Thr Asp
1445                1450                1455 gtg att ggt cac agc agt agt gtt gtt tct gta tcc gaa act ggc        5672
Val Ile Gly His Ser Ser Ser Val Val Ser Val Ser Glu Thr Gly
1460                1465                1470 aac acc aag agt cta aca agt tcc ggg ttg agt act atg tcg caa        5717
Asn Thr Lys Ser Leu Thr Ser Ser Gly Leu Ser Thr Met Ser Gln
1475                1480                1485 cag cct cgt agc aca cca gca agc agc atg gta gga tat agt aca        5762
Gln Pro Arg Ser Thr Pro Ala Ser Ser Met Val Gly Tyr Ser Thr
1490                1495                1500 gct tct tta gaa att tca acg tat gct ggc agt gcc aac agc tta        5807
Ala Ser Leu Glu Ile Ser Thr Tyr Ala Gly Ser Ala Asn Ser Leu
1505                1510                1515 ctg gcc ggt agt ggt tta agt gtc ttc att gcg tcc tta ttg ctg        5852
Leu Ala Gly Ser Gly Leu Ser Val Phe Ile Ala Ser Leu Leu Leu
1520                1525                1530 gca att att taa                                                     5864
Ala Ile Ile
1535

<210> SEQ ID NO 17
<211> LENGTH: 1537
<212> TYPE: PRT
<213> ORGANISM: Saccharomyces cerevisiae

<400> SEQUENCE: 17

Met Thr Met Pro His Arg Tyr Met Phe Leu Ala Val Phe Thr Leu Leu
1               5                   10                  15

Ala Leu Thr Ser Val Ala Ser Gly Ala Thr Glu Ala Cys Leu Pro Ala
            20                  25                  30

Gly Gln Arg Lys Ser Gly Met Asn Ile Asn Phe Tyr Gln Tyr Ser Leu
        35                  40                  45

Lys Asp Ser Ser Thr Tyr Ser Asn Ala Ala Tyr Met Ala Tyr Gly Tyr
    50                  55                  60

Ala Ser Lys Thr Lys Leu Gly Ser Val Gly Gly Gln Thr Asp Ile Ser
65                  70                  75                  80

Ile Asp Tyr Asn Ile Pro Cys Val Ser Ser Gly Thr Phe Pro Cys
                85                  90                  95

Pro Gln Glu Asp Ser Tyr Gly Asn Trp Gly Cys Lys Gly Met Gly Ala
            100                 105                 110

Cys Ser Asn Ser Gln Gly Ile Ala Tyr Trp Ser Thr Asp Leu Phe Gly
        115                 120                 125

Phe Tyr Thr Thr Pro Thr Asn Val Thr Leu Glu Met Thr Gly Tyr Phe
    130                 135                 140

Leu Pro Pro Gln Thr Gly Ser Tyr Thr Phe Lys Phe Ala Thr Val Asp
145                 150                 155                 160

Asp Ser Ala Ile Leu Ser Val Gly Gly Ala Thr Ala Phe Asn Cys Cys
                165                 170                 175

Ala Gln Gln Gln Pro Pro Ile Thr Ser Thr Asn Phe Thr Ile Asp Gly
```

-continued

```
                180                 185                 190
Ile Lys Pro Trp Gly Gly Ser Leu Pro Pro Asn Ile Glu Gly Thr Val
    195                 200                 205

Tyr Met Tyr Ala Gly Tyr Tyr Tyr Pro Met Lys Val Val Tyr Ser Asn
    210                 215                 220

Ala Val Ser Trp Gly Thr Leu Pro Ile Ser Val Thr Leu Pro Asp Gly
225                 230                 235                 240

Thr Thr Val Ser Asp Asp Phe Glu Gly Tyr Val Tyr Ser Phe Asp Asp
                245                 250                 255

Asp Leu Ser Gln Ser Asn Cys Thr Val Pro Asp Pro Ser Asn Tyr Ala
            260                 265                 270

Val Ser Thr Thr Thr Thr Thr Glu Pro Trp Thr Gly Thr Phe Thr
        275                 280                 285

Ser Thr Ser Thr Glu Met Thr Thr Val Thr Gly Thr Asn Gly Val Pro
        290                 295                 300

Thr Asp Glu Thr Val Ile Val Ile Arg Thr Pro Thr Thr Ala Ser Thr
305                 310                 315                 320

Ile Ile Thr Thr Thr Glu Pro Trp Asn Ser Thr Phe Thr Ser Thr Ser
                325                 330                 335

Thr Glu Leu Thr Thr Val Thr Gly Thr Asn Gly Val Arg Thr Asp Glu
            340                 345                 350

Thr Ile Ile Val Ile Arg Thr Pro Thr Thr Ala Thr Thr Ala Ile Thr
        355                 360                 365

Thr Thr Glu Pro Trp Asn Ser Thr Phe Thr Ser Thr Ser Thr Glu Leu
        370                 375                 380

Thr Thr Val Thr Gly Thr Asn Gly Leu Pro Thr Asp Glu Thr Ile Ile
385                 390                 395                 400

Val Ile Arg Thr Pro Thr Thr Ala Thr Thr Ala Met Thr Thr Thr Gln
                405                 410                 415

Pro Trp Asn Asp Thr Phe Thr Ser Thr Ser Thr Glu Leu Thr Thr Val
            420                 425                 430

Thr Gly Thr Asn Gly Leu Pro Thr Asp Glu Thr Ile Ile Val Ile Arg
        435                 440                 445

Thr Pro Thr Thr Ala Thr Thr Ala Met Thr Thr Thr Gln Pro Trp Asn
        450                 455                 460

Asp Thr Phe Thr Ser Thr Ser Thr Glu Leu Thr Thr Val Thr Gly Thr
465                 470                 475                 480

Asn Gly Leu Pro Thr Asp Glu Thr Ile Ile Val Ile Arg Thr Pro Thr
                485                 490                 495

Thr Ala Thr Thr Ala Met Thr Thr Thr Gln Pro Trp Asn Asp Thr Phe
            500                 505                 510

Thr Ser Thr Ser Thr Glu Ile Thr Thr Val Thr Gly Thr Asn Gly Leu
        515                 520                 525

Pro Thr Asp Glu Thr Ile Ile Val Ile Arg Thr Pro Thr Thr Ala Thr
        530                 535                 540

Thr Ala Met Thr Thr Pro Gln Pro Trp Asn Asp Thr Phe Thr Ser Thr
545                 550                 555                 560

Ser Thr Glu Met Thr Thr Val Thr Gly Thr Asn Gly Leu Pro Thr Asp
                565                 570                 575

Glu Thr Ile Ile Val Ile Arg Thr Pro Thr Thr Ala Thr Thr Ala Ile
            580                 585                 590

Thr Thr Thr Glu Pro Trp Asn Ser Thr Phe Thr Ser Thr Ser Thr Glu
        595                 600                 605
```

-continued

```
Met Thr Thr Val Thr Gly Thr Asn Gly Leu Pro Thr Asp Glu Thr Ile
    610                 615                 620

Ile Val Ile Arg Thr Pro Thr Thr Ala Thr Thr Ala Ile Thr Thr Thr
625                 630                 635                 640

Gln Pro Trp Asn Asp Thr Phe Thr Ser Thr Ser Thr Glu Met Thr Thr
                645                 650                 655

Val Thr Gly Thr Asn Gly Leu Pro Thr Asp Glu Thr Ile Ile Val Ile
                660                 665                 670

Arg Thr Pro Thr Thr Ala Thr Thr Ala Met Thr Thr Thr Gln Pro Trp
            675                 680                 685

Asn Asp Thr Phe Thr Ser Thr Ser Thr Glu Ile Thr Thr Val Thr Gly
        690                 695                 700

Thr Thr Gly Leu Pro Thr Asp Glu Thr Ile Ile Val Ile Arg Thr Pro
705                 710                 715                 720

Thr Thr Ala Thr Thr Ala Met Thr Thr Thr Gln Pro Trp Asn Asp Thr
                725                 730                 735

Phe Thr Ser Thr Ser Thr Glu Met Thr Thr Val Thr Gly Thr Asn Gly
                740                 745                 750

Val Pro Thr Asp Glu Thr Val Ile Val Ile Arg Thr Pro Thr Ser Glu
            755                 760                 765

Gly Leu Ile Ser Thr Thr Thr Glu Pro Trp Thr Gly Thr Phe Thr Ser
        770                 775                 780

Thr Ser Thr Glu Met Thr Thr Val Thr Gly Thr Asn Gly Gln Pro Thr
785                 790                 795                 800

Asp Glu Thr Val Ile Val Ile Arg Thr Pro Thr Ser Glu Gly Leu Val
                805                 810                 815

Thr Thr Thr Thr Glu Pro Trp Thr Gly Thr Phe Thr Ser Thr Ser Thr
            820                 825                 830

Glu Met Thr Thr Ile Thr Gly Thr Asn Gly Val Pro Thr Asp Glu Thr
        835                 840                 845

Val Ile Val Ile Arg Thr Pro Thr Ser Glu Gly Leu Ile Ser Thr Thr
850                 855                 860

Thr Glu Pro Trp Thr Gly Thr Phe Thr Ser Thr Ser Thr Glu Met Thr
865                 870                 875                 880

Thr Ile Thr Gly Thr Asn Gly Gln Pro Thr Asp Glu Thr Val Ile Val
                885                 890                 895

Ile Arg Thr Pro Thr Ser Glu Gly Leu Ile Ser Thr Thr Thr Glu Pro
            900                 905                 910

Trp Thr Gly Thr Phe Thr Ser Thr Ser Thr Glu Met Thr His Val Thr
        915                 920                 925

Gly Thr Asn Gly Val Pro Thr Asp Glu Thr Val Ile Val Ile Arg Thr
    930                 935                 940

Pro Thr Ser Glu Gly Leu Ile Ser Thr Thr Thr Glu Pro Trp Thr Gly
945                 950                 955                 960

Thr Phe Thr Ser Thr Ser Thr Glu Val Thr Ile Thr Gly Thr Asn
                965                 970                 975

Gly Gln Pro Thr Asp Glu Thr Val Ile Val Ile Arg Thr Pro Thr Ser
            980                 985                 990

Glu Gly Leu Ile Ser Thr Thr  Glu Pro Trp Thr Gly  Thr Phe Thr
            995                 1000                1005

Ser Thr  Ser Thr Glu Met Thr  Thr Val Thr Gly Thr  Asn Gly Gln
    1010                1015                1020
```

-continued

```
Pro Thr Asp Glu Thr Val Ile Val Ile Arg Thr Pro Thr Ser Glu
1025                1030                1035

Gly Leu Val Thr Thr Thr Glu Pro Trp Thr Gly Thr Phe Thr
1040                1045                1050

Ser Thr Ser Thr Glu Met Ser Thr Val Thr Gly Thr Asn Gly Leu
1055                1060                1065

Pro Thr Asp Glu Thr Val Ile Val Val Lys Thr Pro Thr Thr Ala
1070                1075                1080

Ile Ser Ser Ser Leu Ser Ser Ser Ser Ser Gly Gln Ile Thr Ser
1085                1090                1095

Ser Ile Thr Ser Ser Arg Pro Ile Ile Thr Pro Phe Tyr Pro Ser
1100                1105                1110

Asn Gly Thr Ser Val Ile Ser Ser Ser Val Ile Ser Ser Ser Val
1115                1120                1125

Thr Ser Ser Leu Phe Thr Ser Ser Pro Val Ile Ser Ser Ser Val
1130                1135                1140

Ile Ser Ser Ser Thr Thr Thr Ser Thr Ser Ile Phe Ser Glu Ser
1145                1150                1155

Ser Lys Ser Ser Val Ile Pro Thr Ser Ser Ser Thr Ser Gly Ser
1160                1165                1170

Ser Glu Ser Glu Thr Ser Ser Ala Gly Ser Val Ser Ser Ser Ser
1175                1180                1185

Phe Ile Ser Ser Glu Ser Ser Lys Ser Pro Thr Tyr Ser Ser Ser
1190                1195                1200

Ser Leu Pro Leu Val Thr Ser Ala Thr Ser Gln Glu Thr Ala
1205                1210                1215

Ser Ser Leu Pro Pro Ala Thr Thr Thr Lys Thr Ser Glu Gln Thr
1220                1225                1230

Thr Leu Val Thr Val Thr Ser Cys Glu Ser His Val Cys Thr Glu
1235                1240                1245

Ser Ile Ser Pro Ala Ile Val Ser Thr Ala Thr Val Thr Val Ser
1250                1255                1260

Gly Val Thr Thr Glu Tyr Thr Thr Trp Cys Pro Ile Ser Thr Thr
1265                1270                1275

Glu Thr Thr Lys Gln Thr Lys Gly Thr Thr Glu Gln Thr Thr Glu
1280                1285                1290

Thr Thr Lys Gln Thr Thr Val Val Thr Ile Ser Ser Cys Glu Ser
1295                1300                1305

Asp Val Cys Ser Lys Thr Ala Ser Pro Ala Ile Val Ser Thr Ser
1310                1315                1320

Thr Ala Thr Ile Asn Gly Val Thr Thr Glu Tyr Thr Thr Trp Cys
1325                1330                1335

Pro Ile Ser Thr Thr Glu Ser Arg Gln Gln Thr Thr Leu Val Thr
1340                1345                1350

Val Thr Ser Cys Glu Ser Gly Val Cys Ser Glu Thr Ala Ser Pro
1355                1360                1365

Ala Ile Val Ser Thr Ala Thr Ala Thr Val Asn Asp Val Val Thr
1370                1375                1380

Val Tyr Pro Thr Trp Arg Pro Gln Thr Ala Asn Glu Glu Ser Val
1385                1390                1395

Ser Ser Lys Met Asn Ser Ala Thr Gly Glu Thr Thr Thr Asn Thr
1400                1405                1410

Leu Ala Ala Glu Thr Thr Thr Asn Thr Val Ala Ala Glu Thr Ile
```

|  | 1415 |  |  |  | 1420 |  |  |  |  | 1425 |  |  |  |  |
|---|---|---|---|---|---|---|---|---|---|---|---|---|---|---|

Thr Asn Thr Gly Ala Ala Glu Thr Lys Thr Val Val Thr Ser Ser
    1430                         1435                          1440

Leu Ser Arg Ser Asn His Ala Glu Thr Gln Thr Ala Ser Ala Thr
    1445                         1450                          1455

Asp Val Ile Gly His Ser Ser Val Val Ser Val Ser Glu Thr
    1460                         1465                          1470

Gly Asn Thr Lys Ser Leu Thr Ser Ser Gly Leu Ser Thr Met Ser
    1475                         1480                          1485

Gln Gln Pro Arg Ser Thr Pro Ala Ser Ser Met Val Gly Tyr Ser
    1490                         1495                          1500

Thr Ala Ser Leu Glu Ile Ser Thr Tyr Ala Gly Ser Ala Asn Ser
    1505                         1510                          1515

Leu Leu Ala Gly Ser Gly Leu Ser Val Phe Ile Ala Ser Leu Leu
    1520                         1525                          1530

Leu Ala Ile Ile
    1535

<210> SEQ ID NO 18
<211> LENGTH: 1212
<212> TYPE: DNA
<213> ORGANISM: Saccharomyces cerevisiae

<400> SEQUENCE: 18

| cagcagtcga | atgttcaaga | tgccgtaagt | ttaaaatctt | tcgtatcttt | ccccgatcct | 60 |
|---|---|---|---|---|---|---|
| gtctttcatc | aatgaacttg | aatatcaaga | gtgaaaaaaa | ctcatatggc | ttctcttgaa | 120 |
| gagttagaaa | gataggcaca | tgccaattgt | gtgcatagca | cttactactc | aacgatttca | 180 |
| caacctagca | taatacgcga | aaaaaaaagt | gcatttattt | aggtaagtct | cattacctaa | 240 |
| acgccagttt | gtttcacgta | attggtaacg | atgagggaac | cgcagtagaa | aaaacttttca | 300 |
| ttcacaaacg | attaaagtgt | tatgctagcc | agtttcaggc | tttttgtttt | atgcaagaga | 360 |
| acattcgact | agatgtccag | ttaagtgtgc | gtcacttttc | ctacggtgcc | tcgcacatga | 420 |
| atgttatccg | gcgcacgata | cttatcaccg | aaaaaccta | ttctacggaa | aaccttatt | 480 |
| acattaaagt | tggaaaaatt | tcctcttttt | cctaataagg | tggagctttt | ggcttccagt | 540 |
| atgctttcac | ggaattattt | tcatgtaca | tttagctcca | tttccagtgc | ctccgatagg | 600 |
| gaggcatcat | ggtactaccg | tgacggagaa | tacgtaggct | gacttttcg | tcagtttgtt | 660 |
| gtccgtttac | aaaattggtg | aatgaattct | agccttcctc | tgctcattaa | ttgccctcac | 720 |
| aagaatttgg | aagtgcgtag | acaggtaaaa | gattgtacta | cagaggtatt | gtggaacctt | 780 |
| ctacagtact | tcgaataca | cctaaaaggt | tgttggatgc | taaatttagc | aaaagtcttt | 840 |
| tttagctcac | tattaggctt | gttaaagtct | gaaattgttg | aaaggcactc | aaaaagataa | 900 |
| atcaacaatc | agcattaacg | gcacagttga | agagtcacc | cacttgaaat | tagctcggtt | 960 |
| atcaaatata | attatctctg | gtaaagagct | ctgcagcagg | gttaatctat | tcgcatactt | 1020 |
| acgctgtagg | aacattttat | tattaggatc | cgactactgc | ctacatattt | attcggaagg | 1080 |
| catgatgtcg | aaaattttttg | agcttataaa | aggaacatat | ttcactcttg | ctcgttgatg | 1140 |
| taagctctct | tccgggttct | tattttttaat | tcttgtcacc | agtaaacaga | acatccaaaa | 1200 |
| atgacaatgc | ct |  |  |  |  | 1212 |

<210> SEQ ID NO 19
<211> LENGTH: 4358

```
<212> TYPE: DNA
<213> ORGANISM: Saccharomyces cerevisiae
<220> FEATURE:
<221> NAME/KEY: CDS
<222> LOCATION: (1251)..(4358)

<400> SEQUENCE: 19
```

| | |
|---|---:|
| aaactttcca atgatttctt gataatatcg ggttcgcaaa acattcttaa tgtacacgac | 60 |
| atacaccaaa acggcaaact catctatacc tacgtgtcga gattccccat ccgatgcata | 120 |
| gacatagatc caaggtcgca gataatagcc tacggaatca ccggaaagga tagacataca | 180 |
| ggcgcggaac aagcattagt cgtgatccaa caaattacca gaaataaagt gactttggag | 240 |
| cccgagttcc ccccaccaat caccataaca cttccataca gagatcccat caataccata | 300 |
| caactttcgc acgacgccaa gtatctgaca tgttcgaccg cgctagagtc gcggttcttg | 360 |
| atcatatctt tgcagaaaat aaacgaacca agactgataa tgaaaagtgt tcggtccata | 420 |
| gacacttcct tagaatctga aggtatcact gacacaaaac ttttcccagg aaatccaaat | 480 |
| ctgatgtgta tcacatcaac agcattcaat tcatctccac tggtcataaa caccaaaatc | 540 |
| acccaaatta acggtgtacg gaccgtggca caaccatcca tgcttataag ggtagatgag | 600 |
| attggatgca agattcacaa gtgcgaaata tcaccaagaa acgacgcaat tgccttcctc | 660 |
| gaccgcaacg gatcagttta catcatgtgt gcccccacca tgatggacaa caacgaaaaa | 720 |
| agaaggacaa tcctcgttga aaccgtggca aatgcctaca gggcttatga atcagctact | 780 |
| ttgcggttta acccagaggg caacaagctt tatattctcg acagaaaggg gactttcttt | 840 |
| gtggaagact ttgcatatgg cttgccccaa tctcgcgaaa tcaccaaatg taagcaaata | 900 |
| ttccacaaat aatgcatcta aatatatacg tatgtttaag gttctggtat acaggtatta | 960 |
| aaagaaaaca ctatcaacat tcccaataag atataccaca ccacgtgagc ttatagaagc | 1020 |
| acgtgaccac aattcacccc acaggtgtgg cttttttggt gccgtagaaa agactcattc | 1080 |
| atgaatcgtc ggaaacccat agtcatcttc gagcaaaagg tatatataag caacagaggg | 1140 |
| cagtagttct cgagaccacc atcttttgat tggaaatagt ttcgtttaga tggggtgcac | 1200 |
| atagtttttt tcaactgctt ttcctcgagg tcacccaaat atacaacgag atg cca | 1256 |
|                                                     Met Pro    |      |
|                                                      1         |      |
| gtt gag ttt gct acc aat cct ttt ggc gag gcc aaa aat gca act tca | 1304 |
| Val Glu Phe Ala Thr Asn Pro Phe Gly Glu Ala Lys Asn Ala Thr Ser |      |
|      5               10                  15                    |      |
| ctg cca aaa tat ggt aca ccc gta act gcc att tca tct gtg ctg ttc | 1352 |
| Leu Pro Lys Tyr Gly Thr Pro Val Thr Ala Ile Ser Ser Val Leu Phe |      |
|  20              25                  30                        |      |
| aat aac gtg gac tcc att ttt gct tac aag tcc ttt tct caa ccc gat | 1400 |
| Asn Asn Val Asp Ser Ile Phe Ala Tyr Lys Ser Phe Ser Gln Pro Asp |      |
| 35              40                  45                  50     |      |
| ttg cta cac caa gat cta aaa aaa tgg tct gaa aag cgt ggt aac gaa | 1448 |
| Leu Leu His Gln Asp Leu Lys Lys Trp Ser Glu Lys Arg Gly Asn Glu |      |
|              55                  60                  65        |      |
| tca cgt ggg aag cca ttt ttc caa gag ctg gat atc aga tct ggc gct | 1496 |
| Ser Arg Gly Lys Pro Phe Phe Gln Glu Leu Asp Ile Arg Ser Gly Ala |      |
|          70                  75                  80            |      |
| ggt ttg gct cct tta ggg ttt tct cat gga ttg aag aac act aca gca | 1544 |
| Gly Leu Ala Pro Leu Gly Phe Ser His Gly Leu Lys Asn Thr Thr Ala |      |
|      85                  90                  95                |      |
| att gtt gct cca ggg ttt tcg ctg cca tac ttc att aac tct ttg aaa | 1592 |
| Ile Val Ala Pro Gly Phe Ser Leu Pro Tyr Phe Ile Asn Ser Leu Lys |      |
|     100                 105                 110                |      |

-continued

```
acc gtc tct cat gat ggt aag ttt ctt ttg aat gtt ggt gct tta aac         1640
Thr Val Ser His Asp Gly Lys Phe Leu Leu Asn Val Gly Ala Leu Asn
115                 120                 125                 130 tac gac aat gct acc ggc tct gtc acc aac gat tat gta acc gca ttg         1688
Tyr Asp Asn Ala Thr Gly Ser Val Thr Asn Asp Tyr Val Thr Ala Leu
            135                 140                 145 gat gct gct tcc aag ctg aag tat ggt gtc gtg act ccg att tcc gct         1736
Asp Ala Ala Ser Lys Leu Lys Tyr Gly Val Val Thr Pro Ile Ser Ala
        150                 155                 160 aac gag gta caa agt gtc gcc tta ctg gca ttg gcg att gcc act ttc         1784
Asn Glu Val Gln Ser Val Ala Leu Leu Ala Leu Ala Ile Ala Thr Phe
    165                 170                 175 agt aat aac tcc gga gct atc aat tta ttt gac gga tta aac tac tcg         1832
Ser Asn Asn Ser Gly Ala Ile Asn Leu Phe Asp Gly Leu Asn Tyr Ser
180                 185                 190 aaa acc gtc ttg ccg ttg gtc gaa tct gtt cct gag gca tct att ttg         1880
Lys Thr Val Leu Pro Leu Val Glu Ser Val Pro Glu Ala Ser Ile Leu
195                 200                 205                 210 gca aaa cta tcc aaa gtt att gca cca gat gct gcc ttt gat gat gtc         1928
Ala Lys Leu Ser Lys Val Ile Ala Pro Asp Ala Ala Phe Asp Asp Val
            215                 220                 225 ttg gat aag ttt aat gaa ttg act gga ttg aga cta cat aat ttc caa         1976
Leu Asp Lys Phe Asn Glu Leu Thr Gly Leu Arg Leu His Asn Phe Gln
        230                 235                 240 tac ttt ggt gct cag gat gct gaa act gtg ttt atc act tat ggg tct         2024
Tyr Phe Gly Ala Gln Asp Ala Glu Thr Val Phe Ile Thr Tyr Gly Ser
    245                 250                 255 tta gaa tcc gaa ttg ttc aac tct gcg att agt ggt aat aat tcc aaa         2072
Leu Glu Ser Glu Leu Phe Asn Ser Ala Ile Ser Gly Asn Asn Ser Lys
260                 265                 270 atc ggg tta atc aac gtc aga gtg cca tta cct ttt aac gtt gct aag         2120
Ile Gly Leu Ile Asn Val Arg Val Pro Leu Pro Phe Asn Val Ala Lys
275                 280                 285                 290 ttt gtc act cac gtt cca tcc act acc aaa caa att gtt gtt ata ggc         2168
Phe Val Thr His Val Pro Ser Thr Thr Lys Gln Ile Val Val Ile Gly
            295                 300                 305 caa act ttg gat ggt tct tcg cct tct ttc ttg aga tct caa gtt tca         2216
Gln Thr Leu Asp Gly Ser Ser Pro Ser Phe Leu Arg Ser Gln Val Ser
        310                 315                 320 gcc gcc tta ttt tac cac ggc cgc acc tca att agc gtt tct gag tac         2264
Ala Ala Leu Phe Tyr His Gly Arg Thr Ser Ile Ser Val Ser Glu Tyr
    325                 330                 335 atc tat caa cca gat ttc att tgg tcc cca aaa gct gtc aaa tca att         2312
Ile Tyr Gln Pro Asp Phe Ile Trp Ser Pro Lys Ala Val Lys Ser Ile
340                 345                 350 gta tcg tca ttc atc cct gaa ttc act tac aat gcc gat tca tct ttc         2360
Val Ser Ser Phe Ile Pro Glu Phe Thr Tyr Asn Ala Asp Ser Ser Phe
355                 360                 365                 370 ggc gaa gga ttc att tat tgg gcc tct gat aag agt atc aat att gat         2408
Gly Glu Gly Phe Ile Tyr Trp Ala Ser Asp Lys Ser Ile Asn Ile Asp
            375                 380                 385 gtt gcc tcc aaa ctt gtg aaa gct ctg tct ttg gaa gat ggg aaa ttt         2456
Val Ala Ser Lys Leu Val Lys Ala Leu Ser Leu Glu Asp Gly Lys Phe
        390                 395                 400 gtg tct ttg aga acg aaa ttt gat aac ttg gct aat gct ggt acc ttc         2504
Val Ser Leu Arg Thr Lys Phe Asp Asn Leu Ala Asn Ala Gly Thr Phe
    405                 410                 415 caa gct caa ttt gtg acc tcg aaa gaa cag ata cct gtt tca aac atc         2552
Gln Ala Gln Phe Val Thr Ser Lys Glu Gln Ile Pro Val Ser Asn Ile
```

-continued

```
         420                 425                 430
gat tct acg aaa tta tca gtc gtt gaa gat gtc agt tta ttg aag cat        2600
Asp Ser Thr Lys Leu Ser Val Val Glu Asp Val Ser Leu Leu Lys His
435                 440                 445                 450 tta gac gta gct gct acc gtc gca gaa caa ggt tca att gcg ttg gtt        2648
Leu Asp Val Ala Ala Thr Val Ala Glu Gln Gly Ser Ile Ala Leu Val
            455                 460                 465 tcc caa aag gca gtt aaa gat ttg gat tta aat tct gta gaa agt tac        2696
Ser Gln Lys Ala Val Lys Asp Leu Asp Leu Asn Ser Val Glu Ser Tyr
        470                 475                 480 gtc aag aat ttg gga att cct gaa tca ttc cta ata tct att gcg aag        2744
Val Lys Asn Leu Gly Ile Pro Glu Ser Phe Leu Ile Ser Ile Ala Lys
    485                 490                 495 aaa aac atc aaa ttg ttt atc atc gat ggt gag acc act aac gac gag        2792
Lys Asn Ile Lys Leu Phe Ile Ile Asp Gly Glu Thr Thr Asn Asp Glu
500                 505                 510 tcc aaa ttg tcc ttg ttt atc caa gcc gtt ttc tgg aaa ttg gcc ttc        2840
Ser Lys Leu Ser Leu Phe Ile Gln Ala Val Phe Trp Lys Leu Ala Phe
515                 520                 525                 530 ggt cta gat gtc gca gaa tgt acc aac cgt atc tgg aaa agc att gat        2888
Gly Leu Asp Val Ala Glu Cys Thr Asn Arg Ile Trp Lys Ser Ile Asp
            535                 540                 545 tca ggt gca gac att tca gca gcc tcg att tct gaa ttt ctc act ggt        2936
Ser Gly Ala Asp Ile Ser Ala Ala Ser Ile Ser Glu Phe Leu Thr Gly
        550                 555                 560 gca ttc aaa aac ttc ctc agt gag gtt ccg cta gcg ctg tac act aaa        2984
Ala Phe Lys Asn Phe Leu Ser Glu Val Pro Leu Ala Leu Tyr Thr Lys
    565                 570                 575 ttt tct gaa ata aac att gaa aag aaa gag gat gag gaa gag cct gca        3032
Phe Ser Glu Ile Asn Ile Glu Lys Lys Glu Asp Glu Glu Glu Pro Ala
580                 585                 590 gct tta cca att ttc gtt aat gaa aca tct ttc ctc cca aat aac agt        3080
Ala Leu Pro Ile Phe Val Asn Glu Thr Ser Phe Leu Pro Asn Asn Ser
595                 600                 605                 610 acc att gaa gaa ata cca tta cct gag acc tct gag atc tct gat att        3128
Thr Ile Glu Glu Ile Pro Leu Pro Glu Thr Ser Glu Ile Ser Asp Ile
            615                 620                 625 gcc aag aag ttg tcc ttc aaa gag gca tat gaa gtt gag aat aaa cta        3176
Ala Lys Lys Leu Ser Phe Lys Glu Ala Tyr Glu Val Glu Asn Lys Leu
        630                 635                 640 aga ccc gat tta ccc gtc aag aac ttc gtc gtg aaa gtt aaa gaa aat        3224
Arg Pro Asp Leu Pro Val Lys Asn Phe Val Val Lys Val Lys Glu Asn
    645                 650                 655 aga cgt gtt acg cct gct gat tat gat aga tat att ttc cat att gaa        3272
Arg Arg Val Thr Pro Ala Asp Tyr Asp Arg Tyr Ile Phe His Ile Glu
660                 665                 670 ttc gat att tct ggt act gga atg act tat gac atc ggt gaa gcc ctc        3320
Phe Asp Ile Ser Gly Thr Gly Met Thr Tyr Asp Ile Gly Glu Ala Leu
675                 680                 685                 690 ggt att cat gcc aga aac aat gaa tct ttg gtc aaa gaa ttc tta acc        3368
Gly Ile His Ala Arg Asn Asn Glu Ser Leu Val Lys Glu Phe Leu Thr
            695                 700                 705 ttc tat ggt cta aat gaa tcc gat gtt gtc tta gtc ccc aac aag gac        3416
Phe Tyr Gly Leu Asn Glu Ser Asp Val Val Leu Val Pro Asn Lys Asp
        710                 715                 720 aac cac cat ttg tta gaa aca aga acc gtc tta caa gca ttt gtg gaa        3464
Asn His His Leu Leu Glu Thr Arg Thr Val Leu Gln Ala Phe Val Glu
    725                 730                 735 aat ttg gat att ttc ggt aaa cca cca aaa aga ttt tac gaa tca ttg        3512
```

```
            Asn Leu Asp Ile Phe Gly Lys Pro Pro Lys Arg Phe Tyr Glu Ser Leu
                740                 745                 750 att cca tat gcc tct aac gaa gag gag aag aaa aaa tta gag gat ttg      3560
Ile Pro Tyr Ala Ser Asn Glu Glu Glu Lys Lys Lys Leu Glu Asp Leu
755                 760                 765                 770 gtt act cct gcc ggt gca gta gat ttg aag aga ttt caa gat gtg gag      3608
Val Thr Pro Ala Gly Ala Val Asp Leu Lys Arg Phe Gln Asp Val Glu
                775                 780                 785 tat tat aca tat gct gac att ttt gaa ttg ttc cca tct gtt cgc cca      3656
Tyr Tyr Thr Tyr Ala Asp Ile Phe Glu Leu Phe Pro Ser Val Arg Pro
            790                 795                 800 tct ctt gag gaa ctt gtt act atc att gaa cca ttg aag aga aga gaa      3704
Ser Leu Glu Glu Leu Val Thr Ile Ile Glu Pro Leu Lys Arg Arg Glu
        805                 810                 815 tac tca att gcc tcc tct cag aaa gtt cat cca aat gaa gtt cat tta      3752
Tyr Ser Ile Ala Ser Ser Gln Lys Val His Pro Asn Glu Val His Leu
    820                 825                 830 ttg atc gtt gtt gtt gat tgg gtg gat aat aaa gga aga aaa agg tac      3800
Leu Ile Val Val Val Asp Trp Val Asp Asn Lys Gly Arg Lys Arg Tyr
835                 840                 845                 850 ggt caa gct tct aag tat atc tca gac ctt gct gtc ggt tca gaa ttg      3848
Gly Gln Ala Ser Lys Tyr Ile Ser Asp Leu Ala Val Gly Ser Glu Leu
                855                 860                 865 gtc gtt agc gtt aaa cca tct gtt atg aaa tta cca cca tct cca aag      3896
Val Val Ser Val Lys Pro Ser Val Met Lys Leu Pro Pro Ser Pro Lys
            870                 875                 880 caa cca gtt att atg agt ggt tta ggt act ggt ttg gca cca ttc aag      3944
Gln Pro Val Ile Met Ser Gly Leu Gly Thr Gly Leu Ala Pro Phe Lys
        885                 890                 895 gcc att gtt gaa gag aaa tta tgg caa aag cag caa ggt tat gag att      3992
Ala Ile Val Glu Glu Lys Leu Trp Gln Lys Gln Gln Gly Tyr Glu Ile
    900                 905                 910 ggt gaa gtc ttc cta tat cta ggt tca aga cac aaa aga gaa gaa tat      4040
Gly Glu Val Phe Leu Tyr Leu Gly Ser Arg His Lys Arg Glu Glu Tyr
915                 920                 925                 930 tta tat ggt gag tta tgg gag gct tac aaa gat gca ggt att atc aca      4088
Leu Tyr Gly Glu Leu Trp Glu Ala Tyr Lys Asp Ala Gly Ile Ile Thr
                935                 940                 945 cac atc ggc gct gct ttc tca aga gac caa cct caa aaa att tac att      4136
His Ile Gly Ala Ala Phe Ser Arg Asp Gln Pro Gln Lys Ile Tyr Ile
            950                 955                 960 caa gat cgt atc aaa gag aat ttg gat gaa tta aaa act gca atg att      4184
Gln Asp Arg Ile Lys Glu Asn Leu Asp Glu Leu Lys Thr Ala Met Ile
        965                 970                 975 gat aat aaa ggt tca ttt tac ttg tgt ggc cct act tgg cca gtt cca      4232
Asp Asn Lys Gly Ser Phe Tyr Leu Cys Gly Pro Thr Trp Pro Val Pro
    980                 985                 990 gat att act caa gct ttg  caa gac att ctg gct  aaa gac gcc gag        4277
Asp Ile Thr Gln Ala Leu  Gln Asp Ile Leu Ala  Lys Asp Ala Glu
995                      1000                 1005 gaa aga ggc atc aaa gtc  gac ttg gat gcc gca  att gaa gaa tta        4322
Glu Arg Gly Ile Lys Val  Asp Leu Asp Ala Ala  Ile Glu Glu Leu
1010                     1015                 1020 aag gaa gca tca aga tac  att tta gaa gtc tac  taa                    4358
Lys Glu Ala Ser Arg Tyr  Ile Leu Glu Val Tyr
1025                     1030                 1035

<210> SEQ ID NO 20
<211> LENGTH: 1035
<212> TYPE: PRT
```

<213> ORGANISM: Saccharomyces cerevisiae

<400> SEQUENCE: 20

```
Met Pro Val Glu Phe Ala Thr Asn Pro Phe Gly Glu Ala Lys Asn Ala
1               5                   10                  15

Thr Ser Leu Pro Lys Tyr Gly Thr Pro Val Thr Ala Ile Ser Ser Val
            20                  25                  30

Leu Phe Asn Asn Val Asp Ser Ile Phe Ala Tyr Lys Ser Phe Ser Gln
        35                  40                  45

Pro Asp Leu Leu His Gln Asp Leu Lys Lys Trp Ser Glu Lys Arg Gly
    50                  55                  60

Asn Glu Ser Arg Gly Lys Pro Phe Phe Gln Glu Leu Asp Ile Arg Ser
65                  70                  75                  80

Gly Ala Gly Leu Ala Pro Leu Gly Phe Ser His Gly Leu Lys Asn Thr
                85                  90                  95

Thr Ala Ile Val Ala Pro Gly Phe Ser Leu Pro Tyr Phe Ile Asn Ser
            100                 105                 110

Leu Lys Thr Val Ser His Asp Gly Lys Phe Leu Leu Asn Val Gly Ala
        115                 120                 125

Leu Asn Tyr Asp Asn Ala Thr Gly Ser Val Thr Asn Asp Tyr Val Thr
    130                 135                 140

Ala Leu Asp Ala Ala Ser Lys Leu Lys Tyr Gly Val Val Thr Pro Ile
145                 150                 155                 160

Ser Ala Asn Glu Val Gln Ser Val Ala Leu Leu Ala Leu Ala Ile Ala
                165                 170                 175

Thr Phe Ser Asn Asn Ser Gly Ala Ile Asn Leu Phe Asp Gly Leu Asn
            180                 185                 190

Tyr Ser Lys Thr Val Leu Pro Leu Val Glu Ser Val Pro Glu Ala Ser
        195                 200                 205

Ile Leu Ala Lys Leu Ser Lys Val Ile Ala Pro Asp Ala Ala Phe Asp
    210                 215                 220

Asp Val Leu Asp Lys Phe Asn Glu Leu Thr Gly Leu Arg Leu His Asn
225                 230                 235                 240

Phe Gln Tyr Phe Gly Ala Gln Asp Ala Glu Thr Val Phe Ile Thr Tyr
                245                 250                 255

Gly Ser Leu Glu Ser Glu Leu Phe Asn Ser Ala Ile Ser Gly Asn Asn
            260                 265                 270

Ser Lys Ile Gly Leu Ile Asn Val Arg Val Pro Leu Pro Phe Asn Val
        275                 280                 285

Ala Lys Phe Val Thr His Val Pro Ser Thr Thr Lys Gln Ile Val Val
    290                 295                 300

Ile Gly Gln Thr Leu Asp Gly Ser Ser Pro Ser Phe Leu Arg Ser Gln
305                 310                 315                 320

Val Ser Ala Ala Leu Phe Tyr His Gly Arg Thr Ser Ile Ser Val Ser
                325                 330                 335

Glu Tyr Ile Tyr Gln Pro Asp Phe Ile Trp Ser Pro Lys Ala Val Lys
            340                 345                 350

Ser Ile Val Ser Ser Phe Ile Pro Glu Phe Thr Tyr Asn Ala Asp Ser
        355                 360                 365

Ser Phe Gly Glu Gly Phe Ile Tyr Trp Ala Ser Asp Lys Ser Ile Asn
    370                 375                 380

Ile Asp Val Ala Ser Lys Leu Val Lys Ala Leu Ser Leu Glu Asp Gly
385                 390                 395                 400
```

```
Lys Phe Val Ser Leu Arg Thr Lys Phe Asp Asn Leu Ala Asn Ala Gly
            405                 410                 415
Thr Phe Gln Ala Gln Phe Val Thr Ser Lys Glu Gln Ile Pro Val Ser
        420                 425                 430
Asn Ile Asp Ser Thr Lys Leu Ser Val Val Glu Asp Val Ser Leu Leu
            435                 440                 445
Lys His Leu Asp Val Ala Ala Thr Val Ala Glu Gln Gly Ser Ile Ala
    450                 455                 460
Leu Val Ser Gln Lys Ala Val Lys Asp Leu Asp Leu Asn Ser Val Glu
465                 470                 475                 480
Ser Tyr Val Lys Asn Leu Gly Ile Pro Glu Ser Phe Leu Ile Ser Ile
                485                 490                 495
Ala Lys Lys Asn Ile Lys Leu Phe Ile Ile Asp Gly Glu Thr Thr Asn
            500                 505                 510
Asp Glu Ser Lys Leu Ser Leu Phe Ile Gln Ala Val Phe Trp Lys Leu
            515                 520                 525
Ala Phe Gly Leu Asp Val Ala Glu Cys Thr Asn Arg Ile Trp Lys Ser
    530                 535                 540
Ile Asp Ser Gly Ala Asp Ile Ser Ala Ala Ser Ile Ser Glu Phe Leu
545                 550                 555                 560
Thr Gly Ala Phe Lys Asn Phe Leu Ser Glu Val Pro Leu Ala Leu Tyr
                565                 570                 575
Thr Lys Phe Ser Glu Ile Asn Ile Glu Lys Lys Glu Asp Glu Glu Glu
                580                 585                 590
Pro Ala Ala Leu Pro Ile Phe Val Asn Glu Thr Ser Phe Leu Pro Asn
        595                 600                 605
Asn Ser Thr Ile Glu Glu Ile Pro Leu Pro Gly Thr Ser Glu Ile Ser
        610                 615                 620
Asp Ile Ala Lys Lys Leu Ser Phe Lys Glu Ala Tyr Glu Val Glu Asn
625                 630                 635                 640
Lys Leu Arg Pro Asp Leu Pro Val Lys Asn Phe Val Lys Val Lys
                645                 650                 655
Glu Asn Arg Arg Val Thr Pro Ala Asp Tyr Asp Arg Tyr Ile Phe His
            660                 665                 670
Ile Glu Phe Asp Ile Ser Gly Thr Gly Met Thr Tyr Asp Ile Gly Glu
        675                 680                 685
Ala Leu Gly Ile His Ala Arg Asn Asn Glu Ser Leu Val Lys Glu Phe
    690                 695                 700
Leu Thr Phe Tyr Gly Leu Asn Glu Ser Asp Val Val Leu Val Pro Asn
705                 710                 715                 720
Lys Asp Asn His His Leu Leu Glu Thr Arg Thr Val Leu Gln Ala Phe
                725                 730                 735
Val Glu Asn Leu Asp Ile Phe Gly Lys Pro Lys Arg Phe Tyr Glu
            740                 745                 750
Ser Leu Ile Pro Tyr Ala Ser Asn Glu Glu Lys Lys Leu Glu
                755                 760                 765
Asp Leu Val Thr Pro Ala Gly Ala Val Asp Leu Lys Arg Phe Gln Asp
    770                 775                 780
Val Glu Tyr Tyr Thr Tyr Ala Asp Ile Phe Glu Leu Phe Pro Ser Val
785                 790                 795                 800
Arg Pro Ser Leu Glu Glu Leu Val Thr Ile Ile Glu Pro Leu Lys Arg
            805                 810                 815
Arg Glu Tyr Ser Ile Ala Ser Ser Gln Lys Val His Pro Asn Glu Val
```

```
                820            825             830
His Leu Leu Ile Val Val Asp Trp Val Asp Asn Lys Gly Arg Lys
        835                 840                 845

Arg Tyr Gly Gln Ala Ser Lys Tyr Ile Ser Asp Leu Ala Val Gly Ser
850                     855                 860

Glu Leu Val Val Ser Val Lys Pro Ser Val Met Lys Leu Pro Pro Ser
865                 870                 875                 880

Pro Lys Gln Pro Val Ile Met Ser Gly Leu Gly Thr Gly Leu Ala Pro
                885                 890                 895

Phe Lys Ala Ile Val Glu Glu Lys Leu Trp Lys Gln Gln Gly Tyr
            900                 905                 910

Glu Ile Gly Glu Val Phe Leu Tyr Leu Gly Ser Arg His Lys Arg Glu
            915                 920                 925

Glu Tyr Leu Tyr Gly Glu Leu Trp Glu Ala Tyr Lys Asp Ala Gly Ile
        930                 935                 940

Ile Thr His Ile Gly Ala Ala Phe Ser Arg Asp Gln Pro Gln Lys Ile
945                 950                 955                 960

Tyr Ile Gln Asp Arg Ile Lys Glu Asn Leu Asp Glu Leu Lys Thr Ala
                965                 970                 975

Met Ile Asp Asn Lys Gly Ser Phe Tyr Leu Cys Gly Pro Thr Trp Pro
            980                 985                 990

Val Pro Asp Ile Thr Gln Ala Leu  Gln Asp Ile Leu Ala  Lys Asp Ala
        995                 1000                 1005

Glu Glu  Arg Gly Ile Lys Val  Asp Leu Asp Ala Ala  Ile Glu Glu
    1010                 1015                 1020

Leu Lys  Glu Ala Ser Arg Tyr  Ile Leu Glu Val Tyr
    1025                 1030                 1035

<210> SEQ ID NO 21
<211> LENGTH: 1212
<212> TYPE: DNA
<213> ORGANISM: Saccharomyces cerevisiae

<400> SEQUENCE: 21
tgtacacgac atacaccaaa acggcaaact catctatacc tacgtgtcga gattccccat      60
ccgatgcata gacatagatc caaggtcgca gataatagcc tacggaatca ccggaaagga     120
tagacataca ggcgcggaac aagcattagt cgtgatccaa caaattacca gaaataaagt     180
gactttggag cccgagttcc ccccaccaat caccataaca cttccataca gagatcccat     240
caataccata caactttcgc acgacgccaa gtatctgaca tgttcgaccg cgctagagtc     300
gcggttcttg atcatatctt tgcagaaaat aaacgaacca agactgataa tgaaaagtgt     360
tcggtccata gacacttcct tagaatctga aggtatcact gacacaaaac ttttcccagg     420
aaatccaaat ctgatgtgta tcacatcaac agcattcaat tcatctccac tggtcataaa     480
caccaaaatc acccaaatta acggtgtacg gaccgtggca caaccatcca tgcttataag     540
ggtagatgag attggatgca agattcacaa gtgcgaaata tcaccaagaa acgacgcaat     600
tgccttcctc gaccgcaacg gatcagttta catcatgtgt gcccccacca tgatggacaa     660
caacgaaaaa agaaggacaa tcctcgttga accgtggca aatgcctaca gggcttatga      720
atcagctact ttgcggttta acccagaggg caacaagctt tatattctcg acagaaaggg     780
gactttcttt gtggaagact ttgcatatgg cttccccaa tctcgcgaaa tcaccaaatg      840
taagcaaata ttccacaaat aatgcatcta aatatatacg tatgtttaag gttctggtat     900
```

-continued

```
acaggtatta aaagaaaaca ctatcaacat tcccaataag atataccaca ccacgtgagc      960
ttatagaagc acgtgaccac aattcacccc acaggtgtgg cttttttggt gccgtagaaa     1020
agactcattc atgaatcgtc ggaaacccat agtcatcttc gagcaaaagg tatatataag     1080
caacagaggg cagtagttct cgagaccacc atcttttgat tggaaatagt ttcgtttaga     1140
tggggtgcac atagttttt tcaactgctt ttcctcgagg tcacccaaat atacaacgag      1200
atgccagttg ag                                                         1212

<210> SEQ ID NO 22
<211> LENGTH: 13
<212> TYPE: DNA
<213> ORGANISM: Artificial
<220> FEATURE:
<223> OTHER INFORMATION: Description of Artificial Sequence: supF-
      stuffer fragment junction component

<400> SEQUENCE: 22
ccccggagac gtc                                                          13

<210> SEQ ID NO 23
<211> LENGTH: 10
<212> TYPE: DNA
<213> ORGANISM: Artificial
<220> FEATURE:
<223> OTHER INFORMATION: Description of Artificial Sequence: terminal of
      supF gene

<400> SEQUENCE: 23
tcccccacca                                                              10
```

METHODS OF USING GLUCAN SYNTHASE PATHWAY REPORTER GENES TO SCREEN FOR ANTIFUNGAL COMPOUNDS

1.0 INTRODUCTION

The present invention relates to methods of using nucleotide sequences from the promoter region of at least one of seven *S. cerevisiae* genes whose expression is an indicator of the inhibition or modulation of the glucan synthase pathway in *S. cerevisiae*. This invention envisions using at least one target polynucleotide sequence, each target polynucleotide sequence being operably linked to the promoter region of one of the seven glucan synthase pathway reporter genes, to screen chemical libraries and natural products for molecules which can be used as antifungal agents for use against a variety of fungal pathogens. This invention also envisions using the methods of the invention to assay the efficacy of and/or specificity of antifungal agents, and/or to monitor the activity of the glucan synthase pathway.

2.0 BACKGROUND OF THE INVENTION

Citation of a reference herein shall not be construed as an admission that such reference is prior art to the present invention.

2.1 Fungi and Disease

Fungi are eukaryotic microorganisms comprising a phylogenetic kingdom. The Kingdom Fungi is estimated to contain over 100,000 species and includes species of "yeast", which is the common term for several families of unicellular fungi.

Although fungal infections were once unrecognized as a significant cause of disease, the extensive spread of fungal infections is a major concern in hospitals, health departments and research laboratories. According to a 1988 study, nearly 40% of all deaths from hospital-acquired infections were caused by fungi, not bacteria or viruses (Sternberg, S., 1994, *Science* 266:1632–34).

Immunocompromised patients are particularly at risk for fungal infections. Patients with impaired immune systems due to AIDS, cancer chemotherapy, or those treated with immunosuppressive drugs used to prevent rejection in organ transplant are common hosts for fungal infections. Organisms including but not limited to *Cryptococcus* spp., *Candida* spp., *Hostoplasma* spp., *Coccidioides* spp., and as many as 150 species of fungi have been linked to human or animal diseases (Sternberg, S., 1994, *Science* 266:1632–34). Under immunocompromised conditions, fungi that are normally harmless to the host when maintained in the gastrointestinal system, can be transferred to the bloodstream, eyes, brain, heart, kidneys, and other tissues leading to symptoms ranging in severity from white patches on the tongue, to fever, rupturing of the retina, blindness, pneumonia, heart failure, shock, or sudden catastrophic clotting of the blood (Sternberg, S., 1994, *Science* 266:1632–34). In susceptible burn victims, even *S. cerevisiae* (baker's yeast), common in the human mouth and normally non-virulent, can lead to severe infection (Sternberg, S., 1994, *Science* 266:1632–34). Hospital transmission may also occur via catheters or other invasive equipment (Sternberg, S., 1994, *Science* 266:1632–34).

Fungal infections are not limited to individuals with compromised immune systems. Geological and meterological events have been reported to trigger fungal outbreaks. Following a 1994 earthquake in California, tremors were estimated to have released infectious fungal pores from the soil triggering a 3-year statewide epidemic that led to more than 4,500 cases per year (Sternberg, S., 1994, *Science* 266:1632–34).

Moreover, fungal infections are not limited to humans. Animals and plants are both struck by fungal infections. The worldwide contamination of foods and feeds with mycotoxins, the secondary metabolites of fungi, is a significant problem that has adverse effects on humans, animals and crops and results in substantial illness and economic loss. (Hussein, H. S. and Brasel, J. M., 2001, *Toxicology:*167(2): 101–34). The economic impact of mycotoxins include loss of human and animal life, increased health care and veterinary care costs, reduced livestock production, disposal of contaminated foods and feeds, and investment in research and applications to reduce severity of the mycotoxin problem. (Hussein, H. S. and Brasel, J. M., 2001, *Toxicology:* 167(2):101–34). Clearly, efforts to control the spread of fungi will concomitantly control the often costly byproducts of fungi, mycotoxins.

The widespread dissemination of fungal infection coupled with the recognition of fungi as a significant disease causing factor creates an increasing need for antifungal agents. Existing antifungal therapies harbor many disadvantages as discussed below in Section 2.2, and novel antifungal agents and therapies are needed.

2.2 Antifungal Agents and the Need for Improvement

An effective antifungal agent is toxic to the pathogenic fungi, but not to the host. One way to achieve this goal is to target a structure or pathway that is unique to the pathogen. For example, successful antibacterial therapies often take advantage of the differences between the prokaryotic bacteria and the eukaryotic host. However, since fungal pathogens, like human cells, are eukaryotic, it has been more difficult to identify therapeutic agents that uniquely affect the pathogen. A lack of sufficient pathogen specificity can result in host toxicity. Treatment of fungal diseases is often limited because antifungal agents are often toxic to the mammalian or plant host, frequently resulting in severe side effects. For example, the commonly prescribed drug, Amphotericin B, a mainstay of antifungal therapy, includes such side effects as fever, chills, low blood pressure, headache, nausea, vomiting, inflammation of blood vessels and kidney damage (Sternberg, S., 1994, *Science* 266:1632–34). Further, many of the existing therapies act to inhibit or slow fungal growth, but do not kill the infecting fungi.

Currently, there are five main classes of antifungal compounds: azoles; polyenes; allylamines; flucytosine; and candins. Each class is characterized by its mode and/or site of action. Azoles inhibit the synthesis of ergosterol, the main fungal sterol. Polyenes bind to fungal membrane sterol, resulting in the formation of aqueous pores through which essential cytoplasmic materials leak out. Allylamines block ergosterol biosynthesis, leading to accumulation of squalene, which is toxic to cells. Flucytosine inhibits macromolecular synthesis. Finally, candins inhibit the synthesis of 1,3-β-glucan, the major structural polymer of the fungal cell wall, thereby inhibiting fungal growth. (Balkis, M. M., et al., 2002, *Drugs* 62(7):1025–40).

Additionally, the increased use of antifungal agents in recent years has resulted in the development of fungal resistance to these drugs. The prospect of acquired resistance in fungal pathogens to known antifungal agents is likely to continue to fuel the search for novel and more effective antifungal agents.

2.3 The Cell Wall and the Glucan Synthase Pathway

The fungal cell wall is a complex, dynamic network whose structure and function are both unique and essential to fungal cell life and development. The fungal cell wall thus serves as an ideal target for antifungal agents. In addition to helping a cell maintain its shape and protecting the cell against osmotic forces, the cell wall acts as a filter, controlling uptake and secretion of molecules into and out of the cell. (Wills, E. A., et al., 2000, *Emerging Therapeutic Targets* 4(3):1–32). Interference with fungal cell wall function, structure or synthesis will eventually lead to cell lysis and death. (Wills, E. A., et al., 2000, *Emerging Therapeutic Targets* 4(3):1–32).

The fungal cell wall comprises a meshlike structure of polysaccharides, including 1,3-β-glucan, 1,6-β-glucan, and chitin. (Douglas, et al., 1994, *J. Bacteriology* 176(18): 5686–5696). Significantly, 1,3-β-glucan is the most prominent carbohydrate component of the fungal cell wall. (Wills, E. A., et al., 2000, *Emerging Therapeutic Targets* 4(3): 1–32). Thus, the membrane-bound enzyme which catalyzes the synthesis of 1,3-β-glucan, the enzyme glucan synthase (EC 2.4.1.34 [UDP-glucose: 1,3-β-D-glucan 3-β-glucose transferase]), plays an indispensable role in cell wall biosynthesis. (Douglas, et al., 1994, *J. Bacteriology* 176(18): 5686–5696). Specifically, glucan synthase transfers glucose from UDP-glucose to an acid-insoluble, alkali-soluble, exo-β-1,3-glucan-sensitive polysaccharide. This fundamental role, coupled with the fact that glucan synthase is not found in mammalian cells, makes the glucan synthase pathway an ideal target for antifungal agents. Several known antifungal agents, such as Enfumafungin, Ascosteroside, and dihydropapulacandin, act by inhibiting the glucan synthase pathway. (Gorman, J. A., et al., 1995, *J. Antibiotics*, 49(6):547–52).

Similarly, it is known that disrupting *S. cerevisiae* glucan synthase pathway genes FKS1 and/or FKS2 results in cell wall damage. (Terashima, H., et al., 2000, *Mol. Gen. Genet.* 264:64–74). FKS1 and FKS2 encode alternative catalytic subunits of the glucan synthases that are responsible for the synthesis of 1,3-β-glucan. (Terashima, H., et al., 2000, *Mol. Gen. Genet.* 264:64–74).

Furthermore, a glucan synthase complex or a homologous glucan synthase gene has been documented in the following pathogenic fungal species: *Saccharomyces cerevisiae* (Inoue, S. B., et al, 1995, *Eur. J. Biochem.* 231:845–854); *Candida albicans* (Mio, T., et al., 1997, *J. Bacteriol.*, 179: 4096–4105); *Schizosaccharomyces pombe* (Arellano, M, et al., 1996, *Embo. J.* 15:4584–4591); *Aspergillus nidulans* (Kelly, R., et al., 1996, *J. Bacteriol.* 178: 4381–4391); *Neurospora crassa* (Awald, P., et al., 1994, *Biochim. Biophys. Acta* 1201(2):312–320); and *Cryptococcus neoformans* (Thompson, J. R., et al., 1999, *J. Bacteriol.* 181(2): 444–453).

At present, there is a need in the art for efficient and economical methods to evaluate potential antifungal molecules for their effect on the glucan synthase pathway. Current methods of screening for novel glucan synthase pathway inhibitors include in vitro screening assays for molecules that inhibit polymerization by glucan synthase.

Current methods however, harbor several disadvantages and shortcomings. The primary drawbacks of the in vitro assay are its difficulty to perform and the possibility that molecules which inhibit polymerization by glucan synthase in vitro, may not have that effect in vivo. The methods described in the instant invention can easily be assayed in a non-invasive fashion that is suitable to a broader spectrum of assay conditions and is suitable to high-throughput assays.

2.4 Microarray Technology

Within the past decade, several technologies have made it possible to monitor the expression level of a large number of transcripts at any one time (see, e.g., Schena et al., 1995, Quantitative monitoring of gene expression patterns with a complementary DNA micro-array, *Science* 270:467–470; Lockhart et al., 1996, Expression monitoring by hybridization to high-density oligonucleotide arrays, *Nature Biotechnology* 14:1675–1680; Blanchard et al., 1996, Sequence to array: Probing the genome's secrets, *Nature Biotechnology* 14, 1649; U.S. Pat. No. 5,569,588, issued Oct. 29, 1996 to Ashby et al entitled "Methods for Drug Screening"). In organisms for which the complete genome is known, it is possible to analyze the transcripts of all genes within the cell. With other organisms, such as humans, for which there is an increasing knowledge of the genome, it is possible to simultaneously monitor large numbers of the genes within the cell.

Such monitoring technologies have been applied to the identification of genes which are up-regulated or down-regulated in various diseased or physiological states, the analyses of members of signaling cellular states, and the identification of targets for various drugs. See, e.g., Friend and Hartwell, International Publication WO98/38329 (dated Sep. 3, 1998); Stoughton and Friend, U.S. Pat. No. 5,965, 352 (issued on Oct. 12, 1999); Friend and Hartwell, U.S. Pat. No. 6,165,709 (issued on Dec. 26, 2000), U.S. Pat. No. 6,324,479 (issued on Nov. 27, 2001), all incorporated herein by reference for all purposes.

Levels of various constituents of a cell are known to change in response to drug treatments and other perturbations of the cell's biological state. Measurements of a plurality of such "cellular constituents" therefore contain a wealth of information about the effect of perturbations and their effect on the cell's biological state. Such measurements typically comprise measurements of gene expression levels of the type discussed above, but may also include levels of other cellular components such as, but by no means limited to, levels of protein abundances, or protein activity levels. The collection of such measurements is generally referred to as the "profile" of the cell's biological state.

The number of genes in a *S. cerevisiae* cell is typically on the order of more than 6,000 genes. The profile of a particular cell is therefore typically of high complexity. Any one perturbing agent may cause a small or a large number of cellular constituents to change their abundances or activity levels. Thus, identifying the particular cellular constituents which are associated with a certain biological pathway, such as the glucan synthase pathway, provides a difficult and challenging task.

In order to efficiently monitor and study a particular biological pathway, it is necessary to have a "read-out" or reporter of the pathway which allows measurement of an alteration of the pathway. Many biological pathways, however, do not have reliable reporters associated with them. Therefore, there is a need in the art to identify reporter genes, which are associated with a particular biological pathway. The present invention provides such reporter genes and methods of using such reporters to monitor the state of the glucan synthase pathway in *S. cerevisiae* and additionally, methods of using those reporter genes to screen chemical libraries and natural products for novel antifungal agents.

3.0 SUMMARY OF THE INVENTION

The present invention relates to methods of using nucleotide sequences from the promoter region of at least one of seven *S. cerevisiae* genes whose expression is an indicator of the inhibition or modulation of the glucan synthase pathway in *S. cerevisiae*. This invention envisions using at least one target polynucleotide sequence, each target polynucleotide sequence being operably linked to the promoter region of one of the seven glucan synthase pathway reporter ("GSPR") genes, to screen chemical libraries and natural products for molecules which can be used as antifungal agents for use against a variety of fungal pathogens. This invention also envisions using the methods of the invention to assay the efficacy of and/or specificity of antifungal agents, and/or to monitor the activity of the glucan synthase pathway.

One aspect of the invention provides a method for determining whether a molecule affects the function or activity of a glucan synthase pathway in a *S. cerevisiae* cell comprising: (a) contacting the cell with, or recombinantly expressing within the cell, the molecule; (b) determining whether the RNA expression or protein expression in said cell corresponding to at least one target polynucleotide sequence is changed in step (a) relative to the expression of said target polynucleotide sequence in the absence of the molecule, each said target polynucleotide sequence being regulated by a promoter native to a gene selected from the group consisting of YOL113W (SKM1), YNR066C, YLR121C (YPS3), YHR209W, YKL161C, YAR050W (FLO1), YFR030W (MET10), and homologs of each of the foregoing; and (c) determining that the molecule affects the function or activity of the glucan synthase pathway if the expression is changed, or determining that the molecule does not affect the function or activity of the glucan synthase pathway if the expression is unchanged. In a particular embodiment, the invention further comprises the step of determining that the molecule inhibits glucan synthase synthesis if a cell contacted with the molecule exhibits a lower level of glucan synthase than a cell which is not contacted with said molecule. In a preferred embodiment, the step of determining whether the RNA expression or protein expression of a target polynucleotide sequence regulated by a promoter native to YOL113W (SKM1) is changed. In another embodiment, the step of determining whether the RNA expression or protein expression has changed comprises determining whether RNA expression is changed. In still another embodiment, the step of determining whether the RNA expression or protein expression has changed comprises determining whether protein expression is changed. In a specific embodiment, the step of determining whether the RNA or protein expression in the cell has changed comprises determining whether RNA or protein expression of at least two of said target polynucleotide sequences is changed. In a specific embodiment, the step of determining whether the RNA or protein expression in the cell has changed comprises determining whether RNA or protein expression of at least three of said target polynucleotide sequences is changed. In another embodiment, the step of determining whether said molecule inhibits glucan synthase synthesis, comprises determining that the molecule inhibits glucan synthase synthesis if the expression of said target polynucleotide sequence in step (a) is increased relative to the expression of said target polynucleotide sequence in the absence of the molecule. In a preferred embodiment, the *S. cerevisiae* cell is a cell that recombinantly expresses said target polynucleotide sequence. In a particular embodiment, wherein step (a) comprises contacting the cell with the molecule, step (a) is carried out in a liquid high throughput-like assay. In another embodiment, wherein step (a) comprises contacting the cell with the molecule, step (a) is carried out in a solid plate halo assay. In another embodiment, wherein step (a) comprises contacting the cell with the molecule, step (a) is carried out in an agar overlay assay. In another preferred embodiment, the cell comprises a promoter region of at least one gene selected from the group consisting of YOL113W (SKM1), YNR066C, YLR121C (YPS3), YHR209W, YKL161C, YAR050W (FLO1), YFR030W (MET10), and homologs of each of the foregoing, each promoter region being operably linked to a marker gene; and wherein step (b) comprises determining whether the RNA expression or protein expression of the marker gene(s) is changed in step (a) relative to the expression of said marker gene in the absence of the molecule. In a preferred embodiment, the marker gene is selected from the group consisting of green fluorescent protein, red fluorescent protein, blue fluorescent protein, luciferase, LEU2, LYS2, ADE2, TRP1, CAN1, CYH2, GUS, CUP1 and chloramphenicol acetyl transferase.

Another aspect of the invention provides a method for determining the effect of a molecule upon the function or activity of the glucan synthase pathway comprising: (a) contacting a *S. cerevisiae* cell with, or recombinantly expressing within the cell the molecule; (b) detecting a change in RNA expression or protein expression in said cell of at least one target polynucleotide sequence relative to the expression of said target polynucleotide sequence in the absence of the molecule, each said target polynucleotide sequence being regulated by a promoter native to a gene selected from the group consisting of YOL113W (SKM1), YNR066C, YLR121C (YPS3), YHR209W, YKL161C, YAR050W (FLO1), YFR030W (MET10), and homologs of each of the foregoing; and (c) determining the effect of the molecule upon the function or activity of the glucan synthase pathway based upon the change in RNA expression or protein expression. In one embodiment, step (a) comprises contacting the cell with said molecule. In another embodiment, step (a) comprises recombinantly expressing within the cell the molecule. In yet another embodiment, step (b) comprises detecting an increase in said RNA or protein expression, and step (c) comprises determining that said effect of the molecule is to inhibit the function or activity of the glucan synthase pathway.

Another aspect of the invention provides a method for monitoring the activity of the glucan synthase pathway in a *S. cerevisiae* cell exposed to a molecule comprising (a) contacting the cell with, or recombinantly expressing within the cell, the molecule; (b) determining whether the RNA expression or protein expression in said cell of at least one target polynucleotide sequence is changed in step (a) relative to the expression of said target polynucleotide sequence in the absence of the molecule, each said target polynucleotide sequence being regulated by a promoter native to a gene selected from the group consisting of YOL113W (SKM1), YNR066C, YLR121C (YPS3), YHR209W, YKL161C, YAR050W (FLO1), YFR030W (MET10), and homologs of each of the foregoing; and (c) determining that the activity of the glucan synthase pathway in said cell is changed if the expression is determined to be changed in step (b), or determining that the activity of the glucan synthase pathway in said cell is unchanged if the expression is determined to be unchanged in step (b). In one embodiment of the invention, step (a) comprises contacting the cell with said molecule. In another embodiment of the invention, step (a) comprises recombinantly expressing within the cell the molecule. In yet another embodiment of the invention, step (b) comprises determining that said expression is increased, and step (c) comprises determining that the activity of the glucan synthase pathway is inhibited.

In a preferred embodiment, at least one target polynucleotide sequence comprises YOL113W (SKM1). In another preferred embodiment, at least one target polynucleotide sequence is selected from the group consisting of YOL113W (SKM1), YNR066C, YLR121C (YPS3), YHR209W, YKL161C, YAR050W (FLO1), YFR030W (MET10) and homologs of each of the foregoing.

Another aspect of the invention provides a method for identifying a molecule that modulates the expression of a glucan synthase pathway target polynucleotide sequence comprising: (a) recombinantly expressing in a *S. cerevisiae* cell, or contacting a *S. cerevisiae* cell with, at least one candidate molecule; and (b) measuring the RNA or protein expression in said cell of at least one target polynucleotide sequence, each said target polynucleotide sequence being regulated by a promoter native to a gene selected from the group consisting of YOL113W (SKM1), YNR066C, YLR121C (YPS3), YHR209W, YKL161C, YAR050W (FLO1), YFR030W (MET10), and homologs of each of the foregoing, wherein an increase or decrease in the expression of said target polynucleotide sequence relative to the expression of said target polynucleotide sequence in the absence of said candidate molecule indicates that the molecule modulates expression of the glucan synthase pathway target polynucleotide sequence.

Yet another aspect of the invention provides a method for determining whether a first *S. cerevisiae* cell is mutant for a glucan synthase pathway gene comprising: (a) in said first *S. cerevisiae* cell, determining the RNA or protein expression of at least one target polynucleotide sequence, each target polynucleotide sequence being regulated by a promoter native to a gene selected from the group consisting of YOL113W (SKM1), YNR066C, YLR121C (YPS3), YHR209W, YKL161C, YAR050W (FLO1), YFR030W (MET10), and homologs of each of the foregoing, wherein said cell is not being exposed to an inhibitor of the glucan synthase pathway; (b) determining whether the RNA and/or protein expression of said at least one target polynucleotide sequence determined in step (a) is changed relative to the RNA and/or protein expression of said at least one target polynucleotide sequence in a second *S. cerevisiae* cell which is believed to be wildtype for glucan synthase genes; and (c) determining that the first *S. cerevisiae* cell is mutant for a glucan synthase pathway gene if the expression is determined to be changed in step (a), or determining that the first *S. cerevisiae* cell is not mutant for a glucan synthase pathway gene if the expression is determined to be unchanged in step (b). In another embodiment, the invention further comprises determining the RNA or protein expression of one or both of YAR050W (FLO1) and YFR030W (MET10), and homologs of each of the foregoing, in said first *S. cerevisiae* cell; and wherein step (c) further comprises determining that the first *S. cerevisiae* cell is mutant for said glucan synthase pathway gene if the expression of one or both of YAR050W (FLO1) and YFR030W (MET10) is determined to be unchanged.

4.0 BRIEF DESCRIPTION OF THE DRAWINGS

FIG. 1. Nucleotide sequence of a region of *S. cerevisiae* glucan synthase pathway gene YOL113W (SKM1) (SEQ ID NO: 1) and predicted amino acid sequence (SEQ ID NO: 2). The region comprises 3218 nucleotides. Bolded nucleotide sequence (SEQ ID NO: 3) illustrates promoter region of YOL113W used herein.

FIG. 2. Nucleotide sequence of a region of *S. cerevisiae* glucan synthase pathway gene YNR066C (SEQ ID NO: 4) and predicted amino acid sequence (SEQ ID NO: 5). The region comprises 2561 nucleotides. Bolded nucleotide sequence (SEQ ID NO: 6) illustrates promoter region of YNR066C used herein.

FIG. 3. Nucleotide sequence of a region of *S. cerevisiae* glucan synthase pathway gene YLR121C (YPS3) (SEQ ID NO: 7) and predicted amino acid sequence (SEQ ID NO: 8). The region comprises 2777 nucleotides. Bolded nucleotide sequence (SEQ ID NO: 9) illustrates promoter region of YLR121C (YPS3) used herein.

FIG. 4. Nucleotide sequence of a region of *S. cerevisiae* glucan synthase pathway gene YHR209W (SEQ ID NO: 10) and predicted amino acid sequence (SEQ ID NO: 11). The region comprises 2126 nucleotides. Bolded nucleotide sequence (SEQ ID NO: 12) illustrates promoter region of YHR209W used herein.

FIG. 5. Nucleotide sequence of a region of *S. cerevisiae* glucan synthase gene YKL161C (SEQ ID NO: 13) and predicted amino acid sequence (SEQ ID NO: 14). The region comprises 2552 nucleotides. Bolded nucleotide sequence (SEQ ID NO: 15) illustrates promoter region of YKL161C used herein.

FIG. 6. Nucleotide sequence of a region of *S. cerevisiae* glucan synthase gene YAR050W (FLO1) (SEQ ID NO: 16) and predicted amino acid sequence (SEQ ID NO: 17). The region comprises 5864 nucleotides. Bolded nucleotide sequence (SEQ ID NO: 18) illustrates promoter region of YAR050W (FLO1) used herein.

FIG. 7. Nucleotide sequence of a region of *S. cerevisiae* glucan synthase gene YFR030W (MET10) (SEQ ID NO: 19) and predicted amino acid sequence (SEQ ID NO: 20). The region comprises 4358 nucleotides. Bolded nucleotide sequence (SEQ ID NO: 21) illustrates promoter region of YFR030W (MET10) used herein.

FIG. 8. Change in gene expression of roughly 6,000 reporter genes in a GRM exposed to 5 μg/ml ascosteroside in 1% DMSO.

Figure 9:
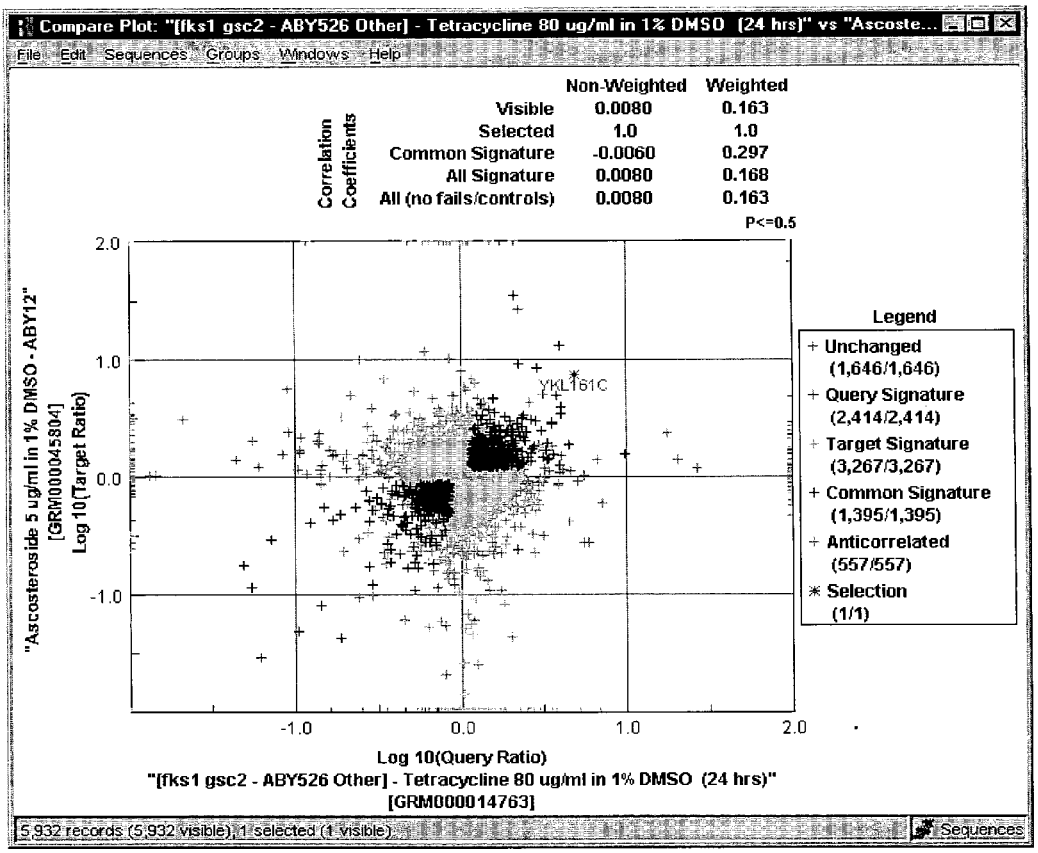

FIG. 9. Comparison of expression profile of GRM exposed to 5 μg/ml ascosteroside in 1% DMSO versus the expression profile for the double-mutant FKS1/GSC2 (consisting of a knockout of the GSC2 (FKS2) gene and downregulation of a tetracycline repressible promoter operatively linked to the FKS 1 gene). Data points marked "selection" are correlated in their expression responses between the two treatments. YKL161C is highly up-regulated in both treatments.

Figure 10:
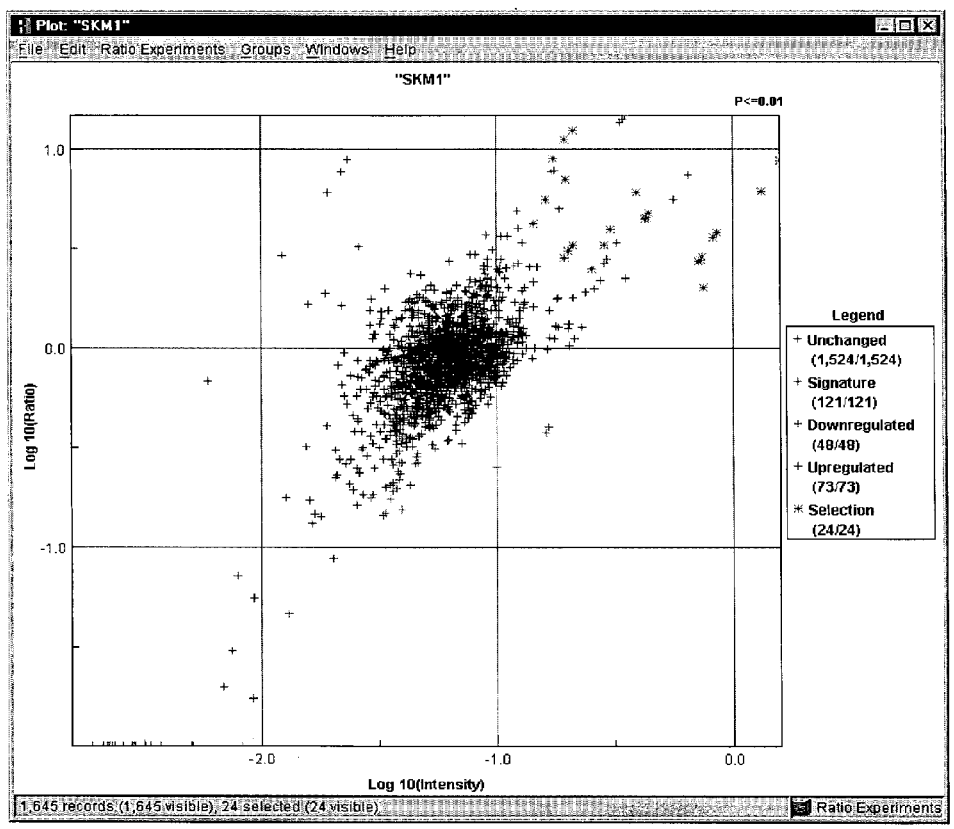

FIG. 10. Expression profile plotting ratio (Log 10) versus intensity (Log 10) for candidate glucan synthase pathway reporter gene YOL 113W (SKM 1) for 1,645 treatments. Data points marked "selection" represent the 24 experiments in the "*S. cerevisiae*/Genome Reporter Matrix" data set that are comprised of either compounds that inhibit glucan synthase or mutations in the glucan synthase genes. These 24 data points are all highly up-regulated indicating that blocks in the glucan synthase pathway cause significant up-regulation of the cited reporter construct.

FIG. 1*l*. Expression profile plotting ratio (Log 10) versus intensity (Log 10) for candidate glucan synthase pathway reporter gene YCR101C for 1,527 treatments. Data points marked "selection" represent the 24 experiments in the "*S. cerevisiae*/Genome Reporter Matrix" data set that are comprised of either compounds that inhibit glucan synthase or mutations in the glucan synthase genes. The low intensity and "wedge type" plot for YCR101C indicate that this reporter produces spurious results that make it a less desirable GS pathway reporter.

Figure 12:
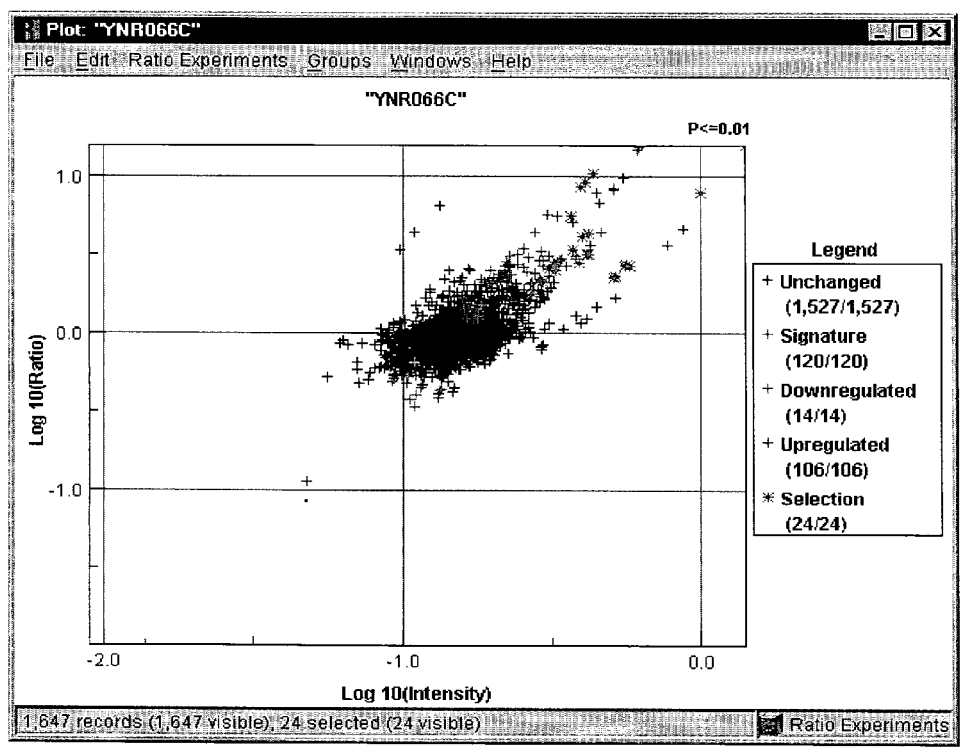

FIG. 12. Expression profile plotting ratio (Log 10) versus intensity (Log 10) for candidate glucan synthase pathway reporter gene YNR066C for 1,647 treatments. Data points marked "selection" represent the 24 experiments in the "S. cerevisiae/Genome Reporter Matrix" data set that are comprised of either compounds that inhibit glucan synthase or mutations in the glucan synthase genes. These 24 data points are all highly up-regulated indicating that blocks in the glucan synthase pathway cause significant up-regulation of the cited reporter construct.

Figure 13:
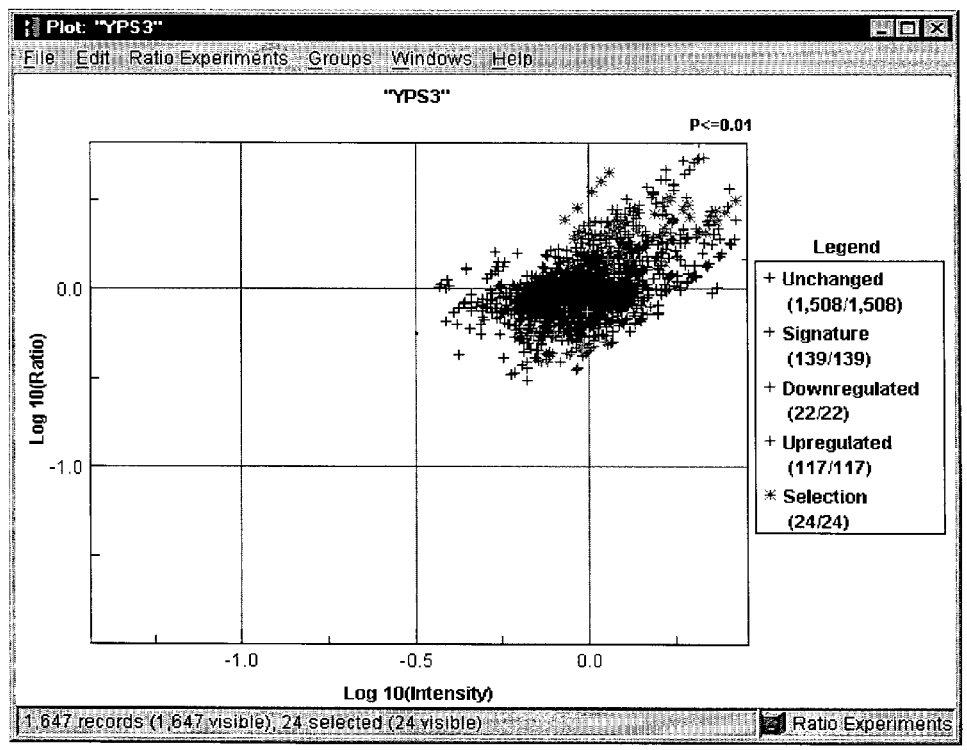

FIG. 13. Expression profile plotting ratio (Log 10) versus intensity (Log 10) for candidate glucan synthase pathway reporter gene YLR121C (YPS3) for 1,647 treatments. Data points marked "selection" represent the 24 experiments in the "S. cerevisiae/Genome Reporter Matrix" data set that are comprised of either compounds that inhibit glucan synthase or mutations in the glucan synthase genes. These 24 data points are all highly up-regulated indicating that blocks in the glucan synthase pathway cause significant up-regulation of the cited reporter construct.

Figure 14:
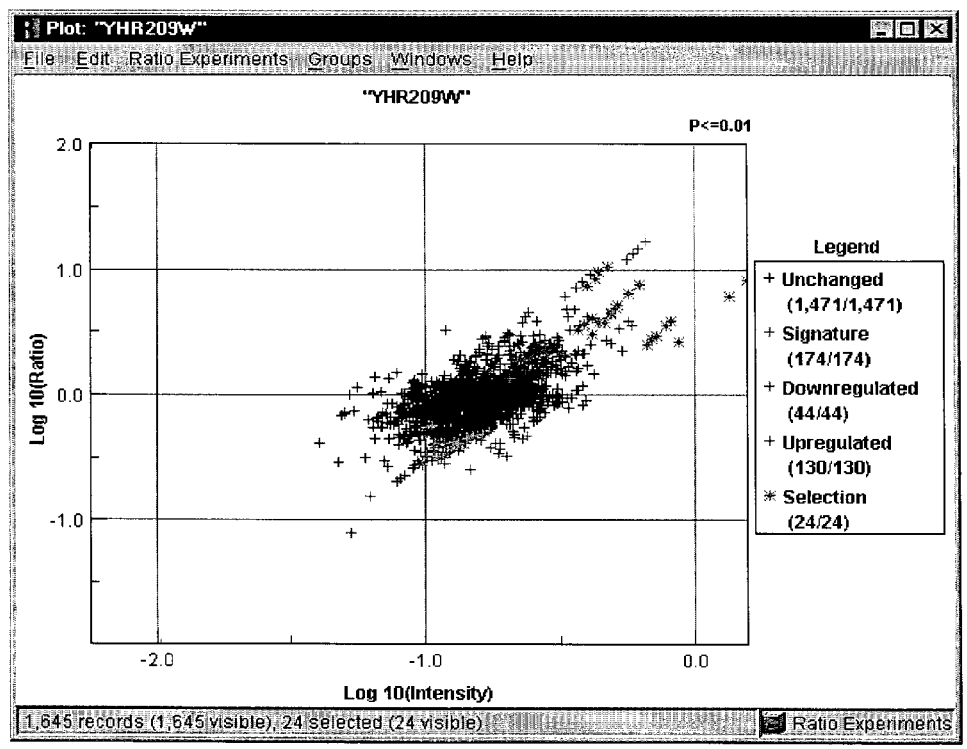

FIG. 14. Expression profile plotting ratio (Log 10) versus intensity (Log 10) for candidate glucan synthase pathway reporter gene YHR209W for 1,645 treatments. Data points marked "selection" represent the 24 experiments in the "S. cerevisiae/Genome Reporter Matrix" data set that are comprised of either compounds that inhibit glucan synthase or mutations in the glucan synthase genes. These 24 data points are all highly up-regulated indicating that blocks in the glucan synthase pathway cause significant up-regulation of the cited reporter construct.

Figure 15:
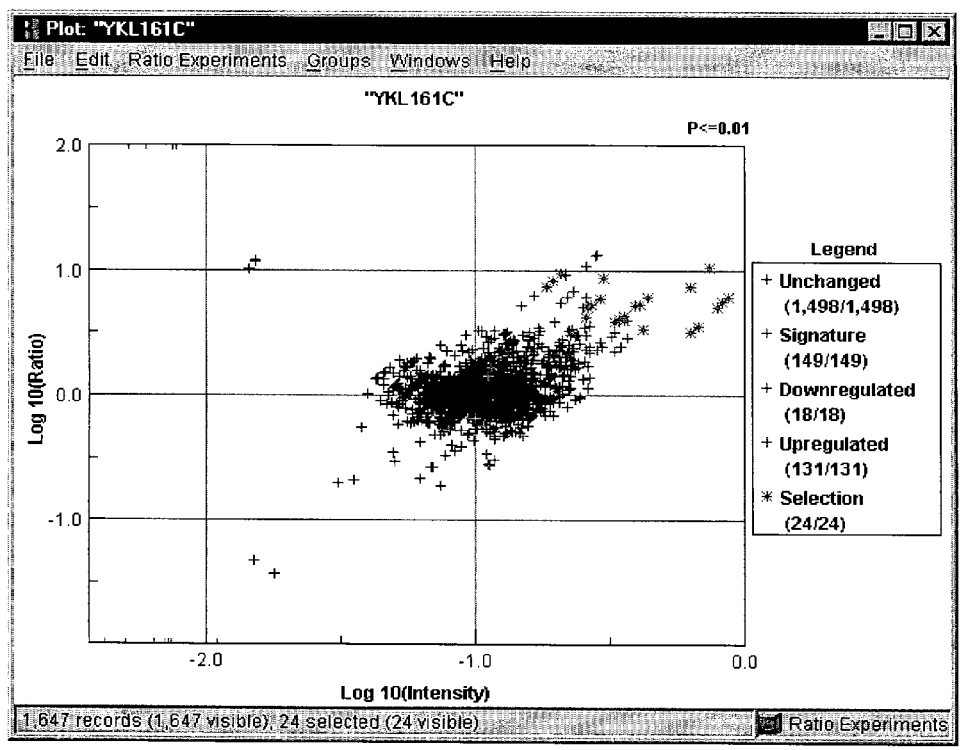

FIG. 15. Expression profile plotting ratio (Log 10) versus intensity (Log 10) for candidate glucan synthase pathway reporter gene YKL161C for 1,647 treatments. Data points marked "selection" represent the 24 experiments in the "S. cerevisiae/Genome Reporter Matrix" data set that are comprised of either compounds that inhibit glucan synthase or mutations in the glucan synthase genes. These 24 data points are all highly up-regulated indicating that blocks in the glucan synthase pathway cause significant up-regulation of the cited reporter construct.

Figure 16:
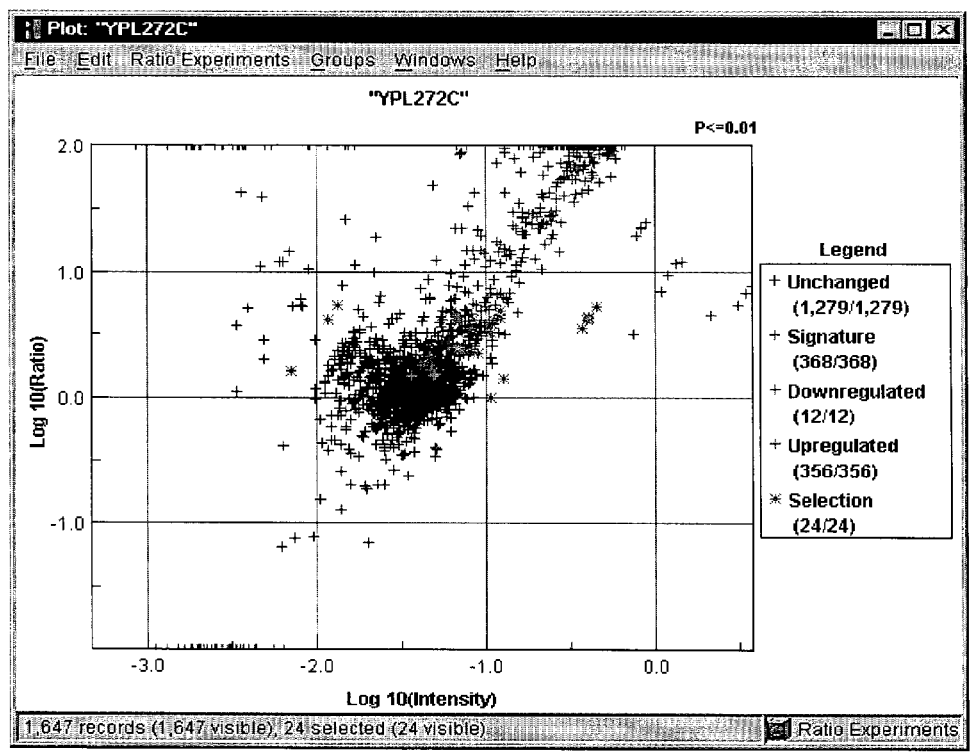

FIG. 16. Expression profile plotting ratio (Log 10) versus intensity (Log 10) for candidate glucan synthase pathway reporter gene YPL272C for 1,647 treatments. Data points marked "selection" represent the 24 experiments in the "S. cerevisiae/Genome Reporter Matrix" data set that are comprised of either compounds that inhibit glucan synthase or mutations in the glucan synthase genes. These 24 data points are either not up-regulated or show some of the lowest ratios of induction out of the 356 experiments that significantly up-regulated YPL272C, indicating that the cited reporter would not make for a useful GS pathway reporter.

Figure 17:
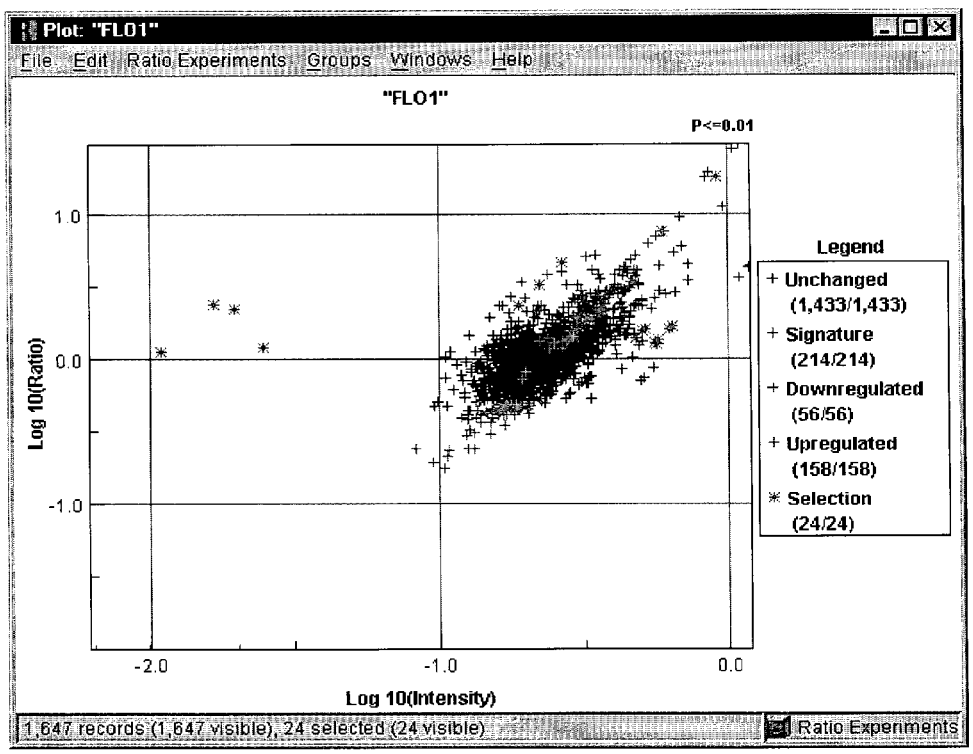

FIG. 17. Expression profile plotting ratio (Log 10) versus intensity (Log 10) for candidate glucan synthase pathway reporter gene YAR050W (FLO1) for 1,647 treatments. Data points marked "selection" represent the 24 experiments in the "S. cerevisiae/Genome Reporter Matrix" data set that are comprised of either compounds that inhibit glucan synthase or mutations in the glucan synthase genes. The cited reporter shows a normal ratio vs. intensity plot.

Figure 18:
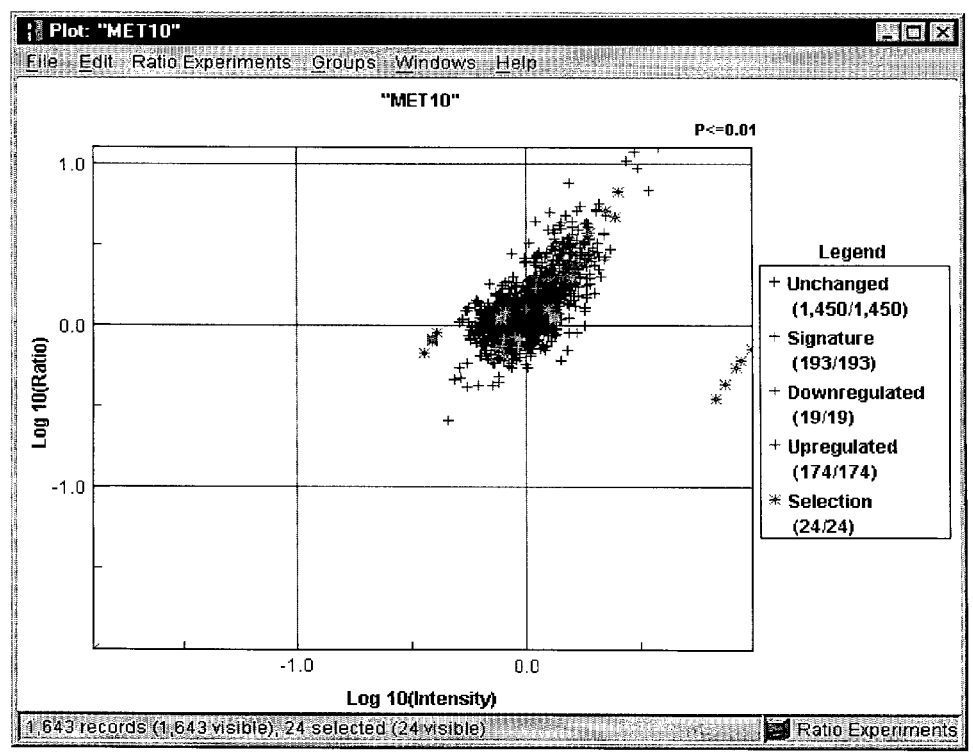

FIG. 18. Expression profile plotting ratio (Log 10) versus intensity (Log 10) for candidate glucan synthase pathway reporter gene YFR030W (MET10) for 1,647 treatments. Data points marked "selection" represent the 24 experiments in the "S. cerevisiae/Genome Reporter Matrix" data set that are comprised of either compounds that inhibit glucan synthase or mutations in the glucan synthase genes. The cited reporter shows a normal ratio vs. intensity plot.

Figure 19:
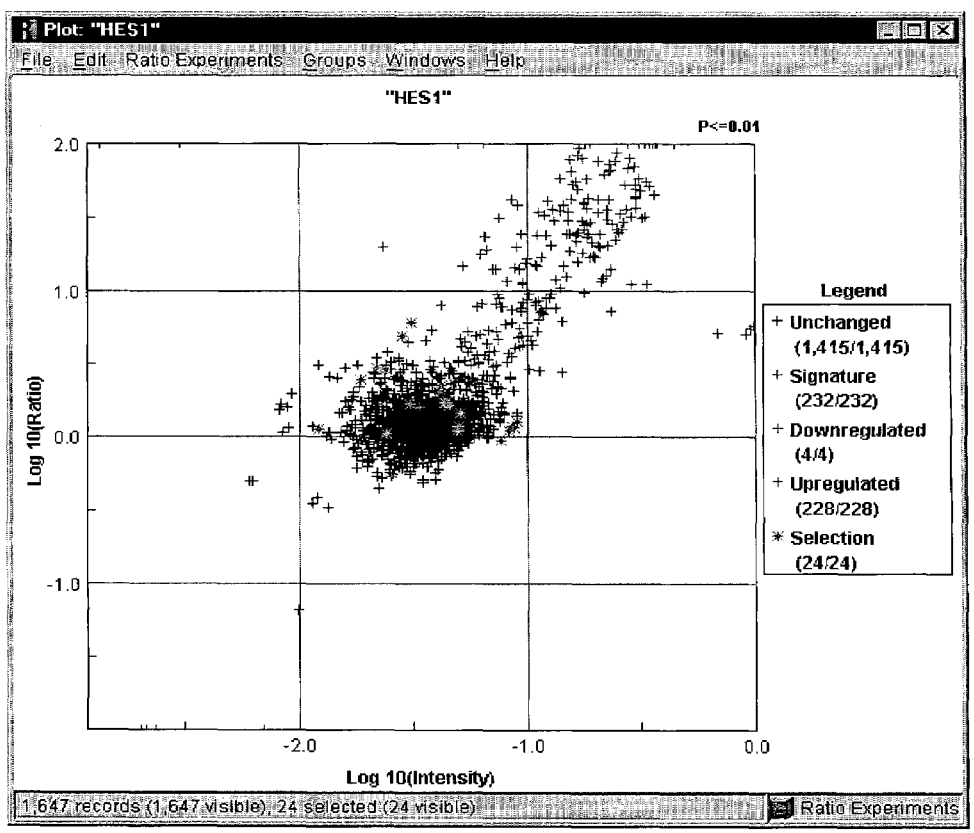

FIG. 19. Expression profile plotting ratio (Log 10) versus intensity (Log 10) sterol biosynthesis pathway reporter gene YOR237W (HES1) for 1,647 treatments. Data points marked "selection" represent the 24 experiments in the "S. cerevisiae/Genome Reporter Matrix" data set that are comprised of either compounds that inhibit glucan synthase or mutations in the glucan synthase genes. Note that the cited reporter is not significantly up-regulated by any of the 24 GS experiments.

Figure 20:
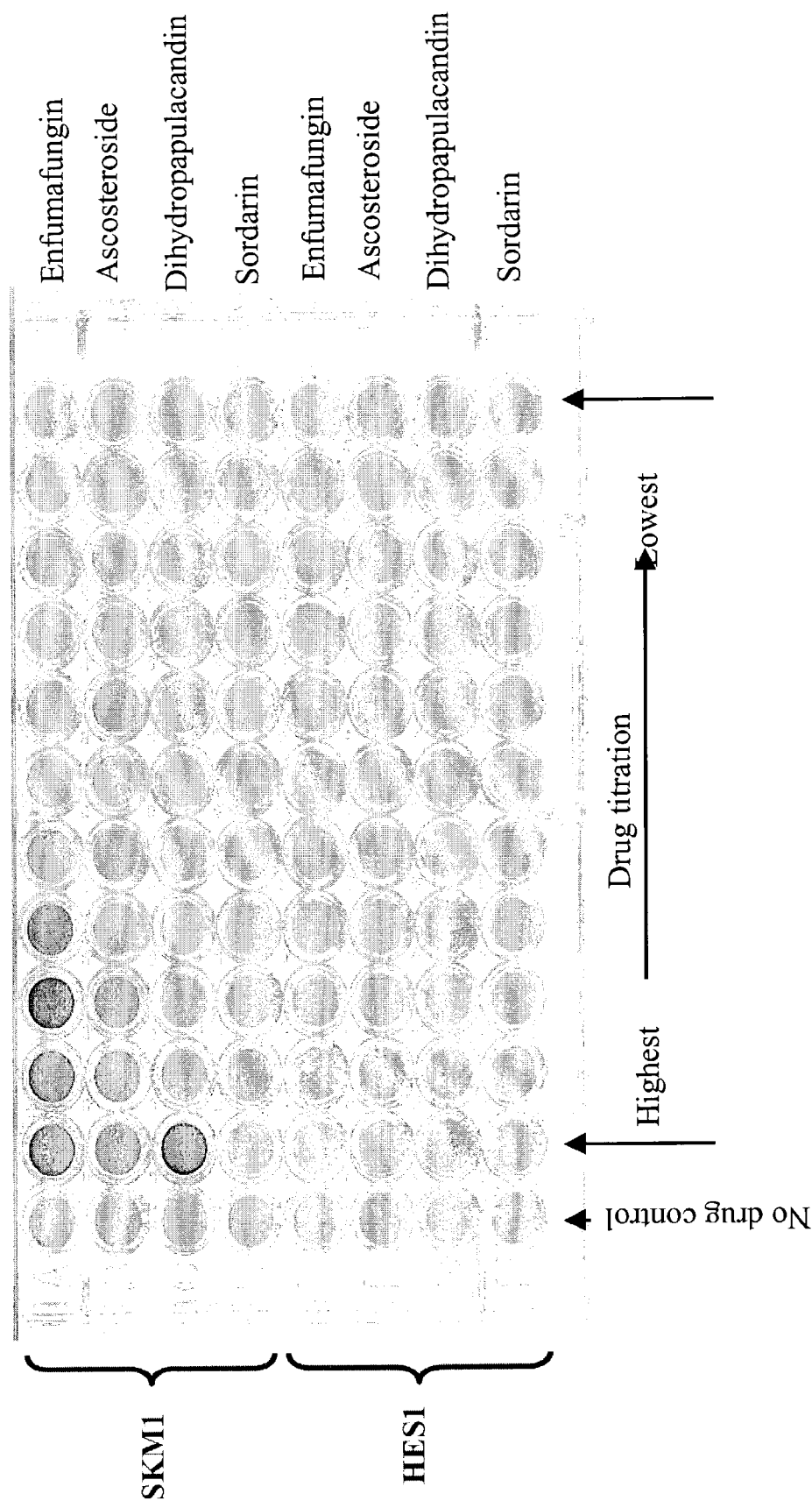

FIG. 20. Fluorescence results of SKM1-GFP fusion and HES1-GFP fusion for serial dilutions of four known antifungal compounds ascosteroside, enfumafungin, dihydropapulacandin, sordarin, with column 1 representing control with no drug added.

Figure 21:
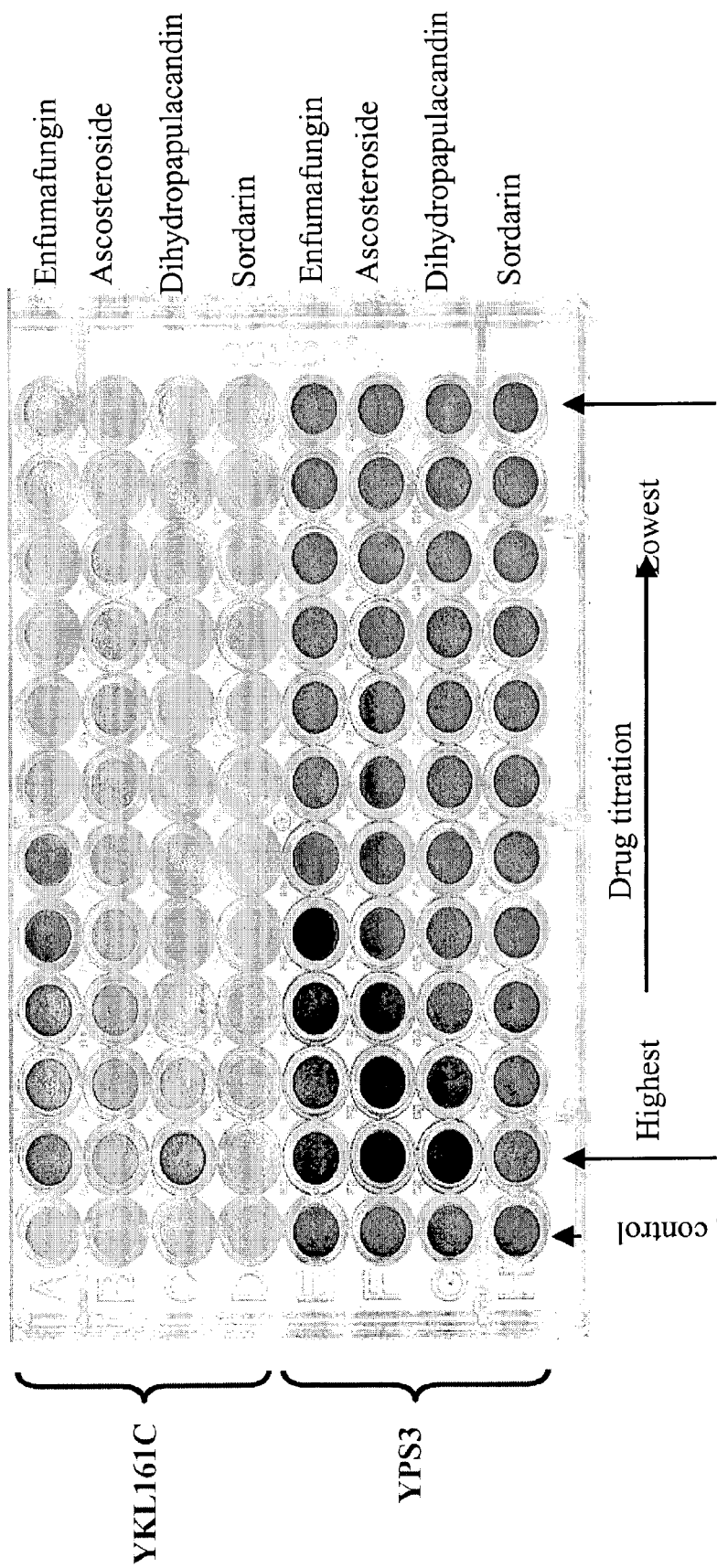

FIG. 21. Fluorescence results of YKL161C-GFP fusion and YPS3-GFP fusion for serial dilutions of four known antifungal compounds ascosteroside, enfumafungin, dihydropapulacandin, sordarin, with column 1 representing control with no drug added.

Figure 22:
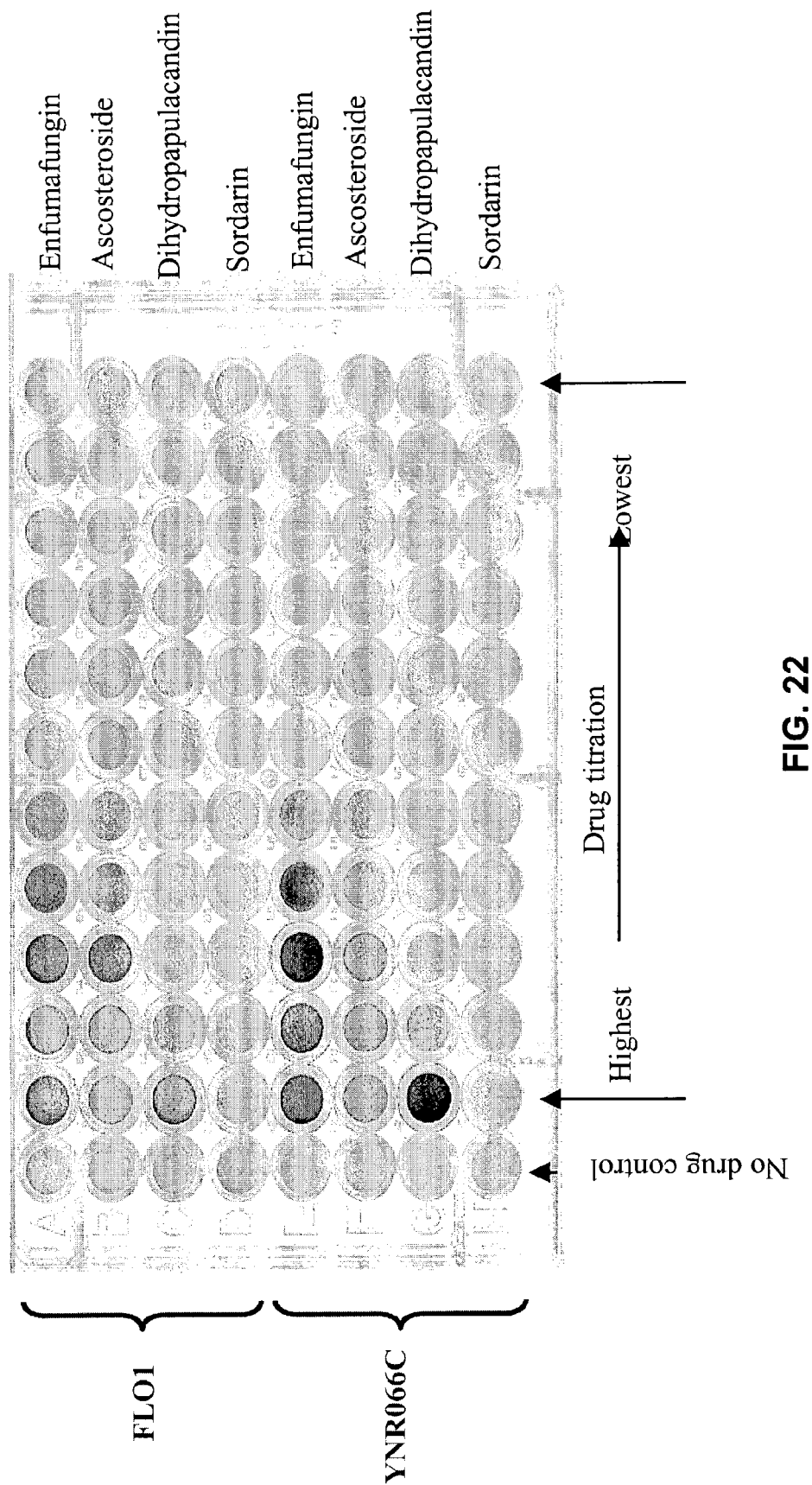

FIG. 22. Fluorescence results of FLO1-GFP fusion and YNR066C-GFP fusion for serial dilutions of four known antifungal compounds ascosteroside, enfumafungin, dihydropapulacandin, sordarin, with column 1 representing control with no drug added.

Figure 23:
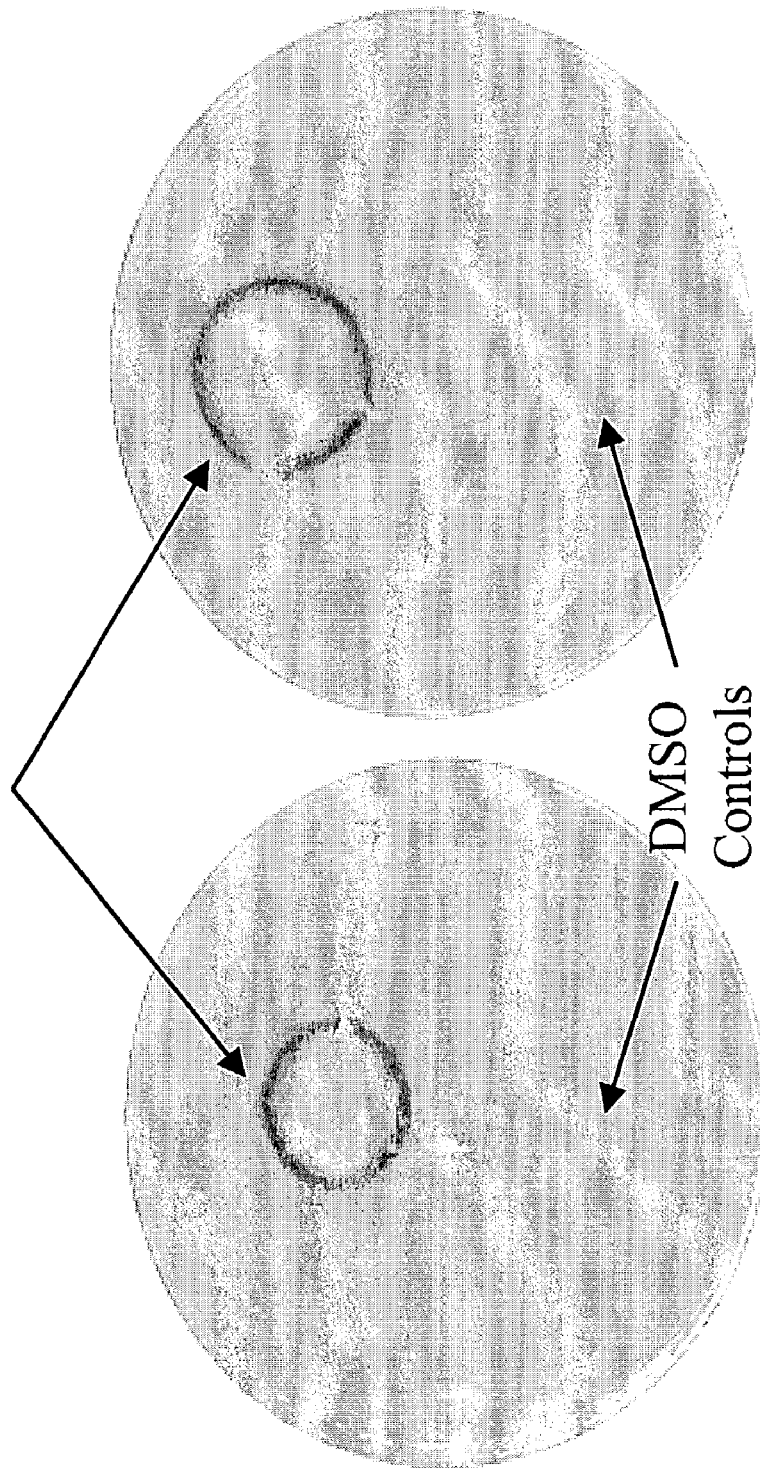

FIG. 23. Results from solid plate halo assay showing different concentrations of enfumafungin (200 µg/ml and 1 mg/ml) upregulating SKM1 reporter and DMSO control showing no zone of growth inhibition and no induction of YOL113W (SKM1) reporter.

5.0 DETAILED DESCRIPTION OF THE INVENTION

The present invention relates to methods of using nucleotide sequences from the promoter region of at least one of seven S. cerevisiae genes whose expression is an indicator of the inhibition or modulation of the glucan synthase pathway in S. cerevisiae. This invention envisions using at least one target polynucleotide sequence, each target polynucleotide sequence being operably linked to the promoter region of one of the seven glucan synthase pathway reporter genes, to screen chemical libraries and natural products for molecules which can be used as antifungal agents for use against a variety of fungal pathogens. This invention also envisions using the methods of the invention to assay the efficacy of and/or specificity of antifungal agents, and/or to monitor the activity of the glucan synthase pathway.

As used herein, a reporter gene for the glucan synthase pathway is any gene for which a change in expression of its encoded RNA or protein is indicative of a change in the activity of the glucan synthase pathway. Thus, the reporter genes of this invention are useful for analyzing the activity of the glucan synthase pathway, e.g., to identify potential antifungal molecules which inhibit or modulate the glucan synthase pathway.

In a preferred embodiment, the cell used in the methods of the invention is a S. cerevisiae cell. A preferred S. cerevisiae strain is one for which the genomic sequence is known, such as strain S288C or substantially isogeneic derivatives of it (see, e.g., Dujon et al., 1994, Nature 369:371–378; Bussey et al, 1995, Proc. Natl. Acad. Sci. U.S.A. 92:3809–3813; Feldmann et al., 1994, E.M.B.O.J. 13:5795–5809; Johnston et al., 1994, Science 265:2077–2082; Galibert et al., 1996, E.M.B.O.J. 15:2031–2049). However, other strains may be used as well. S. cerevisiae strains are available, e.g., from American Type Culture Collection, 10801 University Boulevard, Manassas, Va. 20110–2209. Well-established methods are available for controllably modifying expression of S. cerevisiae genes.

Standard techniques for manipulating *S. cerevisiae* are described in C. Kaiser, S. Michaelis, & A. Mitchell, 1994, *Methods in Yeast Genetics: A Cold Spring Harbor Laboratory Course Manual,* Cold Spring Harbor Laboratory Press, New York; and Sherman et al., 1986, *Methods in Yeast Genetics: A Laboratory Manual,* Cold Spring Harbor Laboratory, Cold Spring Harbor. N.Y. Many other strains commonly known and available in the art can be used.

Although for simplicity the disclosure often makes reference to single cells (e.g., "RNA is isolated from a cell exposed to a particular drug"), it will be understood by those of skill in the art that more often than not, any particular step of the invention will be carried out using a plurality of genetically similar cells, e.g., from a cultured cell line. Such similar cells are referred to herein as a "cell type."

In accordance with the present invention there may be employed conventional molecular biology, biology, microbiology, and recombinant DNA techniques within the skill of the art. Such techniques are explained fully in the literature. See, e.g., Sambrook, Fritsch & Maniatis, *Molecular Cloning: A Laboratory Manual,* Second Edition (1989) Cold Spring Harbor Laboratory Press, Cold Spring Harbor, N.Y. (herein "Sambrook et al., 1989"); *DNA Cloning: A Practical Approach,* Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel et al. (eds.), *Current Protocols in Molecular Biology,* John Wiley & Sons, Inc. (2002).

The invention is illustrated by way of examples set forth in Section 6 below which disclose, inter alia, the identification and characterization of reporters genes of the *S. cerevisiae* glucan synthase pathway, using Genome Reporter Matrix™ ("GRM") technology (see U.S. Pat. No. 5,569, 588, issued Oct. 29, 1996, and U.S. Pat. No. 5,777,888, issued Jul. 7, 1998, both of which are hereby incorporated by reference in their entireties).

For clarity of disclosure, and not by way of limitation, the detailed description of the invention is divided into the subsections which follow.

5.1 Glucan Synthase Pathway Reporter Genes

The present invention relates to methods of using nucleotide sequences from at least one of seven *S. cerevisiae* genes whose expression is an indicator of the inhibition or modulation of the glucan synthase pathway in *S. cerevisiae* ("glucan synthase pathway reporter" genes or "GSPR" genes). The present invention identifies the following genes as glucan synthase pathway reporter genes: YOL113W (SKM1), YNR066C, YLR121C (YPS3), YHR209W, YKL161C, YAR050W (FLO1) and YFR030W (MET10). The nucleotide sequences of the reporter genes that are used in the present invention may comprise the entire glucan synthase pathway reporter gene, the 5' region of the gene including the promoter and all or part of the coding region, or a fragment, conservatively modified variant or homolog thereof which retains the indicator function of the glucan synthase pathway reporter gene. As used herein the term "promoter" refers to a nucleotide sequence that is necessary and sufficient in the presence of the appropriate factors to promote transcription of an operatively linked sequence. In preferred embodiments, the promoter of a GSPR gene is selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, and homologs of each of the foregoing. Homologs of SEQ ID NO: 3, SEQ ID NO: 6, SEQ ID NO: 9, SEQ ID NO: 12, SEQ ID NO: 15, SEQ ID NO: 18, and SEQ ID NO: 21 may contain conservative substitutions, additions or deletions, which do not effect the ability of the sequence to promote transcription of an operatively linked sequence. The ability of a GSPR gene promoter sequence homolog to promote transcription of an operatively linked sequence may be tested by any method known in the art. One non-limiting method comprises linking a detectable marker gene such as GFP to a putative promoter sequence, detecting the transcription level of the marker gene, and comparing said transcription level to that produced in the absence of having promoter sequence.

Specific embodiments of the invention provide methods for using a combination of genes to construct a more specific reporter for the glucan synthase pathway. In this embodiment, more than one glucan synthase pathway reporter gene is used as a reporter for the glucan synthase pathway. By way of example, and not limitation, expression of two glucan synthase pathway reporter genes such as YOL113W (SKM1), and YNR066C, may be detected simultaneously as a reporter for the glucan synthase pathway. Such co-detection can serve to increase the sensitivity of a reporter of the glucan synthase pathway. In another embodiment of the invention, expression from 2 or 3, 3 to 5, or 5 to 7 glucan synthase pathway reporter genes is detected simultaneously as a reporter system for the glucan synthase pathway.

In other embodiments of the invention, the promoter region of a glucan synthase pathway reporter gene or loci are used as reporters for the glucan synthase pathway. In this embodiment, the promoter region of a glucan synthase pathway reporter gene may be operably linked to a marker gene encoding a detectable or selectable product such as but not limited to GFP (green fluorescent protein) or an RNA transcript. Detection or selection of the marker RNA or protein is used to determine the activation or inhibition of the glucan synthase pathway reporter gene in response to controlled stimuli. Additionally, more than one promoter or regulatory region may be utilized simultaneously. For example, the promoter from a first gene such as YOL113W (SKM1) may be fused to a marker such as GFP, and a promoter from a second glucan synthase pathway reporter gene such as YNR066C, may be fused to BFP (blue fluorescent protein). Detection of both protein markers simultaneously can thus provide higher sensitivity than detection of either marker alone. Thus, in this embodiment, the reporter of the glucan synthase pathway is a combination of two or more genes. In another embodiment of the invention, expression from 2 or 3, 3 to 5, or 5 to 7 glucan synthase pathway reporter genes is detected simultaneously as a reporter system for the glucan synthase pathway.

5.2 Methods for Obtaining Glucan Synthase Pathway Reporter Genes

A glucan synthase pathway reporter gene or promoter region thereof can be isolated from any source, preferably from a *S. cerevisiae* cell or genomic library. Methods for obtaining genes are well known in the art, as described in Sambrook et al., 1989, supra.

Alternatively, a glucan synthase pathway reporter gene or promoter region can be obtained by chemical synthesis, by cDNA cloning, or by the cloning of genomic DNA, or fragments thereof, purified from the desired cell (See, for example, Sambrook et al., 1989, supra; Glover, D. M. (ed.), 1985, *DNA Cloning: A Practical Approach,* MRL Press, Ltd., Oxford, U.K. Vol. I, II). Clones derived from genomic DNA may contain regulatory and intron DNA regions in addition to coding regions; clones derived from cDNA will not contain intron sequences.

Any *S. cerevisiae* cell can serve as the nucleic acid source for the molecular cloning of a glucan synthase pathway reporter gene or promoter region. The DNA may be obtained by standard procedures known in the art from cloned DNA (e.g., a DNA "library"), including EST libraries and cDNA libraries prepared from cells with high level expression of the protein.

Identification of a specific DNA fragment containing a desired glucan synthase pathway reporter gene or promoter region can be accomplished by various methods known in the art. For example, a portion of a glucan synthase pathway reporter gene exemplified below can be purified and labeled to prepare a labeled probe, and the generated DNA may be screened by nucleic acid hybridization to the labeled probe (Benton and Davis, *Science* 196:180, 1977; Grunstein and Hogness, *Proc. Natl. Acad. Sci. U.S.A.* 72:3961, 1975). Those DNA fragments with substantial homology to the probe, such as an allelic variant, will hybridize. In a specific embodiment, high stringency hybridization conditions are used to identify an allelic variant of a glucan synthase pathway reporter gene.

Glucan synthase pathway reporter gene sequences can also be obtained, e.g., by polymerase chain reaction (PCR) amplification of genomic DNA or cloned sequences. PCR primers are preferably chosen based on the glucan synthase pathway reporter gene sequences described herein. Computer programs that are well known in the art are useful in the design of primers with the required specificity and optimal amplification properties, such as Oligo version 5.0 (National Biosciences). PCR methods are well known in the art, and are described, for example, in Innis et al., eds., 1990, *PCR Protocols: A Guide to Methods and Applications,* Academic Press Inc., San Diego, Calif.

An alternative means for generating the nucleotide sequences of the invention is by synthesis of synthetic polynucleotides or oligonucleotides, e.g., using N-phosphonate or phosphoramidite chemistries (Froehler et al., 1986, *Nucleic Acid Res.* 14:5399–5407; McBride et al., 1983, *Tetrahedron Lett.* 24:246–248).

A glucan synthase pathway reporter gene derivative can be made by altering encoding nucleotide sequences by substitutions, additions or deletions that provide for functionally equivalent molecules. Alternatively, non-functional mutant forms of the glucan synthase pathway reporter proteins, that may for example compete with the wild-type glucan synthase pathway reporter protein in the glucan synthase pathway, but which are less effective, can be prepared for use in screening potential antifungal molecules.

Due to the degeneracy of nucleotide coding sequences, other DNA sequences which encode substantially the same amino acid sequence as a glucan synthase pathway reporter gene may be used in the practice of the present invention. These include but are not limited to allelic genes and nucleotide sequences comprising all or portions of glucan synthase pathway reporter genes which are altered by the substitution of different codons that encode the same amino acid residue within the sequence, thus producing a silent change.

The nucleotide sequences encoding glucan synthase pathway reporter gene promoter regions, derivatives and analogs of the invention can be produced by various methods known in the art. The manipulations which result in their production can occur at the gene or protein level. For example, a cloned glucan synthase pathway reporter gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of a derivative or analog of a glucan synthase pathway reporter gene, care should be taken to ensure that the modified gene remains within the same translational reading frame as the gene, uninterrupted by translational stop signals, in the gene region where the desired activity is encoded.

Additionally, a glucan synthase pathway reporter gene can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, *J. Biol. Chem.* 253:6551; Zoller and Smith, 1984, *DNA* 3:479–488; Oliphant et al., 1986, Gene 44:177; Hutchinson et al, 1986, *Proc. Natl. Acad. Sci. U.S.A.* 83:710), etc. PCR techniques are preferred for site directed mutagenesis (see Higuchi, 1989, "Using PCR to Engineer DNA", in *PCR Technology: Principles and Applications for DNA Amplification,* H. Erlich, ed., Stockton Press, Chapter 6, pp. 61–70).

5.3 Methods for Measuring Glucan Synthase Pathway Reporter Gene Expression

This invention provides several methods for detecting changes in gene expression or protein expression, including but not limited to the expression of glucan synthase pathway reporter genes, and marker genes operably linked to glucan synthase pathway reporter genes of the invention. Assays for changes in gene expression are well known in the art (see e.g, PCT Publication No. WO 96/34099, published Oct. 31, 1996, which is incorporated by reference herein in its entirety). Such assays may be performed in vitro using transformed cell lines, immortalized cell lines, or recombinant cell lines.

The RNA expression or protein expression of a target polynucleotide sequence, regulated by a promoter native to a glucan synthase pathway reporter gene may be measured by measuring the amount or abundance of RNA (as RNA or cDNA) or protein. The target polynucleotide sequence may be, but is not limited to, a marker gene or a glucan synthase pathway reporter gene coding region. For example, the target polynucleotide may be an untranslated region of a gene. In a specific embodiment, the target polynucleotide sequence is an open reading frame. In a preferred embodiment, the target polynucleotide sequence is a marker gene. In particular, the assays may detect the presence of increased or decreased expression of a target polynucleotide sequence on the basis of increased or decreased mRNA expression (using, e.g., nucleic acid probes), increased or decreased levels of protein products (using, e.g., antibodies thereto), or increased or decreased levels of expression of a marker gene (e.g., GFP) operably linked to a glucan synthase pathway reporter 5' promoter region in a recombinant construct.

The present invention envisions monitoring changes in glucan synthase pathway reporter gene expression or marker gene expression by any expression analysis technique known to one of skill in the art, including but not limited to, differential display, serial analysis of gene expression (SAGE), nucleic acid array technology, oligonucleotide array technology, GeneChip expression analysis, reverse-transcription polymercase chain reaction (RT-PCR), dot blot hybridization, northern blot hybridization, subtractive hybridization, protein chip arrays, Western blot, immunoprecipitation followed by SDS PAGE, immunocytochemistry, proteome analysis and mass-spectrometry of two-dimensional protein gels.

Methods of gene expression profiling to measure changes in gene expression are well-known in the art, as exemplified by the following references describing RT-PCR (Bachmair et al., 2002, *Methods Mol. Biol.* 193:103–116; Muller et al., 2002, *Biotechniques*, 32(6):1372–4, 1376, 1378–9), subtractive hybridization (Wang and Brown, 1991, *Proc. Natl. Acad. Sci. U.S.A.* 88:11505–11509), differential display (Liang and Pardee, 1992, *Science* 257:967–971), SAGE (Velculescu et al., 1995, *Science* 270:484–487), proteome analysis (Humphery-Smith et al., 1997, *Electrophoresis* 18:1217–1242; Dainese et al., 1997, *Electrophoresis* 18:432–442), and hybridization-based methods employing nucleic acid arrays (Heller et al., 1997, *Proc. Natl. Acad. Sci. U.S.A.* 94:2150–2155; Lashkari et al., 1997, *Proc. Natl. Acad. Sci. U.S.A.* 94:13057–13062; Wodicka et al., 1997, *Nature Biotechnol.* 15:1259–1267). Microarray technology is described in more detail below.

In one series of embodiments, various expression analysis techniques may be used to identify molecules which affect glucan synthase pathway reporter gene expression or marker gene expression, by comparing a cell line expressing a glucan synthase pathway reporter gene or marker gene under the control of a glucan synthase pathway reporter gene promoter sequence in the absence of a test molecule to a cell line expressing the same glucan synthase pathway reporter gene or marker gene under the control of a glucan synthase pathway reporter gene promoter sequence in the presence of the test molecule. In a preferred embodiment, expression analysis techniques are used to identify a molecule which upregulates glucan synthase pathway reporter gene or marker gene expression upon treatment of a cell with the molecule.

In a specific embodiment, nucleic acid array technology (preferably small arrays) may be used to determine a glucan synthase pathway reporter gene or marker gene expression pattern in a *S. cerevisiae* cell not exposed to a test molecule for comparison with a glucan synthase pathway reporter gene or marker gene expression pattern of a *S. cerevisiae* cell exposed to a test molecule. In a preferred embodiment, a protocol similar to the one described in *Gene Cloning and Expression Technologies*, 2002, eds. Weiner and Lu, BioTechniques Press, Chpt. 36 is utilized.

5.3.1 Preferred Methods for Monitoring Reporter Gene Expression of a Glucan Synthase Pathway Reporter Gene Heterologous Glucan Synthase Pathway Reporter Gene Construct In a preferred embodiment, the *S. cerevisiae* cell being assayed for glucan synthase pathway reporter gene expression contains a fusion construct of at least one glucan synthase pathway reporter gene transcriptional promoter region, each operably linked to a marker gene expressing a detectable and/or selectable product. In preferred embodiments, the promoter of a GSPR gene is selected from the group consisting of SEQ ID NO: 3, SEQ ID NO: 6, SEQ ID NO: 9, SEQ ID NO: 12, SEQ ID NO: 15, SEQ ID NO: 18 and SEQ ID NO: 21. In one embodiment, the detectable or selectable product is a protein. In another embodiment, the detectable product is a RNA. Increased expression of a marker gene operably linked to a glucan synthase pathway reporter gene promoter indicates increased expression of that glucan synthase pathway reporter gene.

The marker gene is a sequence encoding a detectable or selectable marker, the expression of which is regulated by at least one glucan synthase pathway reporter gene promoter region in the heterologous construct used in the present invention. In one embodiment, the detectable or selectable marker is a protein. In another embodiment, the detectable marker is a RNA. Preferably, the assay is carried out in the absence of background levels of marker gene expression (e.g., in a cell that is mutant or otherwise lacking in the marker gene). If not already lacking in endogenous marker gene activity, cells mutant in the marker gene may be selected by known methods, or the cells can be made mutant in the marker gene by known gene-disruption methods prior to introducing the marker gene (Rothstein, 1983, *Meth. Enzymol.* 101:202–211).

A marker gene of the invention may be any gene which encodes a detectable and/or selectable product. The detectable marker may be any molecule that can give rise to a detectable signal, e.g., a fluorescent protein or a protein that can be readily visualized or that is recognizable by a specific antibody or that gives rise enzymatically to a signal. The selectable marker can be any molecule which can be selected for its expression, e.g., which gives cells a selective advantage over cells not having the selectable marker under appropriate (selective) conditions. In preferred aspects, the selectable marker is an essential nutrient in which the cell in which the interaction assay occurs is mutant or otherwise lacks or is deficient, and the selection medium lacks such nutrient. In one embodiment, one type of marker gene is used to detect gene expression. In another embodiment, more than one type of marker gene is used to detect gene expression.

Preferred marker genes include but are not limited to, green fluorescent protein (GFP) (Cubitt et al., 1995, *Trends Biochem. Sci.* 20:448–455), red fluorescent protein, blue fluorescent protein, luciferase, LEU2, LYS2, ADE2, TRP1, CAN1, CYH2, GUS, CUP1 or chloramphenicol acetyl transferase (CAT). Other marker genes include, but are not limited to, URA3, HIS3 and/or the lacZ genes (see e.g., Rose and Botstein, 1983, *Meth. Enzymol.* 101:167–180) operably linked to GAL4 DNA-binding domain recognition elements. Alam and Cook disclose non-limiting examples of detectable marker genes that can be operably linked to a glucan synthase pathway reporter gene promoter region (Alam and Cook, 1990, *Anal. Biochem.* 188:245–254).

In a specific embodiment of the invention, a marker gene is operably linked to the promoter of one of the following genes: YOL113W (SKM1), YNR066C, YLR121C (YPS3), YHR209W, YKL161C, YAR050W (FLO1) and YFR030W (MET10). In an alternate embodiment, more than one different marker gene is used to detect transcriptional activation, e.g., one encoding a detectable marker, and one or more encoding one or more different selectable marker(s), or e.g., different detectable markers. Expression of the marker genes can be detected and/or selected for by techniques known in the art (see e.g. U.S. Pat. Nos. 6,057,101 and 6,083,693).

Methods to construct a suitable reporter construct are disclosed herein by way of illustration and not limitation and any other methods known in the art may also be used. In a preferred embodiment, the reporter gene construct is a chimeric reporter construct comprising a marker gene that is transcribed under the control of a glucan synthase pathway reporter gene promoter sequence comprising all or a portion of a promoter region of YOL113W (SKM1), YNR066C, YLR121C (YPS3), YHR209W, YKL161C, YAR050W (FLO1) and YFR030W (MET10). If not already a part of the DNA sequence, the translation initiation codon, ATG, is provided in the correct reading frame upstream of the DNA sequence.

Vectors comprising all or portions of the gene sequences of YOL113W (SKM1), YNR066C, YLR121C (YPS3), YHR209W, YKL161C, YAR050W (FLO1) and YFR030W (MET10) useful in the construction of recombinant S. cerevisiae reporter gene constructs and cells are provided. The vectors of this invention also include those vectors comprising DNA sequences which hybridize under stringent conditions to the YOL113W (SKM1), YNR066C, YLR121C (YPS3), YHR209W, YKL161C, YAR050W (FLO1) and YFR030W (MET10) gene sequences, and conservatively modified variations thereof.

The vectors of this invention may be present in transformed or transfected cells, cell lysates, or in partially purified or substantially pure forms. DNA vectors may contain a means for amplifying the copy number of the gene of interest, stabilizing sequences, or alternatively may be designed to favor directed or non-directed integration into the host cell genome.

Given the strategies described herein, one of skill in the art can construct a variety of vectors and nucleic acid molecules comprising functionally equivalent nucleic acids. DNA cloning and sequencing methods are well known to those of skill in the art and are described in an assortment of laboratory manuals, including Sambrook et al., 1989, supra; and Ausubel et al., 2002 Supplement.

Transformation and other methods of introducing nucleic acids into a host cell (e.g., transfection, electroporation, liposome delivery, membrane fusion techniques, high velocity DNA-coated pellets, viral infection and protoplast fusion) can be accomplished by a variety of methods which are well known in the art (see, for instance, Ausubel, supra, and Sambrook, supra). S. cerevisiae cells of the invention can be transformed or transfected with an expression vector, such as a plasmid, a cosmid, or the like, wherein the expression vector comprises the DNA of interest. Alternatively, the cells may be infected by a viral expression vector comprising the DNA or RNA of interest.

Particular details of the transfection and expression of nucleotide sequences are well documented and are understood by those of skill in the art. Further details on the various technical aspects of each of the steps used in recombinant production of foreign genes in expression systems can be found in a number of texts and laboratory manuals in the art (see, e.g., Ausubel et al., 2002, herein incorporated by reference).

Detecting Reporter Gene Expression

In accordance with the present invention, reporter gene expression can be monitored at the RNA or the protein level. In a specific embodiment, molecules which affect reporter gene expression may be identified by detecting differences in the level of marker protein expressed by S. cerevisiae cells contacted with a test molecule versus the level of marker protein expressed by S. cerevisiae cells in the absence of the test molecule.

Protein expression can be monitored using a variety of methods which are well known to those of skill in the art. For example, protein chips or protein microarrays (e.g., ProteinChip™, Ciphergen Biosystem) and two-dimensional electrophoresis (see e.g., U.S. Pat. No. 6,064,754 which is incorporated herein by reference in its entirety) can be utilized to monitor protein expression levels. As used herein "two-dimensional electrophoresis") (2D-electrophoresis) means a technique comprising isoelectric focusing, followed by denaturing electrophoresis, generating a two-dimensional gel (2D-gel) containing a plurality of proteins. Any protocol for 2D-electrophoresis known to one of ordinary skill in the art can be used to analyze protein expression by the reporter genes of the invention. For example, 2D electrophoresis can be performed according to the methods described in O'Farrell, 1975, J. Biol. Chem. 250: 4007–4021.

Liquid High Throughput-Like Assay

In a preferred embodiment, a liquid high throughput-like assay is used to determine the protein expression level of a glucan synthase pathway reporter gene. The following exemplary, but not limiting, assay may be used:

A reporter construct is transformed into a wild-type S. cerevisiae strain, e.g., ABY12. Cultures from solid media plates are used to innoculate liquid cultures in Casamino Acids media or an equivalent media. This liquid culture is grown and then diluted in Casamino Acids media or an equivalent media.

A test molecule is selected for the assay, preferably but not necessarily along with a negative control molecule. The test molecule and negative control molecule are separately added to an assay plate containing multiple wells and serially diluted (e.g., 1 to 2) into Casamino Acids media plus DMSO in sequential columns, so that each plate contains a range of concentrations of each drug. If a negative control is being used, one column of each plate may be used as a "no drug" control, containing only Casamino Acids media plus DMSO. The skilled artisan will note that different assay plates may be used, such as those with 96, 384 or 1536 well format.

An aliquot of liquid reporter strain is added to each well of the serial dilution plates from above and mixed. The assay plates are then incubated. In a preferred embodiment, they are incubated at 30° C. for ~24 hours.

After incubation the assay plates are analyzed for detectable marker gene product. In a preferred embodiment, the assay plates are imaged in a Molecular Dynamics Fluorimager SI to measure the fluorescence from the GFP reporters.

The results are then analyzed, as described above. If the drug is an inhibitor of the glucan synthase pathway, the specific glucan synthase pathway reporters will show increases in fluorescence for the higher drug concentrations versus the lower drug concentrations and/or the no drug controls.

Solid Plate Halo Assay

Additionally, the following exemplary, but not limiting, assay may be used to determine whether a test molecule inhibits the glucan synthase pathway in S. cerevisiae. Although described for YOL113W (SKM1), other glucan synthase pathway reporter genes, and homologs thereof, may be used.

A YOL113W (SKM1) reporter construct is transformed into wild-type S. cerevisiae strain, such as ABY12. The transformed strain is grown on a solid Casamino Acids media or an equivalent media plate. The culture from the solid media plate is used to inoculate a liquid culture in (e.g., Casamino Acids) media. This liquid culture is grown and then diluted in Casamino Acids media or an equivalent media. Cell culture is then spread evenly over the surface of each of two or more solid agar media plates to form a lawn of the YOL113W (SKM1) reporter strain on each plate.

Two blank paper discs are placed on top of the agar surface of each plate evenly spaced apart. In one embodiment, 6 mm diameter paper discs are used. (Becton Dickinson #231039). On one plate, an appropriate amount of the test molecule is spotted onto one of the two paper discs (low concentration treatment) and DMSO is spotted on the other paper disc as a control. On another plate a greater amount of the test molecule is spotted onto one of the two paper discs (high concentration treatment) and DMSO is spotted on the other paper disc as a control. The plates are then incubated.

After incubation, the assay plates are analyzed as described above. In a preferred embodiment, the assay plates are imaged in a Molecular Dynamics Fluorimager SI to measure the fluorescence from the GFP reporters. The results are then examined, an increase in glucan synthase pathway reporter gene expression and a halo of no growth around the test molecule disc indicating inhibition of the glucan synthase pathway and the potential utility of the test molecule as an antifungal agent.

Agar Overlay Method

Agar overlays may be prepared by any method known in the art, including but not limited to the preparation methods described herein below. An agar plate is prepared containing a layer of bacteria or fungi. An second layer, an agar overlay, containing a GSPR strain is placed over the first layer of agar. The plate is incubated and the second GSPR overlay layer is then examined for any effects of the natural products produced by the first agar layer containing the bacteria or fungal natural products. In one embodiment, following incubation, the plate is sprayed with a tetrazolium salt (e.g., MTT) which is converted to a formazan dye by the microorganism, thereby revealing inhibition zones of little or no growth as clear spots against a purple background. In one embodiment, the first agar layer is a grid of test strains, whereas the second agar layer comprises at least one GSPR reporter construct fusion strain. Any agar overlay method known to one of skill in the art may be modified and used in connection with the present invention including but not limited to those described in Rahalison, L. et al., 1991, *Phytochem. Anal.* 2: 199–203 and Rios et al., 1988, *J. Ethnopharmacol.* 23(2–3): 127–49, hereby incorporated by reference in their entireties.

5.3.2 Other Methods for Monitoring Reporter Gene Expression of a Glucan Synthase Pathway Reporter Gene Small Array Assays GSPR gene expression may be monitored on the nucleic acid level or the protein level using small arrays as described in Martel et al., Proc. SPIE Vol. 4626: 35–43, Biomedical Nanotechnology Architectures and Applications, D. Bornhop et al. eds., the contents of which are hereby incorporated by reference in its entirety. In a preferred embodiment, a multiplexed mRNA assay to measure the expression of 16 genes may be conducted as described below.

ArrayPlates contain the same 16-element array at the bottom of each well. In a preferred embodiment, the plate contains 96 wells. Each array element consists of a unique target ("anchor") polynucleotide sequence that incorporates a position-specific sequence. The binding specificity of the array elements may be modified to render them target-specific. This consists of a single hybridization step that modifies the binding specificity of the array elements. This is achieved using programming linker species. Each programming linker contains both an array element-binding oligonucleotide region and a target-specific region. The array is exposed to a mixture of programming linker species, each species hybridizes to its corresponding element in the array and presents its target-specific region at that position. If the target-specific region of the programming linker is also an oligonucleotide, then the array is capable of subsequently immobilizing other nucleic acids. If instead the target-specific region of the programming linker is an antibody, then the linker-modified array element exposes an antibody that can capture the corresponding protein antigen.

Genome Reporter Matrix™ Technology

One method of monitoring the expression of a GSPR gene are GSPR gene fusion constructs that are part of a Genome Reporter Matrix™ (GRM), or an equivalent thereof. The description below of the generation of gene expression profiles utilizing the Genome Reporter Matrix™ has been described essentially in U.S. Pat. Nos. 5,569,588, and 5,777,888, and Dimster-Denk, et al., 1999, *J. Lipid Research,* 40:850–860, all of which are incorporated herein by reference, in their entireties.

The promoter (and optionally, 5' upstream regulatory elements and/or 5' upstream untranslated sequences) of a *S. cerevisiae* glucan synthase pathway reporter ORF or a *S. cerevisiae* glucan synthase pathway reporter gene is fused to a marker gene creating a transcriptional and/or translational fusion of the promoter to the marker gene. The promoter and optional additional sequences comprise all the regulatory elements necessary for transcriptional (and optionally translational) control of an attached coding sequence. The marker gene is a detectable marker gene that can be any gene that, when expressed in a suitable host, encodes a product that can be detected by a quantitative assay. Any suitable assay may be used, including but not limited to enzymatic, calorimetric, fluorescence or other spectrographic assays, fluorescent activated cell sorting assay and immunological assays. Examples of suitable marker genes include, inter alia, green fluorescent protein (GFP), β-lactamase, lacZ, invertase, membrane bound proteins (e.g., CD2, CD4, CD8, the influenza hemagglutinin protein, and others well known in the art) to which high affinity antibodies directed to them exist or can be made routinely, fusion protein comprising membrane bound protein appropriately fused to an antigen tag domain (e.g., hemagglutinin or Myc and others well known in the art). In a preferred embodiment, the marker protein is GFP from the jellyfish *Aequorea victoria.* GFP is a naturally fluorescing protein that does not require the addition of any exogenous substrates for activity. The ability to measure GFP fluorescence in intact living cells makes it an ideal marker protein for the GRM or an equivalent matrix comprising living cells.

In a preferred embodiment, reporter constructs comprise the 5' region of the ORF comprising the promoter of the ORF and other expression regulatory sequences, and generally, the first four codons of the ORF fused in-frame to the green fluorescent protein. In a more preferred embodiment, approximately 1200 base-pairs of 5' regulatory sequence are included in each fusion. Only 228 *S. cerevisiae* ORFs (3.5%) possess introns. Of these 228 intron-containing ORFs, all but four contain only one intron. In these ORFs, fusions are created two to four codons past (3' to) the splice junction. Therefore, these fusions must undergo splicing in order to create a functional reporter fusion.

Each reporter fusion is preferably assembled in an episomal yeast shuttle vector (either CEN or 2 μ plasmid) or on a yeast integrating vector for subsequent insertion into the chromosomal DNA. In a preferred embodiment, the gene reporter constructs are built using a yeast multicopy vector. A multicopy vector is chosen to facilitate easy transfer of the reporter constructs to many different *S. cerevisiae* strain backgrounds. In addition, the vector replicates at an average of 10–20 copies per cell, providing added sensitivity for detecting genes that are expressed at a low level. In another preferred embodiment, the reporter constructs are maintained on episomal plasmids in *S. cerevisiae.*

In one embodiment, a plurality (all or a significant subset) of the resulting glucan synthase pathway reporter gene constructs is transformed into a strain of S. cerevisiae. The resulting strains constitute one embodiment of the Genome Reporter Matrix™. In another embodiment, the Genome Reporter Matrix™ comprises reporter gene constructs for all or a significant subset of the open reading frames of the S. cerevisiae genome.

Expression profiles can be produced by arraying wild type or mutant cells carrying the reporter fusion genes in growth media containing one or more different drugs, chemical compounds, and/or known or potential antifungal molecules and measuring changes in expression of the marker gene by the appropriate assay (see below). In a preferred embodiment, where the marker gene is GFP, measurement of changes in expression are done by measuring the amount of green light produced by the cells over time with an automated fluorescence scanner. Alternatively, the drug(s), chemical compound(s), and/or known or potential antifungal molecule(s) may be added to the S. cerevisiae cells after they have been arrayed onto growth media and then measuring changes in marker gene expression by the appropriate assay. In another embodiment, the test molecules are recombinantly expressed in the S. cerevisiae cells.

In a preferred embodiment, a natural product screen is used in the methods of the invention. In another preferred embodiment, a direct bioautography method is used in the methods of the invention. In a particularly preferred embodiment, an agar overlay screening assay is used.

Over 93% of the markers are detectable over background on rich medium. The reproducibility of individual reporters is high, with expression generally varying by less than 10%.

In one embodiment, the GRM is used to obtain gene expression information. The GRM is preferred to hybridization-based methods of profiling for several reasons. First, because the promoter-marker fusions include the first four amino acids of the native gene product, the response profiles are composites of both transcriptional and translational effects. The importance of being able to monitor both levels of response is underscored by the experience with bacterial antibiotics. Those antibiotics that work at the translational level have a greater therapeutic performance than those affecting transcription. Because hybridization-based methods can reveal only effects on transcription, profiling with the GRM provides a more complete view of the full spectrum of biological effects induced by exposure to drugs, compounds, and/or known or potential antifungal molecules.

Second, the GRM permits profiling of gene expression changes in living cells, which permits one to easily measure the kinetics of changes in gene response profiles in the same population of cells following exposure to different drugs and chemical agents.

Third, hybridization-based methods require relatively sophisticated molecular procedures to produce labeled cDNA, followed by a hybridization of labeled cDNA probes to target DNA arrays on slides or chips. The GRM requires only that being able to produce arrays of colonies and measure emitted light. These procedures are easier to scale up in an industrial setting than are sophisticated molecular biology methods, rendering data that is more straightforward to produce and more reproducible in nature.

Microarray Technology

The invention herein provides methods of using microarray technology to assay glucan synthase pathway reporter gene expression. Microarrays may be prepared by any method known in the art, including but not limited to the preparation methods described herein below.

In one embodiment, hybridization levels are measured by microarrays of probes consisting of a solid phase on the surface of which are immobilized a population of polynucleotides, such as a population of DNA or DNA mimics, or, alternatively, a population of RNA or RNA mimics. In preferred embodiments, a microarray comprises a support or surface with an ordered array of binding (e.g., hybridization) sites or "probes" for products of one or more of the genes in the genome of a cell or organism, preferably one, two, three, four, five, six or all seven of the glucan synthase pathway reporter genes. The polynucleotide molecules which may be analyzed by the present invention are from S. cerevisiae cells containing at least one promoter region from a glucan synthase pathway reporter gene. In a preferred embodiment, the polynucleotide molecules analyzed by the invention comprise RNA, including, but by no means limited to, total cellular RNA, poly(A)$^+$ messenger RNA (mRNA), fraction thereof, or RNA transcribed from cDNA (i.e., cRNA; see, e.g., Linsley & Schelter, U.S. patent application Ser. No. 09/411,074, filed Oct. 4, 1999).

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene.

In preferred embodiments, cDNAs from two different cells are hybridized to the binding sites of the microarray. In the case of drug responses, one cell is exposed to a test compound and another cell of the same type is not exposed to the test compound. The cDNA derived from each of the two cell types are differently labeled so that they can be distinguished. The relative abundance of an mRNA in two cells or cell lines is scored as perturbed (i.e., the abundance is different in the two sources of mRNA tested) or as not perturbed (i.e., the relative abundance is the same). It is, however, also advantageous to determine the magnitude of the relative difference in abundances for an mRNA in two cells or in two cell lines. This can be carried out, as noted above, by calculating the ratio of the emission of the two fluorophores used for differential labeling, or by analogous methods that will be readily apparent to those of skill in the art.

5.4 Molecules that May be Screened by the Methods of the Invention

This invention envisions using the glucan synthase pathway reporter genes of the invention to screen chemical libraries and natural products for molecules which can be used as antifungal agents against a variety of pathogenic fungal species. This invention also envisions using the reporter genes of the invention to assay the efficacy of and/or specificity of antifungal agents, and/or to monitor the activity of the glucan synthase pathway.

Any molecule, e.g. protein or non-protein organic pharmaceutical, with the potential capability of affecting any of the glucan synthase pathway reporter genes may be screened. In a preferred embodiment, a plurality of assay mixtures are run in parallel with different concentrations to obtain a differential response to the various concentrations. In another preferred embodiment, one of these concentrations serves as a negative control, i.e. at zero concentration or below the level of detection. This invention also envisions assaying the efficacy and/or specificity of antifungal agents.

In one embodiment of the invention, test molecules are contacted with the glucan synthase pathway reporter cells of the invention. In another embodiment, test molecules are recombinantly expressed in the glucan synthase pathway reporter cells.

Test molecules may be any of numerous chemical classes. In a specific embodiment, the test molecules are organic molecules, preferably small molecules, i.e., those having a molecular weight of more than 50 and less than about 2,500 daltons. In another specific embodiment, the test molecules comprise biomolecules including, but not limited to: peptides, saccharides, fatty acids, steroids, purines, pyrimidines, derivatives, structural analogs or combinations thereof.

The test molecules to be screened may be selected or derived from a wide variety of sources including libraries of synthetic and/or natural compounds. In a specific embodiment, the test molecules are purified compounds. In another embodiment, the test molecules are produced by an organism such as strains of bacteria or fungi, e.g., agar overlay assay. In a specific embodiment, the test molecules are produced by random and/or directed synthesis of one or more organic compounds, including but not limited to, expression of randomized oligonucleotides, oligopeptides and/or saccharides. Alternatively, libraries of natural compounds in the form of bacterial, fungal, plant and animal extracts are available from e.g. Pan Laboratories (Bothell, Wash.) or MycoSearch (NC), or are readily producible.

Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.).

Additionally, natural and synthetically produced libraries and compounds are readily modified through conventional chemical, physical, and biochemical means (Blondelle et al., Tib Tech, 14:60, 1996). In a specific embodiment, known compounds and/or known antifungal agents may be subjected to directed or random chemical modifications, such as acylation, alkylation, esterification, amidification, etc. to produce structural analogs. In another specific embodiment, test molecules may also be created using methods such as rational drug design or computer modelling.

In a specific embodiment of the invention, the natural products envisioned by the present invention are microorganisms and/or potential antifungal compounds produced by microorganisms. The following non-limiting procedure may be used to isolate microorganisms and/or potential antifungal compounds for use in the screening procedures described herein. The procedure described below was used to isolate the antifungal Ascosteroside, and is provided by way of example and not limitation (Gorman, J. A., et al., 1995, *J. Antibiotics*, 49(6): 547–552).

A sample of soil or other organic matter is collected and suspended in diluent (such as buffered saline), sonicated for several minutes and vortexed. This initial suspension is then diluted and aliquots are plated onto different types of nutrient agar and incubated at room temperature. After several days, colonies are subcultured onto agar medium and incubated for several days at room temperature. Test molecules may be selected from the colonies and then screened by the methods described herein. Other methods known in the art for screening natural products are contemplated by the instant invention, including but not limited to those described in McCormack et al., 1994, *Appl. Envir. Microbiology* 60(3): 927–931 and Bojase et al., 2002, *Planta Med.* 68:615–620, both of which are hereby incorporated by reference in their entireties.

In another specific embodiment, known or potential antifungal agent(s) serve as test molecules to determine the specificity and/or efficacy of the molecule. In a particular embodiment of the invention, known antifungal agents are tested for whether the antifungal agent affects the glucan synthase pathway.

In another embodiment of the invention, antisense oligonucleotides are screened for an ability to inhibit the glucan synthase pathway. More specifically, antisense oligonucleotides can be screened by identifying those oligonucleotides that inhibit transcription or translation of a glucan synthase pathway reporter reporter gene. Methods of producing antisense oligonucleotides are well-known in the art, see Castanotto, D. et al., 1998, *Antisense & Nucleic Acid Drug Development*, 8:1–13, herein incorporated by reference. In a preferred embodiment, antisense oligonucleotides are produced which are complementary to the mRNA of one or more glucan synthase pathway reporter gene(s). In a specific embodiment, antisense oligonucleotides are produced using derivatized or modified nucleotides in order to increase half-life or bioavailability.

In another aspect of the invention, antibodies are screened for their ability to inhibit the glucan synthase pathway by antagonizing or mimicking the activity of a glucan synthase pathway protein encoded by one the glucan synthase pathway reporter genes of the invention. The polypeptides encoded by the glucan synthase pathway reporter genes of this invention may be used to elicit polyclonal or monoclonal antibodies which bind to the glucan synthase pathway reporter gene product using a variety of techniques well known to those of skill in the art. Alternatively, peptides corresponding to specific regions of the polypeptide encoded by the glucan synthase pathway reporter gene may be synthesized and used to create immunological reagents according to well known methods.

Additionally, non-functional mutant forms of glucan synthase pathway proteins, that may for example compete with the wild-type glucan synthase pathway protein in the glucan synthase pathway, but which are less effective, can be screened as potential antifungal molecules.

5.5 Pharmaceutical Applications

Molecules identified by the methods of the present invention as having e.g., antifungal activity, can be used to treat diseases and disorders caused by a fungus, e.g., fungal infections. The present invention envisions the use of molecules identified by the methods of the present invention against several fungal species including but not limited to the pathogenic fungal species disclosed in Section 2.0 of the specification, particularly those listed in Table I below.

TABLE I

Fungi against which the molecules identified by the methods of the present invention may be used

| | |
|---|---|
| *Cryptococcus* spp. | *Candida* spp. |
| *Asperigillus* spp. | *Histoplasma* spp. |
| *Coccidioides* spp. | *Paracoccidioides* spp. |
| *Blastomyces* spp. | *Fusarium* spp. |
| *Sporothrix* spp. | *Trichosporon* spp. |
| *Rhizopus* spp. | *Pseudallescheria* spp. |
| *Paeciliomyces* spp. | *Alternaria* spp. |
| *Curvularia* spp. | *Exophiala* spp. |
| *Wangiella* spp. | *Dematiaceous fungi* |
| *Pneumocystis carninii* | *Fonsecaea pedrosoi* |
| *Scedosporium* spp. | *Acremonium strictum,* |
| *Bipolaris* spp. | *Cladophilophora bantiana,* |
| *Phialophora* spp. | *Pityrosporum* spp. |
| *Geotrichum* spp. | *Epidermophyton* spp. |

TABLE I-continued

Fungi against which the molecules identified
by the methods of the present invention may be used

| | |
|---|---|
| Epidermophyton floccosum | Malassezia spp. |
| Sporothrix spp. | Trichophyton spp. |
| Microsporum spp. | Hendersonula toruloidea |
| Scytalidium spp. | Scopulariopsis brevicaulis |
| Acremonium spp. | Piedraia hortae |

In particularly preferred embodiments, the molecules identified by the methods of the present invention are used against *Saccharomyces cerevisiae, Candida albicans, Schizosaccharomyces pombe, Aspergillus nidulans, Neurospora crassa* and *Cryptococcus neoformans.*

The molecules of the this invention may be used to treat fungal infections in a variety of subjects including but not limited to humans, non-human animals and crops including but not limited to dogs, cats, chickens, bovids, goats, pigs, horses, fish, birds, silkworms, and plants such as corn, wheat, rice and tobacco.

The molecules identified by the methods of the present invention may also be tested in yeast cell systems and heterologous host cell systems (e.g., human cells) to verify that they do not have undesirable side effects. In addition, the GRM can be used to make sure that the compounds do not adversely alter gene transcription (e.g., in an undesirable way). Of course, certain changes in gene expression may be inevitable and many of these will not be deleterious to the patient or host organism. Once lead molecules have been identified, these molecules can be refined further via rational drug design and other standard pharmaceutical techniques.

The molecules of this invention may be formulated into pharmaceutical compositions and administered in vivo at an effective dose to treat a particular disease or condition. Determination of a preferred pharmaceutical formulation and a therapeutically efficient dose regiment for a given application is within the skill of the art taking into consideration, for example, the condition and weight of the patient, the extent of desired treatment and the tolerance of the patient for the treatment.

Administration of the molecules, including isolated and purified forms, their salts or pharmaceutically acceptable derivatives thereof, may be accomplished using any conventionally accepted mode of administration.

The pharmaceutical compositions of this invention may be in a variety of forms, which may be selected according to the preferred modes of administration. These include, for example, solid, semi-solid and liquid dosage forms such as tablets, pills, powders, liquid solutions or suspensions, suppositories, and injectable and infusible solutions. The preferred form depends on the intended mode of administration and therapeutic application. Modes of administration may include oral, parenteral, subcutaneous, intravenous, intralesional or topical administration.

The molecules of this invention may, for example, be placed into sterile, isotonic formulations with or without cofactors which stimulate uptake or stability. The formulation is preferably liquid, or may be lyophilized powder. For example, the inhibitors may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Alternatively, the composition may be pressurized and contain a compressed gas, such as nitrogen or a liquified gas propellant. The liquified propellant medium and indeed the total composition is preferably such that the active ingredient does not dissolve therein to any substantial extent.

Dosage forms for topical or transdermal administration of a molecule of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The pharmaceutical compositions may also be administered using microspheres, microparticulate delivery systems or other sustained release formulations placed in, near, or otherwise in communication with affected tissues or the bloodstream. Suitable examples of sustained release carriers include semipermeable polymer matrices in the form of shaped articles such as suppositories or microcapsules. Implantable or microcapsular sustained release matrices include polylactides (U.S. Pat. No. 3,773,319; EP 58,481), copolymers of L-glutamic acid and gamma ethyl-L-glutamate (Sidman et al., 1985); poly(2-hydroxyethyl-methacrylate) or ethylene vinyl acetate (Langer et al., 1981, Langer, 1982).

The molecules of this invention may also be attached to liposomes, which may optionally contain other agents to aid in targeting or administration of the compositions to the desired treatment site. Attachment of the molecules to liposomes may be accomplished by any known cross-linking agent such as heterobifunctional cross-linking agents that have been widely used to couple toxins or chemotherapeutic agents to antibodies for targeted delivery. Conjugation to liposomes can also be accomplished using the carbohydrate-directed cross-linking reagent 4-(4-maleimidophenyl) butyric acid hydrazide (MPBH) (Duzgunes et al., 1992), herein incorporated by reference.

Liposomes containing pharmaceutical molecules may be prepared by well-known methods (See, e.g. DE 3,218,121; Epstein et al., 1985; Hwang et al.,1980; U.S. Pat. Nos. 4,485,045 and 4,544,545). Ordinarily the liposomes are of the small (about 200–800 Angstroms) unilamellar type in which the lipid content is greater than about 30 mol. % cholesterol. The proportion of cholesterol is selected to control the optimal rate of MAG derivative and inhibitor release.

The compositions also will preferably include conventional pharmaceutically acceptable carriers well known in the art (see, e.g., Remington's Pharmaceutical Sciences, 16th Edition, 1980, Mac Publishing Company). Such pharmaceutically acceptable carriers may include other medicinal agents, carriers, genetic carriers, adjuvants, excipients, etc., such as human serum albumin or plasma preparations. The compositions are preferably in the form of a unit dose and will usually be administered one or more times a day.

6. EXAMPLES

The following examples are provided merely as illustrative of various aspects of the invention and shall not be construed to limit the invention in any way.

A group of *S. cerevisiae* genes have been discovered as novel reporters of the glucan synthase pathway in the model organism *S. cerevisiae*. This invention provides the following examples of the characterization of seven *S. cerevisiae* glucan synthase pathway reporter genes described in detail below.

6.1 Genome Reporter Matrix™ Technology

Genome Reporter Matrix™ (GRM) technology was used to generate the gene expression profiles that the glucan synthase inhibition treatments induced in the yeast *S. cerevisiae*. The GRM was used to generate comprehensive gene expression profiles in the yeast *S. cerevisiae*. The GRM used in the present invention was a matrix of units comprising living *S. cerevisiae* cells, the cells in each unit containing one *S. cerevisiae* reporter fusions (GRM construct) representative of essentially every known gene and hypothetical open reading frame (ORF) of *S. cerevisiae*. The GRM constructs used in the present invention comprised a promoter, 5' upstream untranslated region and usually the first four amino acids from one of each hypothetical ORF fused to a gene encoding the green fluorescent protein (GFP). Detailed descriptions of the concept of the GRM can be found in U.S. Pat. Nos. 5,569,588 and 5,777,888, all of which are hereby incorporated by reference, in their entireties. Detailed descriptions of the GRM and how it is used to generate expression profiles can be found in International Publication No. WO/58521, published Oct. 5, 2000, and in Dimster-Denk, D., et al., 1999, J. of Lipid Research, 40(5): 850–860, which are hereby incorporated by reference in their entireties.

6.1.1 Reporter Gene Construct

In a preferred method for constructing the genome reporter constructs used in this invention, a vector comprising a marker gene having an amber mutation and a supF tRNA gene which suppresses the amber mutation is used as the parent vector. A modified version of the methods found in Ashby, M., et al., International Publication WO 00/5821, dated Oct. 5, 2000, which is hereby incorporated by reference in its entirety, is presented below.

A plasmid cloning vector was constructed which comprises a mutant β-lactamase gene with an amber mutation and a supF tRNA gene. Downstream of the supF tRNA gene there is a "stuffer" DNA fragment which is flanked by BsmBI restriction sites. The BsmBI restriction enzyme cuts outside of its six base pair recognition sequence (see, e.g., New England Biolabs 96/97 Catalog, p. 23) and creates a four nucleotide 5' overhang. When the plasmid cloning vector is digested with BsmBI, the enzyme cleaves within the stuffer DNA and within the adjoining tRNA gene and deletes the four 3' terminal nucleotides of the gene. The deleted supF tRNA gene encodes a tRNA which cannot fold correctly and is non-functional, i.e., it can not suppress the amber mutation in the mutant β-lactamase gene (β-lactamase (amber)). Downstream from the stuffer DNA fragment is the coding region of a modified green fluorescent protein ("GFP") gene.

The stuffer DNA was excised from the vector by digestion with BsmBI. The double-stranded DNA at the supF-stuffer fragment junction, produced by BsmBI digestion, is shown below (SEQ ID NO: 22). The tRNA gene sequences are indicated in bold:

```
5' ..supF .. TC        CCCCGGAGACGTC..stuffer..
          .. AGGGGG         CCTCTGCAG..5'
                     BsmBI
```

The 3' terminal sequence of the supF gene necessary for proper function is TCCCCCACCA (SEQ ID NO: 23). The vector, once cleaved with BsmBI, lacks the supF tRNA ACCA terminal nucleotides if the overhangs self-anneal during re-circularization of the plasmid in the absence of insert.

A DNA insert containing the upstream regulatory sequence from a *S. cerevisiae* ORF was generated as a PCR fragment. Two oligonucleotides were designed to flank the DNA insert sequences of interest on a template DNA and anneal to opposite strands of the template DNA. These oligonucleotides also contained a sequence at their respective 5' ends that, when converted into a 5' overhang (in the double-stranded PCR fragment generated using the oligonucleotides), is complementary to the overhangs on the cloning vector generated by BsmBI endonucleolytic cleavage.

Oligonucleotide #1 comprises the 5' terminal sequence: 5'CCCACCA . . . . The remaining nucleotides 3' to this sequence were designed to anneal to sequences at one end of the DNA insert of choice, in this example, to one of the multitude of *S. cerevisiae* expression control sequences.

As highlighted in bold above, oligonucleotide #1 comprises the base pairs needed to restore the wild-type 3' terminal end of the supf tRNA gene. These base pairs are located immediately 3' to the sequence that allows the insert to anneal to the overhang in the BsmBI-digested pAB4 vector.

Oligonucleotide #2 comprises the 5' terminal sequence: 5' TCCTG . . . . The remaining nucleotides 3' to this sequence were designed to anneal to sequences at the other end of the DNA insert of choice, in this Example, to one of a variety of *S. cerevisiae* expression control sequences which may be used according to this invention.

The DNA template (*S. cerevisiae* genomic DNA) and the two oligonucleotides were annealed and the hybrids were amplified by polymerase chain reaction using Klentaq™ polymerase and PCR buffer according to the manufacturer's instructions (Clontech™). Briefly, 15 ng *S. cerevisiae* genomic DNA served as template DNA in a 10 μl PCR reaction containing 0.2 mM dNTPs, PCR buffer, Klentaq™ polymerase, and 1 μL of an 8 μM solution containing the primer pairs. The PCR reaction mixture was subjected to the following steps: a) 94° C. for 3 min; b) 94° C. for 15 sec; c) 52° C. for 30 sec; d) 72° C. for 1 min. 45 sec; and e) 4° C. indefinitely. Steps b) through d) were repeated for a total of 30 cycles. The PCR amplification product was purified away from other components of the reaction by standard methods.

To generate the desired 5' overhangs on the ends of the PCR amplification product, the PCR fragment was treated with DNA polymerase I in the presence of dTTP and dCTP. Under these conditions, DNA polymerase I fills in 3' overhangs with its 5' to 3' polymerase activity and also generates 5' overhangs with its 3' to 5' exonucleolytic activity, which, in the presence of excess dTTP and dCTP, removes nucleotides in a 3' to 5' direction until thymidine or a cytosine, respectively, is removed and then replaced.

The overhangs generated by this reaction are:

a) At the 5' end (supF tRNA restoring end) of the DNA insert:

```
5' CCCCACCA..     becomes    5' CCCCACCA..
     GGGGTGGT..                       TGGT..
``` b) At the 3' end of the DNA insert (joined to the GFP coding sequence)

```
5' CAGGA..       becomes      5' C
   GTCCT..                       GTCCT ..
```

This DNA insert, now comprising 5' overhangs compatible with one of each of the ends of the BsmBI-cleaved pAB4 vector, was used as substrate in a standard ligation reaction with the BsmBI-cleaved pAB4 vector. The resulting ligation mixture was used to transform competent E. coli cells. The cells were plated on agar plates in the presence of ampicillin.

Colonies that grew in the presence of ampicillin were producing functional β-lactamase enzyme and each harbored the desired recombinant DNA molecule, having a DNA insert with a S. cerevisiae expression control sequence inserted upstream of the modified GFP coding region. The supF gene on vectors which re-ligated without a DNA insert did not express a functional supF tRNA and did not make functional β-lactamase. Thus, they were not found in transformed host cells grown on ampicillin.

6.1.2 Construction of S. cerevisiae Strains

ABY12 (MATa his3Δ1, lev2Δ0, met15Δ0, ura3Δ0) of S. cerevisiae was used. ABY12 is derived from S228c. GRM arrays were grown at 30° C. on solid casamino acid medium (Difco) with 2% glucose and 0.5% Ultrapure Agarose (Gibco BRL). The medium was supplemented with additional amino acids and adenine (Sigma™) at the following concentrations: adenine and tryptophan at 30 μg/ml; histidine, methionine, and tyrosine at 20 μg/ml; leucine and lysine at 40 μg/ml. Stock solutions of the supplements were made at 100× concentrations in water. S. cerevisiae cells were transformed with the reporter plasmids prepared by the method above by electroporation.

6.2 Determining Reporter Gene Expression Levels

Solutions of test compounds were added directly to the solid agar growth media plates prior to addition of S. cerevisiae strains. The individual strains comprising the GRM were maintained as independent colonies (and cultures) in a 96-well format, in medium selecting for the URA2-containing reporter plasmid. Prior to each experiment, fresh dilutions of the reporter-containing strains were inoculated and grown overnight at 30° C. A Hamilton MicroLab 4200, a multichannel gantry robot equipped with a custom pin tool device capable of dispensing 50 nanoliter volumes in a highly reproducible manner, was used to array the matrix of S. cerevisiae strains in a uniform manner onto solid agar growth media at a density of 1536 reporter strains per 110 cm$^2$ plate. Fifty nanoliters of S. cerevisiae liquid cultures arrayed onto solid medium by the Hamilton Microlab 4200 results in colony-to-colony signal reproducibility of less than 5% variation. Once arrayed, each plate was grown at 30° C. for 18 hours or at 25° C. for 24 hours.

The level of fluorescence expressed from each reporter gene fusion was determined using a Molecular Dynamics Fluorimager SI. Custom image analysis software was used to quantitate the fluorescence of each colony in the images. Generally, the drug treatments were performed at several concentrations, with the analysis based upon the concentration producing the most informative expression profile.

6.3 Identification of Glucan Synthase Pathway Reporter Genes

First, comprehensive gene expression profiles for S. cerevisiae grown in the presence of known inhibitors of glucan synthase were constructed. Enfumafungin and Ascosteroside were two known glucan synthase inhibitors used in the present invention. Prior to exposing the GRM to these two glucan synthase inhibitors, growth inhibition studies were performed on wild-type S288C strain in order to determine the appropriate concentrations for GRM profiling. Past experience has shown that the most informative reporter gene expression profiles are generated when the drug or chemical treatment is performed at concentrations that inhibit S. cerevisiae growth. Both Enfumafungin and Ascosteroside were effective in these growth inhibition assays (Table II).

TABLE II

Various inhibition concentrations (in μg/ml) of ascosteroside and enfumafungin.

| Merck Compound | IC25 | IC50 | IC75 |
|---|---|---|---|
| Ascosteroside | 6.3 | 19 | N/A |
| Enfumafungin | 0.54 | 0.69 | 0.9 |

Based on the IC50 of 0.69 μg/ml for Enfumafungin, the GRM was exposed to concentrations of 0.15, 0.30, 0.45, 0.60 and 0.75 μg/ml. The 0.60 μg/ml and 0.75 μg/ml concentrations were too high and caused too much growth inhibition of the GRM to allow generation of reporter gene expression profiles. The lowest three concentrations all yielded informative profiles with the GRM. Based on the IC50 of 19 μg/ml for Ascosteroside the GRM was exposed to Ascosteroside concentrations of 5.0, 10.0 and 20.0 μg/ml. All three concentrations yielded informative profiles with the GRM. Chemical treatment of the GRM routinely causes significant changes in reporter gene expression for many of the genes in the S. cerevisiae genome. Even the lowest concentration of Ascosteroside caused significant ($p<=0.01$) up- or down-regulation of 318 of the roughly 6,000 gene reporters in the GRM (FIG. 8).

Next, the six GRM expression profiles that were generated for Enfumafungin and Ascosteroside were added to the "S. cerevisiae/Genome Reporter Matrix" data set contained in a database stored in a Rosetta Resolver® gene expression data analysis system (Rosetta BioSoftware, Kirkland, Wash.) in Rosetta Inpharmatics' Resolver® database. With the addition of these profiles the GRM data set in Resolver® database contained 1,647 expression profiles for approximately 500 unique compounds/molecules and 60 genetic mutants of the S288C strain at the time of analysis. All compound profiles in this data set were generated using the GRM in the same S288C strain background (Chemical Profiling Strain). This data set also contained 18 profiles generated from strains harboring mutations in the S. cerevisiae Glucan synthase genes. These mutations consist of either a complete knockout of the FKS1 gene, down-regulation of a tetracycline repressible promoter operatively linked to the FKS1 gene, or a double mutant consisting of a knockout of the GSC2 (FKS2) gene and down-regulation of a tetracycline repressible promoter operatively linked to the FKS1 gene.

To find gene reporters that were indicators of inhibiting or disrupting glucan synthase in S. cerevisiae, an analysis was performed to find reporter genes that were significantly up-regulated in both glucan synthase inhibitor profiles and glucan synthase mutant profiles. From the comparison of the expression profile for the 5 μg/ml Ascosteroside treatment and one of the expression profiles for the FKS1/GSC2 double-mutant (FIG. 9), nine candidate single gene reporters that were significantly up-regulated in both expression profiles were selected for further analysis. Additionally four other reporters that were significantly up-regulated in the drug treatments were selected for further analysis. All of these reporter genes are shown in Table III.

TABLE III

Nine candidate single glucan synthase pathway reporters that were significantly up-regulated in both expression profiles, FIG. 8, and four candidate reporters that were significantly up-regulated in the drug treatments.

| pACA | ORF | Gene | p-value (from 5 µg Ascosteroside) | expression units | # treatments up-regulating, p >= 0.5 | treatment causing upregulation |
|---|---|---|---|---|---|---|
| 6768 | YAR010C | — | 0.03 | 0.0–0.5 | 44 | |
| 3578 | YAR050W | FLO1 | $9.6 \times 10^{-6}$ | 0.1–5.3 | 309 | mostly drugs |
| 6597 | YCR101C | — | $1.1 \times 10^{-6}$ | 0.0–1.4 | 189 | all types |
| 3695 | YFR030W | MET10 | $8.5 \times 10^{-7}$ | 0.1–10.5 | 335 | drugs only |
| 4560 | YHR209W | — | $3.3 \times 10^{-7}$ | 0.1–4.6 | 303 | all types |
| 4609 | YIL141W | — | 0.01 | 0.0–0.4 | 30 | very few |
| 7866 | YJR137C | ECM17 | $4 \times 10^{-5}$ | 0.1–10.7 | 605 | mostly drugs |
| 1195 | YKL161C | — | $8.2 \times 10^{-7}$ | 0.1–3.0 | 214 | all types |
| 3133 | YLR121C | YPS3 | $2.3 \times 10^{-4}$ | 0.2–6.8 | 218 | all types |
| 5199 | YNR066C | — | $2.3 \times 10^{-7}$ | 0.1–5.8 | 201 | all types |
| 5263 | YOL113W | SKM1 | $6 \times 10^{-6}$ | 0.1–3.0 | 122 | all types |
| 5784 | YPL272C | — | $1.1 \times 10^{-4}$ | 0.1–12.1 | 492 | not all |
| 6102 | YPR047W | MSF1 | 0.06 | 0.6–71 | 9 | very few |

Analysis of the performance of each of these reporters across the entire data set by examining plots of the log 10 (Ratio) vs. the Log 10 (Intensity) showed that three of the reporters (YAR010C, YIL141W, and YPR047W) exhibited extremely sporadic behavior across the 1,647 expression profiles in the database. This sporadic behavior was also evidenced by that fact that these three reporters all had P values greater than 0.01 in the 5 µg/ml Ascosteroside experiment (Table III). The three reporters (YAR010C, YIL141W, and YPR047W) were dropped from further analysis because of this sporadic behavior.

The remaining ten reporters were rank-ordered based on their specificity towards being up-regulated by glucan synthase inhibitors or mutations in the glucan synthase genes (Table IV) versus being upregulated by other drug treatments or mutations outside of the glucan synthase pathway.

also caused some of the highest expression ratios for YOL113W (SKM1) out of all 1,647 experiments (FIG. 10). The reporter for YOL113W (SKM1) also shows a 30 fold dynamic range throughout the experimental set (Table IV, "expression units"). The high specificity of YOL113W (SKM1), along with the high expression ratios induced by inhibition of glucan synthase, and YOL113W's (SKM1) good dynamic range, make YOL113W (SKM1) the ideal reporter for high throughput screens of chemical libraries and screens of natural product producing strains.

The next five reporters down the rank-ordered list (YCR101C, YNR066C, YLR121C, YHR209W, and YKL161C; Table IV) showed fairly good specificity (ranging from 105 through 131 treatments causing significant up-regulation, Table IV) for glucan synthase inhibition. Four of the five showed good dynamic range (Table IV, "expres-

TABLE IV

Ten candidate glucan synthase pathway reporters rank-ordered based on their specificity towards being up-regulated by glucan synthase inhibitors or mutations in the glucan synthase genes.

| pACA | ORF | Gene | P-VALUE (from 5 µg Ascosteroside) | expression units | # treatments up-regulating, p <= 0.01 | Treatment causing upregulation |
|---|---|---|---|---|---|---|
| 5263 | YOL113W | SKM1 | $6 \times 10^{-6}$ | 0.1–3.0 | 73 | all types |
| 6597 | YCR101C | — | $1.1 \times 10^{-6}$ | 0.0–1.4 | 105 | all types |
| 5199 | YNR066C | — | $2.3 \times 10^{-7}$ | 0.1–5.8 | 106 | all types |
| 3133 | YLR121C | YPS3 | $2.3 \times 10^{-4}$ | 0.2–6.8 | 117 | all types |
| 4560 | YHR209W | — | $3.3 \times 10^{-7}$ | 0.1–4.6 | 130 | all types |
| 1195 | YKL161C | — | $8.2 \times 10^{-7}$ | 0.1–3.0 | 131 | all types |
| 3578 | YAR050W | FL01 | $9.6 \times 10^{-6}$ | 0.1–5.3 | 158 | drugs |
| 3695 | YFR030W | MET10 | $8.5 \times 10^{-7}$ | 0.1–10.5 | 174 | drugs |
| 5784 | YPL272C | — | $1.1 \times 10^{-4}$ | 0.1–12.1 | 356 | not all |
| 7866 | YJR137C | ECM17 | $4 \times 10^{-5}$ | 0.1–10.7 | 418 | drugs |

Figure 11:
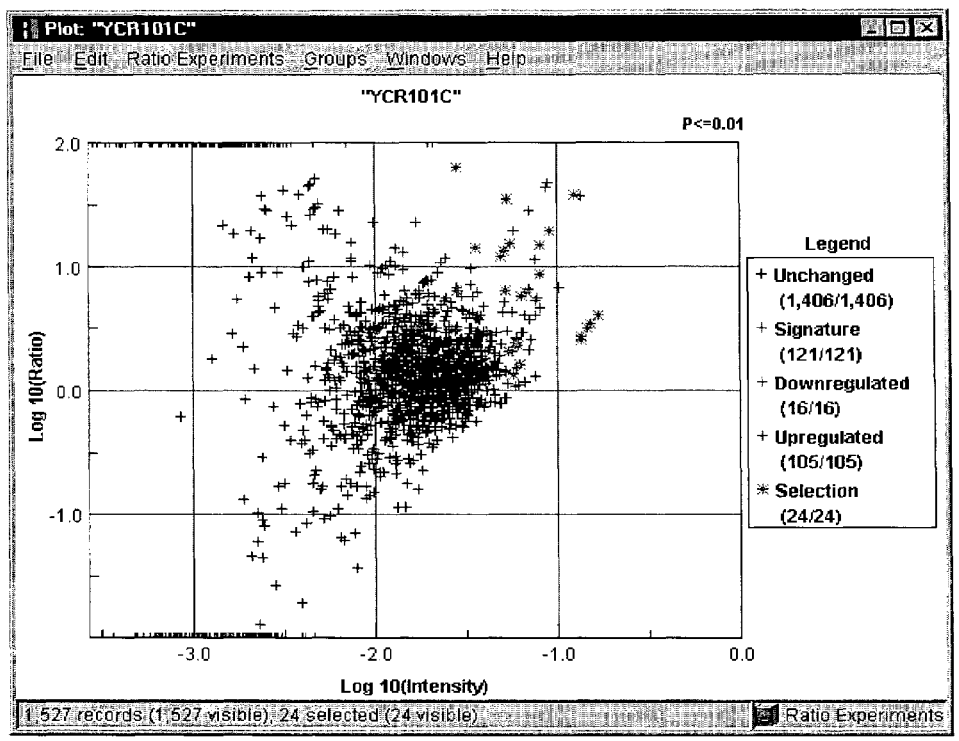

The most specific of these reporters, YOL113W (SKM1) was significantly (P<=0.01, i.e., P less than or equal to 0.01) up-regulated by only 73 out of the 1,647 conditions in the data set (Table IV). Moreover, all 24 experiments in the "*S. cerevisiae*/Genome Reporter Matrix" data set that are comprised of either compounds that inhibit glucan synthase or mutations in the glucan synthase genes were among those 73 experiments significantly up-regulating YOL113W (SKM1) (FIG. 10, "Selection" points). Some of these 24 experiments sion units") with YCR101C being somewhat problematic in this regard, expression range of 0.0–1.4, due to the fact that it is a low intensity reporter (FIG. 11). The wedge type plot of Log 10 (Ratio) vs. Log 10 (Intensity) shows how this low intensity reporter could be very noisy in terms of ratios, producing at times large, but insignificant ratios for many of the 1,647 treatments (FIG. 11). This characteristic makes YCR101C a less desirable reporter for screening than the other four in this group. The other four reporters in this group of five all showed good intensities and normal ratio vs. intensity plots where the 24 glucan synthase experiments highlighted on these plots show strong ratios of induction for these reporters for these glucan synthase perturbing treatments (FIGS. 12–15).

The last four reporters at the bottom of the rank-ordered list (YAR050W, YFR030W, YPL272C, and YJR137C; Table IV) were all selected from being significantly up-regulated in drug treatments, but not by the mutants. All of these were less specific to glucan synthase blocks (Table IV) than those selected from the drug vs. mutant compare plot (FIG. 9). With 356 treatments up-regulating ($p<=0.01$) YPL272C and 418 up-regulating ($p<=0.01$) YJR137C (Table IV), neither of these reporters were promising candidates for single-reporters for screening compound libraries for novel glucan synthase inhibitors. Additionally, the glucan synthase inhibitors that up-regulated YPL272C significantly ($p<=0.01$) generated some of the lowest ratios of induction out of the 356 experiments that significantly up-regulated YPL272C (FIG. 16). The other two reporters in this group (YAR050W and YFR030W) were moderately specific with 158 and 174 treatments up-regulating each respectively (Table IV). They both showed good dynamic ranges (Table IV, "expression units") and normal ratio vs. intensity plots with good baseline intensities (FIGS. 17 and 18). From this analysis the best reporters for assays to detect inhibition of glucan synthase are in order of preference: YOL113W (SKM1); YNR066C; YLR121C (YPS3); YHR209W; YKL161C; YAR050W (FLO1); and YFR030W (MET10). YAR050W (FLO1) and YFR030W (MET10) may have some additional utility due to their ability to differentiate between drugs and mutants.

6.4 Confirmation of Utility 6.4.1 Liquid High-Throughput Like Assay Performance Test The utility of using five of the identified reporters in a liquid based screen for GS inhibitors was demonstrated by selecting five out of the ten reporters shown in Table IV to test in a 96-well liquid assay. The five reporters selected were: YOL113W (SKM1), YNR066C, YLR121C (YPS3), YKL161C, and YAR050W (FLO1). Another reporter, YOR237W (HES1), was selected as a negative control. YOR237W (HES1) is a reporter that is induced by agents that inhibit sterol biosynthesis (WO 00/58521, PCT published application) but is not significantly induced by any of the compounds that inhibit GS, nor by any of the GS mutants profiled in this data set (FIG. 19, GS experiments marked "Selection").

A non-limiting description of the assay as performed is described below:

1. Reporters transformed into wild-type *S. Cerevisiae* strain ABY12 were grown on solid Casamino Acids media plates.

2. The cultures from the solid media plates were used to inoculate 50 ml liquid cultures in Casamino Acids media. These liquid cultures were grown overnight at 30 degrees Celsius. The cultures were all grown to a final $OD_{600}\sim=8$ (Table V).

TABLE V

Final OD of five reporters strains, YOL113W (SKM1), YNR066C, YLR121C (YPS3), YKL161C, and YAR050W, and one control strain, YOR237W (HES1).

| pACA | ORF | Gene | OD600 |
|---|---|---|---|
| 5263 | YOL113W | SKM1 | 7.8 |
| 5199 | YNR066C | — | 7.9 |

TABLE V-continued

Final OD of five reporters strains, YOL113W (SKM1), YNR066C, YLR121C (YPS3), YKL161C, and YAR050W, and one control strain, YOR237W (HES1).

| pACA | ORF | Gene | OD600 |
|---|---|---|---|
| 3133 | YLR121C | YPS3 | 8.4 |
| 1195 | YKL161C | — | 8.2 |
| 3578 | YAR050W | FLO1 | 8.4 |
| 5613 | YOR237W | HES1 | 8.1 |

These cultures were then diluted in Casamino Acids media to and $OD_{600}=2$.

3. The drug-like agents selected for the assay were the GS inhibitors Enfumafungin, Ascosteroside, and Dihydropapulacandin B; along with the Elongation Factor 2 (EF2) inhibitor Sordarin, to be used as a negative control. These four drugs were all added to the second column of each 96-well assay plate and serially diluted (1 to 2) into Casamino Acids media plus 2% DMSO in columns 3–12, so that column 2 of each plate will contain the highest concentration of each drug and column 12 will contain the lowest. The first column of each plate was used as a "no drug" control, containing only Casamino Acids media plus 2% DMSO. The concentrations for each drug that were added to the wells in column 2 are shown in Table VI (Maximum Concentration Tested) along with the rows of each plate they were added to (Table VI, Rows).

TABLE VI

IC25, IC50, IC75, maximum concentration (µg/ml) tested, and row location on FIGS. 20–22 for antifungal compounds ascosteroside, enfumafungin, dihydropapulacandin, sordarin.

| Drug/Compound | IC25* | IC50* | IC75* | Maximum Concentration Tested | Rows |
|---|---|---|---|---|---|
| Ascosteroside | 6.3 | 19 | N/A | 25 | B, F |
| Enfumafungin | 0.54 | 0.69 | 0.9 | 5 | A, E |
| Dihydropapulacandin B | 3.7 | 4.4 | 5.3 | 12.5 | C, G |
| Sordarin | 1.1 | 1.5 | 2.5 | 5 | D, H |

*Concentrations are given in µg/ml

After the serial dilutions were completed each well contained 100 ul of media and/or media plus drug.

4. One-hundred microliters from the liquid reporter strain cultures at $OD_{600}=2$ were added to each of the wells of the 96-well serial dilution plates from above and mixed. Thus at time zero, all GFP-reporter strain cultures were seeded at a density of $OD_{600}=1$. The 96-well assay plates were then incubated at 30 degrees Celsius for ~24 hours.

5. After the 24 hour incubation the 96-well assay plates were imaged in a Molecular Dynamics Fluorimager SI to measure the fluorescence from the GFP reporters. The five reporters that were selected to be specific reporters of GS inhibition all showed increases in fluorescence for the higher drug concentrations of the three GS inhibitors versus the no drug controls (FIGS. 20–22). None of the reporters, however, showed any increase in fluorescence for any of the concentrations of the EF2 inhibitor Sordarin (FIGS. 20–22). Additionally, none of the compounds tested induced increased fluorescence from the reporter for inhibition of sterol biosynthesis, HES1 (FIG. 20). These results demonstrate the utility of these GFP-reporter strains for use as reporters in high-throughput screens for identifying inhibitors of GS. Of note here is the fact that the highest concentrations tested were all substantially greater than the measured IC50's for these compounds in the ABY12 strain (Table VI). Therefore these strains are capable of reporting on inhibition of GS even at drug concentrations that inhibit cell growth. This is an important characteristic of this assay as the preferred method of high-throughput screening would be to perform the screens at one high concentration for every compound assayed. It has been previously shown that the HES1 reporter strain is capable of performing under such assay conditions in a 384-well formatted high-throughput screen of a combinatorial library (WO 00/58521, PCT published application).

6.4.2 Test of YOL113W (SKM1) Reporter in Solid Plate "Halo" Assay

To demonstrate the utility of using these reporters in a solid plate assay for GS inhibitors, a YOL113W (SKM1) reporter was selected to test in a agar plate "halo" assay. This assay is meant to mimic assays where natural product producing strains would be either plated onto a lawn of our ABY12 reporter carrying strains, or an agar overlay containing the ABY12 reporter strain would be placed over a plate containing natural product producing strains, the purpose being identifying strains that are producing molecules that inhibit GS.

A non-limiting description of the assay as performed is described below:

1. The YOL113W (SKM1) reporter transformed into wild-type S. Cerevisiae strain ABY12 was grown on a solid Casamino Acids media plate.

2. The culture from the solid media plate was used to inoculate a 50 ml liquid culture in Casamino Acids media. This liquid culture was grown overnight at 30 degrees Celsius. The culture was grown to a final $OD_{600}$=10.5. This culture was then diluted in Casamino Acids media to an $OD_{600}$=1, or 1×107 cells per milliliter. Five-hundred microliters of cell culture (5×106 cells) was then spread evenly over the surface of each of two 100 mm solid agar-Casamino-acids-media plates to form a lawn of the YOL113W (SKM1) reporter strain on each plate.

3. Two 6 mm diameter blank paper discs (BECTON DICKINSON® #231039) were placed on top of the agar surface of each plate evenly spaced apart. On one plate 20 ul of 200 µg/ml of the GS inhibitor Enfumafungin was spotted onto one of the two paper discs (low concentration treatment) and 20 ul of 2% DMSO was spotted on the other paper disc as a control. On the other plate 20 ul of 1 mg/ml Enfumafungin was spotted onto one of the two paper discs (high concentration treatment) and 20 ul of 10% DMSO was spotted on the other paper disc as a control. The plates were then incubated at 30 degrees Celsius overnight.

4. After a 23 hour incubation the assay plates were imaged in a Molecular Dynamics Fluorimager SI to measure the fluorescence from the GFP reporters. Both the low and high concentrations of Enfumafungin inhibited the growth of the lawn of the YOL113W (SKM1) reporter strain on each plate to form "halo's" of no growth radiating out from each of the paper discs where the drug was spotted down (FIG. 23). At the edge of each halo where the lawn begins to grow is a zone of high fluorescence where the YOL113W (SKM1) reporter has been significantly induced by the GS inhibitor Enfumafungin (FIG. 23). In both cases the DMSO controls cause no zone of growth inhibition and no induction of the YOL113W (SKM1) reporter (FIG. 23). These results demonstrate the utility of these reporters for use in this type of solid plate assay for discovering agents that block fungal GS.

The present invention is not be to be limited in scope by the specific embodiments described herein. Indeed, various modifications of the invention in addition to those described herein will become apparent to those skilled in the art from the foregoing description and accompanying drawings. Such modifications are intended to fall within the scope of the appended claims.

Various references are cited herein above, including patent applications, patents, and publications, the disclosures of which are hereby incorporated by reference in their entireties.

What is claimed is:

1. A method for determining whether a molecule affects the function or activity of a glucan synthase pathway in a S. cerevisiae cell comprising:
   (a) contacting the cell with, or recombinantly expressing within the cell, the molecule;
   (b) determining whether the RNA expression or protein expression in said cell of at least one target polynucleotide sequence is changed in step (a) relative to the expression of said target polynucleotide sequence in the absence of the molecule, each said target polynucleotide sequence being operatively linked to a promoter native to a gene selected from the group consisting of YOL113W (SKM1), YNR066C, YLR121C (YPS3), YHR209W, YKL161C, YAR050W (FLO1), and YFR030W (MET10); and
   (c) determining that the molecule affects the function or activity of the glucan synthase pathway if the expression of said target polynucleotide is changed, or determining that the molecule does not affect the function or activity of the glucan synthase pathway if the expression of said target polynucleotide sequence is unchanged.

2. The method of claim 1, wherein each target polynucleotide sequence comprises a marker gene; wherein step (b) comprises determining whether the RNA expression or protein expression of the marker gene(s) is changed in step (a) relative to the expression of said marker gene in the absence of the molecule; and wherein step (c) comprises determining that the molecule affects the function or activity of the glucan synthase pathway if the expression of said marker gene is changed, or determining that the molecule does not affect the function or activity of the glucan synthase pathway if the expression of the marker gene is unchanged.

3. The method of claim 1 which is a method for determining whether the molecule inhibits glucan synthase synthesis such that a cell contacted with the molecule exhibits a lower level of glucan synthase than a cell which is not contacted with said molecule.

4. The method of claim 1, wherein step (b) comprises determining whether RNA or protein expression of a target polynucleotide sequence regulated by a promoter native to YOL113W (SKM1) is changed.

5. The method of claim 1, wherein step (b) comprises determining whether RNA expression is changed.

6. The method of claim 1, wherein step (b) comprises determining whether protein expression is changed.

7. The method of claim 1, wherein step (b) comprises determining whether RNA or protein expression of at least two of said target polynucleotide sequences is changed.

8. The method of claim 1 which is a method for determining whether said molecule inhibits glucan synthase synthesis, and wherein step (c) comprises determining that the molecule inhibits glucan synthase synthesis if the expression of said target polynucleotide sequence in step (a)

is increased relative to the expression of said target polynucleotide sequence in the absence of the molecule.

9. The method of claim 1, wherein the *S. cerevisiae* cell is a cell that recombinantly expresses said target polynucleotide sequence.

10. The method of claim 1, wherein step (a) comprises contacting the cell with the molecule, and wherein step (a) is carried out in a liquid high throughput-like assay.

11. The method of claim 1, wherein step (a) comprises contacting the cell with the molecule, and wherein step (a) is carried out in a solid plate halo assay.

12. The method of claim 1, wherein step (a) comprises contacting the cell with the molecule, and wherein step (a) is carried out in an agar overlay assay.

13. A method for determining the effect of a molecule upon the function or activity of the glucan synthase pathway comprising:
  (a) contacting a *S. cerevisiae* cell with, or recombinantly expressing within the cell the molecule;
  (b) detecting a change in RNA expression or protein expression in said cell of at least one target polynucleotide sequence relative to the expression of said target polynucleotide sequence in the absence of the molecule, each said target polynucleotide sequence being regulated by a promoter native to a gene selected from the group consisting of YOL113W (SKM1), YNR066C, YLR121C (YPS3), YHR209W, YKL161C, YAR050W (FLO1), and YFR030W (MET10); and
  (c) determining the effect of the molecule upon the function or activity of the glucan synthase pathway based upon the change in RNA expression or protein expression.

14. A method for monitoring the activity of the glucan synthase pathway in a *S. cerevisiae* cell exposed to a molecule comprising:
  (a) contacting the cell with, or recombinantly expressing within the cell, the molecule;
  (b) determining whether the RNA expression or protein expression in said cell of at least one target polynucleotide sequence is changed in step (a) relative to the expression of said target polynucleotide sequence in the absence of the molecule, each said target polynucleotide sequence being regulated by a promoter native to a gene selected from the group consisting of YOL113W (SKM1), YNR066C, YLR121C (YPS3), YHR209W, YKL161C, YAR050W (FLO1), and YFR030W (MET10); and
  (c) determining that the activity of the glucan synthase pathway in said cell is changed if the expression is determined to be changed in step (b), or determining that the activity of the glucan synthase pathway in said cell is unchanged if the expression is determined to be unchanged in step (b).

15. The method of claim 13, wherein step (a) comprises contacting the cell with said molecule.

16. The method of claim 14, wherein step (a) comprises contacting the cell with said molecule.

17. The method of claim 13, wherein step (a) comprises recombinantly expressing within the cell the molecule.

18. The method of claim 14, wherein step (a) comprises recombinantly expressing within the cell the molecule.

19. The method of claim 13, wherein step (b) comprises detecting an increase in said RNA or protein expression, and step (c) comprises determining that said effect of the molecule is to inhibit the function or activity of the glucan synthase pathway.

20. The method of claim 14, wherein step (b) comprises determining that said expression is increased, and step (c) comprises determining that the activity of the glucan synthase pathway is inhibited.

21. The method of claim 13, 14, 15, 16, 17, 18, 19 or 20, wherein said at least one target polynucleotide sequence comprises YOL113W (SKM1).

22. The method of claim 13, 14, 15, 16, 17, 18, 19 or 20, wherein said at least one target polynucleotide sequence is selected from the group consisting of YOL113W (SKM1), YNR066C, YLR121C (YPS3), YHR209W, YKL161C, YFR030W (FLO1), and YFR030W (MET10).

23. A method for identifying a molecule that modulates the expression of a glucan synthase pathway target polynucleotide sequence comprising:
  (a) recombinantly expressing in a *S. cerevisiae* cell, or contacting a *S. cerevisiae* cell with, at least one candidate molecule; and
  (b) measuring the RNA or protein expression in said cell of at least one target polynucleotide sequence, each said target polynucleotide sequence being regulated by a promoter native to a gene selected from the group consisting of YOL113W (SKM1), YNR066C, YLR121C (YPS3), YHR209W, YKL161C, YAR050W (FLO1), and YFR030W (MET10), wherein an increase or decrease in the expression of said target polynucleotide sequence relative to the expression of said target polynucleotide sequence in the absence of said candidate molecule indicates that the molecule modulates expression of the glucan synthase pathway target polynucleotide sequence.

24. The method of claim 1 wherein the promoter is selected from the group consisting of SEQ ID NO:3, SEQ ID NO:6, SEQ ID NO:9, SEQ ID NO:12, SEQ ID NO:15, SEQ ID NO:18, and SEQ ID NO:21.

25. The method of claim 2 wherein the marker gene is selected from the group consisting of green fluorescent protein, red fluorescent protein, blue fluorescent protein, luciferase, LEU2, LYS2, ADE2, TRP1, CAN1, CYH2, GUS, CUP1 and chloramphenicol acetyl transferase.

26. A method for determining whether a first *S. cerevisiae* cell is mutant for a glucan synthase pathway gene comprising:
  (a) in said first *S. cerevisiae* cell, determining the RNA or protein expression of at least one target polynucleotide sequence, each target polynucleotide sequence being regulated by a promoter native to a gene selected from the group consisting of YOL113W (SKM1 1), YNR066C, YLR121C (YPS3), YHR209W, and YKL161C, wherein said cell is not being exposed to an inhibitor of the glucan synthase pathway;
  (b) determining whether the RNA and/or protein expression of said at least one target polynucleotide sequence determined in step (a) is changed relative to the RNA and/or protein expression of said at least one target polynucleotide sequence in a second *S. cerevisiae* cell which is wildtype for glucan synthase genes; and
  (c) determining that the first *S. cerevisiae* cell is mutant for a glucan synthase pathway gene if the expression is determined to be changed in step (a), or determining that the first *S. cerevisiae* cell is not mutant for a glucan synthase pathway gene if the expression is determined to be unchanged in step (b).

27. The method of claim 26, which further comprises determining the RNA or protein expression of one or both of YAR050W (FLO1) and YFR030W (MET10), in said first *S. cerevisiae* cell; and wherein step (c) further comprises determining that the first *S. cerevisiae* cell is mutant for said glucan synthase pathway gene if the expression of one or both of YAR050W (FLO1) and YFR030W (MET10) is determined to be unchanged.

28. The method of claim 1, wherein the molecule is selected from the group consisting of natural products, proteins, and small molecules.

29. The method of claim 28, wherein the molecule is purified.

30. The method of claim 29, wherein the molecule is not substantially purified.

31. The method of claim 1, wherein step (a) comprises contacting the cell with a second, test cell, wherein the test cell produces the molecule.

32. The method of claim 31, wherein the molecule is released by the test cell.

33. The method of claim 32, wherein the molecule is secreted by the test cell.

* * * * *